(12) United States Patent
Keyt et al.

(10) Patent No.: US 11,542,342 B2
(45) Date of Patent: Jan. 3, 2023

(54) BINDING MOLECULES WITH MODIFIED J-CHAIN

(71) Applicant: IGM Biosciences, Inc., Mountain View, CA (US)

(72) Inventors: Bruce A. Keyt, Hillsborough, CA (US); Leonard G. Presta, San Francisco, CA (US); Ramesh Baliga, Redwood City, CA (US)

(73) Assignee: IGM Biosciences, Inc., Mountain View, CA (US)

( * ) Notice: Subject to any disclaimer, the term of this patent is extended or adjusted under 35 U.S.C. 154(b) by 298 days.

(21) Appl. No.: 16/745,059

(22) Filed: Jan. 16, 2020

(65) Prior Publication Data

US 2020/0255546 A1  Aug. 13, 2020

Related U.S. Application Data

(63) Continuation of application No. 15/764,859, filed as application No. PCT/US2016/055041 on Sep. 30, 2016, now Pat. No. 10,618,978.

(60) Provisional application No. 62/235,518, filed on Sep. 30, 2015.

(51) Int. Cl.
| | | |
|---|---|---|
| C07K 16/46 | (2006.01) | |
| C07K 16/28 | (2006.01) | |
| A61K 39/395 | (2006.01) | |
| A61K 39/00 | (2006.01) | |
| A61P 35/02 | (2006.01) | |
| A61P 27/00 | (2006.01) | |

(52) U.S. Cl.
CPC ...... *C07K 16/468* (2013.01); *A61K 39/39541* (2013.01); *A61K 39/39558* (2013.01); *C07K 16/28* (2013.01); *C07K 16/2809* (2013.01); *C07K 16/2881* (2013.01); *C07K 16/2887* (2013.01); *A61K 2039/505* (2013.01); *A61P 27/00* (2018.01); *A61P 35/02* (2018.01); *C07K 2317/24* (2013.01); *C07K 2317/31* (2013.01); *C07K 2317/35* (2013.01); *C07K 2317/52* (2013.01); *C07K 2317/569* (2013.01); *C07K 2317/622* (2013.01); *C07K 2317/734* (2013.01); *C07K 2317/90* (2013.01); *C07K 2319/31* (2013.01); *C07K 2319/735* (2013.01); *C07K 2319/91* (2013.01)

(58) Field of Classification Search
CPC .. C07K 16/468; C07K 16/28; C07K 16/2809; C07K 16/2881; C07K 16/2887; C07K 2317/24; C07K 2317/31; C07K 2317/35; C07K 2317/52; C07K 2317/569; C07K 2317/622; C07K 2317/734; C07K 2317/90; C07K 2319/31; C07K 2319/735; C07K 2319/91; A61K 39/39541; A61K 39/39558; A61K 2039/505; A61P 27/00; A61P 35/02; A61P 19/02; A61P 25/28; A61P 27/02; A61P 29/00; A61P 35/00

See application file for complete search history.

(56) References Cited

U.S. PATENT DOCUMENTS

| | | |
|---|---|---|
| 4,816,567 A | 3/1989 | Cabilly |
| 5,434,340 A | 7/1995 | Krimpenfort |
| 5,798,229 A | 8/1998 | Strittmatter |
| 5,831,034 A | 11/1998 | Katinger |
| 5,911,989 A | 6/1999 | Katinger |
| 6,165,463 A | 12/2000 | Platz |
| 6,284,536 B1 | 9/2001 | Morrison |
| 6,476,198 B1 | 11/2002 | Kang |
| 6,676,924 B2 | 1/2004 | Hansen |
| 7,074,403 B1 | 7/2006 | Goldenberg |
| 7,109,304 B2 | 9/2006 | Hansen |
| 7,138,496 B2 | 11/2006 | Hua |
| 7,151,164 B2 | 12/2006 | Hansen |
| 7,238,785 B2 | 7/2007 | Govindan |
| 7,251,164 B2 | 7/2007 | Okhonin |
| 7,282,567 B2 | 10/2007 | Goldenberg |
| 7,300,655 B2 | 11/2007 | Hansen |
| 7,311,912 B1 | 12/2007 | Hein |
| 7,312,318 B2 | 12/2007 | Hansen |
| 7,387,773 B2 | 6/2008 | Murray |
| 7,402,312 B2 | 7/2008 | Rosen |
| 7,541,440 B2 | 6/2009 | Goldenberg |
| 7,601,351 B1 | 10/2009 | Rosen |
| 7,612,180 B2 | 11/2009 | Goldenberg |
| 7,709,615 B2 | 5/2010 | Irie |
| 7,932,360 B2 | 4/2011 | Van Berkel |
| 7,951,378 B2 | 5/2011 | Larrick |
| 8,066,994 B2 | 11/2011 | Gillies |
| 8,114,965 B2 | 2/2012 | Maddon |

(Continued)

FOREIGN PATENT DOCUMENTS

| | | |
|---|---|---|
| AU | 697387 | 3/1996 |
| AU | 708301 | 5/1996 |

(Continued)

OTHER PUBLICATIONS

Baliga, R., et al., (2016) "High Avidity Anti-CD20 IgM Antibody for enhanced Complement-Dependent Cell Killing of Low CD20 Expressing Tumor Cells", Poster Presented at the PEGS Boston Meeting Apr. 25-29, 2016.

(Continued)

*Primary Examiner* — Phuong Huynh

(57) ABSTRACT

The present invention concerns binding molecules that comprise an IgM, IgA, IgG/IgM or IgG/IgA antibody with a J-chain modified to include an ADME-modulating moiety, and their uses.

27 Claims, 29 Drawing Sheets

Specification includes a Sequence Listing.

(56) References Cited

U.S. PATENT DOCUMENTS

| | | | |
|---|---|---|---|
| 8,153,125 B2 | 4/2012 | Watkins | |
| 8,257,703 B2 | 9/2012 | Irie | |
| 8,333,971 B2 | 12/2012 | Goldenberg | |
| 8,337,844 B2 | 12/2012 | Carr | |
| 8,377,435 B2 | 2/2013 | Bhat | |
| 8,871,216 B2 | 10/2014 | Chang | |
| 9,173,961 B2 | 11/2015 | Deckert | |
| 9,409,976 B2 | 8/2016 | Teng | |
| 9,458,241 B2 | 10/2016 | Bhat | |
| 9,938,347 B2 | 4/2018 | Wang | |
| 9,951,134 B2 * | 4/2018 | Keyt | A61P 31/12 |
| 10,351,631 B2 | 7/2019 | Keyt | |
| 10,400,038 B2 * | 9/2019 | Keyt | C07K 16/18 |
| 10,604,559 B2 | 3/2020 | Carroll | |
| 10,618,978 B2 | 4/2020 | Keyt | |
| 10,689,449 B2 | 6/2020 | Wang | |
| 10,787,520 B2 | 9/2020 | Keyt | |
| 10,899,835 B2 | 1/2021 | Baliga | |
| 10,954,302 B2 | 3/2021 | Keyt | |
| 10,975,147 B2 * | 4/2021 | Keyt | C07K 16/468 |
| 11,192,941 B2 | 12/2021 | Keyt | |
| 11,401,337 B2 | 8/2022 | Baliga | |
| 2002/0006630 A1 | 1/2002 | Sirbasku | |
| 2002/0168367 A1 | 11/2002 | Larrick | |
| 2003/0224443 A1 | 12/2003 | Hiatt | |
| 2004/0005318 A1 | 1/2004 | Davis | |
| 2004/0137001 A1 | 7/2004 | Schreiber | |
| 2004/0156826 A1 | 8/2004 | Dangond | |
| 2005/0003431 A1 | 1/2005 | Wucherpfennig | |
| 2005/0129616 A1 | 6/2005 | Salcedo | |
| 2005/0202026 A1 | 9/2005 | Hiatt | |
| 2005/0287153 A1 | 12/2005 | Dennis | |
| 2006/0063234 A1 | 3/2006 | Jones | |
| 2006/0153854 A1 | 7/2006 | Bhat | |
| 2007/0014720 A1 | 1/2007 | Gazit-Bomstein | |
| 2007/0154469 A1 | 7/2007 | Irie | |
| 2007/0248601 A1 | 10/2007 | Cogne | |
| 2007/0249812 A1 | 10/2007 | Hayasaka | |
| 2008/0044413 A1 | 2/2008 | Hammond | |
| 2008/0145420 A1 | 6/2008 | Simon | |
| 2009/0022738 A1 | 1/2009 | Hofmeister | |
| 2009/0130089 A9 | 5/2009 | Smith | |
| 2009/0291899 A1 | 11/2009 | Ferrante | |
| 2010/0093979 A1 | 4/2010 | Lazar | |
| 2010/0172899 A1 | 7/2010 | Irie | |
| 2010/0184959 A1 | 7/2010 | Guler-Gane | |
| 2010/0279932 A1 | 11/2010 | Er | |
| 2010/0279939 A1 | 11/2010 | Fries | |
| 2011/0110852 A1 | 5/2011 | Miller | |
| 2011/0129412 A1 | 6/2011 | Gazit-Bornstein | |
| 2011/0318339 A1 | 12/2011 | Smider | |
| 2012/0039870 A9 | 2/2012 | Dolk | |
| 2012/0045432 A9 | 2/2012 | Yu | |
| 2012/0258126 A1 | 10/2012 | Joergen | |
| 2012/0269830 A1 | 10/2012 | Horowitz | |
| 2013/0095097 A1 | 4/2013 | Blankenship | |
| 2013/0164283 A1 | 6/2013 | Bhat | |
| 2013/0189258 A1 | 7/2013 | Rother | |
| 2013/0280167 A1 | 10/2013 | Rodriguez | |
| 2014/0010809 A1 | 1/2014 | Ledbetter | |
| 2014/0044739 A1 | 2/2014 | Teng | |
| 2014/0088295 A1 | 3/2014 | Smith et al. | |
| 2014/0154252 A1 | 6/2014 | Thompson | |
| 2014/0249044 A1 | 9/2014 | Braz Gonçalves | |
| 2015/0004167 A1 | 1/2015 | Wu | |
| 2015/0038682 A1 | 2/2015 | Tsurushita | |
| 2015/0259420 A1 | 9/2015 | Triebel | |
| 2016/0222132 A1 | 8/2016 | Keyt | |
| 2016/0326233 A1 | 11/2016 | Mondelli | |
| 2016/0368971 A1 | 12/2016 | Keyt | |
| 2017/0183409 A1 | 6/2017 | Keyt | |
| 2017/0283510 A1 | 10/2017 | Keyt | |
| 2017/0320955 A1 | 11/2017 | Wang | |
| 2018/0009897 A1 | 1/2018 | Wang | |
| 2018/0118814 A1 | 5/2018 | Carroll | |
| 2018/0118816 A1 | 5/2018 | Keyt | |
| 2018/0265596 A1 | 9/2018 | Keyt | |
| 2019/0002566 A1 | 1/2019 | Keyt | |
| 2019/0100597 A1 | 4/2019 | Keyt | |
| 2019/0185570 A1 | 6/2019 | Keyt | |
| 2019/0330360 A1 | 10/2019 | Wang | |
| 2019/0330374 A1 | 10/2019 | Wang | |
| 2019/0338031 A1 | 11/2019 | Keyt | |
| 2019/0338040 A1 | 11/2019 | Keyt | |
| 2019/0338041 A1 | 11/2019 | Baliga | |
| 2020/0190190 A1 | 6/2020 | Keyt | |
| 2020/0239572 A1 | 7/2020 | Baliga | |
| 2020/0377577 A1 | 12/2020 | Keyt | |
| 2021/0002353 A1 | 1/2021 | Carroll | |
| 2021/0032357 A1 | 2/2021 | Keyt | |
| 2021/0087273 A1 | 3/2021 | Baliga | |
| 2021/0147567 A1 | 5/2021 | Baliga | |
| 2021/0163600 A1 | 6/2021 | Keyt | |
| 2021/0380701 A1 | 12/2021 | Baliga | |
| 2021/0388098 A1 | 12/2021 | Keyt | |
| 2022/0106398 A1 | 4/2022 | Baliga | |
| 2022/0106399 A1 | 4/2022 | Baliga | |
| 2022/0169751 A1 | 6/2022 | Wang | |
| 2022/0177595 A1 | 6/2022 | Wang | |
| 2022/0267415 A1 | 8/2022 | Ku | |
| 2022/0289856 A1 | 9/2022 | Amoury | |

FOREIGN PATENT DOCUMENTS

| | | | |
|---|---|---|---|
| AU | 2004297218 | 6/2005 | |
| CA | 2358520 | 7/2000 | |
| CA | 2662701 | 10/2008 | |
| EP | 642585 | 3/1995 | |
| EP | 1169352 | 1/2002 | |
| EP | 1301541 | 4/2003 | |
| EP | 1617870 | 1/2006 | |
| EP | 1833848 | 9/2007 | |
| EP | 2219458 | 8/2010 | |
| EP | 2254592 | 12/2010 | |
| EP | 2264163 | 12/2010 | |
| EP | 2300498 | 3/2011 | |
| EP | 2465871 | 6/2012 | |
| EP | 2649184 | 10/2013 | |
| EP | 2655415 | 10/2013 | |
| EP | 2771361 | 9/2014 | |
| EP | 2962103 | 1/2016 | |
| JP | 2004525630 | 8/2004 | |
| JP | 2005522998 | 8/2005 | |
| WO | 1989001975 | 3/1989 | |
| WO | 1998030591 | 7/1998 | |
| WO | 1998030592 | 7/1998 | |
| WO | 2001012820 | 2/2001 | |
| WO | 2001014424 | 3/2001 | |
| WO | 2004110143 | 12/2004 | |
| WO | 2005103081 | 11/2005 | |
| WO | 2006052641 | 5/2006 | |
| WO | 2006130458 | 12/2006 | |
| WO | 2008140477 | 11/2008 | |
| WO | 2009013620 | 1/2009 | |
| WO | 2009130575 | 10/2009 | |
| WO | 2010105256 | 9/2010 | |
| WO | 2013061098 | 5/2013 | |
| WO | 2013087913 | 6/2013 | |
| WO | 2013120012 | 8/2013 | |
| WO | 2013150138 | 10/2013 | |
| WO | 2013158748 | 10/2013 | |
| WO | 2013188870 | 12/2013 | |
| WO | 2014022592 | 2/2014 | |
| WO | 2014124457 | 8/2014 | |
| WO | WO-2014165093 A2 * | 10/2014 | ........... C07K 14/765 |
| WO | 2014207064 | 12/2014 | |
| WO | 2015037000 | 3/2015 | |
| WO | 2015053887 | 4/2015 | |
| WO | 2015103072 | 7/2015 | |
| WO | 2015120474 | 8/2015 | |
| WO | 2015151081 | 10/2015 | |
| WO | 2015153912 | 10/2015 | |
| WO | 2016118641 | 7/2016 | |
| WO | 2016141303 | 9/2016 | |

(56) References Cited

FOREIGN PATENT DOCUMENTS

| | | |
|---|---|---|
| WO | 2016154593 | 9/2016 |
| WO | 2016168758 | 10/2016 |
| WO | 2017059380 | 4/2017 |
| WO | 2017059387 | 4/2017 |
| WO | 2017196867 | 11/2017 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |
| WO | 2020163646 | 8/2020 |
| WO | 2021030688 | 2/2021 |
| WO | 2021034646 | 2/2021 |
| WO | 2021041250 | 3/2021 |
| WO | 2021055765 | 3/2021 |
| WO | 2021141902 | 7/2021 |
| WO | 2021216756 | 10/2021 |
| WO | 2021231639 | 11/2021 |
| WO | 2022026475 | 2/2022 |
| WO | 2022109023 | 5/2022 |
| WO | 2022177870 | 8/2022 |
| WO | 2022178047 | 8/2022 |

OTHER PUBLICATIONS

Cao, Y., et al., (2011), "Targeting cell surface β2-microglobulin by pentameric IgM antibodies", Br J Haematol, 154(1):111-121.

Casset, F., et al., (2003), "A peptide mimetic of an anti-CD4 monoclonal antibody by rational design", Biochemical and biophysical Research Communications, 307:198-205.

Chen, Y., et al., (1999), Selection and Analysis of an Optimized Anti-VEGF Antibody: Crystal Structure of an Affinity-matured Fab in Complex with Antigen, 293: 865-881.

De Pascalis, R., et al., (2002), "Grafting of "Abbreviated" Complementarity-Determining Regions Containing specificity-Determining Residues Essential for Ligand Contact to Engineer a Less Immunogenic Humanized Monoclonal Antibody", The Journal of Immunology, 169: 3076-3084.

Duramad, O., et al., (2014), "IGM-55.5 a novel monoclonal human recombinant IgM antibody with potent activity against B cell leukemia and lymphoma" IGM Biosciences, Inc.—Research and Development SRI International—Cancer Pharmacology, Stanford—Department of Obstetrics and Gynecology, Abstract No. 645 AACR Annual Meeting, Apr. 5-9, 2014, San Diego CA.

Gaetano, N., et al., (2003), "Complement Activation Determines the Therapeutic Activity of Rituximab in Vivo", The Journal of Immunology, 171: 1581-1587.

Johnson, R., et al. (2012) "Biological Activity of Anti-CD20 Multivalent HPMA Copolymer-Fab' Conjugates", Biomacromolecules, vol. 13, pp. 727-735.

Lamminmäki, U., et al., (2001), "Crystal Structure of a Recombinant Anti-estradiol Fab Fragment in Complex with 17β Estradiol", The Journal of Biological Chemistry, vol. 276(39): 36687-36694.

MacCallum R., et al. (1996), "Antibody-antigen Interactions: Contact Analysis and binding Site Topography", J. Mol. Bio. 262: 732-745.

Padlan, E., et al., (1989), "Structure of an antibody-antigen complex: crystal structure of the HyHel-10 Fab-lysozyme complex;". Proc. Natl Acad. Sci. USA, vol. 86: 5938-5942.

Pascal, V., et al. (2012) "Anti-CD20 IgA can protect mice against lymphoma development: evaluation of the direct impact of IgA and cytotoxic effector recruitment on CD20 Target cells", Haematologica, the Hematology Journal, vol. 97(11), pp. 1686-1694.

Randall, T., et al., (1992), "Direct Evidence That J Chain Regulates the Polymeric Structure of IgM in Antibodysecreting B Cells", The Journal of Biological Chemistry, vol. 267(25), 18002-18007.

Rossi, E., et al. (2008) "Novel Designs of Multivalent Anti-CD20 Humanized Antibodies as Improved Lymphoma Therapeutics", Cancer Res, vol. 68(20), pp. 8384-8392.

Rudikoff, S., et al., (1982), "Single amino acid substitution altering antigen-binding specificity", Proc. Natl. Acad. Sci. USA, 79: 1979-1983.

Vajdos, F., et al., (2002), "Comprehensive Functional Maps of the Antigen-binding Site of an Anti-ErbB2 Antibody Obtained with Shotgun Scanning Mutagenesis", J. Mol. Biol. 320: 415-428.

Weiskopf, K., et al. (2013) "Engineered SIRPa Variants as Immunotherapeutic Adjuvants to Anticancer Antibodies", Science Express, vol. 341, pp. 89-91 with supplemental materials, 36 pages.

Woof et al.,"Structure and Function Relationships in IgA", Mucosal Immunology, Nov. 2011, pp. 590-597, vol. 4 No. 6.

Wu, H., et al., (1999), "Humanization of a Murine Monoclonal Antibody by simultaneous Optimization of Framework and CDR Residues", J Mol. Biol. 294: 151-162.

Lederman, S., et al. (1991), "A Single Amino Acid Substitution in a Common African Allele of the CD4 Molecule Ablates Binding of the Monoclonal Antibody, OKT4", Molecular Immunology, 28(11): 1171-1181.

Lewis, A.K., et al., 2014, "Open and Closed Conformations of the Isolated Transmembrane Domain of Death Receptor 5 Support a New Model of Activation" Biophys J 106, L21-L24.

Liedtke, M., et al., (2012), "Phase I trial of a novel human monoclonal antibody mAb216 in patients with relapsed or refractory B-cell acute lymphoblastic leukemia" Haematologica 97, 30-37.

Lines, J., et al., (2014), "VISTA Is an Immune Checkpoint Molecule for Human T Cells", Cancer Research 74(7): 1924-1932.

Liu, X., et al., (2005), "Preliminary study on recombination of J-HNP-1 and its antibacterial effect in vitro" Shijie Huaren Kiaohua Zazhi, 13(22), 2640-2644, English Abstract Only Available.

Liu, Xianhua, et al., 2006, "Expression Detection of the gene of α-defensin-1 with J chain in the transfected COS-7 cells". Chin Crit Care Med, vol. 18, No. 2, pp. 71 to 73 with Full English translation.

Lloyd, C., et al., (2009), "Modelling the human immune response: performance of a 10" human antibody repertoire against a broad panel of therapeutically relevant antigens", Protein Engineering, Design & Selection, 22(3), 159-168.

Maekawa, N., et al., (2014), "Expression of PD-L1 on Canine Tumor Cells and Enhancement of IFN-γ Production from Tumor-Infiltrating Cells by PD-L1 Blockade", PLOS One, vol. 9(6), e98415.

Mariuzza, R. A., (1987), "The Structural Basis of Antigen-Antibody Recognition", vol. 16: 139-159.

Marks et al., "By-passing immunization. Human antibodies from V-gene libraries displayed on phage," J. Mol. Biol. 1991, vol. 222, pp. 582-597.

Mestecky, J., et al., (1973), "J-chain of polymeric IgA myeloma proteins", Protides of the Biological Fluids, vol. 20: 279-283 , Abstract Only Available.

Meyer et al., "Improved In Vivo Anti-Tumor Effects of IgA-Her2 Antibodies Through Half-Life Extension and Serum Exposure Enhancement by FcRn Targeting", mAbs, Jan. 2016, pp. 87-98, vol. 8, Issue 1.

Mongini, P., et al., (1995), "Human B Cell Activation, Effect of T Cell Cytokines on the Physicochemical Binding Requirements for Achieving Cell cycle Progression Via the Membrane IgM Signaling Pathway", The Journal of Immunology, 155: 3385-3400.

Mordenti, J., et al. (1999), "Intraocular Pharmacokinetics and Safety of a Humanized Monoclonal Antibody in Rabbits after Intravitreal Administration of a Solution or a PLGA Microsphere Formulation", Toxicological Sciences, 52: 101-106.

Mordenti, J., et al., (1999), "Comparisons of the Intraocular Tissue Distribution, Pharmacokinetics, and Safety of 125I-Labeled Full-Length and Fab Antibodies in Rhesus Monkeys Following Intravitreal Administration", Investigative Pathology, vol. 27, No. 5, pp. 536-544.

Morrison et al., "Chimeric human antibody molecules: mouse antigen-binding domains with human constant region domains," PNAS 1984, vol. 81, pp. 6851-6855.

(56) References Cited

OTHER PUBLICATIONS

Mosmann, T.R., et al. (1978), "Modification and Fate of J. Chain in myeloma cells in the presence and absence of polymeric immunoglobulin secretion", Eur. J. Immunol. 8: 84-101.
Müller, M et al., (2012), "Improving the pharmacokinetic properties of biologies by fusion to an anti-HSA shark VNAR domain" MAbs 4, 673-685.
NCBI Reference Sequence: NP_653247.1,17.04.2013, Immunoglobulin J chain precursor [*Homo sapiens*].
Niwa, H., Yamamura, K., Miyazaki, J., 1991. Efficient selection for high-expression transfectants with a novel eukaryotic vector. Gene 108, 193-199.
Nocentini, G., et al., (1997), "A new member of the tumor necrosis factor/nerve growth factor receptor family inhibits T cell receptor-induced apoptosis", Proc. Natl. Acad. Sci. U .S. A. 94, 6216-6221.
Non-Final Office Action issued in U.S. Appl. No. 15/764,859 dated Aug. 6, 2019.
Noren et al., "A general method for site-specific incorporation of unnatural amino acids into proteins," Science 1989, vol. 244, p. 182-188.
Ofei et al., "Effects of an engineered human anti-TNF-a antibody (CDP571) on insulin sensitivity and glycemic control inpatients with NIDDM," Diabetes 1996, vol. 45, pp. 881-885.
Office Action dated Sep. 27, 2019 in U.S. Appl. No. 15/764,870.
Palanichamy Arumugam et al., "Rituximab efficiently depletes increased CD20-expressing T cells in multiple sclerosis patients.", Journal of Immunology (Baltimore, MD.: 1950) Jul. 15, 2014, (Jul. 15, 2014), vol. 193, No. 2, pp. 580-586.
Pardoll, D.M., (2012), "The blockade of immune checkpoints in cancer immunotherapy" Nat. Rev. Cancer 12(4): 252-264.
Paterson, J., et al., (2006), "The differential expression of LCK and BAFF-receptor and their role in apoptosis in human lymphomas", Haematologica 91: 772-780.
Paulik et al., "Drug-antibody conjugates with anti-HIV activity," Biochem. Pharmacol. 1999, vol. 58, pp. 1781-1790.
Ponders and Richards, "Tertiary templates for proteins. Use of packing criteria in the enumeration of allowed sequences for different structural classes," J. Mol. Biol. 1987, vol. 193, pp. 775-791.
Postow, M., et al., (2015), "Immune Checkpoint Blockade in Cancer Therapy", J. Clin. Oncol. 33(17): 1974-1982.
Presta, "Antibody engineering," Curr. Op. Struct. Biol. 1992, vol. 2, pp. 593-596.
Rabbitts et al. "Human immunoglobulin heavy chain genes: evolutionary comparisons of C mu, C delta and C gamma genes and associated switch sequences," GenBank Accession No. CAB37838, Nucleic Acids Research 1981 vol. 9, No. 18, pp. 4509-4524.
Raju et al., "Potential therapeutic roles for antibody mixtures," Exp. Op. Biol. Ther. 2013, vol. 13, No. 10, pp. 1347-1352.
Redwan et al., "Recombinant human J-chain: fix the protein aggregations and yield maximize," Human Antibodies 2006, vol. 15, pp. 95-102.
Redwan, E., et al. (2006), "Recombinant human J-chain: fix the protein aggregations and yield maximize" Human Antibodies 15, 95-102.
Riechmann et al., "Reshaping human antibodies for therapy," Nature 1988, vol. 332, pp. 323-329.
Roopenian, D., et al., (2007), "FcRn: the neonatal Fc receptor comes of age", Nature Reviews, vol. 7, 715-725.
Seifert, O., et al., (2012), "The IgM CH2 domain as covalently linked homodimerization module for the generation of fusion proteins with dual specificty", Protein engineering, Design & Selection, vol. 25(10): 603-612.
Singer, M., et al., "Genes and Genomes", Moscow, "Mir", 1998, vol. 1: 63-64, no translation available, reference is believed to be a standard textbook reference on antibody structure.
Smith, R. et al., (1995), "Addition of a mu-tailpiece to IgG results in polymeric antibodies with enhanced effector functions including complement-mediated cytolysis by IgG4" The Journal of Immunology 154, 2226-2236.

Sørensen, V., et al., (2000), "Structural requirements for incorporation of J chain into human IgM and IgA.", Int. Immunol. 12, 19-27.
Stancovski, I., et al. (1991), "Mechanistic aspects of the opposing effects of monoclonal antibodies to the ERBB2 receptor on tumor growth", Cell Biology, Proc Natl. Acad. Sci. USA, vol. 88, 8691-8695.
Symersky, J., et al., (2000), "Expression of the recombinant human immunoglobulin J Chain in *Escherichia coli*", Molecular Immunology, 37: 133-140.
Tabrizi, M., et al. (2010), "Biodistribution Mechanisms of Therapeutic Monoclonal Antibodies in Health and Disease", The AAPS Journal, vol. 12, No. 1, pp. 33-43.
Tavolaro, S., et al. (2013), "IgD cross-linking induces gene expression profiling changes and enhances apoptosis in chronic lymphocytic leukemia cells", Leukemia Research, 37: 455-462.
Tchoudakova, A., et al., 2009, "High level expression of functional human IgMs in human PER.C6 cells", MAbs 1, 163-171.
Tussiwand, R., et al., (2012), "BAFF-R expression correlates with positive selection of immature B cells", European Journal of Immunology, 42: 206-216.
Valley, C., et al., "Tumor Necrosis Factor-related Apoptosis-inducing Ligand (TRAIL) Induces Death Receptor 5 Networks That Are Highly Organized", The Journal of Biological chemistry, vol. 287, No. 25, pp. 21265-21278.
Vasquez, K., et al., (2011), "Quantitative Whole Body biodistribution of fluorescent-labeled Agents by Non-Invasive Tomographic Imaging", PLOS one, vol. 6, Issue 6, e20594.
Request for Supplement Examination as filed on Jun. 18, 2021 with USPTO re U.S. Pat. No. 9,951,134, issued Apr. 24, 2018.
Supplemental Examination Certificate dated Aug. 16, 2021 with USPTO re U.S. Pat. No. 9,951,134.
Vcelar et al., "Reassessment of autoreactivity of the broadly neutralizing HIV antibodies 4E10 and 2F5 and retrospective analysis of clinical safety data," AIDS 2007, vol. 21, No. 16, pp. 2161-2170.
Wajant, H. (2015), "Principles of antibody-mediated TNF receptor activation", Cell Death and Differentiation, 22: 1727-1741.
Wang, W., et al. (2008), "Monoclonal Antibody Pharmacokinetis and Pharmacodynamics", State of the Art, vol. 84, No. 5, pp. 548-558.
Wang, Y., et al., (2007), "The design, construction and function of a new chimeric anti-CD20 antibody", Journal of Biotechnology, 129: 726-731.
Wood, C.R., et al., (1990), "High level synthesis of immunoglobulins in Chinese hamster ovary cells". J. Immunol. 145, 3011-3016.
Koo et al., "Structural requirements for polymeric immunoglobulin assembly and association with J chain," J. Biol. Chem. 1999, vol. 274, No. 47, pp. 33771-33777.
Ku, L., et al. (2008), "Interaction between bevacizumab and Murine VEGF-A: A Reassessment", Investigative Opthalmology & Visual-Science, 49(2), 522-527.
Yu, X., et al., 2009, "The surface protein TIGIT suppresses T cell activation by promoting the generation of mature immunoregulatory dendritic cells," Nat Immunol. 10, 48-57.
Yu, Y., et al. (2014), "Therapeutic bispecific antibodies cross the blood-brain barter in nonhuman primates", Antibody Therapeutics, vol. 6, Issue 261, 261ra154, 11 pages.
Zuchero, Y., et al., (2015), "Discovery of Novel Blood-Brain Barrier Targets to Enhance Brain Uptake of Therapeutic Antibodies", Neuron 89: 70-82.
Arnold, J., et al., (2005), "Human serum IgM glycosylation: identification of glycoforms that can bind to mannan-binding lectin", The Journal of Biological Chemistry, vol. 280(32): 29080-29087.
Bacac, M., et al., (2018), "CD20-TCB with Obinutuzumab Pretreatment as Next-Generation Treatment of Hematologic Malignancies", Clinical Cancer Research, 24(19): 4785-4797, includes supplementary methods, Binding to CD20- and CD3-expressing cells, 24 additional pages.
Baliga, R., et al., (2019), "IGM-2323: High Avidity IgM-based CD20 x CD3 Bispecific Antibody for Enhanced T-Cell Dependent Killing with Minimal Cytokine Release", Abstract 1574 at American Society of Hematology Annual Meeting, Dec. 7-10, 2019, Orlando, FL.

(56) References Cited

OTHER PUBLICATIONS

Beers, S., et al., (2010), "Antigenic modulation limits the efficacy of anti-CD20 antibodies: implications for antibody selection", Blood, 115(25): 5191-5201.

Bornstein, G., et al., (2010), "Development of a new fully human anti-CD20 monoclonal antibody for the treatment of B-cell malignancies", Invest New Drugs, 28:561-574.

Bortoletto, N., et al., (2002), "Optimizing anti-CD3 affinity for effective T cell targeting against tumor cells", Eur. J. Immunol, 32: 3102-3107.

Bowles, J., et al., (2006), "Anti-CD20 monoclonal antibody with enhanced affinity for CD16 activates NK cells at lower concentrations and more effectively than rituximab", Blood, 108(8): 2648-2654.

Brüggemann M., et al., (1987), "Comparison of the effector functions of human immunoglobulins using a matched set of chimeric antibodies", J Exp. Med, 166: 1351-1361.

Castro, C., et al., (2014), "Putting J chain back on the map: how might its expression define plasma cell development?", The Journal of Immunology, 193: 3248-3255.

Chu, S., et al., (2014), "Immunotherapy with Long-Lived Anti-CD20 x Anti-CD3 Bispecific Antibodies Stimulates Potent T Cell-mediated Killing of Human B Cell lines and Circulating and Lymphoid B Cells in Monkeys: A Potential Therapy tor B Cell Lymphomas and Leukemias", Xencor, Inc., Monrovia, California 91016 USA, Poster.

Cregger, M., et al., (2006), "Immunohistochemistry and Quantitative Analysis of Protein Expression", Arch Pathol Lab Med., 130: 1026-1030.

Czuczman, M., et al., (2008), "Acquirement of rituximab resistance in lymphoma cell lines is associated with both global CD20 gene and protein down-regulation regulated at the pretranscriptional and posttranscriptional levels", Clin Cancer Res, 14(5): 1561-1570.

Davis, T., et al., (1999), "Single-agent monoclonal antibody efficacy in bulky non-Hodgkin's lymphoma: results of a phase II trial of rituximab", J. Clin Oncol. 17:1851-1857.

Davis, T., et al., (2000), "Rituximab anti-CD20 monoclonal antibody therapy in non-Hodgkin's lymphoma: safety and efficacy of re-treatment", Journal of Clinical Oncology, 18(17): 3135-3143.

Ghielmini, M., (2004), "Prolonged treatment with rituximab in patients with follicular lymphoma significantly increases event-free survival and response duration compared with the standard weekly x 4 schedule", Blood, 103(12):4416-4423.

Hagenbeek, A., et al., (2009), "Evaluation of Ofatumumab, a Novel Human CD20 Monoclonal Antibody, as Single Agent Therapy in Rituximab-Refractory Follicular Lymphoma", Blood, 114(22): 935, 6 pages.

Haidar, JH., et al., (2003), "Loss of CD20 expression in relapsed lymphomas after rituximab therapy", Eur J. Haematol, 70: 330-332.

Hensel, F., et al., (2013), "Early development of PAT-SM6 for the treatment of melanoma", Melanoma Research, 23 (4): 264-275.

Hsu, D., et al., (1999), "A humanized anti-CD3 antibody, HuM291, with low mitogenic activity, mediates complete and reversible T-cell depletion in chimpanzees", Transplantation, 68(4): 545-554.

Klimovich, V. B., (2011), "IgM and Its Receptors: Structural and Functional Aspects", Biochemistry, 76(5): 654-672.

Liu, X., et al., (2005), "Recombinant of J chain-HNP-1 cDNA and the construction of expression vector", Di-San Junyi Oaxue Xuebao, 27(8), 697-699. English Abstract Only Available.

Maloney, D., et al., (1997), "IDEC-C2B8 (Rituximab) anti-CD20 monoclonal antibody therapy in patients with relapsed low-grade non-Hodgkin's lymphoma", Blood, 90(6): 2188-2195.

Mandikian, D., et al., (2018), "Relative Target Affinities of T Cell-Dependent Bispecific Antibodies Determine Biodistribution in a Solid Tumor Mouse Model", Mol Cancer Ther., 17(4): 776-785, doi: 10.1158/1535-7163. MCT-17-0657.

Marcus, R., et al., (2017), "Obinutuzumab for the First-Line Treatment of Follicular Lymphoma", N. Engl. J. Med. 377 (14): 1331-44.

Mølhøj, M., et al., (2007), "CD19-/CD3-bispecific antibody of the BiTE class is far superior to tandem diabody with respect to redirected tumor cell lysis", Molecular Immunology 44: 1935-1943.

Miles, M., et al., (1995), "Polymer IgM assembly and secretion in lymphoid and nonlymphoid cell lines: evidence that J chain is required for pentamer IgM synthesis", Proc. Natl. Acad. Sci. USA, 92:2884-2888.

Rasche, L., et al., (2015), "GRP78-directed immunotherapy in relapsed or refractory multiple myeloma—results from a phase 1 trial with the monoclonal immunoglobulin M antibody PAT-SM6", Haematologica, 100(3): 377-384.

Rezvani, A., et al., (2011), "Rituximab Resistance", Best Pract Res Clin Haematol, 24(2): 203-216.

Saber, H., et al., (2017), "An FDA oncology analysis of CD3 bispecific constructs and first-in-human dose selection", Regulatory Toxicology and Pharmacology, 90: 144-152.

Smith, E., et al., (2015), "A novel, native-format bispecific antibody triggering T-cell killing of B-cells is robustly active in mouse tumor models and cynomolgus monkeys", Scientific Reports, 5: 17943, 12 pages.

Strohl, W., et al., (2015), "Fusion Proteins for Half-Life Extension of Biologies as a Strategy to Make Biobetters", BioDrugs, 29: 215-239.

Sun, L., et al., (2015), "Anti-CD20/CD3 T cell-dependent bispecific antibody for the treatment of B cell malignancies", Immunotherapy, vol. 7(287), 287ra70, 11 pages.

Teachey, D., et al., (2013), "Cytokine release syndrome after blinatumomab treatment related to abnormal macrophage activation and ameliorated with cytokine directed therapy", Blood Journal, DOI 10.1182/blood-2013-02-485623.

Van Imhoff, G., et al., (2017), "Ofatumumab Versus Rituximab Salvage Chemoimmunotherapy in Relapsed or Refractory Diffuse Large B-Cell Lymphoma: The ORCHARRD Study", Journal of Clinical Oncology, 35(5): 544-551.

Vitolo, U., et al., (2017), "Obinutuzumab or Rituximab Plus Cyclophosphamide, Doxorubicin, Vincristine, and Prednisone in Previously Untreated Diffuse Large B-Cell Lymphoma", Journal of Clinical Oncology, 35(31): 3529-3537.

Wing, M., (2008), "Monoclonal Antibody First Dose Cytokine Release Syndromes-Mechanisms and Prediction", Journal of Immunotoxicology, 5: 11-18.

Wu, J., et al., (2015), "Blinatumomab: a bispecific T cell engager (BiTE) antibody against CD19/CD3 for refractory acute lymphoid leukemia", Journal of Hematology & Oncology, 8:104, DOI 10.1186/13045-015-0195-4, 7 pages.

Aggarwal, B., et al., "Historical perspectives on tumor necrosis factor and its superfamily: 25 years later, a golden journey", 2012, Blood, vol. 119 (No. 3), pp. 651-665.

Albrecht, H., et al. (2006), "Recombinant Antibodies: From the Laboratory to the Clinic", Cancer Biotherapy & Radiopharmaceuticals, vol. 21: 285-304.

Ammann, J., et al. (2014), "Development and use of IgM/J-Chain Fusion Proteins for Chacterization of Immunoglobulin Superfamily Ligand-Receptor Interactions", Current Protocols in Protein Science, 19.24.1-19.24.11, Supplement 75.

Ammann, J., et al., (2012), "Detection of weak receptor-ligand interactions using IgM and J-chain-based fusion proteins", European Journal of Immunology, 42:1354-1356.

Andersen, J., et al., "Extending Serum Half-life of Albumin by Engineering Neonatal Fc Receptor (FcRn) Binding", 2014, Journal of Biological Chemistry, vol. 289, No. 19, pp. 13492-13502.

Azuma, Y., et al., "Recombinant Human Hexamer-Dominant IgM Monoclonal Antibody to Ganglioside GM3 for Treatment of Melanoma", 2007, Clin Cancer Res, vol. 13 (No. 9), pp. 2745-2750 with correction on article.

Bakema et al, "Immunoglobulin A, A next generation of therapeutic antibodies?", mAbs, Aug. 2011, vol. 3, No. 4, 352-361.

Binz, et al., "Engineering novel binding proteins from nonimmunoglobulin domains," Nature Biotechnology 2005, vol. 23, No. 10, pp. 1257-1268.

Braathen, R., et al. (2002), "The Carboxyl-terminal Domanins of IgA and IgM Direct Isotype-specific Polymerization and Interaction with the Polymeric Immunoglobulin Receptor", The Journal of Biological Chemistry, vol. 277, No. 45, pp. 42755-42762.

Brodska et al., "Correlation of PD-L1 Surface Expression on Leukemia Cells with the Ratio of PD-L1 mRNA Variants and with

(56) References Cited

OTHER PUBLICATIONS

Electrophoretic Mobility", Cancer Immunology Research, Aug. 2016, pp. 815-819, vol. 4, No. 10.
Cao, Y., et al., (2011), "Targeting cell surface Beta2-microglobulin by pentameric IgM antibodies", British Journal of Haematology, 154: 111-121.
Cazet et al., "Tumour-associated carbohydrate antigens in breast cancer," Breast Cancer Research 2010, vol. 12, No. 3, p. 204.
Chintalacharuvu et al., "Hybrid IgA2/igG1 Antibodies with Tailor-Made Effector Functions", Clinical Immunology, Oct. 2001, pp. 21-31, vol. 101, No. 1, pp. 21-31.
Ćirić B., et al. (2009), "Effect of Valency on Binding Properties of the Antihuman IgM Monoclonal Antibody 202", Hybridoma, vol. 14. No. 6, pp. 537-544.
Clackson et al.," Making antibody fragments using phage display libraries" Nature 1991, vol. 352, pp. 624-628.
Colman, P.M. (1994) "Effects of amino acid sequence changes on antibody-antigen interactions", Biomolecular Research Institute, 55th Forum in Immunology, pp. 33-35.
Czajkowsky and Shao,"The human IgM pentamer is a mushroom-shaped molecule with a flexural bias," PNAS 2009, vol. 106, No. 35, pp. 14960-14965.
Davis et al., "On the structure of polymeric IgM," Eur. J. Immunol. 1988, vol. 18, No. 7, pp. 1001-1008.
Davis, A., et al., (1989), "IgM—Molecular requirements for its assembly and function", Immunology Today, 10(4): 7 pages.
Dennis, M., et al. (2002), "Albumin Binding as a General Strategy for Improving the Pharmacokinetics of Proteins", J. Biol. Chem. 277(38): 35035-35043.
Dennis, M., et al., (2012), "Transferrin Antibodies into the Brain", Neuropsychopharmacology Reviews, 37: 302-303.
Dorai et al., "The complete nucleotide sequence of a human immunoglobulin genomic Cu gene," GenBank Accession No. X14940. 1, Nucleic Acids Research 1989, vol. 17, No. 15, p. 6412.
Ducry, L., et al., "Antibody-drug conjugates: linking cytotoxic payloads to monoclonal antibodies", 2010, Bioconjug. Chem. 21, 5-13.
Edwards, B., et al., (2003), "The Remarkable Flexibility of the Human Antibody Repertoire; Isolation of Over One Thousand Different Antibodies to a Single Protein, BLyS", J. Mol. Biol, 334: 103-118.
Ellman, "Biosynthetic method for introducing unnatural amino acids site-specifically into proteins," Meth. Enzym. 1991, vol. 202, pp. 301-336.
Fournier et al., "Bispecific antibodies and trispecific immunocytokines for targeting the immune system against cancer preparing for the future," BioDrugs 2013, vol. 27, No. 1, pp. 35-53.
Frutiger, S., et al., 1992, "Disulfide Bond Assignment in Human J Chain and its Covalent Pairing with Immunoglobulin M", Biochemistry, vol. 31, pp. 12643-12647.
Fukushima, N., et al., (2002), "Chacterization of Recombinant Monoclonal IgA Anti-PDC-E2 Autoantibodies Derived From patients with PBC", Hepatology: 35: 1383-1392.
Garcia-Pardo et al., "J chain is covalently bound to both monomer subunits in human secretory IgA," J. Biol. Chem. 1981, vol. 256, pp. 11734-11738.
Gibson Josefine, "Anti-PD-L1 for metastatic triple-negative breast cancer.", The Lancet. Oncology Jun. 2015, (Jun. 2015), vol. 16, No. 6, ISSN 1474-5488, p. e264, XP002765988.
Gilmour, J.E.M., et al. (2008), "Effect of the presence or absence of J Chain on expresion of recombinant anti-kell immunoglobulin", Transfusion Medicine, 18: 167-174.

Golay, J., et al. (2012), "Mechanism of action of therapeutic monoclonal antibodies: Promises and pitfalls of in vitro and in vivo assays", Archives of Biochemistry and Biophysics, 526: 146-153.
Goswami et al., "Developments and challenges for mAb-Based therapeutics," Antibodies 2013, vol. 2, No. 3, pp. 452-500.
Harao et al., "Abstract LB-263: Enhancing of CD8+ tumor-infiltrating lymphocyte expansion from triple-negative breast cancer patients using of 41BB costimulation", (Oct. 1, 2014), American Associaton for Cancer Research, URL: http://cancerres.aacrjournals.org/content/74/19_Supplement/LB-263, (Jan. 16, 2017), XP002765987.
Hay, M., et al., (2014), "Clinical development success rates for investigational drugs", Nature Biology, 32(1): 40-51.
Hirayasu, K. and Arase, H., "Immunoglobulin mu heavy chain, partial [*Homo sapiens*]," GenBank Accession No. AFM37312, Jun. 18, 2012 (2 pages).
Hopp, J., et al., (2010), "The effects of affinity and valency of an albumin-binding domain (ABD) on the half-life of a single-chain diabody-ABD fusion protein", vol. 23(11): 827-834.
Houghton, J., et al., (2015), "Site-specifically labeled CA19.9-targeted immunoconjugates for the PET, NIRF, and multimodal PET/NIRF imaging of pancreatic cancer", PNAS, vol. 112, No. 52: 15850-15855.
Jeon, H., et al., (2014), "Structure and Cancer Immunotherapy of the B7 Family Member B7x", Cell Rep., vol. 9(3): 1089-1098.
Johansen, F., et al., (2000), "Role of J Chain in Secretory Immunoglobulin Formation", Scand. J. Immunol., 52: 240-248.
Johansen, F., et al., (2001), "The J Chain Is Essential for Polymeric Ig Receptor-Mediated Epithelial Transport of IgA", The Journal of Immunology, 167: 5185-5192.
Jones et al., "Replacing the complementarity-determining regions in a human antibody with those from a mouse," Nature 1986, vol. 321, pp. 522-525.
Jones, A., et al., (2007), "Blood-Brain Barrier Transport of Therapeutics via Receptor-Mediation", Pharm Res., 24(9): 1759-1771.
Joos, B., et al., 2006, "Long-Term Multiple-Dose Pharmacokinetics of Human Monoclonal Antibodies (MAbs) against Human Immunodeficiency Virus Type 1 Envelope gp120 (MAb 2G12) and gp41 (MAbs 4E10 and 2F5)", Antimicrob Agents Chemother 50, 1773-1779.
Jubala, C.M., et al. (2005), "CD20 Expression in Normal Canine B Cells and in Canine non-Hodgkin Lymphoma" Vet Pathol 42: 468-476.
Klein, J., et al., (2014,) "Design and characterization of structured protein linkers with differing flexibilities" Protein Eng Des Sel 27, 325-330.
Kohler et al., "Continuous cultures of fused cells secreting antibody of predefined specificity," Nature 1975, vol. 256, No. 495-7.
Kragten, E., et al., (1995), "Site-specific analysis of the N-Glycans on Murine Polymeric Immunoglobulin A. Using Liquid Chromatography/Electrospray Mass Spectrometry", vol. 30, 1679-1686.
Krugmann, S., et al. (1997), "Structural Requirements for Assembly of Dimeric IgA Probed by Site-Directed Mutagenesis of J Chain and a Cysteine Residue of the α-chain CH2 Domain", The Journal of Immunology, 159: 244-249.
Ksiezak-Reding, H., et al., 1988, "Alz 50, a monoclonal antibody to Alzheimer's disease antigen, cross-reacts with tau proteins from bovine and normal human brain", J. Biol. Chem. 263, 7943-7947.
U.S. Appl. No. 18/052,388, Specification, Claims, Abstract and Drawings as filed Nov. 3, 2022 with U.S. Patent Office.
U.S. Appl. No. 17/998,307, Specification, Claims, Abstract and Drawings as filed Nov. 9, 2022 with U.S. Patent Office.
U.S. Appl. No. 18/054,776, Specification, Claims, Abstract and Drawings as filed Nov. 11, 2022 with U.S. Patent Office.
U.S. Appl. No. 18/055,340, Specification, Claims, Abstract and Drawings as filed Nov. 14, 2022 with U.S. Patent Office.

\* cited by examiner

FIG. 3

Mature Human J Chain

QEDERIVLVDNKCKCARITSRIIRSSEDPNEDIVERNI
RIIVPLNNRENISDPTSPLRTRFVYHLSDLCKKCDPT
EVELDNQIVTATQSNICDEDSATETCYTYDRNKCYT
AVVPLVYGGETKMVETALTPDACYPD (SEQ ID NO: 1)

- Number of amino acids: 137
- Molecular weight: 15594.4
- Theoretical pI: 4.59

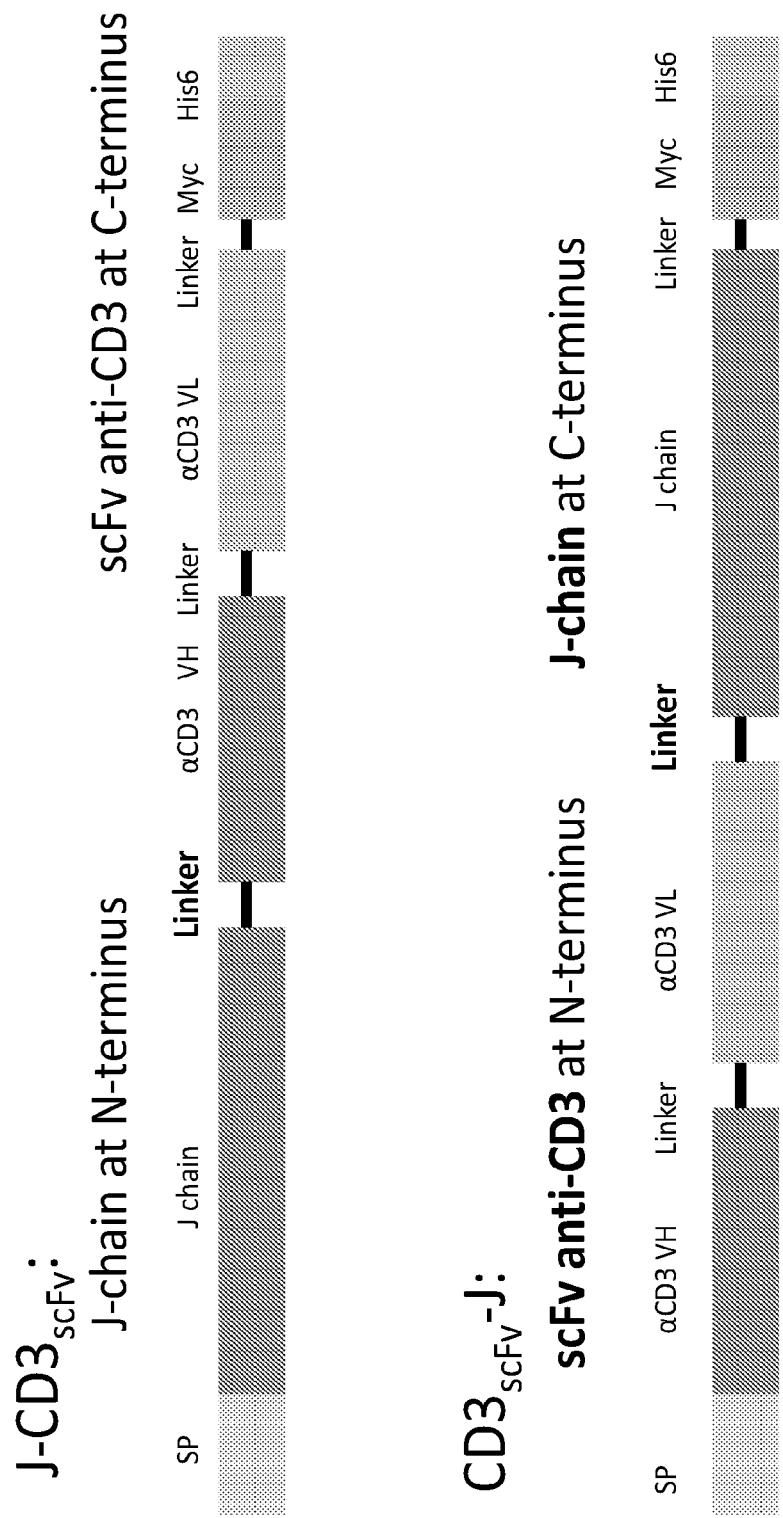

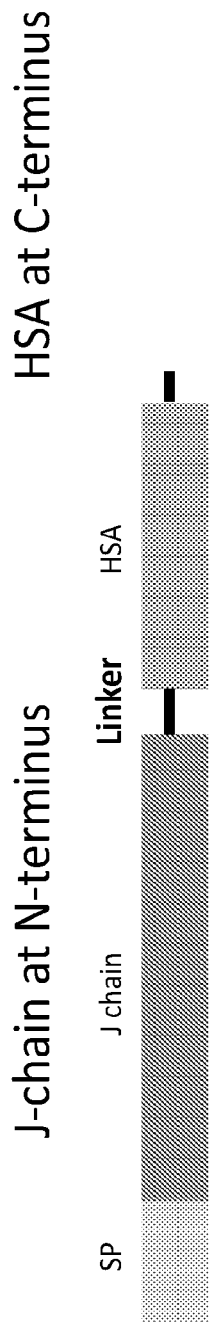
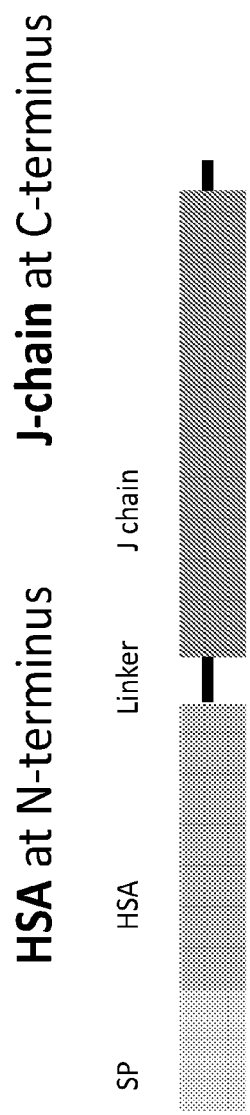
FIG. 4B
Orientation of J-chain Constructs

Asymmetric IgM Pentamer with modified J-chain

Anti-CD20$_{IgM}$ x Anti-CD3$_J$ bi-specific IgM can be expressed and assembled into pentamer with various scFv at either N- or C- terminus of J-chain Anti-CD20 $_{IgM}$ x Anti-CD3$_J$ Bi-specific IgM Induces T-cell activation in presence of target cells Multimer specific ELISA for CD20 IgMs

FIG. 11
Panel A
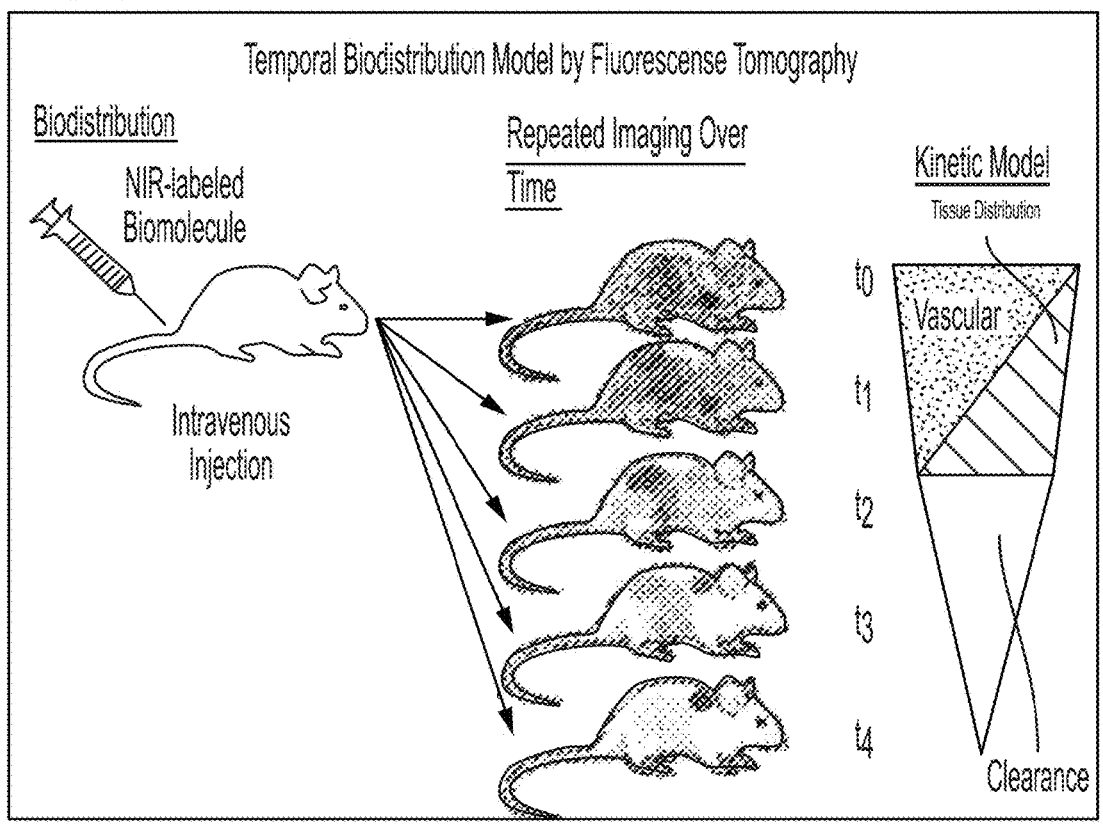
Panel B
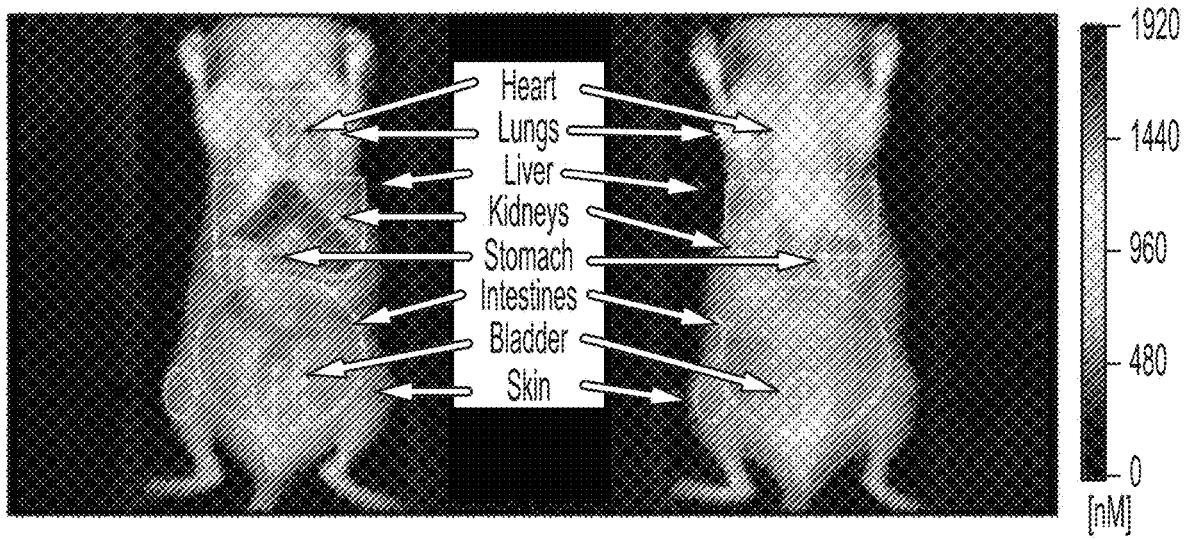

FIG. 12
Site Specific labeling of IgM glycans using chemo-enzymatic approaches
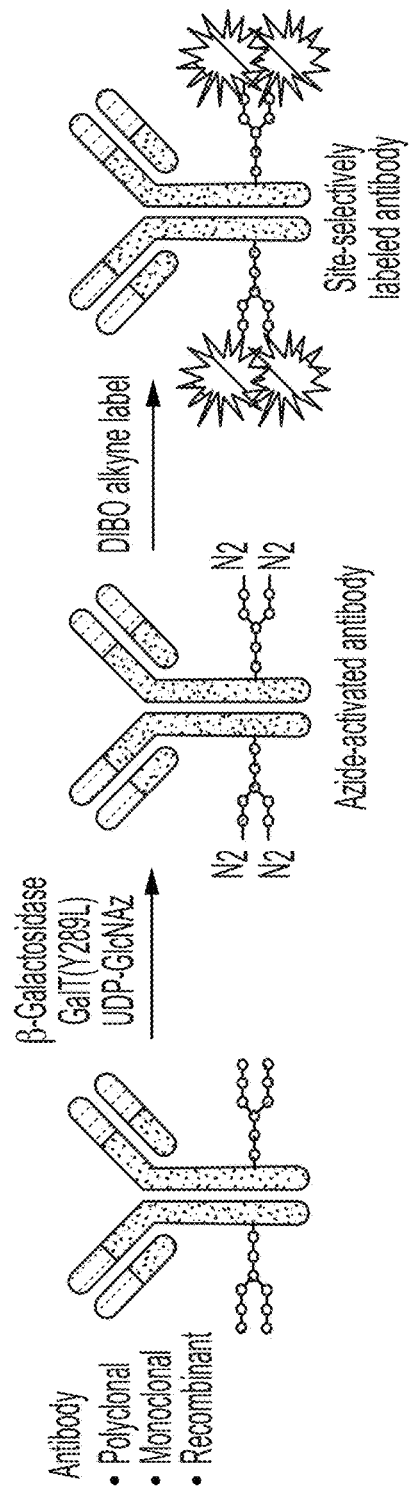
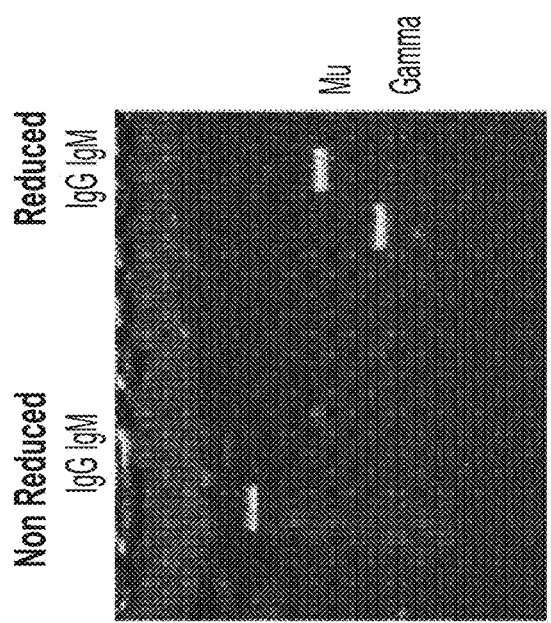
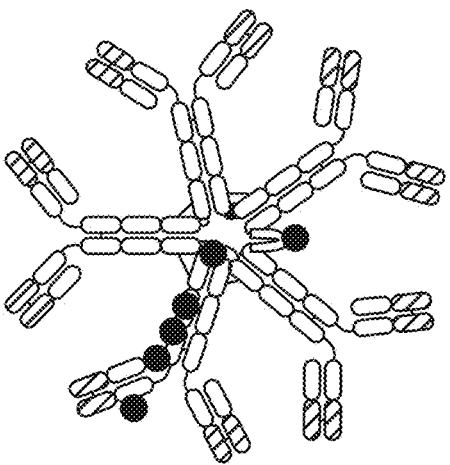

FIG. 13

Combinatorial approach to compartmentalization uses of J-chain binding molecules:

Antibody Target

Super agonist targets:
CD137 (4-1BB), OX40, CD40, GITR, CD27, HVEM

Low expression level targets:
EGFR, HER2, HER3, EpCAM, CEACAM, Gp100, MAGE1

Low affinity targets:
NY-ESO-1, Sialyl Lewis X antigen, Tn antigen

Hematologic cancer targets:
CD19, CD20, CD22, CD33, CD38, CD52, CD70

Other binding targets:
VEGF, TNF alpha, amyloid beta, BACE

J-chain binding moiety target

Targets for regulating half-life
Human serum albumin (HSA)
HSA binding peptides
Neonatal Fc Receptor (FcRn)
Fc domain Targets for regulating bio-distribution
Transferrin, Transferrin receptor (TfR)
Insulin, Insulin Receptor
IGF-1, IGF-1 receptor
Leptin, Leptin receptor
basigin
Glut1
CD98hc Target for retention in intra-ocular or intra-articular compartments
Hyaluronic Acid
TSG-6

Alternating units of 1,4-linked N-acetylglucosamine and glucuronic acid

Panel A:

Panel B:

| Antibody | $t_{1/2}\,\alpha$ (hrs) | $t_{1/2}\,\beta$ (hrs) | $AUC_{0-\infty}$ (µg/ml*hr) |
|---|---|---|---|
| Rituximab | 2.4 | 158.7 | 12180 |
| Polyclonal IgM | 0.99 | 14.3 | 1412 |
| 55.5 (CHO IgM) | 0.2 | 4.7 | 549 |

Panel A:

Panel B:

Panel A:

Panel B:

| Antibody | $t_{1/2}\alpha$ (hrs) | $t_{1/2}\beta$ (hrs) | $AUC_{0-\infty}$ (µg/ml*hr) |
|---|---|---|---|
| Rituximab | 2.4 | 158.7 | 12180 |
| αCD20 IgM+V15J | 0.23 | 4.0 | 82 |
| αCD20 IgM+A15J | 3.2 | 32.4 | 1341 |

FIG. 22

| Antibody | $t_{1/2}\,\alpha$ (hrs) | $t_{1/2}\,\beta$ (hrs) | $AUC_{0-\infty}$ (µg/ml*hr) |
|---|---|---|---|
| Rituximab | 2.4 | 158.7 | 12180 |
| 1.5.3 IgM+V15J | 0.23 | 4.0 | 82 |
| 1.5.3 IgM+J15A | 3.2 | 32.4 | 1341 |
| 1.5.3 IgM+A15J | 0.85 | 10.3 | 1196 |
| 1.5.3 IgM+J15H | 2.3 | 14.5 | 1380 |
| 1.5.3 IgM+H15J | 0.71 | 17.7 | 1259 |

FIG. 26
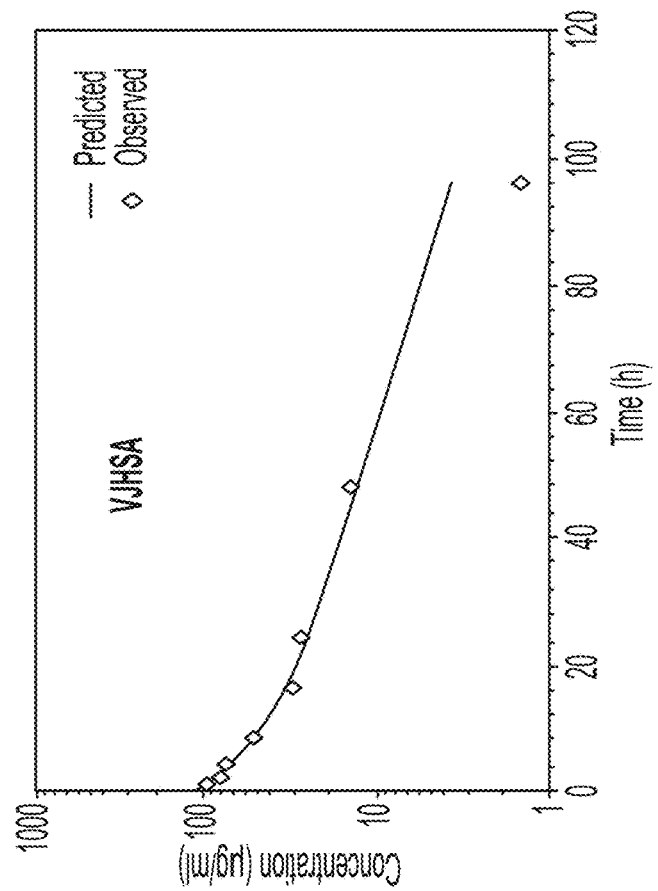
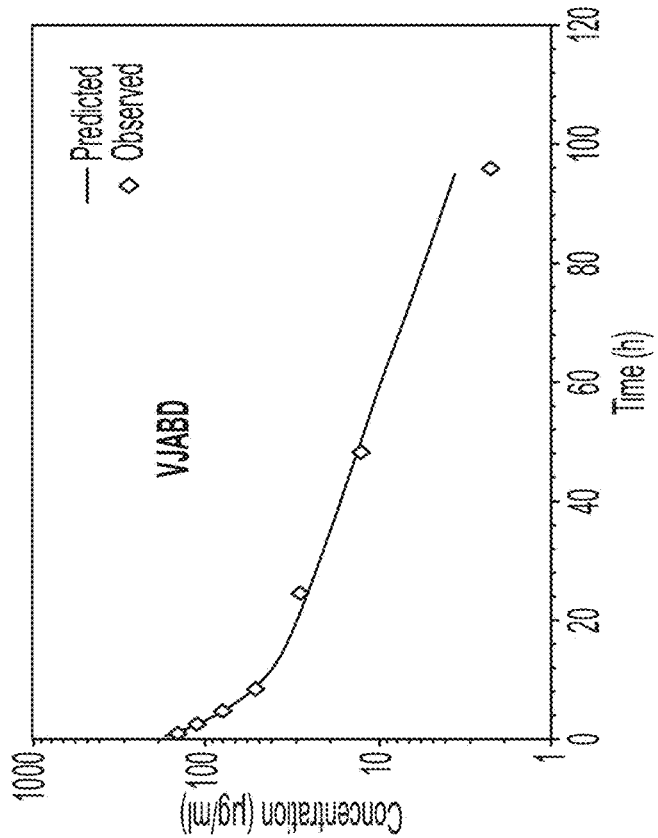

FIG. 27

| | t₁/₂ Alpha | t₁/₂ Beta | AUC₀-inf |
|---|---|---|---|
| 153 IgM HSAJ | 0.78 | 17.8 | 1260 |
| 153 IgM JHSA | 2.33 | 14.5 | 1380 |
| 153 IgM VJABD | 3.22 | 26.0 | 2212 |
| 153 IgM VJHSA | 4.22 | 25.6 | 2167 |

FIG. 28
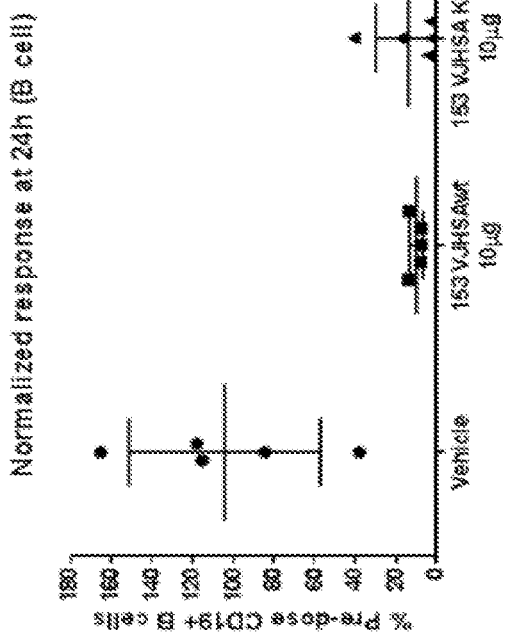
Panel A
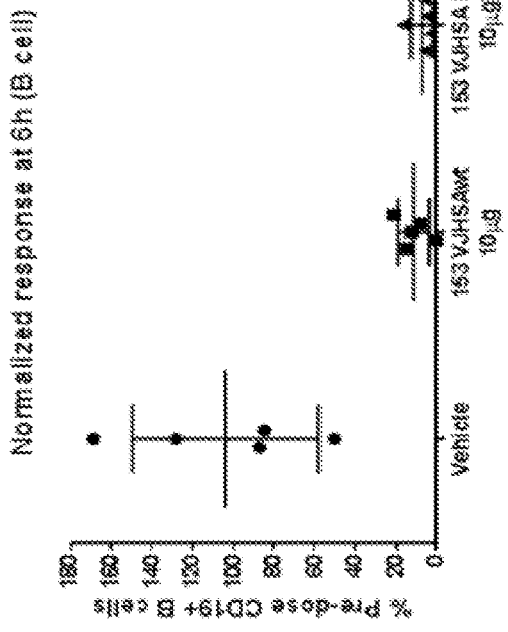
Panel B

SEQUENCE LISTING

<160> NUMBER OF SEQ ID NOS: 104

<210> SEQ ID NO 1
<211> LENGTH: 137
<212> TYPE: PRT
<213> ORGANISM: Homo sapiens

<400> SEQUENCE: 1

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
                20                  25                  30

Ile Val Glu Arg Asn Ile Arg Ile Ile Val Pro Leu Asn Asn Arg Glu
                35                  40                  45

Asn Ile Ser Asp Pro Thr Ser Pro Leu Arg Thr Arg Phe Val Tyr His
        50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
                100                 105                 110

Val Val Pro Leu Val Tyr Gly Gly Glu Thr Lys Met Val Glu Thr Ala
                115                 120                 125

Leu Thr Pro Asp Ala Cys Tyr Pro Asp
    130                 135

<210> SEQ ID NO 2
<211> LENGTH: 11
<212> TYPE: PRT
<213> ORGANISM: Unknown
<220> FEATURE:
<221> NAME/KEY: source
<223> OTHER INFORMATION: /note="Description of Unknown: Albumin binding
    peptide"

<400> SEQUENCE: 2

Asp Leu Cys Leu Arg Asp Trp Gly Cys Leu Trp
1               5                   10

<210> SEQ ID NO 3
<211> LENGTH: 11
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 3

Asp Ile Cys Leu Pro Arg Trp Gly Cys Leu Trp
1               5                   10

<210> SEQ ID NO 4
<211> LENGTH: 15
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 4

Met Glu Asp Ile Cys Leu Pro Arg Trp Gly Cys Leu Trp Gly Asp
1               5                   10                  15

<210> SEQ ID NO 5
<211> LENGTH: 20
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 5

Gln Arg Leu Met Glu Asp Ile Cys Leu Pro Arg Trp Gly Cys Leu Trp
1               5                   10                  15

Glu Asp Asp Glu
            20

<210> SEQ ID NO 6
<211> LENGTH: 20
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 6

Gln Gly Leu Ile Gly Asp Ile Cys Leu Pro Arg Trp Gly Cys Leu Trp
1               5                   10                  15

Gly Arg Ser Val
            20

<210> SEQ ID NO 7
<211> LENGTH: 21
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 7

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 8

```
<211> LENGTH: 15
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 8

Glu Asp Ile Cys Leu Pro Arg Trp Gly Cys Leu Trp Glu Asp Asp
1               5                   10                  15

<210> SEQ ID NO 9
<211> LENGTH: 18
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 9

Arg Leu Met Glu Asp Ile Cys Leu Pro Arg Trp Gly Cys Leu Trp Glu
1               5                   10                  15

Asp Asp

<210> SEQ ID NO 10
<211> LENGTH: 16
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 10

Met Glu Asp Ile Cys Leu Pro Arg Trp Gly Cys Leu Trp Glu Asp Asp
1               5                   10                  15

<210> SEQ ID NO 11
<211> LENGTH: 15
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 11

Met Glu Asp Ile Cys Leu Pro Arg Trp Gly Cys Leu Trp Glu Asp
1               5                   10                  15

<210> SEQ ID NO 12
<211> LENGTH: 18
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 12

Arg Leu Met Glu Asp Ile Cys Leu Ala Arg Trp Gly Cys Leu Trp Glu
1               5                   10                  15

Asp Asp

<210> SEQ ID NO 13
```

```
<211> LENGTH: 20
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 13

Glu Val Arg Ser Phe Cys Thr Arg Trp Pro Ala Glu Lys Ser Cys Lys
1               5                   10                  15

Pro Leu Arg Gly
            20

<210> SEQ ID NO 14
<211> LENGTH: 20
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 14

Arg Ala Pro Glu Ser Phe Val Cys Tyr Trp Glu Thr Ile Cys Phe Glu
1               5                   10                  15

Arg Ser Glu Gln
            20

<210> SEQ ID NO 15
<211> LENGTH: 11
<212> TYPE: PRT
<213> ORGANISM: Unknown
<220> FEATURE:
<221> NAME/KEY: source
<223> OTHER INFORMATION: /note="Description of Unknown: Albumin binding
      peptide"

<400> SEQUENCE: 15

Glu Met Cys Tyr Phe Pro Gly Ile Cys Trp Met
1               5                   10

<210> SEQ ID NO 16
<211> LENGTH: 593
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Gly Trp Ser Tyr Ile Ile Leu Phe Leu Val Ala Thr Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95
```

```
Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ser Gly Ser Ala Ser
        130                 135                 140

Ala Pro Thr Leu Phe Pro Leu Val Ser Cys Glu Asn Ser Pro Ser Asp
145                 150                 155                 160

Thr Ser Ser Val Ala Val Gly Cys Leu Ala Gln Asp Phe Leu Pro Asp
                165                 170                 175

Ser Ile Thr Phe Ser Trp Lys Tyr Lys Asn Asn Ser Asp Ile Ser Ser
            180                 185                 190

Thr Arg Gly Phe Pro Ser Val Leu Arg Gly Gly Lys Tyr Ala Ala Thr
            195                 200                 205

Ser Gln Val Leu Leu Pro Ser Lys Asp Val Met Gln Gly Thr Asp Glu
            210                 215                 220

His Val Val Cys Lys Val Gln His Pro Asn Gly Asn Lys Glu Lys Asn
225                 230                 235                 240

Val Pro Leu Pro Val Ile Ala Glu Leu Pro Pro Lys Val Ser Val Phe
                245                 250                 255

Val Pro Pro Arg Asp Gly Phe Phe Gly Asn Pro Arg Lys Ser Lys Leu
                260                 265                 270

Ile Cys Gln Ala Thr Gly Phe Ser Pro Arg Gln Ile Gln Val Ser Trp
            275                 280                 285

Leu Arg Glu Gly Lys Gln Val Gly Ser Gly Val Thr Thr Asp Gln Val
            290                 295                 300

Gln Ala Glu Ala Lys Glu Ser Gly Pro Thr Thr Tyr Lys Val Thr Ser
305                 310                 315                 320

Thr Leu Thr Ile Lys Glu Ser Asp Trp Leu Ser Gln Ser Met Phe Thr
                325                 330                 335

Cys Arg Val Asp His Arg Gly Leu Thr Phe Gln Gln Asn Ala Ser Ser
            340                 345                 350

Met Cys Val Pro Asp Gln Asp Thr Ala Ile Arg Val Phe Ala Ile Pro
        355                 360                 365

Pro Ser Phe Ala Ser Ile Phe Leu Thr Lys Ser Thr Lys Leu Thr Cys
    370                 375                 380

Leu Val Thr Asp Leu Thr Thr Tyr Asp Ser Val Thr Ile Ser Trp Thr
385                 390                 395                 400

Arg Gln Asn Gly Glu Ala Val Lys Thr His Thr Asn Ile Ser Glu Ser
                405                 410                 415

His Pro Asn Ala Thr Phe Ser Ala Val Gly Glu Ala Ser Ile Cys Glu
            420                 425                 430

Asp Asp Trp Asn Ser Gly Glu Arg Phe Thr Cys Thr Val Thr His Thr
        435                 440                 445

Asp Leu Pro Ser Pro Leu Lys Gln Thr Ile Ser Arg Pro Lys Gly Val
    450                 455                 460

Ala Leu His Arg Pro Asp Val Tyr Leu Leu Pro Pro Ala Arg Glu Gln
465                 470                 475                 480

Leu Asn Leu Arg Glu Ser Ala Thr Ile Thr Cys Leu Val Thr Gly Phe
                485                 490                 495

Ser Pro Ala Asp Val Phe Val Gln Trp Met Gln Arg Gly Gln Pro Leu
            500                 505                 510

Ser Pro Glu Lys Tyr Val Thr Ser Ala Pro Met Pro Glu Pro Gln Ala
```

```
                515                 520                 525
Pro Gly Arg Tyr Phe Ala His Ser Ile Leu Thr Val Ser Glu Glu Glu
    530                 535                 540

Trp Asn Thr Gly Glu Thr Tyr Thr Cys Val Val Ala His Glu Ala Leu
545                 550                 555                 560

Pro Asn Arg Val Thr Glu Arg Thr Val Asp Lys Ser Thr Gly Lys Pro
                565                 570                 575

Thr Leu Tyr Asn Val Ser Leu Val Met Ser Asp Thr Ala Gly Thr Cys
            580                 585                 590

Tyr
```

<210> SEQ ID NO 17
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Met Asp Met Arg Val Pro Ala Gln Leu Leu Gly Leu Leu Leu Leu Trp
1               5                   10                  15

Leu Arg Gly Ala Arg Cys Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 18
<211> LENGTH: 417
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 18

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Lys
225                 230                 235                 240

Gly Gly Gly Gly Ser Gly Gly Gly Ser Gly Gly Gly Ser Gln
                245                 250                 255

Glu Asp Glu Arg Ile Val Leu Val Asp Asn Lys Cys Lys Cys Ala Arg
            260                 265                 270

Ile Thr Ser Arg Ile Ile Arg Ser Ser Glu Asp Pro Asn Glu Asp Ile
        275                 280                 285

Val Glu Arg Asn Ile Arg Ile Ile Val Pro Leu Asn Asn Arg Glu Asn
    290                 295                 300

Ile Ser Asp Pro Thr Ser Pro Leu Arg Thr Arg Phe Val Tyr His Leu
305                 310                 315                 320

Ser Asp Leu Cys Lys Lys Cys Asp Pro Thr Glu Val Glu Leu Asp Asn
                325                 330                 335

Gln Ile Val Thr Ala Thr Gln Ser Asn Ile Cys Asp Glu Asp Ser Ala
            340                 345                 350

Thr Glu Thr Cys Tyr Thr Tyr Asp Arg Asn Lys Cys Tyr Thr Ala Val
        355                 360                 365

Val Pro Leu Val Tyr Gly Gly Glu Thr Lys Met Val Glu Thr Ala Leu
    370                 375                 380

Thr Pro Asp Ala Cys Tyr Pro Asp Gly Gly Gly Ser Glu Gln Lys Leu
```

```
385                 390                 395                 400
Ile Ser Glu Glu Asp Leu Asn Ser Ala Val Asp His His His His
                405                 410                 415
His
```

<210> SEQ ID NO 19
<211> LENGTH: 413
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
                20                  25                  30

Ile Val Glu Arg Asn Ile Arg Ile Ile Val Pro Leu Asn Asn Arg Glu
            35                  40                  45

Asn Ile Ser Asp Pro Thr Ser Pro Leu Arg Thr Arg Phe Val Tyr His
        50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp Gly Gly Gly Ser Gly Gly
130                 135                 140

Gly Gly Ser Gly Gly Gly Gly Ser Gln Val Gln Leu Gln Gln Ser Gly
145                 150                 155                 160

Ala Glu Leu Ala Arg Pro Gly Ala Ser Val Lys Met Ser Cys Lys Ala
                165                 170                 175

Ser Gly Tyr Thr Phe Thr Arg Tyr Thr Met His Trp Val Lys Gln Arg
            180                 185                 190

Pro Gly Gln Gly Leu Glu Trp Ile Gly Tyr Ile Asn Pro Ser Arg Gly
        195                 200                 205

Tyr Thr Asn Tyr Asn Gln Lys Phe Lys Asp Lys Ala Thr Leu Thr Thr
    210                 215                 220

Asp Lys Ser Ser Ser Thr Ala Tyr Met Gln Leu Ser Ser Leu Thr Ser
225                 230                 235                 240

Glu Asp Ser Ala Val Tyr Tyr Cys Ala Arg Tyr Tyr Asp Asp His Tyr
                245                 250                 255

Ser Leu Asp Tyr Trp Gly Gln Gly Thr Thr Leu Thr Val Ser Ser Gly
            260                 265                 270

Gly Gly Gly Ser Gly Gly Gly Gly Ser Gly Gly Gly Gly Ser Gln Ile
        275                 280                 285

Val Leu Thr Gln Ser Pro Ala Ile Met Ser Ala Ser Pro Gly Glu Lys
    290                 295                 300

Val Thr Met Thr Cys Ser Ala Ser Ser Ser Val Ser Tyr Met Asn Trp
305                 310                 315                 320
```

```
Tyr Gln Gln Lys Ser Gly Thr Ser Pro Lys Arg Trp Ile Tyr Asp Thr
                325                 330                 335

Ser Lys Leu Ala Ser Gly Val Pro Ala His Phe Arg Gly Ser Gly Ser
            340                 345                 350

Gly Thr Ser Tyr Ser Leu Thr Ile Ser Gly Met Glu Ala Glu Asp Ala
        355                 360                 365

Ala Thr Tyr Tyr Cys Gln Gln Trp Ser Ser Asn Pro Phe Thr Phe Gly
    370                 375                 380

Ser Gly Thr Lys Leu Glu Ile Lys Glu Gln Lys Leu Ile Ser Glu Glu
385                 390                 395                 400

Asp Leu Asn Ser Ala Val Asp His His His His His His
                405                 410

<210> SEQ ID NO 20
<211> LENGTH: 412
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ile Ser Tyr Thr Met His Trp Val Arg Gln Ala Pro Gly Gln Gly Leu
    50                  55                  60

Glu Trp Met Gly Tyr Ile Asn Pro Arg Ser Gly Tyr Thr His Tyr Asn
65                  70                  75                  80

Gln Lys Leu Lys Asp Lys Ala Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
            180                 185                 190

Pro Gly Lys Ala Pro Lys Arg Leu Ile Tyr Asp Thr Ser Lys Leu Ala
        195                 200                 205

Ser Gly Val Pro Ser Arg Phe Ser Gly Ser Gly Ser Gly Thr Asp Phe
    210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
                245                 250                 255

Leu Glu Ile Lys Gly Gly Gly Gly Ser Gly Gly Gly Gly Ser Gly Gly
```

-continued

```
                260                 265                 270
Gly Gly Ser Gln Glu Asp Glu Arg Ile Val Leu Val Asp Asn Lys Cys
            275                 280                 285

Lys Cys Ala Arg Ile Thr Ser Arg Ile Ile Arg Ser Ser Glu Asp Pro
        290                 295                 300

Asn Glu Asp Ile Val Glu Arg Asn Ile Arg Ile Ile Val Pro Leu Asn
305                 310                 315                 320

Asn Arg Glu Asn Ile Ser Asp Pro Thr Ser Pro Leu Arg Thr Arg Phe
                325                 330                 335

Val Tyr His Leu Ser Asp Leu Cys Lys Lys Cys Asp Pro Thr Glu Val
            340                 345                 350

Glu Leu Asp Asn Gln Ile Val Thr Ala Thr Gln Ser Asn Ile Cys Asp
        355                 360                 365

Glu Asp Ser Ala Thr Glu Thr Cys Tyr Thr Tyr Asp Arg Asn Lys Cys
    370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp
                405                 410

<210> SEQ ID NO 21
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp Gly
145                 150                 155                 160

Gly Gly Gly Ser Gly Gly Gly Ser Gly Gly Gly Ser Gln Val
                165                 170                 175

Gln Leu Val Gln Ser Gly Ala Glu Val Lys Lys Pro Gly Ala Ser Val
            180                 185                 190

Lys Val Ser Cys Lys Ala Ser Gly Tyr Thr Phe Ile Ser Tyr Thr Met
        195                 200                 205
```

His Trp Val Arg Gln Ala Pro Gly Gln Gly Leu Glu Trp Met Gly Tyr
    210                 215                 220
Ile Asn Pro Arg Ser Gly Tyr Thr His Tyr Asn Gln Lys Leu Lys Asp
225                 230                 235                 240
Lys Ala Thr Leu Thr Ala Asp Lys Ser Ala Ser Thr Ala Tyr Met Glu
                245                 250                 255
Leu Ser Ser Leu Arg Ser Glu Asp Thr Ala Val Tyr Tyr Cys Ala Arg
            260                 265                 270
Ser Ala Tyr Tyr Asp Tyr Asp Gly Phe Ala Tyr Trp Gly Gln Gly Thr
        275                 280                 285
Leu Val Thr Val Ser Ser Gly Gly Gly Ser Gly Gly Gly Gly Ser
    290                 295                 300
Gly Gly Gly Gly Ser Asp Ile Gln Met Thr Gln Ser Pro Ser Ser Leu
305                 310                 315                 320
Ser Ala Ser Val Gly Asp Arg Val Thr Ile Thr Cys Ser Ala Ser Ser
                325                 330                 335
Ser Val Ser Tyr Met Asn Trp Tyr Gln Gln Lys Pro Gly Lys Ala Pro
            340                 345                 350
Lys Arg Leu Ile Tyr Asp Thr Ser Lys Leu Ala Ser Gly Val Pro Ser
        355                 360                 365
Arg Phe Ser Gly Ser Gly Ser Gly Thr Asp Phe Thr Leu Thr Ile Ser
    370                 375                 380
Ser Leu Gln Pro Glu Asp Phe Ala Thr Tyr Tyr Cys Gln Gln Trp Ser
385                 390                 395                 400
Ser Asn Pro Pro Thr Phe Gly Gly Gly Thr Lys Leu Glu Ile Lys
                405                 410                 415

<210> SEQ ID NO 22
<211> LENGTH: 56
<212> TYPE: PRT
<213> ORGANISM: Homo sapiens

<400> SEQUENCE: 22

Gln His Asp Glu Ala Val Asp Ala Asn Ser Leu Ala Glu Ala Lys Val
1               5                   10                  15
Leu Ala Asn Arg Glu Leu Asp Lys Tyr Gly Val Ser Asp Tyr Tyr Lys
            20                  25                  30
Asn Leu Ile Asn Asn Ala Lys Thr Val Glu Gly Val Lys Ala Leu Ile
        35                  40                  45
Asp Glu Ile Leu Ala Ala Leu Pro
    50                  55

<210> SEQ ID NO 23
<211> LENGTH: 208
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln His Asp Glu Ala Val Asp Ala Asn Ser Leu Ala Glu Ala Lys Val
1               5                   10                  15
Leu Ala Asn Arg Glu Leu Asp Lys Tyr Gly Val Ser Asp Tyr Tyr Lys
            20                  25                  30
Asn Leu Ile Asn Asn Ala Lys Thr Val Glu Gly Val Lys Ala Leu Ile

```
                35                  40                  45
Asp Glu Ile Leu Ala Ala Leu Pro Gly Gly Gly Ser Gly Gly
        50                  55                  60
Gly Ser Gly Gly Gly Ser Gln Glu Asp Glu Arg Ile Val Leu Val
65                  70                  75                  80
Asp Asn Lys Cys Lys Cys Ala Arg Ile Thr Ser Arg Ile Ile Arg Ser
                85                  90                  95
Ser Glu Asp Pro Asn Glu Asp Ile Val Glu Arg Asn Ile Arg Ile Ile
                100                 105                 110
Val Pro Leu Asn Asn Arg Glu Asn Ile Ser Asp Pro Thr Ser Pro Leu
                115                 120                 125
Arg Thr Arg Phe Val Tyr His Leu Ser Asp Leu Cys Lys Lys Cys Asp
        130                 135                 140
Pro Thr Glu Val Glu Leu Asp Asn Gln Ile Val Thr Ala Thr Gln Ser
145                 150                 155                 160
Asn Ile Cys Asp Glu Asp Ser Ala Thr Glu Thr Cys Tyr Thr Tyr Asp
                165                 170                 175
Arg Asn Lys Cys Tyr Thr Ala Val Val Pro Leu Val Tyr Gly Gly Glu
                180                 185                 190
Thr Lys Met Val Glu Thr Ala Leu Thr Pro Asp Ala Cys Tyr Pro Asp
        195                 200                 205

<210> SEQ ID NO 24
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Ala Gln Val Gln Leu Leu Glu Ser Gly Gly Gly Leu Val Gln Pro
1               5                   10                  15
Gly Gly Ser Leu Arg Leu Ser Cys Ala Ala Ser Gly Phe Ile Phe Asn
                20                  25                  30
Thr Glu Tyr Met Ala Trp Val Arg Gln Ala Pro Gly Lys Gly Leu Glu
        35                  40                  45
Trp Val Ser Ala Ile Lys Glu Gln Ser Gly Ser Thr Tyr Tyr Ala Asp
        50                  55                  60
Ser Val Lys Gly Arg Phe Thr Ile Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Ala Gln Met His His Glu Ala Glu Val Lys Phe Trp Gly
                100                 105                 110
Gln Gly Thr Leu Val Thr Val Ser
        115                 120

<210> SEQ ID NO 25
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25
```

Met Ala Gln Val Gln Leu Leu Glu Ser Gly Gly Gly Leu Val Gln Pro
1               5                   10                  15

Gly Gly Ser Leu Arg Leu Ser Cys Ala Ala Ser Gly Phe Ile Phe Asn
            20                  25                  30

Thr Glu Tyr Met Ala Trp Val Arg Gln Ala Pro Gly Lys Gly Leu Glu
        35                  40                  45

Trp Val Ser Ala Ile Lys Glu Gln Ser Gly Ser Thr Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Ala Gln Met His His Glu Ala Glu Val Lys Phe Trp Gly
            100                 105                 110

Gln Gly Thr Leu Val Thr Val Ser Gly Gly Gly Ser Gly Gly Gly
        115                 120                 125

Gly Ser Gly Gly Gly Ser Gln Glu Asp Glu Arg Ile Val Leu Val
    130                 135                 140

Asp Asn Lys Cys Lys Cys Ala Arg Ile Thr Ser Arg Ile Ile Arg Ser
145                 150                 155                 160

Ser Glu Asp Pro Asn Glu Asp Ile Val Glu Arg Asn Ile Arg Ile Ile
                165                 170                 175

Val Pro Leu Asn Asn Arg Glu Asn Ile Ser Asp Pro Thr Ser Pro Leu
            180                 185                 190

Arg Thr Arg Phe Val Tyr His Leu Ser Asp Leu Cys Lys Lys Cys Asp
        195                 200                 205

Pro Thr Glu Val Glu Leu Asp Asn Gln Ile Val Thr Ala Thr Gln Ser
    210                 215                 220

Asn Ile Cys Asp Glu Asp Ser Ala Thr Glu Thr Cys Tyr Thr Tyr Asp
225                 230                 235                 240

Arg Asn Lys Cys Tyr Thr Ala Val Val Pro Leu Val Tyr Gly Gly Glu
                245                 250                 255

Thr Lys Met Val Glu Thr Ala Leu Thr Pro Asp Ala Cys Tyr Pro Asp
            260                 265                 270

<210> SEQ ID NO 26
<211> LENGTH: 157
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp Gly Gly Gly Ser Gly Gly
    130                 135                 140

Gly Gly Ser Gly Gly Gly Ser Leu Leu Gln Gly Ala
145                 150                 155

<210> SEQ ID NO 27
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Tyr Asn Met His
1               5

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Ile Tyr Pro Gly Asn Gly Asp Thr Ser Tyr Asn Gln Lys Phe Lys

<210> SEQ ID NO 30
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Ser Thr Tyr Tyr Gly Gly Asp Trp Tyr Phe Asn Val
1               5                   10

<210> SEQ ID NO 31
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Arg Ala Ser Ser Ser Val Ser Tyr Ile His
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Ala Thr Ser Asn Leu Ala Ser
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gln Gln Trp Thr Ser Asn Pro Pro Thr
1               5

<210> SEQ ID NO 35
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr
        195                 200

<210> SEQ ID NO 36
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 36

Val Val Tyr Tyr Ser Asn Ser Tyr Trp Tyr Phe Asp Val
1               5                   10

<210> SEQ ID NO 37
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu
        195                 200

<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Arg Ala Ser Ser Ser Val Ser Tyr Met His
1               5                   10

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 39

Ala Pro Ser Asn Leu Ala Ser
1               5

<210> SEQ ID NO 40
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Gln Trp Ser Phe Asn Pro Pro Thr
1               5

<210> SEQ ID NO 41
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser
        115                 120

<210> SEQ ID NO 42
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Ile Tyr Pro Leu Thr Gly Asp Thr Ser Tyr Asn Gln Lys Ser Lys
1               5                   10                  15

Leu

<210> SEQ ID NO 43
<211> LENGTH: 12
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Thr Tyr Val Gly Gly Asp Trp Gln Phe Asp Val
1               5                   10

<210> SEQ ID NO 44
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys
            100                 105

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ala Ser Ser Ser Val Pro Tyr Ile His
1               5                   10

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ala Thr Ser Ala Leu Ala Ser
1               5

<210> SEQ ID NO 47
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 47

Gln Gln Trp Leu Ser Asn Pro Pro Thr
1               5

<210> SEQ ID NO 48
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Val Gln Leu Gln Gln Pro Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Thr
        35                  40                  45

Gly Ala Ile Tyr Pro Gly Asn Gly Asp Thr Ser Tyr Asn Gln Lys Phe
    50                  55                  60

Lys Gly Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 49
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Gln Gln Pro Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110
```

```
Ala Gly Thr Thr Val Thr Val Ser Ala
        115                 120
```

<210> SEQ ID NO 50
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Gln Ile Val Leu Ser Gln Ser Pro Ala Ile Ile Thr Ala Ser Pro Gly
1               5                   10                  15

Glu Lys Val Thr Met Thr Cys Arg Ala Ser Thr Ser Ala Ser Tyr Ile
            20                  25                  30

His Trp Phe Gln Gln Lys Pro Thr Ser Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105
```

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

```
Arg Ala Ser Thr Ser Ala Ser Tyr Ile His
1               5                   10
```

<210> SEQ ID NO 52
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

```
Gln Ile Val Leu Ser Gln Ser Pro Ala Ile Ile Thr Ala Ser Pro Gly
1               5                   10                  15

Glu Lys Val Thr Met Thr Cys Arg Ala Ser Thr Ser Val Ser Tyr Ile
            20                  25                  30

His Trp Phe Gln Gln Lys Pro Thr Ser Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
```

```
                    85                  90                  95

Phe Gly Gly Gly Thr Lys Leu Glu Ile Lys
            100                 105

<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Arg Ala Ser Thr Ser Val Ser Tyr Ile His
1               5                   10

<210> SEQ ID NO 54
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Ile Val Leu Ser Gln Ser Pro Ala Ile Ile Thr Ala Ser Pro Gly
1               5                   10                  15

Glu Lys Val Thr Met Thr Cys Arg Ala Ser Thr Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 55
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Ile Val Leu Ser Gln Ser Pro Ala Ile Ile Thr Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80
```

```
Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 56
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Val Gln Leu Gln Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Tyr Tyr Gly Ser Ser Tyr Trp Phe Phe Asp Val Trp
            100                 105                 110

Gly Thr Gly Thr Thr Val Thr Val Ser Ser
        115                 120

<210> SEQ ID NO 57
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Asn Tyr Tyr Gly Ser Ser Tyr Trp Phe Phe Asp Val
1               5                   10

<210> SEQ ID NO 58
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Leu Thr Gln Ser Pro Ala Ile Ile Thr Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45
```

```
Ala Thr Ser Asn Leu Ala Ser Gly Val Pro Ser Arg Phe Ser Gly Ser
        50                  55                  60
Gly Ser Gly Thr Thr Tyr Ser Met Thr Ile Ser Ser Leu Glu Ala Glu
 65                  70                  75                  80
Asp Ala Ala Thr Tyr Tyr Cys Gln Gln Trp Ser Phe Asn Pro Pro Thr
                    85                  90                  95
Phe Gly Gly Gly Thr Lys Leu Glu Ile Lys
                100                 105
```

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

```
Arg Ala Ser Ser Ser Val Asn Tyr Met Asp
 1               5                  10
```

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

```
Gln Gln Trp Ser Phe Asn Pro Pro Thr
 1               5
```

<210> SEQ ID NO 61
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Gln Val Gln Leu Gln Gln Ser Gly Ala Glu Val Lys Lys Pro Gly Ser
 1               5                  10                  15
Ser Val Lys Val Ser Cys Lys Ala Ser Gly Tyr Thr Phe Thr Ser Tyr
                20                  25                  30
Asn Met His Trp Val Lys Gln Ala Pro Gly Gln Gly Leu Glu Trp Ile
            35                  40                  45
Gly Ala Ile Tyr Pro Gly Asn Gly Asp Thr Ser Tyr Asn Gln Lys Phe
        50                  55                  60
Lys Gly Lys Ala Thr Leu Thr Ala Asp Glu Ser Thr Asn Thr Ala Tyr
 65                  70                  75                  80
Met Glu Leu Ser Ser Leu Arg Ser Glu Asp Thr Ala Phe Tyr Tyr Cys
                    85                  90                  95
Ala Arg Ser Thr Tyr Tyr Gly Gly Asp Trp Tyr Phe Asp Val Trp Gly
                100                 105                 110
Gln Gly Thr Thr Val Thr Val Ser Ser
            115                 120
```

```
<210> SEQ ID NO 62
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ser Thr Tyr Tyr Gly Gly Asp Trp Tyr Phe Asp Val
1               5                   10

<210> SEQ ID NO 63
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
                20                  25                  30

Ser Val Gly Asp Arg Val Thr Met Thr Cys Arg Ala Ser Ser Ser Val
            35                  40                  45

Ser Tyr Ile His Trp Phe Gln Gln Lys Pro Gly Lys Ala Pro Lys Pro
        50                  55                  60

Trp Ile Tyr Ala Thr Ser Asn Leu Ala Ser Gly Val Pro Val Arg Phe
65                  70                  75                  80

Ser Gly Ser Gly Ser Gly Thr Asp Tyr Thr Phe Thr Ile Ser Ser Leu
                85                  90                  95

Gln Pro Glu Asp Ile Ala Thr Tyr Tyr Cys Gln Gln Trp Thr Ser Asn
            100                 105                 110

Pro Pro Thr Phe Gly Gly Gly Thr Lys Leu Glu Ile Lys
        115                 120                 125

<210> SEQ ID NO 64
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95
```

Ala Arg His Pro Ser Tyr Gly Ser Gly Ser Pro Asn Phe Asp Tyr Trp
            100                 105                 110

Gly Gln Gly Thr Leu Val Thr Val Ser Ser
        115                 120

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gly Tyr Ser Phe Thr Ser Tyr Trp Ile Gly
1               5                   10

<210> SEQ ID NO 66
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ile Ile Tyr Pro Gly Asp Ser Asp Thr Arg Tyr Ser Pro Ser Phe Gln
1               5                   10                  15

Gly

<210> SEQ ID NO 67
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

His Pro Ser Tyr Gly Ser Gly Ser Pro Asn Phe Asp Tyr
1               5                   10

<210> SEQ ID NO 68
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile

```
            65                  70                  75                  80
Ser Arg Val Glu Ala Glu Asp Val Gly Val Tyr Tyr Cys Val Gln Ala
                    85                  90                  95
Thr Gln Phe Pro Leu Thr Phe Gly Gly Gly Thr Lys Val Glu Ile Lys
            100                 105                 110
```

<210> SEQ ID NO 69
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

```
Arg Ser Ser Gln Ser Leu Val Tyr Ser Asp Gly Asn Thr Tyr Leu Ser
1               5                   10                  15
```

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

```
Lys Ile Ser Asn Arg Phe Ser
1               5
```

<210> SEQ ID NO 71
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

```
Val Gln Ala Thr Gln Phe Pro Leu Thr
1               5
```

<210> SEQ ID NO 72
<211> LENGTH: 1347
<212> TYPE: DNA
<213> ORGANISM: Homo sapiens

<400> SEQUENCE: 72

```
gccccaaccc ttttccccct cgtctcctgt gagaattccc cgtcggatac gagcagcgtg     60
gccgttggct gcctcgcaca ggacttcctt cccgactcca tcactttctc ctggaaatac    120
aagaacaact tgacatcag cagcacccgg ggcttcccat cagtcctgag aggggggcaag    180 cacgcagcca cctcacaggt gctgctgcct tccaaggacg tcatgcaggg cacagacgaa    240
cacgtggtgt gcaaagtcca gcaccccaac ggcaacaaag aaaagaacgt gcctcttcca    300
gtgattgctg agctgcctcc caaagtgagc gtcttcgtcc caccccgcga cggcttcttc    360 ggcaacccc gcaagtccaa gctcatctgc caggccacgg gtttcagtcc ccggcagatt    420
caggtgtcct ggctgcgcga ggggaagcag gtggggtctg cgtcaccac ggaccaggtg    480 caggctgagg caaaggagtc tgggccacg acctacaagg tgaccagcac actgaccatc    540
```

```
aaagagagcg actggctcag ccagagcatg ttcacctgcc gcgtggatca caggggcctg    600
accttccagc agaatgcgtc ctccatgtgt ggccccgatc aagacacagc catccgggtc    660
ttctccatcc ccccatcctt tgccagcatc ttcctcacca agtccaccaa gttgacctgc    720
ctggtcacag acctgaccac ctatgacagc gtgaccatct cctggacccg ccagaatggc    780
gaagctgtga aacccacac caacatctcc gagagccacc ccaatgccac tttcagcgcc    840
gtgggtgagg ccagcatctg cgaggatgac tggaattccg gggagaggtt cacgtgcacc    900
gtgacccaca cagacctgcc ctcgccactg aagcagacca tctcccggcc caagggggtg    960
gccctgcaca ggccccgatgt ctacttgctg ccaccagccc gggagcagct gaacctgcgg   1020
gagtcggcca ccatcacgtg cctggtgacg ggcttctctc ccgcggacgt cttcgtgcag   1080
tggatgcaga gggggcagcc cttgtccccg gagaagtatg tgaccagcgc ccaatgcct    1140 gagccccagg ccccaggccg gtacttcgcc cacagcatcc tgaccgtgtc cgaagaggaa   1200
tggaacacgg gggagaccta cacctgcgtg gtggcccatg aggccctgcc caacagggtc   1260
accgagagga ccgtggacaa gtccaccggt aaacccaccc tgtacaacgt gtccctggtc   1320
atgtccgaca cagctggcac tgctac                                        1347
```

<210> SEQ ID NO 73
<211> LENGTH: 453
<212> TYPE: PRT
<213> ORGANISM: Homo sapiens

<400> SEQUENCE: 73

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
        210                 215                 220

Phe Ala Ile Pro Pro Ser Phe Ala Ser Ile Phe Leu Thr Lys Ser Thr
```

```
                225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
                260                 265                 270

Ile Ser Glu Ser His Pro Asn Ala Thr Phe Ser Ala Val Gly Glu Ala
                275                 280                 285

Ser Ile Cys Glu Asp Asp Trp Asn Ser Gly Arg Phe Thr Cys Thr
        290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                    325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
                355                 360                 365

Gly Gln Pro Leu Ser Pro Glu Lys Tyr Val Thr Ser Ala Pro Met Pro
        370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                    405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
                435                 440                 445

Ala Gly Thr Cys Tyr
        450

<210> SEQ ID NO 74
<211> LENGTH: 480
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
atgaagaacc atttgctttt ctggggagtc ctggcggttt ttattaaggc tgttcatgtg      60
aaagcccaag aagatgaaag gattgttctt gttgacaaca aatgtaagtg tgcccggatt     120
acttccagga tcatccgttc ttccgaagat cctaatgagg acattgtgga gagaaacatc     180
cgaattattg ttcctctgaa caacagggag aatatctctg atcccacctc accattgaga     240
accagatttg tgtaccattt gtctgacctc tgtaaaaaat gtgatcctac agaagtggag     300
ctggataatc agatagttac tgctacccag agcaatatct gtgatgaaga cagtgctaca     360
gagacctgct acacttatga cagaaacaag tgctacacag ctgtggtccc actcgtatat     420
ggtggtgaga ccaaaatggt ggaaacagcc ttaaccccag atgcctgcta tcctgactaa     480

<210> SEQ ID NO 75
<211> LENGTH: 158
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 75

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Ile Val Pro
    50                  55                  60

Leu Asn Asn Arg Glu Asn Ile Ser Asp Pro Thr Ser Pro Leu Arg Thr
65                  70                  75                  80

Arg Phe Val Tyr His Leu Ser Asp Leu Cys Lys Cys Asp Pro Thr
                85                  90                  95

Glu Val Glu Leu Asp Asn Gln Ile Val Thr Ala Thr Gln Ser Asn Ile
            100                 105                 110

Cys Asp Glu Asp Ser Ala Thr Glu Thr Cys Tyr Thr Tyr Asp Arg Asn
        115                 120                 125

Lys Cys Tyr Thr Ala Val Val Pro Leu Val Tyr Gly Gly Glu Thr Lys
    130                 135                 140

Met Val Glu Thr Ala Leu Thr Pro Asp Ala Cys Tyr Pro Asp
145                 150                 155

<210> SEQ ID NO 76
<211> LENGTH: 297
<212> TYPE: PRT
<213> ORGANISM: Homo sapiens

<400> SEQUENCE: 76

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

```
Ile Leu Ser Val Met Leu Ile Phe Ala Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Gly Pro Pro Gln Asp Gln Glu Ser
        275                 280                 285

Ser Pro Ile Glu Asn Asp Ser Ser Pro
    290                 295
```

<210> SEQ ID NO 77
<211> LENGTH: 1725
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 77

```
caggttcagc tgcagcagcc cggagccgag ctggtcaaac ctggcgctag tgtgaaaatg      60
tcatgcaagg catccggata cacattcact agctataaca tgcactgggt gaagcagacc     120
cccggcaggg gtctggagtg gatcggagct atctaccccg gcaacggaga cacatcttat     180
aatcagaagt ttaaaggcaa ggccacccty acagctgata agtccagctc taccgcatac     240
atgcagctga gttcactgac aagcgaggac tccgccgtgt actattgcgc ccggtccact     300
tactatggcg agattggta tttcaatgtg tggggagcag gcaccacagt caccgtctcg     360
agcggcagtg ctagcgcccc aacccttttc cccctcgtct cctgtgagaa ttccccgtcg     420
gatacgagca gcgtggccgt tggctgcctc gcacaggact ccttcccgac tccatcact     480 ttctcctgga atacaagaa caactctgac atcagcagca cccggggctt ccatcagtc     540 ctgagagggg gcaagtacgc agccacctca caggtgctgc tgccttccaa ggacgtcatg     600
cagggcacag acgaacacgt ggtgtgcaaa gtccagcacc caacggcaa caaagaaaag     660 aacgtgcctc ttccagtgat tgctgagctg cctcccaaag tgagcgtctt cgtcccaccc     720
cgcgacggct tcttcggcaa ccccgcaag tccaagctca tctgccaggc cacgggtttc     780
agtccccggc agattcaggt gtcctggctg cgcgagggga gcaggtggg gtctggcgtc     840 accacggacc aggtgcaggc tgaggccaaa gagtctgggc ccacgaccta caaggtgacc     900
agcacactga ccatcaaaga gagcgactgg ctcagccaga gcatgttcac ctgccgcgtg     960
gatcacaggg gcctgacctt ccagcagaat gcgtcctcca tgtgtgtccc cgatcaagac    1020
acagccatcc gggtcttcgc catcccccca tcctttgcca gcatcttcct caccaagtcc    1080
accaagttga cctgcctggt cacagacctg accacctatg acagcgtgac catctcctgg    1140
acccgccaga tggcgaagc tgtgaaaacc cacaccaaca tctccgagag ccaccccaat    1200
gccactttca gcgccgtggg tgaggccagc atctgcgagg atgactggaa ttccggggag    1260
aggttcacgt gcaccgtgac ccacacagac ctgccctcgc cactgaagca gaccatctcc    1320
cggcccaagg gggtggccct gcacaggccc gatgtctact gctgccacc agcccgggag    1380
```

-continued

```
cagctgaacc tgcgggagtc ggccaccatc acgtgcctgg tgacgggctt ctctcccgcg   1440
gacgtcttcg tgcagtggat gcagaggggg cagcccttgt ccccggagaa gtatgtgacc   1500
agcgccccaa tgcctgagcc ccaggcccca ggccggtact tcgcccacag catcctgacc   1560
gtgtccgaag aggaatggaa cacggggag  acctacacct gcgtggtggc ccatgaggcc   1620
ctgcccaaca gggtcaccga gaggaccgtg acaagtcca  ccggtaaacc caccctgtac   1680
aacgtgtccc tggtcatgtc cgacacagct ggcacctgct actga                  1725
```

<210> SEQ ID NO 78
<211> LENGTH: 574
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
```

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
        355                 360                 365

Asp Leu Thr Thr Tyr Asp Ser Val Thr Ile Ser Trp Thr Arg Gln Asn
370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
    450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
        515                 520                 525

Gly Glu Thr Tyr Thr Cys Val Val Ala His Glu Ala Leu Pro Asn Arg
    530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 79
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 79
caaattgtgc tgtctcagag tccagctatc ctgagcgcat ctcccggaga gaaggtgacc      60
atgacatgca gagcctccag ctctgtctcc tacatccact ggttccagca gaagcccggc     120
tcctccccaa aaccctggat ctacgccacc tctaacctgg ctagtggtgt gcctgtcagg     180
tttagtggat cagggtccgg caccagctac tctctgacaa tcagccgggt ggaggctgaa     240
gacgccgcta catactattg ccagcagtgg acttctaatc cccctacctt cggcggaggg     300
acaaagctgg agatcaagcg tacggtggct gcaccatctg tcttcatctt cccgccatct     360
gatgagcagt tgaaatctgg aactgcctct gttgtgtgcc tgctgaataa cttctatccc     420

```
agagaggcca aagtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                      642
```

<210> SEQ ID NO 80
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 81
<211> LENGTH: 1728
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
gaggtgcagc tggtgcagtc cggcgccgag gtgaagaagc ccggcgagtc cctgaagatc     60
tcctgcaagg gctccggcta ctccttcacc tcctactgga tcggctgggt gaggcagatg    120
cccggcaagg gcctggagtg gatgggcatc atctaccccg gcgactccga caccaggtac    180
```

```
tcccccctcct tccagggcca ggtgaccatc tccgccgaca agtccatcac caccgcctac    240
ctgcagtggt cctccctgaa ggcctccgac accgccatgt actactgcgc caggcacccc    300
tcctacggct ccggctcccc caacttcgac tactggggcc agggcaccct ggtgaccgtg    360
tcctccggca gtgctagcgc cccaacccct tccccctcg  tctcctgtga gaattccccg    420
tcggatacga gcagcgtggc cgttggctgc ctcgcacagg acttccttcc cgactccatc    480
actttctcct ggaaatacaa gaacaactct gacatcagca gcacccgggg cttcccatca    540
gtcctgagag ggggcaagta cgcagccacc tcacaggtgc tgctgccttc caaggacgtc    600
atgcagggca cagacgaaca cgtggtgtgc aaagtccagc accccaacgg caacaaagaa    660
aagaacgtgc ctcttccagt gattgctgag ctgcctccca agtgagcgt  cttcgtccca    720 ccccgcgacg gcttcttcgg caaccccgc  aagtccaagc tcatctgcca ggccacgggt    780
ttcagtcccc ggcagattca ggtgtcctgg ctgcgcgagg ggaagcaggt ggggtctggc    840
gtcaccacgg accaggtgca ggctgaggcc aaagagtctg ggcccacgac ctacaaggtg    900
accagcacac tgaccatcaa agagagcgac tggctcagcc agagcatgtt cacctgccgc    960
gtggatcaca ggggcctgac cttccagcag aatgcgtcct ccatgtgtgt ccccgatcaa   1020
gacacagcca tccgggtctt cgccatcccc ccatcctttg ccagcatctt cctcaccaag   1080
tccaccaagt tgacctgcct ggtcacagac ctgaccacct atgacagcgt gaccatctcc   1140
tggacccgcc agaatggcga agctgtgaaa acccacacca catctccga  gagccacccc   1200 aatgccactt tcagcgccgt gggtgaggcc agcatctgcg aggatgactg gaattccggg   1260
gagaggttca cgtgcaccgt gacccacaca gacctgccct cgccactgaa gcagaccatc   1320
tcccggccca aggggtggc  cctgcacagg cccgatgtct acttgctgcc accagcccgg   1380
gagcagctga acctgcggga gtcggccacc atcacgtgcc tggtgacggg cttctctccc   1440
gcggacgtct tcgtgcagtg gatgcagagg gggcagccct gtccccgga  gaagtatgtg   1500 accagcgccc caatgcctga gccccaggcc caggccggt  acttcgccca gcatcctg    1560 accgtgtccg aagaggaatg gaacacgggg gagacctaca cctgcgtggt ggcccatgag   1620
gccctgccca acagggtcac cgagaggacc gtggacaagt ccaccggtaa acccacccctg   1680 tacaacgtgt ccctggtcat gtccgacaca gctggcacct gctactga                1728
```

<210> SEQ ID NO 82
<211> LENGTH: 575
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg His Pro Ser Tyr Gly Ser Gly Ser Pro Asn Phe Asp Tyr Trp
            100                 105                 110

Gly Gln Gly Thr Leu Val Thr Val Ser Ser Gly Ser Ala Ser Ala Pro
        115                 120                 125

Thr Leu Phe Pro Leu Val Ser Cys Glu Asn Ser Pro Ser Asp Thr Ser
    130                 135                 140

Ser Val Ala Val Gly Cys Leu Ala Gln Asp Phe Leu Pro Asp Ser Ile
145                 150                 155                 160

Thr Phe Ser Trp Lys Tyr Lys Asn Asn Ser Asp Ile Ser Ser Thr Arg
                165                 170                 175

Gly Phe Pro Ser Val Leu Arg Gly Gly Lys Tyr Ala Ala Thr Ser Gln
            180                 185                 190

Val Leu Leu Pro Ser Lys Asp Val Met Gln Gly Thr Asp Glu His Val
        195                 200                 205

Val Cys Lys Val Gln His Pro Asn Gly Asn Lys Glu Lys Asn Val Pro
    210                 215                 220

Leu Pro Val Ile Ala Glu Leu Pro Pro Lys Val Ser Val Phe Val Pro
225                 230                 235                 240

Pro Arg Asp Gly Phe Phe Gly Asn Pro Arg Lys Ser Lys Leu Ile Cys
                245                 250                 255

Gln Ala Thr Gly Phe Ser Pro Arg Gln Ile Gln Val Ser Trp Leu Arg
            260                 265                 270

Glu Gly Lys Gln Val Gly Ser Gly Val Thr Thr Asp Gln Val Gln Ala
        275                 280                 285

Glu Ala Lys Glu Ser Gly Pro Thr Thr Tyr Lys Val Thr Ser Thr Leu
    290                 295                 300

Thr Ile Lys Glu Ser Asp Trp Leu Ser Gln Ser Met Phe Thr Cys Arg
305                 310                 315                 320

Val Asp His Arg Gly Leu Thr Phe Gln Gln Asn Ala Ser Ser Met Cys
                325                 330                 335

Val Pro Asp Gln Asp Thr Ala Ile Arg Val Phe Ala Ile Pro Pro Ser
            340                 345                 350

Phe Ala Ser Ile Phe Leu Thr Lys Ser Thr Lys Leu Thr Cys Leu Val
        355                 360                 365

Thr Asp Leu Thr Thr Tyr Asp Ser Val Thr Ile Ser Trp Thr Arg Gln
    370                 375                 380

Asn Gly Glu Ala Val Lys Thr His Thr Asn Ile Ser Glu Ser His Pro
385                 390                 395                 400

Asn Ala Thr Phe Ser Ala Val Gly Glu Ala Ser Ile Cys Glu Asp Asp
                405                 410                 415

Trp Asn Ser Gly Glu Arg Phe Thr Cys Thr Val Thr His Thr Asp Leu
            420                 425                 430

Pro Ser Pro Leu Lys Gln Thr Ile Ser Arg Pro Lys Gly Val Ala Leu
        435                 440                 445

His Arg Pro Asp Val Tyr Leu Leu Pro Pro Ala Arg Glu Gln Leu Asn
    450                 455                 460

Leu Arg Glu Ser Ala Thr Ile Thr Cys Leu Val Thr Gly Phe Ser Pro
465                 470                 475                 480

Ala Asp Val Phe Val Gln Trp Met Gln Arg Gly Gln Pro Leu Ser Pro
                485                 490                 495
```

```
Glu Lys Tyr Val Thr Ser Ala Pro Met Pro Glu Pro Gln Ala Pro Gly
                500                 505                 510

Arg Tyr Phe Ala His Ser Ile Leu Thr Val Ser Glu Glu Glu Trp Asn
            515                 520                 525

Thr Gly Glu Thr Tyr Thr Cys Val Val Ala His Glu Ala Leu Pro Asn
        530                 535                 540

Arg Val Thr Glu Arg Thr Val Asp Lys Ser Thr Gly Lys Pro Thr Leu
545                 550                 555                 560

Tyr Asn Val Ser Leu Val Met Ser Asp Thr Ala Gly Thr Cys Tyr
                565                 570                 575

<210> SEQ ID NO 83
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
gacatcgtga tgacccagac ccccctgtcc tcccccgtga ccctgggcca gcccgcctcc      60
atctcctgca ggtcctccca gtccctggtg tactccgacg gcaacaccta cctgtcctgg     120
ctgcagcaga ggcccggcca gccccccagg ctgctgatct acaagatctc aacaggttc     180 tccggcgtgc ccgacaggtt ctccggctcc ggcgccggca ccgacttcac cctgaagatc     240 tccaggtgg aggccgagga cgtgggcgtg tactactgcg tgcaggccac ccagttcccc     300
ctgaccttcg gcggcggcac caaggtggag atcaagcgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 84
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95
```

```
Thr Gln Phe Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215

<210> SEQ ID NO 85
<211> LENGTH: 353
<212> TYPE: PRT
<213> ORGANISM: Homo sapiens

<400> SEQUENCE: 85

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
            210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255
```

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
        290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 86
<211> LENGTH: 340
<212> TYPE: PRT
<213> ORGANISM: Homo sapiens

<400> SEQUENCE: 86

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

```
Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
305                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 87
<211> LENGTH: 764
<212> TYPE: PRT
<213> ORGANISM: Homo sapiens

<400> SEQUENCE: 87

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
```

```
                290             295             300
Asp Gly Ser Phe Ser Val Val Ile Thr Gly Leu Arg Lys Glu Asp Ala
305             310             315             320

Gly Arg Tyr Leu Cys Gly Ala His Ser Asp Gly Gln Leu Gln Glu Gly
                325             330             335

Ser Pro Ile Gln Ala Trp Gln Leu Phe Val Asn Glu Glu Ser Thr Ile
                340             345             350

Pro Arg Ser Pro Thr Val Val Lys Gly Val Ala Gly Gly Ser Val Ala
                355             360             365

Val Leu Cys Pro Tyr Asn Arg Lys Glu Ser Lys Ser Ile Lys Tyr Trp
370             375             380

Cys Leu Trp Glu Gly Ala Gln Asn Gly Arg Cys Pro Leu Leu Val Asp
385             390             395             400

Ser Glu Gly Trp Val Lys Ala Gln Tyr Glu Gly Arg Leu Ser Leu Leu
                405             410             415

Glu Glu Pro Gly Asn Gly Thr Phe Thr Val Ile Leu Asn Gln Leu Thr
                420             425             430

Ser Arg Asp Ala Gly Phe Tyr Trp Cys Leu Thr Asn Gly Asp Thr Leu
                435             440             445

Trp Arg Thr Thr Val Glu Ile Lys Ile Ile Glu Gly Glu Pro Asn Leu
                450             455             460

Lys Val Pro Gly Asn Val Thr Ala Val Leu Gly Glu Thr Leu Lys Val
465             470             475             480

Pro Cys His Phe Pro Cys Lys Phe Ser Ser Tyr Glu Lys Tyr Trp Cys
                485             490             495

Lys Trp Asn Asn Thr Gly Cys Gln Ala Leu Pro Ser Gln Asp Glu Gly
                500             505             510

Pro Ser Lys Ala Phe Val Asn Cys Asp Glu Asn Ser Arg Leu Val Ser
                515             520             525

Leu Thr Leu Asn Leu Val Thr Arg Ala Asp Glu Gly Trp Tyr Trp Cys
                530             535             540

Gly Val Lys Gln Gly His Phe Tyr Gly Glu Thr Ala Ala Val Tyr Val
545             550             555             560

Ala Val Glu Glu Arg Lys Ala Ala Gly Ser Arg Asp Val Ser Leu Ala
                565             570             575

Lys Ala Asp Ala Ala Pro Asp Glu Lys Val Leu Asp Ser Gly Phe Arg
                580             585             590

Glu Ile Glu Asn Lys Ala Ile Gln Asp Pro Arg Leu Phe Ala Glu Glu
                595             600             605

Lys Ala Val Ala Asp Thr Arg Asp Gln Ala Asp Gly Ser Arg Ala Ser
                610             615             620

Val Asp Ser Gly Ser Ser Glu Glu Gln Gly Gly Ser Ser Arg Ala Leu
625             630             635             640

Val Ser Thr Leu Val Pro Leu Gly Leu Val Leu Ala Val Gly Ala Val
                645             650             655

Ala Val Gly Val Ala Arg Ala Arg His Arg Lys Asn Val Asp Arg Val
                660             665             670

Ser Ile Arg Ser Tyr Arg Thr Asp Ile Ser Met Ser Asp Phe Glu Asn
                675             680             685

Ser Arg Glu Phe Gly Ala Asn Asp Asn Met Gly Ala Ser Ser Ile Thr
                690             695             700

Gln Glu Thr Ser Leu Gly Gly Lys Glu Glu Phe Val Ala Thr Thr Glu
705             710             715             720
```

-continued

```
Ser Thr Thr Glu Thr Lys Glu Pro Lys Lys Ala Lys Arg Ser Ser Lys
                725             730             735

Glu Glu Ala Glu Met Ala Tyr Lys Asp Phe Leu Leu Gln Ser Ser Thr
            740             745             750

Val Ala Ala Glu Ala Gln Asp Gly Pro Gln Glu Ala
        755             760

<210> SEQ ID NO 88
<211> LENGTH: 585
<212> TYPE: PRT
<213> ORGANISM: Homo sapiens

<400> SEQUENCE: 88

Lys Ser Pro Ile Phe Gly Pro Glu Val Asn Ser Val Glu Gly Asn
1               5                   10                  15

Ser Val Ser Ile Thr Cys Tyr Tyr Pro Pro Thr Ser Val Asn Arg His
                20                  25                  30

Thr Arg Lys Tyr Trp Cys Arg Gln Gly Ala Arg Gly Gly Cys Ile Thr
            35                  40                  45

Leu Ile Ser Ser Glu Gly Tyr Val Ser Ser Lys Tyr Ala Gly Arg Ala
        50                  55                  60

Asn Leu Thr Asn Phe Pro Glu Asn Gly Thr Phe Val Val Asn Ile Ala
65                  70                  75                  80

Gln Leu Ser Gln Asp Asp Ser Gly Arg Tyr Lys Cys Gly Leu Gly Ile
                85                  90                  95

Asn Ser Arg Gly Leu Ser Phe Asp Val Ser Leu Glu Val Ser Gln Gly
            100                 105                 110

Pro Gly Leu Leu Asn Asp Thr Lys Val Tyr Thr Val Asp Leu Gly Arg
        115                 120                 125

Thr Val Thr Ile Asn Cys Pro Phe Lys Thr Glu Asn Ala Gln Lys Arg
130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
                165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro
    210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
    290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
```

325                 330                 335
Ser Pro Thr Val Val Lys Gly Val Ala Gly Ser Val Ala Val Leu
            340                 345                 350
Cys Pro Tyr Asn Arg Lys Glu Ser Lys Ser Ile Lys Tyr Trp Cys Leu
        355                 360                 365
Trp Glu Gly Ala Gln Asn Gly Arg Cys Pro Leu Leu Val Asp Ser Glu
    370                 375                 380
Gly Trp Val Lys Ala Gln Tyr Glu Gly Arg Leu Ser Leu Leu Glu Glu
385                 390                 395                 400
Pro Gly Asn Gly Thr Phe Thr Val Ile Leu Asn Gln Leu Thr Ser Arg
            405                 410                 415
Asp Ala Gly Phe Tyr Trp Cys Leu Thr Asn Gly Asp Thr Leu Trp Arg
        420                 425                 430
Thr Thr Val Glu Ile Lys Ile Ile Glu Gly Pro Asn Leu Lys Val
    435                 440                 445
Pro Gly Asn Val Thr Ala Val Leu Gly Glu Thr Leu Lys Val Pro Cys
450                 455                 460
His Phe Pro Cys Lys Phe Ser Ser Tyr Glu Lys Tyr Trp Cys Lys Trp
465                 470                 475                 480
Asn Asn Thr Gly Cys Gln Ala Leu Pro Ser Gln Asp Glu Gly Pro Ser
            485                 490                 495
Lys Ala Phe Val Asn Cys Asp Glu Asn Ser Arg Leu Val Ser Leu Thr
        500                 505                 510
Leu Asn Leu Val Thr Arg Ala Asp Glu Gly Trp Tyr Trp Cys Gly Val
    515                 520                 525
Lys Gln Gly His Phe Tyr Gly Glu Thr Ala Ala Val Tyr Val Ala Val
530                 535                 540
Glu Glu Arg Lys Ala Ala Gly Ser Arg Asp Val Ser Leu Ala Lys Ala
545                 550                 555                 560
Asp Ala Ala Pro Asp Glu Lys Val Leu Asp Ser Gly Phe Arg Glu Ile
            565                 570                 575
Glu Asn Lys Ala Ile Gln Asp Pro Arg
        580                 585

<210> SEQ ID NO 89
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 89
atggaatgga gctgggtctt tctcttcttc ctgtcagtaa cgactggtgt ccactcccag      60
gaagatgagc ggatcgtgct ggtggacaac aagtgcaagt gcgcccggat cacctcccgg     120
atcatccggt cctccgagga tcccaacgag gacatcgtgg aacggaacat cagaatcatc     180
gtgcccctga caaccgcga gaacatctcc gaccccacca gccctctgcg gaccagattc     240
gtgtaccacc tgtccgacct gtgcaagaag tgcgaccccta ccgaggtgga actggacaac     300
cagatcgtga ccgccaccca gtccaacatc tgcgacgagg actccgccac cgagacatgc     360
tacacctacg accggaacaa gtgctacacc gccgtggtgc ctctggtgta cggcggcgag     420
acaaagatgt ggaaaccgc cctgaccccc gacgcctgct atcctgatgg aggcggagga     480
tctggtggcg gtggttctgg cgggggggc tctcagcacg atgaggccgt ggacgccaat     540

-continued

```
tctctggccg aggctaaggt gctggccaac agagagctgg ataagtacgg cgtgtccgac      600
tactacaaga acctgatcaa caacgccaag accgtggaag cgtgaaggc cctgatcgac      660 gagatcctgg ctgccctgcc ttga                                            684
```

<210> SEQ ID NO 90
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

```
Met Glu Trp Ser Trp Val Phe Leu Phe Phe Leu Ser Val Thr Thr Gly
1               5                   10                  15

Val His Ser Gln Glu Asp Glu Arg Ile Val Leu Val Asp Asn Lys Cys
                20                  25                  30

Lys Cys Ala Arg Ile Thr Ser Arg Ile Ile Arg Ser Ser Glu Asp Pro
            35                  40                  45

Asn Glu Asp Ile Val Glu Arg Asn Ile Arg Ile Val Pro Leu Asn
        50                  55                  60

Asn Arg Glu Asn Ile Ser Asp Pro Thr Ser Pro Leu Arg Thr Arg Phe
65                  70                  75                  80

Val Tyr His Leu Ser Asp Leu Cys Lys Lys Cys Asp Pro Thr Glu Val
                85                  90                  95

Glu Leu Asp Asn Gln Ile Val Thr Ala Thr Gln Ser Asn Ile Cys Asp
                100                 105                 110

Glu Asp Ser Ala Thr Glu Thr Cys Tyr Thr Tyr Asp Arg Asn Lys Cys
            115                 120                 125

Tyr Thr Ala Val Val Pro Leu Val Tyr Gly Gly Glu Thr Lys Met Val
130                 135                 140

Glu Thr Ala Leu Thr Pro Asp Ala Cys Tyr Pro Asp Gly Gly Gly Gly
145                 150                 155                 160

Ser Gly Gly Gly Gly Ser Gly Gly Gly Gly Ser Gln His Asp Glu Ala
                165                 170                 175

Val Asp Ala Asn Ser Leu Ala Glu Ala Lys Val Leu Ala Asn Arg Glu
            180                 185                 190

Leu Asp Lys Tyr Gly Val Ser Asp Tyr Tyr Lys Asn Leu Ile Asn Asn
        195                 200                 205

Ala Lys Thr Val Glu Gly Val Lys Ala Leu Ile Asp Glu Ile Leu Ala
    210                 215                 220

Ala Leu Pro
225
```

<210> SEQ ID NO 91
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

```
atggaatgga gctgggtctt tctcttcttc ctgtcagtaa cgactggtgt ccactcccag      60
cacgatgagg ccgtggacgc caattctctg gccgaggcta aggtgctggc caacagagag     120
```

```
ctggataagt acggcgtgtc cgactactac aagaacctga tcaacaacgc caagaccgtg      180
gaaggcgtga aggccctgat cgacgagatc ctggctgccc tgcctggagg cggaggatct      240
ggtggcggtg gttctggcgg agggggctct caggaagatg agcggatcgt gctggtggac      300
aacaagtgca gtgcgcccg gatcacctcc cggatcatcc ggtcctccga ggatcccaac       360
gaggacatcg tggaacggaa catcagaatc atcgtgcccc tgaacaaccg cgagaacatc      420
tccgacccca ccagccctct gcggaccaga ttcgtgtacc acctgtccga cctgtgcaag      480
aagtgcgacc ctaccgaggt ggaactggac aaccagatcg tgaccgccac ccagtccaac      540
atctgcgacg aggactccgc caccgagaca tgctacacct acgaccggaa caagtgctac      600
accgccgtgg tgcctctggt gtacggcggc gagacaaaga tggtggaaac cgccctgacc      660
cccgacgcct gctatcctga ttga                                             684
```

<210> SEQ ID NO 92
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 92

```
Met Glu Trp Ser Trp Val Phe Leu Phe Phe Leu Ser Val Thr Thr Gly
1               5                   10                  15

Val His Ser Gln His Asp Glu Ala Val Asp Ala Asn Ser Leu Ala Glu
            20                  25                  30

Ala Lys Val Leu Ala Asn Arg Glu Leu Asp Lys Tyr Gly Val Ser Asp
        35                  40                  45

Tyr Tyr Lys Asn Leu Ile Asn Asn Ala Lys Thr Val Glu Gly Val Lys
    50                  55                  60

Ala Leu Ile Asp Glu Ile Leu Ala Ala Leu Pro Gly Gly Gly Gly Ser
65                  70                  75                  80

Gly Gly Gly Gly Ser Gly Gly Gly Ser Gln Glu Asp Glu Arg Ile
            85                  90                  95

Val Leu Val Asp Asn Lys Cys Lys Cys Ala Arg Ile Thr Ser Arg Ile
            100                 105                 110

Ile Arg Ser Ser Glu Asp Pro Asn Glu Asp Ile Val Glu Arg Asn Ile
        115                 120                 125

Arg Ile Ile Val Pro Leu Asn Asn Arg Glu Asn Ile Ser Asp Pro Thr
    130                 135                 140

Ser Pro Leu Arg Thr Arg Phe Val Tyr His Leu Ser Asp Leu Cys Lys
145                 150                 155                 160

Lys Cys Asp Pro Thr Glu Val Glu Leu Asp Asn Gln Ile Val Thr Ala
                165                 170                 175

Thr Gln Ser Asn Ile Cys Asp Glu Asp Ser Ala Thr Glu Thr Cys Tyr
            180                 185                 190

Thr Tyr Asp Arg Asn Lys Cys Tyr Thr Ala Val Val Pro Leu Val Tyr
        195                 200                 205

Gly Gly Glu Thr Lys Met Val Glu Thr Ala Leu Thr Pro Asp Ala Cys
    210                 215                 220

Tyr Pro Asp
225
```

<210> SEQ ID NO 93
<211> LENGTH: 2286
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

| | | | | | |
|---|---|---|---|---|---|
| atgaaatggg | tcacctttat | ctccctgctg | ttcctgttct | cctccgccta | ctctcggggc | 60 |
| gtgttcagaa | gagacgccca | caaatcggag | gtagcgcacc | ggttcaaaga | cttgggagaa | 120 |
| gaaaacttta | aggcccttgt | actcattgcg | tttgcgcagt | atttgcagca | gtgcccattc | 180 |
| gaggaccatg | tcaaacttgt | caacgaagtg | acagagtttg | cgaaaacttg | cgtcgccgac | 240 |
| gaatccgcgg | agaactgtga | caagtcgctg | catacgttgt | tcggggataa | gctctgtacc | 300 |
| gtagcgacct | tgagggaaac | ttacggggaa | atggcggact | gttgcgctaa | gcaggagccg | 360 |
| gaacggaacg | agtgtttcct | tcagcataag | gatgacaacc | ccaacctccc | tagattggtc | 420 |
| agacccgaag | tggatgtgat | gtgcacagca | ttccatgaca | atgaggaaac | ctttctcaaa | 480 |
| aagtatttgt | acgagattgc | ccgacgcaca | ccctatttct | acgctcccga | gttgctcttc | 540 |
| ttcgcgaaac | ggtataaagc | tgcctttact | gaatgctgtc | aagcagcgga | caaggccgca | 600 |
| tgcctccttc | ccaaattgga | tgaactccgc | gatgaaggga | aggcgtcatc | ggccaaacag | 660 |
| cggcttaagt | gcgcatcgct | tcagaaattc | ggagagaggg | cgttcaaagc | gtgggccgtc | 720 |
| gcgagactgt | cgcagagatt | ccctaaggcg | gaatttgcag | aggtatcgaa | gctcgtgaca | 780 |
| gacctcacaa | aggtccacac | cgaatgttgc | catggagacc | tgcttgagtg | cgccgatgat | 840 |
| agggcagacc | tcgcaaagta | catttgtgag | aatcaggaca | gcattagctc | caagctgaaa | 900 |
| gagtgctgtg | agaagccttt | gctggaaaaa | tcccactgta | tcgccgaggt | agaaaacgat | 960 |
| gaaatgcccg | ctgatcttcc | ctcgctggcg | gcagacttcg | tcgagtcgaa | ggacgtctgc | 1020 |
| aagaattacg | cagaggcaaa | agatgtgttt | cttggaatgt | tcctttatga | gtatgcgaga | 1080 |
| aggcacccgg | attattccgt | ggtactgctc | ttgcgattgg | cgaaaacgta | cgaaacaacg | 1140 |
| cttgagaagt | gttgtgcggc | tgccgacccg | catgagtgct | acgccaaggt | atttgatgag | 1200 |
| tttaaacctc | ttgtcgagga | accccagaat | cttatcaagc | agaactgcga | gcttttcaag | 1260 |
| cagttgggtg | aatacaaatt | ccagaacgcg | cttctggtga | ggtataccaa | gaaagtacct | 1320 |
| caagtctcaa | cacccacact | cgtcgaggtg | tcacggaacc | tcgggaaagt | agggtcgaag | 1380 |
| tgctgtaaac | acccagaggc | caagcgcatg | ccctgtgcgg | aggactacct | ctcggtagtg | 1440 |
| ttgaatcaac | tgtgtgtcct | ccacgaaaag | acgccggtgt | cagaccgcgt | cacaaagtgc | 1500 |
| tgcacggaga | gcctggtcaa | tagacgcccc | tgcttctcag | cgctggaggt | ggatgagaca | 1560 |
| tacgtcccga | agagtttaa | cgccgaaacg | tttactttc | atgctgatat | ctgtacgttg | 1620 |
| tcagagaagg | aaaggcaaat | caagaaacaa | actgcgcttg | tggaactggt | gaagcacaaa | 1680 |
| ccgaaggcga | ctaaggaaca | gctgaaggcg | gtgatggatg | actttgccgc | gttcgtagag | 1740 |
| aaatgctgta | aagcagacga | taaggagact | tgttttgcgg | aagagggacc | taaacttgtt | 1800 |
| gctgcaagtc | aagctgcctt | aggcttagga | ggcggaggat | ctggtggcgg | tggttctggc | 1860 |
| ggaggggct | ctcaggaaga | tgagcggatc | gtgctggtgg | acaacaagtg | caagtgcgcc | 1920 |
| cggatcacct | cccggatcat | ccggtcctcc | gaggatccca | acgaggacat | cgtggaacgg | 1980 |
| aacatcagaa | tcatcgtgcc | cctgaacaac | cgcgagaaca | tctccgaccc | caccagccct | 2040 |

-continued

```
ctgcggacca gattcgtgta ccacctgtcc gacctgtgca agaagtgcga ccctaccgag      2100
gtggaactgg acaaccagat cgtgaccgcc acccagtcca acatctgcga cgaggactcc      2160
gccaccgaga catgctacac ctacgaccgg aacaagtgct acaccgccgt ggtgcctctg      2220
gtgtacggcg gcgagacaaa gatggtggaa accgccctga ccccgacgc ctgctatcct       2280 gattag                                                                 2286
```

<210> SEQ ID NO 94
<211> LENGTH: 761
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300
```

```
Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Lys Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Pro Lys Leu Val Ala Ala Ser Gln Ala Ala Leu Gly
        595                 600                 605

Leu Gly Gly Gly Ser Gly Gly Gly Ser Gly Gly Gly Ser
    610                 615                 620

Gln Glu Asp Glu Arg Ile Val Leu Val Asp Asn Lys Cys Lys Cys Ala
625                 630                 635                 640

Arg Ile Thr Ser Arg Ile Ile Arg Ser Ser Glu Asp Pro Asn Glu Asp
                645                 650                 655

Ile Val Glu Arg Asn Ile Arg Ile Ile Val Pro Leu Asn Asn Arg Glu
            660                 665                 670

Asn Ile Ser Asp Pro Thr Ser Pro Leu Arg Thr Arg Phe Val Tyr His
        675                 680                 685

Leu Ser Asp Leu Cys Lys Lys Cys Asp Pro Thr Glu Val Glu Leu Asp
    690                 695                 700

Asn Gln Ile Val Thr Ala Thr Gln Ser Asn Ile Cys Asp Glu Asp Ser
705                 710                 715                 720

Ala Thr Glu Thr Cys Tyr Thr Tyr Asp Arg Asn Lys Cys Tyr Thr Ala
```

```
                            725                 730                 735
Val Val Pro Leu Val Tyr Gly Gly Glu Thr Lys Met Val Glu Thr Ala
                740                 745                 750
Leu Thr Pro Asp Ala Cys Tyr Pro Asp
        755                 760

<210> SEQ ID NO 95
<211> LENGTH: 2280
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
atgaagaacc atctgctgtt ctggggcgtg ctggccgtgt tcatcaaggc cgtgcacgtg      60
aaggcccagg aagatgagcg gatcgtgctg gtggacaaca agtgcaagtg cgcccggatc     120
acctcccgga tcatccggtc ctccgaggat cccaacgagg acatcgtgga cggaacatc     180 agaatcatcg tgcccctgaa caaccgcgag aacatctccg accccaccag ccctctgcgg     240
accagattcg tgtaccacct gtccgacctg tgcaagaagt gcgaccctac cgaggtggaa     300
ctggacaacc agatcgtgac cgccacccag tccaacatct gcgacgagga ctccgccacc     360
gagacatgct acacctacga ccggaacaag tgctacaccg ccgtggtgcc tctggtgtac     420
ggcggcgaga caaagatggt ggaaaccgcc ctgaccccg acgcctgcta tcctgatgga     480
ggcggaggat ctggtggcgg tggttctggc ggagggggct ctgacgccca caatcggag     540 gtagcgcacc ggttcaaaga cttgggagaa gaaaacttta aggcccttgt actcattgcg     600
tttgcgcagt atttgcagca gtgcccattc gaggaccatg tcaaacttgt caacgaagtg     660
acagagtttg cgaaaacttg cgtcgccgac gaatccgcgg agaactgtga caagtcgctg     720
catacgttgt tcggggataa gctctgtacc gtagcgacct tgagggaaac ttacggggaa     780
atggcggact gttgcgctaa gcaggagccg gaacggaacg agtgtttcct tcagcataag     840
gatgacaacc caacctccc tagattggtc agacccgaag tggatgtgat gtgcacagca     900
ttccatgaca atgaggaaac ctttctcaaa agtatttgt acgagattgc ccgacgacac     960
ccctatttct acgctcccga gttgctcttc ttcgcgaaac ggtataaagc tgcctttact    1020
gaatgctgtc aagcagcgga caaggccgca tgcctccttc caaattgga tgaactccgc    1080 gatgaaggga aggcgtcatc ggccaaacag cggcttaagt cgcatcgct tcagaaattc    1140 ggagagaggg cgttcaaagc gtgggccgtc gcgagactgt cgcagagatt ccctaaggcg    1200
gaatttgcag aggtatcgaa gctcgtgaca gacctcacaa aggtccacac cgaatgttgc    1260
catggagacc tgcttgagtg cgccgatgat agggcagacc tcgcaaagta catttgtgag    1320
aatcaggaca gcattagctc caagctgaaa gagtgctgtg agaagccttt gctggaaaaa    1380
tcccactgta tcgccgaggt agaaaacgat gaaatgcccg ctgatcttcc ctcgctggcg    1440
gcagacttcg tcgagtcgaa ggacgtctgc aagaattacg cagaggcaaa agatgtgttt    1500
cttggaatgt tcctttatga gtatgcgaga aggcacccgg attattccgt ggtactgctc    1560
ttgcgattgg cgaaaacgta cgaaacaacg cttgagaagt gttgtgcggc tgccgacccg    1620
catgagtgct acgccaaggt atttgatgag tttaaacctc ttgtcgagga accccagaat    1680
cttatcaagc agaactgcga gcttttcaag cagttgggga atacaaatt ccagaacgcg    1740 cttctggtga ggtataccaa gaaagtacct caagtctcaa cacccacact cgtcgaggtg    1800
```

-continued

```
tcacggaacc tcgggaaagt agggtcgaag tgctgtaaac acccagaggc caagcgcatg    1860
ccctgtgcgg aggactacct ctcggtagtg ttgaatcaac tgtgtgtcct ccacgaaaag    1920
acgccggtgt cagaccgcgt cacaaagtgc tgcacggaga gcctggtcaa tagacgcccc    1980
tgcttctcag cgctggaggt ggatgagaca tacgtcccga aagagtttaa cgccgaaacg    2040
tttacttttc atgctgatat ctgtacgttg tcagagaagg aaaggcaaat caagaaacaa    2100
actgcgcttg tggaactggt gaagcacaaa ccgaaggcgc taaggaaca gctgaaggcg    2160 gtgatggatg actttgccgc gttcgtagag aaatgctgta aagcagacga taaggagact    2220
tgttttgcgg aagagggacc taaacttgtt gctgcaagtc aagctgcctt aggcttatag    2280
```

```
<210> SEQ ID NO 96
<211> LENGTH: 759
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96
```

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Arg Ser Ser
            35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
    115                 120                 125

Asn Lys Cys Tyr Thr Ala Val Val Pro Leu Val Tyr Gly Gly Glu Thr
130                 135                 140

Lys Met Val Glu Thr Ala Leu Thr Pro Asp Ala Cys Tyr Pro Asp Gly
145                 150                 155                 160

Gly Gly Gly Ser Gly Gly Gly Ser Gly Gly Gly Ser Asp Ala
                165                 170                 175

His Lys Ser Glu Val Ala His Arg Phe Lys Asp Leu Gly Glu Glu Asn
            180                 185                 190

Phe Lys Ala Leu Val Leu Ile Ala Phe Ala Gln Tyr Leu Gln Gln Cys
        195                 200                 205

Pro Phe Glu Asp His Val Lys Leu Val Asn Glu Val Thr Glu Phe Ala
    210                 215                 220

Lys Thr Cys Val Ala Asp Glu Ser Ala Glu Asn Cys Asp Lys Ser Leu
225                 230                 235                 240

His Thr Leu Phe Gly Asp Lys Leu Cys Thr Val Ala Thr Leu Arg Glu
                245                 250                 255

Thr Tyr Gly Glu Met Ala Asp Cys Cys Ala Lys Gln Glu Pro Glu Arg
            260                 265                 270

```
Asn Glu Cys Phe Leu Gln His Lys Asp Asp Pro Asn Leu Pro Arg
        275                 280                 285

Leu Val Arg Pro Glu Val Asp Val Met Cys Thr Ala Phe His Asp Asn
        290                 295                 300

Glu Glu Thr Phe Leu Lys Lys Tyr Leu Tyr Glu Ile Ala Arg Arg His
305                 310                 315                 320

Pro Tyr Phe Tyr Ala Pro Glu Leu Leu Phe Phe Ala Lys Arg Tyr Lys
                325                 330                 335

Ala Ala Phe Thr Glu Cys Cys Gln Ala Ala Asp Lys Ala Ala Cys Leu
                340                 345                 350

Leu Pro Lys Leu Asp Glu Leu Arg Asp Glu Gly Lys Ala Ser Ser Ala
        355                 360                 365

Lys Gln Arg Leu Lys Cys Ala Ser Leu Gln Lys Phe Gly Glu Arg Ala
        370                 375                 380

Phe Lys Ala Trp Ala Val Ala Arg Leu Ser Gln Arg Phe Pro Lys Ala
385                 390                 395                 400

Glu Phe Ala Glu Val Ser Lys Leu Val Thr Asp Leu Thr Lys Val His
                405                 410                 415

Thr Glu Cys Cys His Gly Asp Leu Leu Glu Cys Ala Asp Asp Arg Ala
                420                 425                 430

Asp Leu Ala Lys Tyr Ile Cys Glu Asn Gln Asp Ser Ile Ser Ser Lys
        435                 440                 445

Leu Lys Glu Cys Cys Glu Lys Pro Leu Leu Glu Lys Ser His Cys Ile
        450                 455                 460

Ala Glu Val Glu Asn Asp Glu Met Pro Ala Asp Leu Pro Ser Leu Ala
465                 470                 475                 480

Ala Asp Phe Val Glu Ser Lys Asp Val Cys Lys Asn Tyr Ala Glu Ala
                485                 490                 495

Lys Asp Val Phe Leu Gly Met Phe Leu Tyr Glu Tyr Ala Arg Arg His
                500                 505                 510

Pro Asp Tyr Ser Val Val Leu Leu Leu Arg Leu Ala Lys Thr Tyr Glu
        515                 520                 525

Thr Thr Leu Glu Lys Cys Cys Ala Ala Ala Asp Pro His Glu Cys Tyr
        530                 535                 540

Ala Lys Val Phe Asp Glu Phe Lys Pro Leu Val Glu Glu Pro Gln Asn
545                 550                 555                 560

Leu Ile Lys Gln Asn Cys Glu Leu Phe Lys Gln Leu Gly Glu Tyr Lys
                565                 570                 575

Phe Gln Asn Ala Leu Leu Val Arg Tyr Thr Lys Lys Val Pro Gln Val
                580                 585                 590

Ser Thr Pro Thr Leu Val Glu Val Ser Arg Asn Leu Gly Lys Val Gly
        595                 600                 605

Ser Lys Cys Cys Lys His Pro Glu Ala Lys Arg Met Pro Cys Ala Glu
        610                 615                 620

Asp Tyr Leu Ser Val Val Leu Asn Gln Leu Cys Val Leu His Glu Lys
625                 630                 635                 640

Thr Pro Val Ser Asp Arg Val Thr Lys Cys Cys Thr Glu Ser Leu Val
                645                 650                 655

Asn Arg Arg Pro Cys Phe Ser Ala Leu Glu Val Asp Glu Thr Tyr Val
                660                 665                 670

Pro Lys Glu Phe Asn Ala Glu Thr Phe Thr Phe His Ala Asp Ile Cys
        675                 680                 685
```

Thr Leu Ser Glu Lys Glu Arg Gln Ile Lys Lys Gln Thr Ala Leu Val
    690                 695                 700

Glu Leu Val Lys His Lys Pro Lys Ala Thr Lys Glu Gln Leu Lys Ala
705                 710                 715                 720

Val Met Asp Asp Phe Ala Ala Phe Val Glu Lys Cys Cys Lys Ala Asp
                725                 730                 735

Asp Lys Glu Thr Cys Phe Ala Glu Glu Gly Pro Lys Leu Val Ala Ala
            740                 745                 750

Ser Gln Ala Ala Leu Gly Leu
        755

<210> SEQ ID NO 97
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97

```
atggggtggt cctacattat cctgttcctc gtggccaccg ccactggcgt gcactcacag      60
gtgcagctgg tgcagtctgg cgccgaagtg aagaaacctg gcgcctccgt gaaggtgtcc     120
tgcaaggcct ccggctacac cttcatcagc tacaccatgc actgggtgcg acaggcccct     180
ggacagggcc tggaatggat gggctacatc aaccctagat ctggctacac ccactacaac     240
cagaagctga aggacaaggc caccctgacc gccgacaagt ctgcctccac cgcctacatg     300
gaactgtcct ccctgcggag cgaggacacc gccgtgtact actgtgccag atccgcctac     360
tacgactacg acggcttcgc ctattggggc cagggcaccc tcgtgacagt gtctagcgtt     420
ggcggaggat ctggcggagg cggtagtggc ggtggcggat ctgatatcca gatgacccag     480
tccccctcca gcctgtctgc ctctgtgggc gacagagtga caattacctg ctccgccagc     540
tcctccgtgt cttacatgaa ctggtatcag cagaagcccg gcaaggcccc caagcggctg     600
atctacgaca cctccaagct ggcctctggc gtgccctcca gattctccgg ctctggctct     660
ggcaccgact ttaccctgac catcagctcc ctgcagcccg aggacttcgc cacctactac     720
tgccagcagt ggtcctccaa ccctcccacc tttggcggag gcaccaaggt ggaaatcaaa     780
ggcggcggag aagcgggggg aggcggttct gggggtggtg gatctcagga agatgagcgg     840
atcgtgctgg tggacaacaa gtgcaagtgc gcccggatca cctcccggat catccggtcc     900
tccgaggatc ccaacgagga catcgtggaa cggaacatca gaatcatcgt gcccctgaac     960
aaccgcgaga acatctccga ccccaccagc cctctgcgga ccagattcgt gtaccacctg    1020
tccgacctgt gcaagaagtg cgaccctacc gaggtggaac tggacaacca gatcgtgacc    1080
gccacccagt ccaacatctg cgacgaggac tccgccaccg agacatgcta cacctacgac    1140
cggaacaagt gctacaccgc cgtggtgcct ctggtgtacg gcggcgagac aaagatggtg    1200
gaaaccgccc tgacccccga cgcctgctat cctgatggag gcggaggatc tggtggcggt    1260
ggttctggcg gagggggctc tcagcacgat gaggccgtgg acgccaattc tctggccgag    1320
gctaaggtgc tggccaacag agagctggat aagtacggcg tgtccgacta ctacaagaac    1380
ctgatcaaca cgccaagac cgtggaaggc gtgaaggccc tgatcgacga gatcctggct    1440
gccctgcctt ga                                                        1452
```

<210> SEQ ID NO 98

<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

```
Met Gly Trp Ser Tyr Ile Ile Leu Phe Leu Val Ala Thr Ala Thr Gly
1               5                   10                  15
Val His Ser Gln Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
            35                  40                  45
Ile Ser Tyr Thr Met His Trp Val Arg Gln Ala Pro Gly Gln Gly Leu
        50                  55                  60
Glu Trp Met Gly Tyr Ile Asn Pro Arg Ser Gly Tyr Thr His Tyr Asn
65                  70                  75                  80
Gln Lys Leu Lys Asp Lys Ala Thr Leu Thr Ala Asp Lys Ser Ala Ser
                85                  90                  95
Thr Ala Tyr Met Glu Leu Ser Ser Leu Arg Ser Glu Asp Thr Ala Val
            100                 105                 110
Tyr Tyr Cys Ala Arg Ser Ala Tyr Tyr Asp Tyr Asp Gly Phe Ala Tyr
        115                 120                 125
Trp Gly Gln Gly Thr Leu Val Thr Val Ser Ser Gly Gly Gly Gly Ser
130                 135                 140
Gly Gly Gly Gly Ser Gly Gly Gly Ser Asp Ile Gln Met Thr Gln
145                 150                 155                 160
Ser Pro Ser Ser Leu Ser Ala Ser Val Gly Asp Arg Val Thr Ile Thr
                165                 170                 175
Cys Ser Ala Ser Ser Ser Val Ser Tyr Met Asn Trp Tyr Gln Gln Lys
            180                 185                 190
Pro Gly Lys Ala Pro Lys Arg Leu Ile Tyr Asp Thr Ser Lys Leu Ala
        195                 200                 205
Ser Gly Val Pro Ser Arg Phe Ser Gly Ser Gly Ser Gly Thr Asp Phe
    210                 215                 220
Thr Leu Thr Ile Ser Ser Leu Gln Pro Glu Asp Phe Ala Thr Tyr Tyr
225                 230                 235                 240
Cys Gln Gln Trp Ser Ser Asn Pro Pro Thr Phe Gly Gly Gly Thr Lys
                245                 250                 255
Val Glu Ile Lys Gly Gly Gly Gly Ser Gly Gly Gly Gly Ser Gly Gly
            260                 265                 270
Gly Gly Ser Gln Glu Asp Glu Arg Ile Val Leu Val Asp Asn Lys Cys
        275                 280                 285
Lys Cys Ala Arg Ile Thr Ser Arg Ile Ile Arg Ser Ser Glu Asp Pro
    290                 295                 300
Asn Glu Asp Ile Val Glu Arg Asn Ile Arg Ile Ile Val Pro Leu Asn
305                 310                 315                 320
Asn Arg Glu Asn Ile Ser Asp Pro Thr Ser Pro Leu Arg Thr Arg Phe
                325                 330                 335
Val Tyr His Leu Ser Asp Leu Cys Lys Lys Cys Asp Pro Thr Glu Val
            340                 345                 350
Glu Leu Asp Asn Gln Ile Val Thr Ala Thr Gln Ser Asn Ile Cys Asp
        355                 360                 365
```

-continued

```
Glu Asp Ser Ala Thr Glu Thr Cys Tyr Thr Tyr Asp Arg Asn Lys Cys
370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp Gly Gly Gly
                405                 410                 415

Ser Gly Gly Gly Gly Ser Gly Gly Gly Ser Gln His Asp Glu Ala
                420                 425                 430

Val Asp Ala Asn Ser Leu Ala Glu Ala Lys Val Leu Ala Asn Arg Glu
                435                 440                 445

Leu Asp Lys Tyr Gly Val Ser Asp Tyr Tyr Lys Asn Leu Ile Asn Asn
450                 455                 460

Ala Lys Thr Val Glu Gly Val Lys Ala Leu Ile Asp Glu Ile Leu Ala
465                 470                 475                 480

Ala Leu Pro
```

<210> SEQ ID NO 99
<211> LENGTH: 3039
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

| | | |
|---|---|---|
| atggggtggt cctacattat cctgttcctc gtggccaccg ccactggcgt gcactcacag | 60 |
| gtgcagctgg tgcagtctgg cgccgaagtg aagaaacctg gcgcctccgt gaaggtgtcc | 120 |
| tgcaaggcct ccggctacac cttcatcagc tacaccatgc actgggtgcg acaggcccct | 180 |
| ggacagggcc tggaatggat gggctacatc aaccctagat ctggctacac ccactacaac | 240 |
| cagaagctga aggacaaggc caccctgacc gccgacaagt ctgcctccac cgcctacatg | 300 |
| gaactgtcct ccctgcggag cgaggacacc gccgtgtact actgtgccag atccgcctac | 360 |
| tacgactacg acggcttcgc ctattgggc agggcacccc tcgtgacagt gtctagcggt | 420 |
| ggcggaggat ctggcggagg cggtagtggc ggtggcggat ctgatatcca gatgacccag | 480 |
| tccccctcca gcctgtctgc ctctgtgggc gacagagtga caattacctg ctccgccagc | 540 |
| tcctccgtgt cttacatgaa ctggtatcag cagaagcccg gcaaggcccc caagcggctg | 600 |
| atctacgaca cctccaagct ggcctctggc gtgccctcca gattctccgg ctctggctct | 660 |
| ggcaccgact ttaccctgac catcagctcc ctgcagcccg aggacttcgc cacctactac | 720 |
| tgccagcagt ggtcctccaa ccctcccacc tttggcggag caccaaggt ggaaatcaaa | 780 |
| ggcggcggag gaagcggggg aggcggttct gggggtggtg atctcagga agatgagcgg | 840 |
| atcgtgctgg tggacaacaa gtgcaagtgc gcccggatca cctcccggat catccggtcc | 900 |
| tccgaggatc ccaacgagga catcgtggaa cggaacatca gaatcatcgt gcccctgaac | 960 |
| aaccgcgaga acatctccga ccccaccagc cctctgcgga ccagattcgt gtaccacctg | 1020 |
| tccgacctgt gcaagaagtg cgaccctacc gaggtggaac tggacaacca gatcgtgacc | 1080 |
| gccacccagt ccaacatctg cgacgaggac tccgccaccg agacatgcta cacctacgac | 1140 |
| cggaacaagt gctacaccgc cgtggtgcct ctggtgtacg gcggcgagac aaagatggtg | 1200 |
| gaaaccgccc tgacccccga cgcctgctat cctgatggag cggaggatc tggtggcggt | 1260 |
| ggttctggcg aggggggctc tgacgcccac aaatcggagg tagcgcaccg gttcaaagac | 1320 |

```
ttgggagaag aaaactttaa ggcccttgta ctcattgcgt ttgcgcagta tttgcagcag      1380
tgcccattcg aggaccatgt caaacttgtc aacgaagtga cagagtttgc gaaaacttgc      1440
gtcgccgacg aatccgcgga gaactgtgac aagtcgctgc atacgttgtt cggggataag      1500
ctctgtaccg tagcgacctt gagggaaact tacggggaaa tggcggactg ttgcgctaag      1560
caggagccgg aacggaacga gtgtttcctt cagcataagg atgacaaccc caacctccct      1620
agattggtca gacccgaagt ggatgtgatg tgcacagcat ccatgacaa tgaggaaacc      1680 tttctcaaaa agtatttgta cgagattgcc cgacgacacc cctatttcta cgctcccgag      1740
ttgctcttct tcgcgaaacg gtataaagct gcctttactg aatgctgtca agcagcggac      1800
aaggccgcat gcctccttcc caaattggat gaactccgcg atgaagggaa ggcgtcatcg      1860
gccaaacagc ggcttaagtg cgcatcgctt cagaaattcg agagagggc gttcaaagcg      1920 tgggccgtcg cgagactgtc gcagagattc cctaaggcgg aatttgcaga ggtatcgaag      1980
ctcgtgacag acctcacaaa ggtccacacc gaatgttgcc atggagacct gcttgagtgc      2040
gccgatgata gggcagacct cgcaaagtac atttgtgaga atcaggacag cattagctcc      2100
aagctgaaag agtgctgtga gaagcctttg ctggaaaaat cccactgtat cgccgaggta      2160
gaaaacgatg aaatgcccgc tgatcttccc tcgctggcgg cagacttcgt cgagtcgaag      2220
gacgtctgca gaattacgc agaggcaaaa gatgtgtttc ttggaatgtt cctttatgag      2280
tatgcgagaa ggcaccccga ttattccgtg gtactgctct tgcgattggc gaaaacgtac      2340
gaaacaacgc ttgagaagtg ttgtgcggct gccgacccgc atgagtgcta cgccaaggta      2400
tttgatgagt ttaaacctct tgtcgaggaa ccccagaatc ttatcaagca gaactgcgag      2460
cttttcaagc agttgggtga atacaaattc cagaacgcgc ttctggtgag gtataccaag      2520
aaagtacctc aagtctcaac acccacactc gtcgaggtgt cacggaacct cgggaaagta      2580
gggtcgaagt gctgtaaaca cccagaggcc aagcgcatgc cctgtgcgga ggactacctc      2640
tcggtagtgt tgaatcaact gtgtgtcctc cacgaaaaga cgccggtgtc agaccgcgtc      2700
acaaagtgct gcacggagag cctggtcaat agacgcccct gcttctcagc gctggaggtg      2760
gatgagacat acgtcccgaa agagtttaac gccgaaacgt ttacttttca tgctgatatc      2820
tgtacgttgt cagagaagga aaggcaaatc aagaaacaaa ctgcgcttgt ggaactggtg      2880
aagcacaaac cgaaggcgac taaggaacag ctgaaggcgg tgatggatga ctttgccgcg      2940
ttcgtagaga aatgctgtaa agcagacgat aaggagactt gttttgcgga agagggacct      3000
aaacttgttg ctgcaagtca agctgcctta ggcttatag                            3039
```

<210> SEQ ID NO 100
<211> LENGTH: 1012
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Ile Ser Tyr Thr Met His Trp Val Arg Gln Ala Pro Gly Gln Gly Leu
 50                  55                  60

Glu Trp Met Gly Tyr Ile Asn Pro Arg Ser Gly Tyr Thr His Tyr Asn
 65                  70                  75                  80

Gln Lys Leu Lys Asp Lys Ala Thr Leu Thr Ala Asp Lys Ser Ala Ser
                 85                  90                  95

Thr Ala Tyr Met Glu Leu Ser Ser Leu Arg Ser Glu Asp Thr Ala Val
                100                 105                 110

Tyr Tyr Cys Ala Arg Ser Ala Tyr Tyr Asp Tyr Asp Gly Phe Ala Tyr
                115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Ser Val Ser Tyr Met Asn Trp Tyr Gln Gln Lys
                180                 185                 190

Pro Gly Lys Ala Pro Lys Arg Leu Ile Tyr Asp Thr Ser Lys Leu Ala
                195                 200                 205

Ser Gly Val Pro Ser Arg Phe Ser Gly Ser Gly Ser Gly Thr Asp Phe
210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
                245                 250                 255

Val Glu Ile Lys Gly Gly Gly Ser Gly Gly Gly Gly Ser Gly Gly
                260                 265                 270

Gly Gly Ser Gln Glu Asp Glu Arg Ile Val Leu Val Asp Asn Lys Cys
                275                 280                 285

Lys Cys Ala Arg Ile Thr Ser Arg Ile Ile Arg Ser Ser Glu Asp Pro
290                 295                 300

Asn Glu Asp Ile Val Glu Arg Asn Ile Arg Ile Ile Val Pro Leu Asn
305                 310                 315                 320

Asn Arg Glu Asn Ile Ser Asp Pro Thr Ser Pro Leu Arg Thr Arg Phe
                325                 330                 335

Val Tyr His Leu Ser Asp Leu Cys Lys Lys Cys Asp Pro Thr Glu Val
                340                 345                 350

Glu Leu Asp Asn Gln Ile Val Thr Ala Thr Gln Ser Asn Ile Cys Asp
                355                 360                 365

Glu Asp Ser Ala Thr Glu Thr Cys Tyr Thr Tyr Asp Arg Asn Lys Cys
370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp Gly Gly Gly Gly
                405                 410                 415

Ser Gly Gly Gly Gly Ser Gly Gly Gly Ser Asp Ala His Lys Ser
                420                 425                 430

Glu Val Ala His Arg Phe Lys Asp Leu Gly Glu Glu Asn Phe Lys Ala
                435                 440                 445

Leu Val Leu Ile Ala Phe Ala Gln Tyr Leu Gln Gln Cys Pro Phe Glu
450                 455                 460

Asp His Val Lys Leu Val Asn Glu Val Thr Glu Phe Ala Lys Thr Cys

```
465                 470                 475                 480
Val Ala Asp Glu Ser Ala Glu Asn Cys Asp Lys Ser Leu His Thr Leu
                    485                 490                 495
Phe Gly Asp Lys Leu Cys Thr Val Ala Thr Leu Arg Glu Thr Tyr Gly
                    500                 505                 510
Glu Met Ala Asp Cys Cys Ala Lys Gln Glu Pro Glu Arg Asn Glu Cys
                    515                 520                 525
Phe Leu Gln His Lys Asp Asp Asn Pro Asn Leu Pro Arg Leu Val Arg
                    530                 535                 540
Pro Glu Val Asp Val Met Cys Thr Ala Phe His Asp Asn Glu Glu Thr
545                 550                 555                 560
Phe Leu Lys Lys Tyr Leu Tyr Glu Ile Ala Arg Arg His Pro Tyr Phe
                    565                 570                 575
Tyr Ala Pro Glu Leu Leu Phe Phe Ala Lys Arg Tyr Lys Ala Ala Phe
                    580                 585                 590
Thr Glu Cys Cys Gln Ala Ala Asp Lys Ala Ala Cys Leu Leu Pro Lys
                    595                 600                 605
Leu Asp Glu Leu Arg Asp Glu Gly Lys Ala Ser Ser Ala Lys Gln Arg
                    610                 615                 620
Leu Lys Cys Ala Ser Leu Gln Lys Phe Gly Glu Arg Ala Phe Lys Ala
625                 630                 635                 640
Trp Ala Val Ala Arg Leu Ser Gln Arg Phe Pro Lys Ala Glu Phe Ala
                    645                 650                 655
Glu Val Ser Lys Leu Val Thr Asp Leu Thr Lys Val His Thr Glu Cys
                    660                 665                 670
Cys His Gly Asp Leu Leu Glu Cys Ala Asp Asp Arg Ala Asp Leu Ala
                    675                 680                 685
Lys Tyr Ile Cys Glu Asn Gln Asp Ser Ile Ser Ser Lys Leu Lys Glu
                    690                 695                 700
Cys Cys Glu Lys Pro Leu Leu Glu Lys Ser His Cys Ile Ala Glu Val
705                 710                 715                 720
Glu Asn Asp Glu Met Pro Ala Asp Leu Pro Ser Leu Ala Ala Asp Phe
                    725                 730                 735
Val Glu Ser Lys Asp Val Cys Lys Asn Tyr Ala Glu Ala Lys Asp Val
                    740                 745                 750
Phe Leu Gly Met Phe Leu Tyr Glu Tyr Ala Arg Arg His Pro Asp Tyr
                    755                 760                 765
Ser Val Val Leu Leu Leu Arg Leu Ala Lys Thr Tyr Glu Thr Thr Leu
770                 775                 780
Glu Lys Cys Cys Ala Ala Ala Asp Pro His Glu Cys Tyr Ala Lys Val
785                 790                 795                 800
Phe Asp Glu Phe Lys Pro Leu Val Glu Glu Pro Gln Asn Leu Ile Lys
                    805                 810                 815
Gln Asn Cys Glu Leu Phe Lys Gln Leu Gly Glu Tyr Lys Phe Gln Asn
                    820                 825                 830
Ala Leu Leu Val Arg Tyr Thr Lys Lys Val Pro Gln Val Ser Thr Pro
                    835                 840                 845
Thr Leu Val Glu Val Ser Arg Asn Leu Gly Lys Val Gly Ser Lys Cys
                    850                 855                 860
Cys Lys His Pro Glu Ala Lys Arg Met Pro Cys Ala Glu Asp Tyr Leu
865                 870                 875                 880
Ser Val Val Leu Asn Gln Leu Cys Val Leu His Glu Lys Thr Pro Val
                    885                 890                 895
```

```
Ser Asp Arg Val Thr Lys Cys Cys Thr Glu Ser Leu Val Asn Arg Arg
            900                 905                 910

Pro Cys Phe Ser Ala Leu Glu Val Asp Glu Thr Tyr Val Pro Lys Glu
        915                 920                 925

Phe Asn Ala Glu Thr Phe Thr Phe His Ala Asp Ile Cys Thr Leu Ser
    930                 935                 940

Glu Lys Glu Arg Gln Ile Lys Lys Gln Thr Ala Leu Val Leu Val
945                 950                 955                 960

Lys His Lys Pro Lys Ala Thr Lys Glu Gln Leu Lys Ala Val Met Asp
                965                 970                 975

Asp Phe Ala Ala Phe Val Glu Lys Cys Cys Lys Ala Asp Asp Lys Glu
            980                 985                 990

Thr Cys Phe Ala Glu Glu Gly Pro Lys Leu Val Ala Ala Ser Gln Ala
        995                 1000                1005

Ala Leu Gly Leu
    1010
```

<210> SEQ ID NO 101
<211> LENGTH: 3039
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 101

| | |
|---|---|
| atggggtggt cctacattat cctgttcctc gtggccaccg ccactggcgt gcactcacag | 60 |
| gtgcagctgg tgcagtctgg cgccgaagtg aagaaacctg gcgcctccgt gaaggtgtcc | 120 |
| tgcaaggcct ccggctacac cttcatcagc tacaccatgc actgggtgcg acaggcccct | 180 |
| ggacagggcc tggaatggat gggctacatc aaccctagat ctggctacac ccactacaac | 240 |
| cagaagctga aggacaaggc caccctgacc gccgacaagt ctgcctccac cgcctacatg | 300 |
| gaactgtcct ccctgcggag cgaggacacc gccgtgtact actgtgccag atccgcctac | 360 |
| tacgactacg acggcttcgc ctattggggc cagggcaccc tcgtgacagt gtctagcggt | 420 |
| ggcggaggat ctggcggagg cggtagtggc ggtggcggat ctgatatcca gatgacccag | 480 |
| tccccctcca gcctgtctgc ctctgtgggc gacagagtga caattacctg ctccgccagc | 540 |
| tcctccgtgt cttacatgaa ctggtatcag cagaagcccg gcaaggcccc caagcggctg | 600 |
| atctacgaca cctccaagct ggcctctggc gtgccctcca gattctccgg ctctggctct | 660 |
| ggcaccgact taccctgac catcagctcc ctgcagcccg aggacttcgc cacctactac | 720 |
| tgccagcagt ggtcctccaa ccctcccacc tttggcggag gcaccaaggt ggaaatcaaa | 780 |
| ggcggcggag gaagcggggg aggcggttct ggggtggtg atctcagga agatgagcgg | 840 |
| atcgtgctgg tggacaacaa gtgcaagtgc gcccggatca cctcccggat catccggtcc | 900 |
| tccgaggatc ccaacgagga catcgtggaa cggaacatca gaatcatcgt gcccctgaac | 960 |
| aaccgcgaga acatctccga ccccaccagc cctctgcgga ccagattcgt gtaccacctg | 1020 |
| tccgacctgt gcaagaagtg cgaccctacc gaggtggaac tggacaacca gatcgtgacc | 1080 |
| gccacccagt ccaacatctg cgacgaggac tccgccaccg agacatgcta cacctacgac | 1140 |
| cggaacaagt gctacaccgc cgtggtgcct ctggtgtacg gcggcgagac aaagatggtg | 1200 |
| gaaaccgccc tgacccccga cgcctgctat cctgatggag gcggaggatc tggtggcggt | 1260 |

```
ggttctggcg agggggctc tgacgcccac aaatcggagg tagcgcaccg gttcaaagac    1320
ttgggagaag aaactttaa ggcccttgta ctcattgcgt ttgcgcagta tttgcagcag    1380
tgcccattcg aggaccatgt caaacttgtc aacgaagtga cagagtttgc gaaaacttgc    1440
gtcgccgacg aatccgcgga gaactgtgac aagtcgctgc atacgttgtt cggggataag    1500
ctctgtaccg tagcgacctt gagggaaact tacggggaaa tggcggactg ttgcgctaag    1560
caggagccgg aacggaacga gtgtttcctt cagcataagg atgacaaccc caacctccct    1620
agattggtca gacccgaagt ggatgtgatg tgcacagcat tccatgacaa tgaggaaacc    1680
tttctcaaaa agtatttgta cgagattgcc cgacgacacc cctatttcta cgctcccgag    1740
ttgctcttct tcgcgaaacg gtataaagct gcctttactg aatgctgtca agcagcggac    1800
aaggccgcat gcctccttcc caaattggat gaactccgcg atgaagggaa ggcgtcatcg    1860
gccaaacagc ggcttaagtg cgcatcgctt cagaaattcg agagagggc gttcaaagcg    1920 tgggccgtcg cgagactgtc gcagagattc cctaaggcgg aatttgcaga ggtatcgaag    1980
ctcgtgacag acctcacaaa ggtccacacc gaatgttgcc atggagacct gcttgagtgc    2040
gccgatgata gggcagacct cgcaaagtac atttgtgaga atcaggacag cattagctcc    2100
aagctgaaag agtgctgtga agcctttg ctggaaaaat cccactgtat cgccgaggta    2160
gaaaacgatg aaatgcccgc tgatcttccc tcgctggcgg cagacttcgt cgagtcgaag    2220
gacgtctgca agaattacgc agaggcaaaa gatgtgtttc ttggaatgtt cctttatgag    2280
tatgcgagaa ggcacccgga ttattccgtg gtactgctct tgcgattggc gaaaacgtac    2340
gaaacaacgc ttgagaagtg ttgtgcggct gccgacccgc atgagtgcta cgccaaggta    2400
tttgatgagt ttaaacctct tgtcgaggaa ccccagaatc ttatcaagca gaactgcgag    2460
cttttcaagc agttgggtga atacaaattc cagaacgcgc ttctggtgag gtataccaag    2520
aaagtacctc aagtctcaac acccacactc gtcgaggtgt cacggaacct cgggaaagta    2580
gggtcgaagt gctgtaaaca cccagaggcc aagcgcatgc cctgtgcgga ggactacctc    2640
tcggtagtgt tgaatcaact gtgtgtcctc cacgaaaaga cgccggtgtc agaccgcgtc    2700
acaaagtgct gcacggagag cctggtcaat agacgcccct gcttctcagc gctggaggtg    2760
gatgagacat acgtcccgaa agagtttaac gccgaaacgt ttactttca tgctgatatc    2820 tgtacgttgt cagagaagga aaggcaaatc aagaaacaaa ctgcgcttgt ggaactggtg    2880
aagcacaaac cgaaggcgac taaggaacag ctgaaggcgg tgatggatga ctttgccgcg    2940
ttcgtagaga aatgctgtaa agcagacgat aaggagactt gttttgcgga agagggaaag    3000
aaacttgttg ctgcaagtca agctgcctta ggcttatag                          3039
```

<210> SEQ ID NO 102  
<211> LENGTH: 1012  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 102

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe

```
                35                  40                  45
Ile Ser Tyr Thr Met His Trp Val Arg Gln Ala Pro Gly Gln Gly Leu
 50                  55                  60
Glu Trp Met Gly Tyr Ile Asn Pro Arg Ser Gly Tyr Thr His Tyr Asn
 65                  70                  75                  80
Gln Lys Leu Lys Asp Lys Ala Thr Leu Thr Ala Asp Lys Ser Ala Ser
                 85                  90                  95
Thr Ala Tyr Met Glu Leu Ser Ser Leu Arg Ser Glu Asp Thr Ala Val
                100                 105                 110
Tyr Tyr Cys Ala Arg Ser Ala Tyr Tyr Asp Tyr Asp Gly Phe Ala Tyr
                115                 120                 125
Trp Gly Gln Gly Thr Leu Val Thr Val Ser Ser Gly Gly Gly Gly Ser
130                 135                 140
Gly Gly Gly Gly Ser Gly Gly Gly Gly Ser Asp Ile Gln Met Thr Gln
145                 150                 155                 160
Ser Pro Ser Ser Leu Ser Ala Ser Val Gly Asp Arg Val Thr Ile Thr
                165                 170                 175
Cys Ser Ala Ser Ser Val Ser Tyr Met Asn Trp Tyr Gln Gln Lys
                180                 185                 190
Pro Gly Lys Ala Pro Lys Arg Leu Ile Tyr Asp Thr Ser Lys Leu Ala
                195                 200                 205
Ser Gly Val Pro Ser Arg Phe Ser Gly Ser Gly Ser Gly Thr Asp Phe
210                 215                 220
Thr Leu Thr Ile Ser Ser Leu Gln Pro Glu Asp Phe Ala Thr Tyr Tyr
225                 230                 235                 240
Cys Gln Gln Trp Ser Ser Asn Pro Pro Thr Phe Gly Gly Gly Thr Lys
                245                 250                 255
Val Glu Ile Lys Gly Gly Gly Gly Ser Gly Gly Gly Gly Ser Gly Gly
                260                 265                 270
Gly Gly Ser Gln Glu Asp Glu Arg Ile Val Leu Val Asp Asn Lys Cys
                275                 280                 285
Lys Cys Ala Arg Ile Thr Ser Arg Ile Ile Arg Ser Ser Glu Asp Pro
                290                 295                 300
Asn Glu Asp Ile Val Glu Arg Asn Ile Arg Ile Ile Val Pro Leu Asn
305                 310                 315                 320
Asn Arg Glu Asn Ile Ser Asp Pro Thr Ser Pro Leu Arg Thr Arg Phe
                325                 330                 335
Val Tyr His Leu Ser Asp Leu Cys Lys Lys Cys Asp Pro Thr Glu Val
                340                 345                 350
Glu Leu Asp Asn Gln Ile Val Thr Ala Thr Gln Ser Asn Ile Cys Asp
                355                 360                 365
Glu Asp Ser Ala Thr Glu Thr Cys Tyr Thr Tyr Asp Arg Asn Lys Cys
                370                 375                 380
Tyr Thr Ala Val Val Pro Leu Val Tyr Gly Gly Glu Thr Lys Met Val
385                 390                 395                 400
Glu Thr Ala Leu Thr Pro Asp Ala Cys Tyr Pro Asp Gly Gly Gly Gly
                405                 410                 415
Ser Gly Gly Gly Gly Ser Gly Gly Gly Gly Ser Asp Ala His Lys Ser
                420                 425                 430
Glu Val Ala His Arg Phe Lys Asp Leu Gly Glu Glu Asn Phe Lys Ala
                435                 440                 445
Leu Val Leu Ile Ala Phe Ala Gln Tyr Leu Gln Gln Cys Pro Phe Glu
                450                 455                 460
```

```
Asp His Val Lys Leu Val Asn Glu Val Thr Glu Phe Ala Lys Thr Cys
465                 470                 475                 480

Val Ala Asp Glu Ser Ala Glu Asn Cys Asp Lys Ser Leu His Thr Leu
            485                 490                 495

Phe Gly Asp Lys Leu Cys Thr Val Ala Thr Leu Arg Glu Thr Tyr Gly
        500                 505                 510

Glu Met Ala Asp Cys Cys Ala Lys Gln Glu Pro Glu Arg Asn Glu Cys
        515                 520                 525

Phe Leu Gln His Lys Asp Asp Asn Pro Asn Leu Pro Arg Leu Val Arg
530                 535                 540

Pro Glu Val Asp Val Met Cys Thr Ala Phe His Asp Asn Glu Glu Thr
545                 550                 555                 560

Phe Leu Lys Lys Tyr Leu Tyr Glu Ile Ala Arg Arg His Pro Tyr Phe
                565                 570                 575

Tyr Ala Pro Glu Leu Leu Phe Phe Ala Lys Arg Tyr Lys Ala Ala Phe
            580                 585                 590

Thr Glu Cys Cys Gln Ala Ala Asp Lys Ala Ala Cys Leu Leu Pro Lys
        595                 600                 605

Leu Asp Glu Leu Arg Asp Glu Gly Lys Ala Ser Ser Ala Lys Gln Arg
610                 615                 620

Leu Lys Cys Ala Ser Leu Gln Lys Phe Gly Glu Arg Ala Phe Lys Ala
625                 630                 635                 640

Trp Ala Val Ala Arg Leu Ser Gln Arg Phe Pro Lys Ala Glu Phe Ala
                645                 650                 655

Glu Val Ser Lys Leu Val Thr Asp Leu Thr Lys Val His Thr Glu Cys
            660                 665                 670

Cys His Gly Asp Leu Leu Glu Cys Ala Asp Asp Arg Ala Asp Leu Ala
        675                 680                 685

Lys Tyr Ile Cys Glu Asn Gln Asp Ser Ile Ser Ser Lys Leu Lys Glu
690                 695                 700

Cys Cys Glu Lys Pro Leu Leu Glu Lys Ser His Cys Ile Ala Glu Val
705                 710                 715                 720

Glu Asn Asp Glu Met Pro Ala Asp Leu Pro Ser Leu Ala Ala Asp Phe
                725                 730                 735

Val Glu Ser Lys Asp Val Cys Lys Asn Tyr Ala Glu Ala Lys Asp Val
            740                 745                 750

Phe Leu Gly Met Phe Leu Tyr Glu Tyr Ala Arg Arg His Pro Asp Tyr
        755                 760                 765

Ser Val Val Leu Leu Leu Arg Leu Ala Lys Thr Tyr Glu Thr Thr Leu
770                 775                 780

Glu Lys Cys Cys Ala Ala Ala Asp Pro His Glu Cys Tyr Ala Lys Val
785                 790                 795                 800

Phe Asp Glu Phe Lys Pro Leu Val Glu Glu Pro Gln Asn Leu Ile Lys
                805                 810                 815

Gln Asn Cys Glu Leu Phe Lys Gln Leu Gly Glu Tyr Lys Phe Gln Asn
            820                 825                 830

Ala Leu Leu Val Arg Tyr Thr Lys Lys Val Pro Gln Val Ser Thr Pro
        835                 840                 845

Thr Leu Val Glu Val Ser Arg Asn Leu Gly Lys Val Gly Ser Lys Cys
        850                 855                 860

Cys Lys His Pro Glu Ala Lys Arg Met Pro Cys Ala Glu Asp Tyr Leu
865                 870                 875                 880
```

-continued

```
Ser Val Val Leu Asn Gln Leu Cys Val Leu His Glu Lys Thr Pro Val
                    885                 890                 895

Ser Asp Arg Val Thr Lys Cys Cys Thr Glu Ser Leu Val Asn Arg Arg
            900                 905                 910

Pro Cys Phe Ser Ala Leu Glu Val Asp Glu Thr Tyr Val Pro Lys Glu
            915                 920                 925

Phe Asn Ala Glu Thr Phe Thr Phe His Ala Asp Ile Cys Thr Leu Ser
        930                 935                 940

Glu Lys Glu Arg Gln Ile Lys Lys Gln Thr Ala Leu Val Glu Leu Val
945                 950                 955                 960

Lys His Lys Pro Lys Ala Thr Lys Glu Gln Leu Lys Ala Val Met Asp
                965                 970                 975

Asp Phe Ala Ala Phe Val Glu Lys Cys Cys Lys Ala Asp Asp Lys Glu
                980                 985                 990

Thr Cys Phe Ala Glu Glu Gly Lys  Lys Leu Val Ala Ala   Ser Gln Ala
            995                1000                1005

Ala Leu  Gly Leu
    1010

<210> SEQ ID NO 103
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Leu Leu Gln Gly Ala
1               5

<210> SEQ ID NO 104
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 104

His His His His His His
1               5
```

BINDING MOLECULES WITH MODIFIED J-CHAIN

CROSS REFERENCE TO RELATED APPLICATIONS

This application is a continuation of U.S. patent application Ser. No. 15/764,859, filed Mar. 29, 2018, which is a US National Stage Entry of PCT Application No. PCT/US2016/055041, filed Sep. 30, 2016, which claims priority benefit of the filing date of U.S. Provisional Patent Application Ser. No. 62/235,518, filed on Sep. 30, 2015, the disclosures of which applications are incorporated herein by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Mar. 6, 2018, is named Sequence-Listing and is 172934 bytes in size.

FIELD OF THE INVENTION

The present invention concerns binding molecules that comprise an IgM, IgA, IgG/IgM or IgG/IgA antibody comprising a modified J-chain.

BACKGROUND OF THE INVENTION

J-chain is an acidic 15-kDa polypeptide, which is associated with pentameric IgM and dimeric IgA via disulfide bonds involving the penultimate cysteine residue in the 18-amino acid secretory tail-piece (tp) at the C-terminus of the IgM μ or IgA α heavy chain. The three disulfide bridges are formed between Cys 12 and 100, Cys 71 and 91, and Cys 108 and 133, respectively. See, e.g., Frutiger et al. 1992, *Biochemistry* 31, 12643-12647. Structural requirements for incorporation of the J-chain into human IgM and IgA and for polymeric immunoglobulin assembly and association with the J-chain are reported by Sorensen et al. 2000, *Int. Immunol.* 12(1): 19-27 and Yoo et al. 1999, *J. Biol. Chem.* 274(47):33771-33777, respectively. Recombinant production of soluble J-chain in *E coli* is reported by Redwan et al. 2006, *Human Antibodies* 15:95-102.

Methods for making hybrid IgA/IgG and IgM/IgG antibodies are known in the art. Thus, recombinant production of hybrid IgA2/IgG1 antibodies is reported in Chintalacharuvu et al. 2001, *Clin Immunol* 101(1):21-31. It has been reported that addition of αtp or μtp at the end of IgG γ heavy chain facilitates polymerization and enhances effector function such as complement activation (Smith et al., *J. Immunol* 1995, 154:2226-2236). The IgA/IgG hybrid antibodies possess properties of both IgA and IgG. Methods for recombinant production of IgM antibodies are also known in the art. E.g., Tchoudakova A, et al., High level expression of functional human IgMs in human PER. C6 cells. *mAbs.* 2009; 1(2):163-171.

Despite the advances made in the design of antibodies, there remains a need for modified antibodies with improved properties, such as improved affinity, specificity and/or avidity, as well as the ability to bind to multiple binding targets.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g., antibody-drug conjugates). Another approach to improving antibody function takes advantage of the bivalent binding of the immunoglobulin G (IgG) structure which allows one IgG molecule to bind two antigens. Indeed, in certain applications, there exists good potential for asymmetric antibodies to exert useful functions by simultaneously binding two different target antigens. To address this need, a variety of constructs have been produced to yield a single molecule that can bind two different antigens, allowing for functions never before seen in nature. An example of this bi-specific approach is "blinatumomab" (MT103 or AMG103) which binds the CD3 and CD19 receptors, on T- and B-cells, respectively. This tethering of a cytotoxic T-cell to a cancerous B-cell, allows for effective treatment of B-cell leukemia.

The blockade of immune checkpoints has emerged as a promising area for the advancement of cancer treatment. Immune checkpoints refer to inhibitory signaling pathways that are encoded into the immune system, and which play a vital role in maintaining self-tolerance, as well as modulating the duration and amplitude of immune responses. See, e.g., Pardoll, Drew M. "The blockade of immune checkpoints in cancer immunotherapy." *Nature Reviews Cancer* 12.4 (2012): 252-264; Postow, Michael A. et al., "Immune Checkpoint Blockade in Cancer Therapy," *J Clin Oncol.* 2015 Jun. 10; 33(17):1974-82. doi: 10.1200/JCO.2014.59.4358.

Despite positive proof of concept results in preclinical models, investigators have reported that monoclonal IgG blocking antibodies directed against T-cell inhibitory signaling pathway components (for example, ipilimumab (Bristol-Myers Squibb) and tremelimumab (MedImmune/AstraZenica), both directed against CTLA4) have only achieved minimal efficacy results in a clinical setting. E.g., Postow et al., pp. 1-2. In addition, treatments involving monoclonal IgG antibodies have resulted in immune-related adverse events, such as dermatologic, GI, hepatic, endocrine and other inflammatory events. E.g., Id. at p. 4. As such, the use of monoclonal IgG antibodies in immune checkpoint blockade may be limited by the therapeutic index of such molecules, in that the dose of a monoclonal IgG antibody required to elicit the desired therapeutic effect also causes immune-related adverse events.

Accordingly, there is a need for binding molecules with increased avidity that will provide increased potency so that lower dosage levels can be used, thereby preventing the occurrence of immune-related adverse events, while still achieving effective blockade of T-cell inhibitory signaling pathways.

The pharmacokinetics and pharmacodynamics of monoclonal antibodies are complex, and depend on both the structure of the monoclonal antibody, as well as the physiological system that it targets. Moreover, different antibody classes are typically processed within a subject via different cellular and physiological systems. For example, secretion into the bile is an important pathway of elimination for IgA antibodies, whereas this route is not a significant contributor to the elimination of IgG antibodies. Rather, the majority of IgG elimination occurs via intracellular catabolism, following fluid-phase or receptor-mediated endocytosis. E.g., Wang et al., *Nature* 84:5 (2008). Furthermore, full-length IgG antibodies have been shown to be primarily distributed within the blood stream, while smaller IgG antibody fragments appear to distribute within the extra-vascular space to a greater extent. E.g., Tabrizi et al., *AAPS J.* 2010 March; 12(1): 33-43. The blood brain barrier generally prevents immunoglobulin molecules from entering the central nervous system via the circulation. E.g., Yu et al., *Science Translational Medicine* 16:261 (2014). Furthermore, immunoglobulins that are directly injected into an extra-vascular space, such as the eyeball, typically only remain in the space on the order of hours. See., e.g., Mordenti, J. et al., *Toxicological Sciences* 52, 101-106 (1999); Mordenti, J. et al., *Toxicological Sciences* 27(5), 536-544 (1999). As such, control and manipulation of factors that influence the absorption, distribution, metabolism and/or excretion (ADME) characteristics of monoclonal antibodies is an important consideration when designing a therapeutic antibody composition.

Accordingly, there is a need for binding molecules whose ADME characteristics can be controlled and modulated to achieve a desired therapeutic effect.

SUMMARY OF THE INVENTION

The present invention is based, at least in part, on the recognition that the J-chain of an IgM or IgA antibody can be modified by introducing one or more ADME-modulating moieties into a native J-chain sequence, and the modified J-chain can be introduced into IgM, IgA, IgG/IgM or IgG/IgA antibodies without compromising the functionality of the recipient antibody or the ADME-modulating moiety. This allows the IgM, IgA, IgG/IgM or IgG/IgA antibody to achieve improved properties, such as an increased concentration and/or an increased half-life in a subject.

The invention is further based on the recognition that due to their multivalent nature, IgM, IgA, IgG/IgM or IgG/IgA antibodies can provide increased avidity between the antibody and a target antigen, thereby facilitating binding of antigens with low level expression and/or low binding affinity. Furthermore, the optional multi-specific nature of the IgM, IgA, IgG/IgM or IgG/IgA portion of the subject binding molecules allows binding between specific numbers and/or specific types of binding targets, thereby facilitating binding between specific combinations of antigen targets. The modified J-chain portion of the subject binding molecules comprises an ADME-modulating moiety, which facilitates an increased concentration and/or an increased half-life in a target tissue.

Aspects of the invention include binding molecules comprising an IgM, IgA, IgG/IgM or IgG/IgA antibody with a modified J-chain, or an antigen binding fragment thereof, wherein the modified J-chain comprises an ADME-modulating moiety. In some embodiments, the ADME-modulating moiety is selected from the group consisting of: antibodies, antigen-binding fragments of antibodies, antibody-like molecules, antigen-binding fragments of antibody-like molecules, proteins, ligands and receptors. In some embodiments, the ADME-modulating moiety is an antigen-binding fragment of an antibody, and is selected from the group consisting of: F(ab')$_2$, F(ab)$_2$, Fab', Fab, Fv, scFv, V$_H$H, scFab and dAb.

In some embodiments, the ADME-modulating moiety reduces clearance of the binding molecule from a subject's circulation. In some embodiments, the ADME-modulating moiety comprises an albumin protein, or a fragment of an albumin protein. In some embodiments, the ADME-modulating moiety comprises an albumin-binding peptide. In some embodiments, the ADME-modulating moiety comprises an albumin-binding antibody fragment. In some embodiments, the albumin-binding antibody fragment is selected from the group consisting of: Fab, scFv, V$_H$H, scFab and dAb. In some embodiments, the ADME-modulating moiety comprises an FcRn-binding peptide. In some embodiments, the ADME-modulating moiety comprises an FcRn-binding antibody fragment. In some embodiments, the FcRn-binding antibody fragment is selected from the group consisting of: Fab, scFv, V$_H$H, scFab and dAb. In some embodiments, the ADME-modulating moiety comprises an Fc domain.

In some embodiments, the ADME-modulating moiety increases a concentration of the binding molecule in a central nervous system tissue of a subject. In some embodiments, the ADME-modulating moiety binds to a member of a receptor mediated transcytosis (RMT) pathway. In some embodiments, the ADME-modulating moiety comprises a ligand that is a member of an RMT pathway. In some embodiments, the ADME-modulating moiety comprises a transferrin protein. In some embodiments, the ADME-modulating moiety comprises a transferrin receptor-binding antibody fragment. In some embodiments, the transferrin receptor-binding antibody fragment is selected from the group consisting of: Fab, scFv, V$_H$H, scFab and dAb. In some embodiments, the ADME-modulating moiety comprises a transferrin-binding antibody fragment. In some embodiments, the transferrin-binding antibody fragment is selected from the group consisting of: Fab, scFv, V$_H$H, scFab and dAb. In some embodiments, the IgM, IgA, IgG/IgM or IgG/IgA antibody binds to beta-secretase 1 (BACE). In some embodiments, the ADME-modulating moiety comprises an insulin receptor-binding antibody fragment. In some embodiments, the insulin receptor-binding antibody fragment is selected from the group consisting of: Fab, scFv, V$_H$H, scFab and dAb. In some embodiments, the ADME-modulating moiety comprises an IGF-1 receptor-binding antibody fragment. In some embodiments, the IGF-1 receptor-binding antibody fragment is selected from the group consisting of: Fab, scFv, V$_H$H, scFab and dAb. In some embodiments, the ADME-modulating moiety comprises a leptin protein. In some embodiments, the ADME-modulating moiety comprises a leptin receptor-binding antibody fragment. In some embodiments, the leptin receptor-binding antibody fragment is selected from the group consisting of: Fab, scFv, V$_H$H, scFab and dAb.

In some embodiments, the ADME-modulating moiety increases retention of the binding molecule in an extra-vascular space of a subject. In some embodiments, the extra-vascular space is an intra-articular space. In some embodiments, the extra-vascular space is an intra-vitreal space. In some embodiments, the ADME-modulating moiety comprises a hyaluronic acid binding protein (HABP). In some embodiments, the ADME-modulating moiety comprises a hyaluronic acid-binding antibody fragment. In some embodiments, the hyaluronic acid-binding antibody fragment is selected from the group consisting of: Fab, scFv, V$_H$H, scFab and dAb. In some embodiments, the ADME-modulating moiety comprises a TSG-6 protein. In some embodiments, the ADME-modulating moiety comprises a TSG-6-binding antibody moiety. In some embodiments, the TSG-6-binding antibody moiety is selected from the group consisting of: Fab, scFv, V$_H$H, scFab and dAb.

In some embodiments, the modified J-chain comprises a modified human J-chain sequence, or a functional fragment thereof. In some embodiments, the modified human J-chain sequence comprises the native human J-chain sequence of SEQ ID NO: 1. In some embodiments, the ADME-modulating moiety is introduced into the native human J-chain sequence of SEQ ID NO: 1 by direct or indirect fusion. In some embodiments, the ADME-modulating moiety is introduced by indirect fusion through a peptide linker. In some embodiments, the indirect fusion is through a peptide linker at or around a C- and/or an N-terminus of the half-life extending moiety. In some embodiments, the ADME-modulating moiety is introduced into the native human J-chain sequence of SEQ ID NO: 1 at or around the C-terminus. In some embodiments, the ADME-modulating moiety is introduced into the native human J-chain sequence of SEQ ID NO: 1 within about 10 residues from the C-terminus. In some embodiments, the ADME-modulating moiety is introduced into the native human J-chain sequence of SEQ ID NO: 1 at or around the N-terminus. In some embodiments, the ADME-modulating moiety is introduced into the native human J-chain sequence of SEQ ID NO: 1 within about 10 amino acid residues from the N-terminus. In some embodiments, the ADME-modulating moiety is introduced into the native human J-chain sequence in between cysteine residues 92 and 101 of SEQ ID NO: 1. In some embodiments, he ADME-modulating moiety is introduced into the native human J-chain sequence of SEQ ID NO: 1 at or near a glycosylation site. In some embodiments, the peptide linker is about 10 to 20 amino acids long. In some embodiments, the peptide linker is about 15 to 20 amino acids long. In some embodiments, the peptide linker is 15 amino acids long. In some embodiments, the ADME-modulating moiety is introduced into the native human J-chain sequence of SEQ ID NO: 1 by chemical or chemo-enzymatic derivatization. In some embodiments, the ADME-modulating moiety is introduced into the native human J-chain sequence of SEQ ID NO: 1 by a chemical linker. In some embodiments, the chemical linker is a cleavable or non-cleavable linker. In some embodiments, the cleavable linker is a chemically labile linker or an enzyme-labile linker. In some embodiments, the linker is selected from the group consisting of N-succinimidyl-3-(2-pyridyldithio) propionate (SPDP), succinimidyl-4-(N-maleimidomethyl) cyclohexane-1-carboxylate (SMCC), N-succinimidyl-4-(2-pyridylthio) pentanoate (SPP), iminothiolane (IT), bifunctional derivatives of imidoesters, active esters, aldehydes, bis-azido compounds, bis-diazonium derivatives, diisocyanates, and bis-active fluorine compounds. In some embodiments, the modified J-chain is modified by insertion of an enzyme recognition site, and by post-translationally attaching an ADME-modulating moiety at the enzyme recognition site through a peptide or non-peptide linker.

In some embodiments, the modified J-chain is in an ADME-linker-J orientation, with the ADME-modulating moiety at an N-terminus of the modified J-chain. In some embodiments, the modified J-chain is in a J-linker-ADME orientation, with the ADME-modulating moiety at a C-terminus of the modified J-chain. In some embodiments, the modified J-chain further comprises a second binding moiety. In some embodiments, the ADME-modulating moiety is located at an N-terminus of the modified J-chain, and the second binding moiety is located at a C-terminus of the modified J-chain. In some embodiments, the ADME-modulating moiety is located at a C-terminus of the modified J-chain, and the second binding moiety is located at an N-terminus of the modified J-chain. In some embodiments, the binding molecule comprises an IgM antibody comprising a heavy chain amino acid sequence of SEQ ID NO: 82, a light chain amino acid sequence of SEQ ID NO: 84, and a J-chain amino acid sequence of SEQ ID NO: 102. In some embodiments, the second binding moiety is a second ADME-modulating moiety.

In some embodiments, the IgM, IgA, IgG/IgM or IgG/IgA antibody is a bispecific antibody. In some embodiments, the IgM, IgA, IgG/IgM or IgG/IgA antibody is a multispecific antibody.

Aspects of the invention include pharmaceutical compositions for the treatment of cancer, wherein the pharmaceutical composition comprises an effective amount of a binding molecule and a pharmaceutically acceptable carrier. In some embodiments, aspects of the invention include use of a binding molecule in the preparation of a medicament for treating cancer. In some embodiments, the cancer is a hematologic cancer, an epithelial cancer or a central nervous system cancer. In some embodiments, the hematologic cancer is a leukemia, lymphoma, myeloma, or myelodysplastic syndrome. In some embodiments, the leukemia is an acute myeloid leukemia, acute lymphoblastic leukemia, chronic myelogenous leukemia, or chronic lymphocytic leukemia. In some embodiments, the lymphoma is Hodgkin's lymphoma or non-Hodgkin's lymphoma. In some embodiments, the epithelial cancer is a melanoma, non-small-cell lung, nasopharyngeal, colorectal, liver, urinary bladder, ovarian, gastric, esophageal, pancreatic, renal, thyroid or breast cancer. In some embodiments, the breast cancer is hormone receptor negative or triple negative breast cancer. In some embodiments, the central nervous system cancer is a glioma, astrocytoma, meningioma, neuroma and oligodendroglioma. In some embodiments, the medicament further comprises an effective amount of a second therapeutic agent.

Aspects of the invention include pharmaceutical compositions for the treatment of rheumatoid arthritis, wherein the pharmaceutical composition comprises an effective amount of a binding molecule and a pharmaceutically acceptable carrier. In some embodiments, aspects of the invention include use of a binding molecule in the preparation of a medicament for treating rheumatoid arthritis.

Aspects of the invention include pharmaceutical compositions for the treatment of age-related macular degeneration, wherein the pharmaceutical composition comprises an effective amount of a binding molecule and a pharmaceutically acceptable carrier. In some embodiments, aspects of the invention include use of a binding molecule in the preparation of a medicament for treating age-related macular degeneration.

Aspects of the invention include pharmaceutical compositions for the treatment of Alzheimer's disease, wherein the pharmaceutical composition comprises an effective amount of a binding molecule and a pharmaceutically acceptable carrier. In some embodiments, aspects of the invention include use of a binding molecule in the preparation of a medicament for treating Alzheimer's disease.

BRIEF DESCRIPTION OF THE DRAWINGS

FIG. 3 shows the amino acid sequence of mature human J-chain (SEQ ID NO: 1).

FIG. 4A illustrates two different orientations of J-chain constructs comprising a modified J-chain with a moiety that binds to CD3. The top illustration is an example of a modified J-chain that is in the J-linker-V orientation, with a binding moiety (e.g., an anti-CD3 scFv antibody fragment) positioned at the C-terminus of the modified J-chain. The bottom illustration is an example of a modified J-chain that is in the V-linker-J orientation, with a binding moiety (e.g., an anti-CD3 scFv antibody fragment) positioned at the N-terminus of the modified J-chain.

FIG. 4B illustrates two different orientations of J-chain constructs comprising a modified J-chain with an HSA-containing moiety. The top illustration is an example of a modified J-chain that is in the J-linker-ADME orientation, with an ADME modulating moiety (e.g., a human serum albumin (HSA) polypeptide) positioned at the C-terminus of the modified J-chain. The bottom illustration is an example of a modified J-chain that is in the ADME-linker-J orientation, with an ADME modulating moiety (e.g., a human serum albumin (HSA) polypeptide) positioned at the N-terminus of the modified J-chain.

FIG. 11, Panel A shows an illustration of a temporal biodistribution model. Panel B shows data for the biodistribution of IGM-55.5 in vivo using conjugated far infra-red dye Vivo Tag 680 (Perkin Elmer).

FIG. 12 Panel A is a schematic illustration depicting site specific labeling of glycans on IgG using chemoenzymatic approach. Panel B shows the position of glycans on IgM heavy chain and J-chain. Panel C shows the non-reduced and reduced gels for the labeled products after using chemoenzymatic labeling.

FIG. 13 lists IgM, IgA, IgG/IgM or IgG/IgA antibody targets and ADME-modulating moieties that can be placed on the J-chain. Any of the antibody targets listed in the left column can be combined with any of the ADME-modulating moieties on a J-chain listed in the right column.

FIG. 22 is a table showing alpha and beta half-life in hours and AUC for 6 different antibodies.

FIG. 26, Panel A, is a graph showing concentration as a function of time for an IgM antibody that has a V-J-ABD bidentate J-chain configuration. Panel B is a graph showing concentration as a function of time for an IgM antibody that has a V-J-HSA bidentate J-chain configuration.

FIG. 27 is a table showing alpha and beta half-life in hours and AUC parameters for 4 different antibodies with various configurations of their J-chains.

FIG. 28, Panel A and Panel B are graphs showing percentage of pre-dose CD19+ B-cells as a function of dose (ng/mouse) for various constructs (e.g., 1.5.3V15J15HSAwt and 1.5.3V15J15HSA (K573P)).

DETAILED DESCRIPTION OF THE INVENTION

I. Definitions

Figure 1:
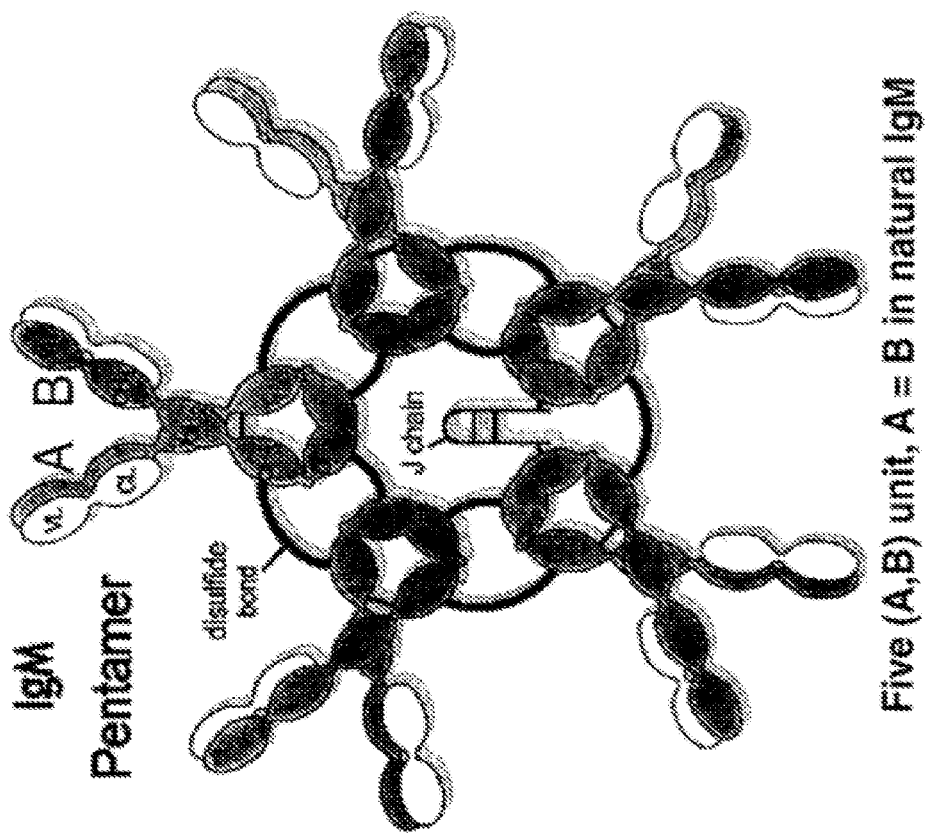
FIG. 1 illustrates the structure of an IgM pentamer, comprising a J-chain, wherein chains A and B are identical in native IgM.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

All publications mentioned herein are expressly incorporated herein by reference to disclose and describe the methods and/or materials in connection with which the publications are cited.

The term "ADME" as used herein is an abbreviation for absorption, distribution, metabolism, and excretion, and is used in the broadest sense to describe the disposition of a pharmaceutical compound within an organism.

The term "ADME-modulating moiety" is used herein in the broadest sense to encompass any chemical entity capable of modulating one or more of the absorption, distribution, metabolism and excretion characteristics of a molecule to which it is attached. Examples of ADME-modulating moieties include, without limitation, antibodies, antigen-binding fragments of antibodies, antibody-drug conjugates, antibody-like molecules, antigen-binding fragments of antibody-like molecules, ligands, receptors, proteins, and polypeptides (including peptides). Preferred binding moieties are antigen-binding fragments of antibodies, preferably with a biological function. An example of a biological function is the ability of an ADME-modulating moiety to bind to a target that extends the half-life of a subject binding molecule.

The term "antibody" includes monoclonal antibodies (including full length antibodies which have an immunoglobulin Fc region), single-chain molecules, as well as antibody fragments (e.g., Fab, F(ab')$_2$, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. Unless noted otherwise, the term "antibody" is used herein in the broadest sense and specifically includes all isotypes, sub-classes and forms of antibodies, including IgG, IgM, IgA, IgD, and IgE antibodies and their fragments, preferably antigen-binding fragments. Preferred antibodies herein include IgM and IgA antibodies and their antigen-binding fragments, which may be modified to include sequences from other isotypes, such as IgG to produce chimeric antibodies.

In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

IgM is a glycoprotein which forms polymers where multiple immunoglobulins are covalently linked together with disufide bonds. IgM mostly exists as a pentamer but also as a hexamer and therefore contains 10 or 12 antigen binding sites. The pentameric form typically contains an additional polypeptide, called the J-chain, but can also be made in the absence of J-chain. The pentameric IgM molecule has a molecular weight of approximately 970 kDa. Due to its polymeric nature, IgM possesses high avidity and is particularly effective in complement activation. Unlike in IgG, the heavy chain in IgM monomers is composed of one variable and four constant domains. The IgM constant domains are designated herein as CM1 or Cμ1, CM2 or Cμ2, CM3 or Cμ3, and CM4 or Cμ4, wherein the "CM" and "Cμ" designations are used interchangeably. The structure of an IgM pentamer is illustrated in FIG. 1.

The term "IgM" is used herein in the broadest sense and specifically includes mono-, and multi-specific (including bispecific) IgM molecules, such as, for example, the multi-specific IgM binding molecules disclosed in PCT Application No. PCT/US2014/054079, the entire disclosure of which is expressly incorporated by reference herein.

The term "IgM binding unit" or "IgM antibody binding unit" is used in the broadest sense and specifically covers an IgM antibody heavy chain constant region polypeptide, comprising at least a CM4 constant domain, fused to a variable domain sequence ($V_H$) binding to a target (e.g., antigen), with or without an associated antibody light chain variable domain ($V_L$) sequence.

The term "bispecific IgM binding unit" or "bispecific IgM antibody binding unit" is used in the broadest sense and specifically covers a pair of IgM antibody heavy chain constant region polypeptides, comprising at least a CM4 constant domain, fused to a variable domain sequence ($V_H$), each variable domain sequence binding to a different target, with or without associated antibody light chain variable domain ($V_L$) sequences. In one embodiment, the bispecific IgM antibody comprises two $V_HV_L$ antigen binding regions, each capable of binding to a different epitope on one antigen or epitopes on two different antigens. The bispecific IgM antibody binding units can be full length from a single species, or be chimerized or humanized. The bispecific IgM antibodies of the present invention have a penta- or hexameric ring structure comprising five or six bispecific IgM binding units.

The term "multi-specific IgM" is used herein in the broadest sense to refer to IgM antibodies with two or more binding specificities. Thus, the term "multi-specific" includes "bispecific", e.g., bispecific antibodies or bispecific binding units, including IgM pentamers comprising at least two monospecific subunits, each binding to a different antigen (AA, BB), or five or six bispecific subunits, each binding to two different antigens (AB, AB). Thus, the bispecific and multi-specific IgM pentamers may include five identical bispecific binding units, monospecific IgM binding units, at least two of them have different binding specificities, or any combination thereof.

A "full length IgM antibody heavy chain" is a polypeptide consisting in N-terminal to C-terminal direction of an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4). The bispecific full length IgM antibodies as defined herein comprise five or six monomers (binding units), each with two antigen binding sites, which specifically bind to two different binding targets (epitopes). The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

Figure 2:
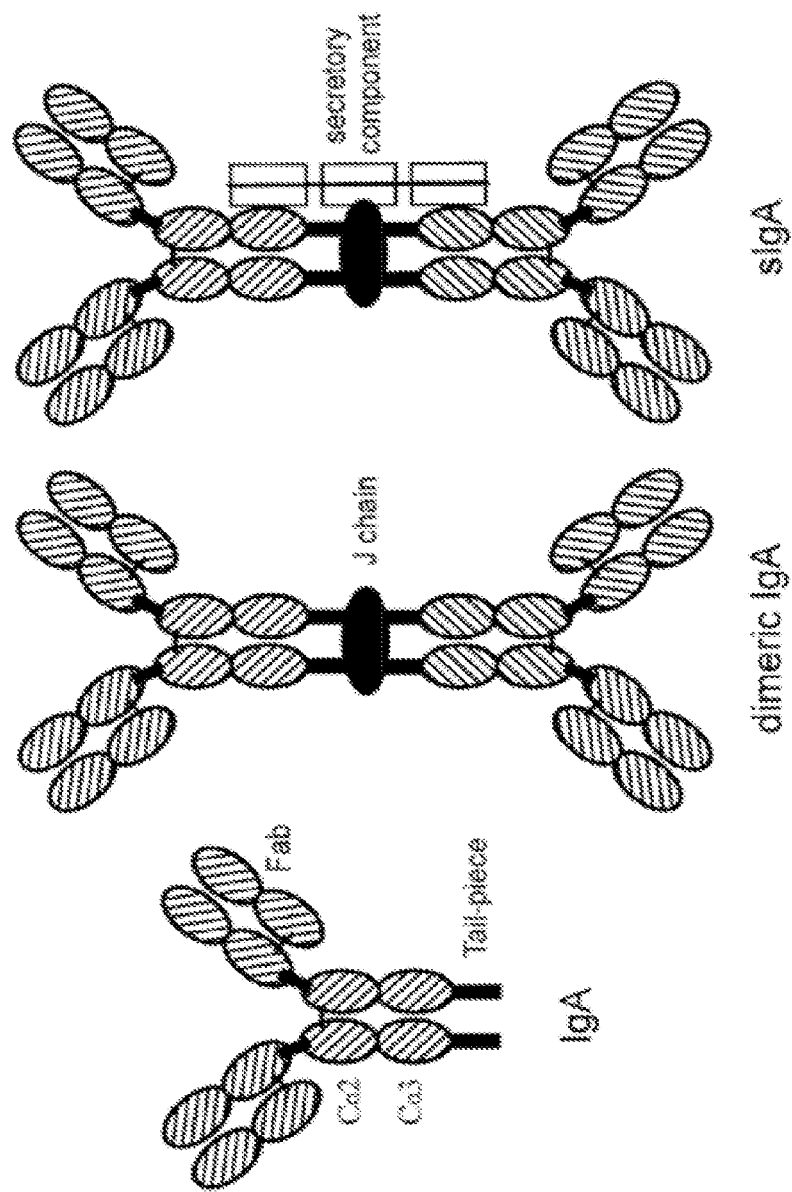
FIG. 2 shows the schematic structures of IgA, dimeric IgA with J-chain, and dimeric J-chain integrated IgA with secretory IgA (sIgA).

Native IgA is a tetrameric protein comprising two identical light chains (κ or λ) and two identical heavy chains (α). In the human, there are two IgA isotypes, IgA1 and IgA2. IgA, similarly to IgG, contains three constant domains (CA1-CA3 or Cα1-Cα3), with a hinge region between the Cα1 and Cα2 domains, wherein the "CA" and "Cα" designations are used interchangeably. All IgA isotypes have an 18 amino acid "tailpiece", which is located C-terminal to the Cα3 domain, which enables polymeric Ig formation (see, e.g., Garcia-Pardo et al., 1981, *J. Biol. Chem.* 256, 11734-11738 and Davis et al., 1988, *Eur. J. Immunol.* 18, 1001-1008). Serum IgA is a monomer but can also polymerize. In its secretory form IgA comprises from 2-5 of the basic 4-chain units, linked by a J-chain, which may include a tail-piece, and may be associated by a secretory component. The structures of tail-piece, dimeric IgA and secretory IgA, associated with a secretory component (sIgA) are illustrated in FIG. 2. IgA antibodies can be further divided into IgA1 and IgA2 sub-classes. The term "IgA" antibody is used herein to specifically include all sub-classes, i.e., IgA1 and IgA2 antibodies, including dimeric and multimeric forms, with and without a secretory component, as well as fragments, preferably antigen-binding fragments, of such antibodies. For the purposes of the present invention, the IgA antibody preferably is a dimer, where two tail-pieces are connected by a J-chain (see, FIG. 2).

The term "IgA" is used herein in the broadest sense and specifically includes mono-, and multi-specific IgA molecules, such as, for example, the multi-specific IgA binding molecules disclosed in PCT Application No. PCT/US2015/015268, the entire disclosure of which is expressly incorporated by reference herein.

The term "multi-specific IgA" is used herein in the broadest sense to refer to IgA antibodies with two or more binding specificities. Thus, the term "multi-specific" includes "bispecific", e.g., bispecific antibodies or bispecific binding units, including IgA dimers comprising two monospecific subunits, each binding to a different antigen (AA, BB), or two bispecific subunits, each binding to two different antigens (AB, AB).

In one embodiment, the dimeric multi-specific IgA molecules consist of two monospecific binding units, each binding unit having binding specificity to a different binding target (AA, BB). In another embodiment, in the dimeric IgA molecules at least one of the two binding units has two different binding specificities (i.e., is a bispecific, e.g., AA, A,B or AA, BC). In another embodiment, each of the two binding units has two specificities, which may be the same (AB, AB) or different (AC, CD or AB, AC, for example).

The term "bispecific IgA antibody binding unit" is used in the broadest sense and specifically covers a pair of IgA antibody heavy chain constant region polypeptides, comprising at least a CA3 constant domain, fused to a variable domain sequence ($V_H$), each variable domain sequence binding to a different target, with or without associated antibody light chain variable domain ($V_L$) sequences. In one embodiment, the bispecific IgA antibody comprises two $V_H V_L$ antigen binding regions, each capable of binding to a different epitope on one antigen or epitopes on two different antigens. The bispecific IgA antibody binding units can be full length from a single species, or be chimerized or humanized.

A "full length IgA antibody heavy chain" is a polypeptide consisting in N-terminal to C-terminal direction of an antibody heavy chain variable domain (VH), an antibody constant heavy chain constant domain 1 (CA1 or Cα1), an antibody constant heavy chain constant domain 2 (CA2 or Cα2), and an antibody heavy chain constant domain 3 (CA3 or Cα3). The bi- or multi-specific full length IgA antibodies according to the invention comprise two monomers (binding units), each of which may be mono- or bispecific, with or without a secretory component. Thus, the multi-specific IgA antibodies of the present invention may include monospecific and bispecific binding units, provided that the resultant IgA antibody has at least two binding specificities. The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

For further details of the structure and properties of the different classes of antibodies, see e.g., Basic and Clinical Immunology, 8th Edition, Daniel P. Stites, Abba I. Terr and Tristram G. Parslow (eds), Appleton & Lange, Norwalk, Conn., 1994, page 71 and Chapter 6.

The term "interface", as used herein, is used to refer to a region, which comprises those "contact" amino acid residues (or other non-amino acid groups such as, for example, carbohydrate groups,) in a first IgM heavy chain constant region which interact with one or more "contact" amino acid residues (or other non-amino acid groups) in a second IgM heavy chain constant region.

The term "asymmetric interface" is used to refer to an interface (as hereinabove defined) formed between two antibody chains, such as a first and a second IgM heavy chain constant region and/or between an IgM heavy chain constant region and its matching light chain, wherein the contact residues in the first and the second chains are different by design, comprising complementary contact residues. The asymmetric interface can be created by knobs/holes interactions and/or salt bridges coupling (charge swaps) and/or other techniques known in the art, such as for example, by the CrossMab approach for coupling a μ heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g., by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e., genetically engineered or mutated) to encode a protuberance or cavity. The original or starting nucleic acid may be a naturally occurring nucleic acid or may comprise a nucleic acid which has been subjected to prior alteration (e.g., a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g., by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g., a humanized monoclonal antibody).

Preferably the import amino acid residue for forming the protuberance has a relatively small number of "rotamers" (e.g., about 3-6). A "rotamer" is an energetically favorable conformation of an amino acid side chain. The number of rotamers for the various amino acid residues are reviewed in Ponders and Richards, J. Mol. Biol. 193: 775-791 (1987).

Unless stated otherwise, the term "antibody" specifically includes native human and non-human IgG1, IgG2, IgG3, IgG4, IgE, IgA, IgD and IgM antibodies, including naturally occurring variants. Thus, for example, the human IgM sequence is available under GenBank Accession Number X14940.1, while variants have been reported as GenBank CAB37838.1, CAC20458.1, AFM37312.1, X57331.1, and J00260.1.

The term "native" with reference to a polypeptide (e.g., an antibody or a J-chain) is used herein to refer to a polypeptide having a sequence that occurs in nature, regardless of its mode of preparation. Thus, the terms "native" and "native sequence" are used herein interchangeably, and expressly encompass recombinant polypeptides with a sequence that is found in nature.

The term "native sequence J-chain" or "native J-chain" as used herein refers to J-chain of native sequence IgM or IgA antibodies of any animal species, including mature human J-chain, the amino acid sequence of which is shown in FIG. 3 (SEQ ID NO: 1).

The term "modified J-chain" is used herein to refer to variants of native sequence J-chain polypeptides comprising an extraneous ADME-modulating moiety introduced into the native sequence. The introduction can be achieved by any means, including direct or indirect fusion of an extraneous ADME-modulating moiety or by attachment through a chemical linker. The term "modified human J-chain" specifically encompasses, without limitation, a native sequence human J-chain of the amino acid sequence of SEQ ID NO: 1 modified by the introduction of an ADME-modulating moiety. The term specifically encompasses, without limitation, a native sequence human J-chain of the amino acid sequence of SEQ ID NO: 1 modified by the introduction of an extraneous ADME-modulating moiety which does not interfere with efficient polymerization (dimerization) of IgM or IgA and binding of such polymers (dimers) to a target The term "polypeptide" is used herein in the broadest sense and includes peptide sequences. The term "peptide" generally describes linear molecular chains of amino acids containing up to about 60, preferably up to about 30 amino acids covalently linked by peptide bonds.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or nonproteinaceous solutes, as well as undesired byproducts of the production. In a preferred embodiment, an isolated antibody herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of a amino acid sequencer, or (3) to homogeneity by SDS-PAGE under reducing or non-reducing conditions using Coomassie blue or, preferably, silver stain. Ordinarily, an isolated antibody will be prepared by at least one purification step.

The term "specific binding" or "specifically binds to" or is "specific for" refers to the binding of two members of a binding pair, such as the binding of an antibody to a target antigen, e.g., an epitope on a particular polypeptide, peptide, or other target (e.g., a glycoprotein target), and means binding that is measurably different from a non-specific interaction (e.g., a non-specific interaction may be binding to bovine serum albumin or casein). Specific binding can be measured, for example, by determining binding of a half-life extending moiety, or an antibody, or an antibody modified by introduction of a half-life extending moiety, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CM5 chips at about 10 response units (RU).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin.

The term "valent" as used herein denotes the presence of a specified number of binding sites in an antibody. As such, the terms "bivalent", "tetravalent", and "hexavalent" denote the presence of two binding sites, four binding sites, and six binding sites, respectively. Thus, if in a bispecific IgA antibody according to the present invention each binding unit is bivalent, the bispecific IgA antibody will have 4 valencies.

The term "epitope" includes any molecular determinant capable of specific binding to an antibody. In certain embodiments, epitope determinants include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. A "binding region" is a region on a binding target bound by a binding molecule.

"Polyepitopic specificity" refers to the ability to specifically bind to two or more different epitopes on the same or different target(s). "Monospecific" refers to the ability to bind only one epitope. According to one embodiment the bispecific IgM antibody binds to each epitope with an affinity of at least $10^{-7}$ M, or $10^{-8}$ M or better.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes, as defined above.

As used herein, the term "immunogenic" refers to substances that elicit the production of antibodies, and/or activate T-cells and/or other reactive immune cells directed against an antigen of the immunogen.

An "antigen-binding site" or "antigen-binding region" of an antibody of the present invention typically contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs may be sufficient for binding to some binding targets. Thus, in some instances, the CDRs of a $V_H$ or a $V_L$ domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "extraneous" with reference to an "ADME-modulating moiety" is used herein to refer to an ADME-modulating moiety not present in a reference native polypeptide sequence at the same location. Thus, an extraneous polypeptide sequence (including peptide sequences), might be comprised within the corresponding native sequence but at a different location. In a preferred embodiment, the "extraneous" sequence is not present in the corresponding native sequence in any location. The term "antagonist" as used herein refers to a molecule that causes a decrease in a function or activity as compared to the same function or activity in the absence of the molecule. An "antagonist" of a signaling pathway is therefore a molecule whose presence causes a decrease in a function or activity of the signaling pathway. The term "antagonize" as used herein refers to causing a decrease in a function or activity.

The term "agonist" as used herein refers to a molecule that causes an increase in a function or activity as compared to the same function or activity in the absence of the molecule. An "agonist" of a signaling pathway is therefore a molecule whose presence causes an increase in a function or activity of the signaling pathway. The term "agonize" as used herein refers to causing an increase in a function or activity.

The term "T-cell inhibitory signaling pathway" as used herein refers to a T-cell signaling pathway that leads to a qualitative or quantitative decrease in, blocking or, or halting of a T-cell immune response.

The term "T-cell stimulatory signaling pathway" as used herein refers to a T-cell signaling pathway that leads to a qualitative or quantitative increase in or maintenance of a T-cell immune response.

The term "low level expression target" as used herein refers to a target whose expression level on a target cell ranges from 0 to 1+, as determined by immunohistochemistry (IHC) tissue analysis, preferably performed on frozen, formalin-fixed, paraffin-embedded tissue sections. Guidelines for determining expression level via IHC are provided, for example, by the College of American Pathologists (CAP), and are exemplified by the ASCO-CAP HER2 Test Guideline Recommendations, available at http://www.cap.org/apps/docs/committees/immunohistochemistry/summary_of_recommendations.pdf.

The term "low affinity target" as used herein refers to a target whose binding interaction with an antibody has a dissociation constant $K_d$ that is greater than or equal to a value ranging from about 10 to 100 nM, such as about 25 to about 75 nM, as measured by ELISA.

The term "half-life" is used herein in the broadest sense to refer to the period of time required for the concentration or amount of a binding molecule to be reduced by one-half in the body of a subject.

The term "albumin-binding polypeptide" as used herein refers to a polypeptide that specifically binds to an albumin protein.

The term "Fc domain" as used herein broadly refers to a C-terminal region of an immunoglobulin heavy chain, including native sequence Fc domains and variant Fc domains.

The terms "extra-vascular" and "extra-vascular space" as used herein broadly refer to a portion of a subject that is situated outside of the subject's blood vessels (e.g., arteries and veins).

The term "intra-articular space" as used herein refers to any portion of a subject that is situated inside of a joint that is located, e.g., between two bones (e.g., the inside of a knee joint).

The term "intra-vitreal space" as used herein refers to any portion of a subject that is situated inside of an eyeball.

DETAILED DESCRIPTION

Design and Production of Binding Molecules with Modified J-Chain

IgM is the first immunoglobulin produced by B cells in response to stimulation by antigen, and is present at around 1.5 mg/ml in serum with a half-life of 5 days. IgM is a pentameric or hexameric molecule. Just as IgG, IgM monomers consist of two light and two heavy chains. However, while IgG contains three heavy chain constant domains ($C_H1$, $C_H2$ and $C_H3$), the heavy (μ) chain of IgM additionally contains a fourth constant domain ($C_H4$), similarly to the ε heavy chains in IgE. This extra constant domain is located in place of the IgG and IgA proline-rich hinge region that is responsible for the rotational flexibility of the antigen-binding Fab domains relative to the Fc domain of IgG and IgA antibodies.

Five IgM monomers form a complex with an additional small polypeptide chain (the J-chain) to form a native IgM molecule. The J-chain is considered to facilitate polymerization of μ chains before IgM is secreted from antibody-producing cells. While crystallization of IgM has proved to be notoriously challenging, Czajkowsky and Shao (PNAS 106(35):14960-14965, 2009) recently published a homology-based structural model of IgM, based on the structure of the IgE Fc domain and the known disulfide pairings. The authors report that the human IgM pentamer is a mushroom-shaped molecule with a flexural bias. The IgM heavy (μ) chain contains five N-linked glycosylation sites: Asn-171, Asn-332, Asn-395, Asn-402 and Asn-563.

Immunoglobulin A (IgA), as the major class of antibody present in the mucosal secretions of most mammals, represents a key first line of defense against invasion by inhaled and ingested pathogens. IgA is also found at significant concentrations in the serum of many species, where it functions as a second line of defense mediating elimination of pathogens that have breached the mucosal surface. Receptors specific for the Fc region of IgA, FcαR, are key mediators of IgA effector function. Human IgA may have two different IgA heavy constant region (Cα) genes which give rise to the two subclasses, IgA1 and IgA2. The main difference between IgA1 and IgA2 resides in the hinge region that lies between the two Fab arms and the Fc region. IgA1 has an extended hinge region due to the insertion of a duplicated stretch of amino acids, which is absent in IgA2. IgA has the capacity to form dimers, in which two monomer units, each comprising two heavy chains and light chains, are postulated to be arranged in an end-to-end configuration stabilized by disulfide bridges and incorporation of a J-chain. Dimeric IgA, produced locally at mucosal sites, is transported across the epithelial cell boundary and out into the secretions by interaction with the polymeric immunoglobulin receptor (pIgR). During this process, the pIgR is cleaved and the major fragment, termed secretory component (SC), becomes covalently attached to the IgA dimer.

Both IgA and IgM possess an 18-amino acid extension in the C terminus called the "tail-piece" (tp). The IgM (μtp) and IgA (αtp) tail-pieces differ at seven amino acid positions. The IgM and IgA tail-piece is highly conserved among various animal species. The conserved penultimate cysteine residue in the IgA and IgM tail-pieces has been demonstrated to be involved in polymerization. Both tail-pieces contain an N-linked carbohydrate addition site, the presence of which is required for dimer formation in IgA and J-chain incorporation and pentamer formation in IgM. However, the structure and composition of the N-linked carbohydrates in the tail-pieces differ, suggesting differences in the accessibility of the glycans to processing by glycosyltransferases.

The nucleotide and/or protein sequences of J-chains of human, and various vertebrate animal species, such as cow, mouse, avian, amphibian, and rabbit, have been reported. The human J-chain contains eight cysteine residues, two (Cys13 and Cys69) are involved in disulfide bridges with the α or μ-chains (in IgA and IgM, respectively), and six are involved in intrachain disulfide bridges (Cys13: Cys101, Cys72: Cys92, Cys109: Cys134). The three-dimensional crystal structure of the J-chain has not been reported.

Figure 5:
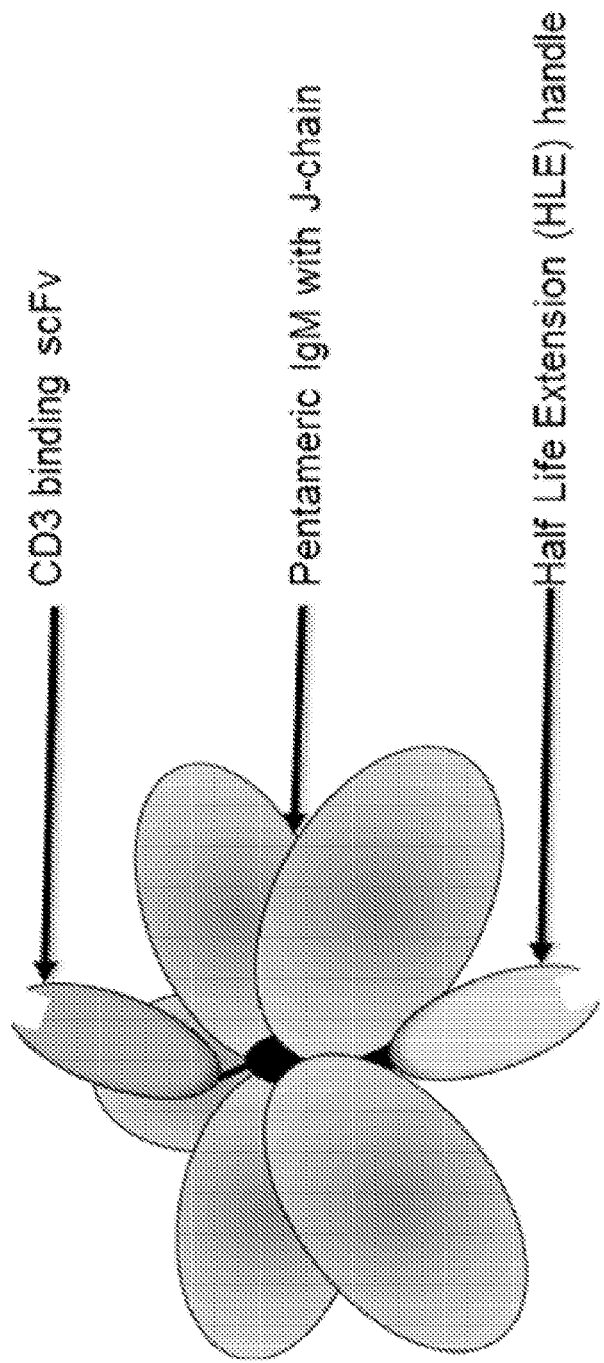
FIG. 5 is a schematic illustration of an asymmetric IgM pentamer with binding specificity for a target antigen, comprising an ADME-modulating moiety fused to the J-chain at one end, and a CD3 binding moiety at the opposite end of the J-chain.

The binding molecules of the present invention include a J-chain that comprises an ADME-modulating moiety that modulates one or more ADME characteristics of the binding molecule, without interfering with the ability of the IgM, IgA, IgG/IgM or IgG/IgA antibody to bind to its binding target(s). A binding molecule can, for example, be an IgM antibody, an IgA antibody, or an IgG/IgM or IgG/IgA hybrid antibody, which may contain an IgM or IgA tail-piece at the IgG heavy chain and thus combine the properties of IgG and IgA or IgA, including the ability to incorporate and form polymers with a modified J-chain whose ADME-modulating moiety modulates an ADME characteristic of the binding molecule. For further details on IgG/IgM and IgG/IgA hybrid antibodies see, e.g., Koteswara et al., *Clinical Immu-* nology 2001, 101(1):21-31. An illustration of an example binding molecule in accordance with aspects of the invention is depicted in FIG. 5. The depicted binding molecule comprises an IgM pentamer with binding specificity for a target antigen, and comprises an ADME-modulating moiety attached to the J-chain.

An ADME-modulating moiety in accordance with embodiments of the invention can include, without limitation, antibodies, antigen-binding fragments of antibodies, antibody-like molecules, antigen-binding fragments of antibody-like molecules, proteins, ligands and receptors. It is emphasized that any type of ADME-modulating moiety can be introduced into a J-chain, following the teaching of the present disclosure, by appropriately selecting the location and type of addition (e.g., direct or indirect fusion, chemical tethering, etc.).

In some embodiments, a binding molecule comprises an amino acid sequence listed in Table 10. In some embodiments, a binding molecule comprises an amino acid sequence that is substantially similar to an amino acid sequence listed in Table 10, for example, has at least about 80% amino acid sequence identity, alternatively, has about 81%, 82%, 83%, 84%, 85%, 86%, 87%, 88%, 89%, 90%, 91%, 92%, 93%, 94%, 95%, 96%, 97%, 98%, 99%. 99.5%, or about 99.9% amino acid sequence identity to an amino acid sequence that is listed in Table 10.

In a preferred embodiment, an ADME-modulating moiety comprises an antibody or an antigen-binding fragment of an antibody (also referred to as an "antibody fragment"), including monospecific, bispecific, and multi-specific antibodies and antibody fragments, that modulates an ADME characteristic of the binding molecule. The term "antibody fragment" is used in the broadest sense and includes, without limitation, Fab, Fab', F(ab')$_2$, scFab, scFv, and (scFv)$_2$ fragments, complementarity determining region (CDR) fragments, linear antibodies, single-chain antibody molecules, minibodies, and multi-specific antibodies formed from antibody fragments. In a preferred embodiment, the antibody fragment is an scFv.

In another preferred embodiment, an ADME-modulating moiety comprises an antibody-like molecule, such as, for example, a human domain antibody (dAb), Dual-Affinity Re-Targeting (DART) molecule, a diabody, a di-diabody, dual-variable domain antibody, a Stacked Variable Domain antibody, a Small Modular ImmunoPharmaceutical (SMIP), a Surrobody, a strand-exchange engineered domain (SEED)-body, VHH (e.g., a camelid-like antibody molecule), or TandAb that functions by modulating an ADME characteristic of the binding molecule.

An ADME-modulating moiety can be introduced into a native J-chain sequence at any location that allows the ADME-modulating moiety to modulate an ADME characteristic of the binding molecule without interfering with the binding of the recipient IgM, IgA, IgG/IgM or IgG/IgA molecule to its binding target or binding targets. Preferred locations include at or near the C-terminus, at or near the N-terminus or at an internal location that, based on the three-dimensional structure of the J-chain, is accessible. In preferred embodiments, an ADME-modulating moiety is introduced into a native sequence J-chain within about 10 residues from the C-terminus or within about 10 amino acid residues from the N-terminus, where the native sequence J-chain preferably is human J-chain of SEQ ID NO: 1. In another embodiment, an ADME-modulating moiety is introduced into the native sequence human J-chain of SEQ ID NO: 1 in between cysteine residues 92 and 101 of SEQ ID NO: 1, or at an equivalent location of another native sequence J-chain. In a further embodiment, an ADME-modulating moiety is introduced into a native sequence J-chain, such as a J-chain of SEQ ID NO: 1, at or near a glycosylation site. Most preferably, an ADME-modulating moiety is introduced into the native sequence human J-chain of SEQ ID NO: 1 within about 10 amino acid residues from the C-terminus.

Introduction can be accomplished by direct or indirect fusion, i.e., by the combination of an ADME-modulating moiety amino acid sequences in one polypeptide chain by in-frame combination of their coding nucleotide sequences, with or without a peptide linker. The peptide linker (indirect fusion), if used, may, for example, be about 1 to 50, or about 1 to 40, or about 1 to 30, or about 1 to 20, or about 1 to 10, or about 10 to 20 amino acid residues, and may be present at one or both ends of an ADME-modulating moiety to be introduced into a J-chain sequence. In a preferred embodiment, the peptide linker is about 10 to 20, or 10 to 15 amino acids long. In another preferred embodiment, the peptide linker is 15 amino acids long.

An ADME-modulating moiety can also be appended to a native J-chain sequence by chemical linkage using heterobifunctional protein crosslinkers containing two different functional groups, which have their own reactivity and selectivity. These crosslinkers can be used in a one step process or can be used to create activated proteins, which can often be preserved and reacted with the second biomolecule in a separate step. Thus, for example, a heterobifunctional crosslinking reagent can be used to form conjugates between a J-chain and an ADME-modulating moiety. The reactive groups include, without limitation, imine reactive groups (such as NHS or sulfo-NHS), maleimide groups, and the like. Such crosslinkers, which can be cleavable or non-cleavable, have been used, for example, in the formation of hapten carrier proteins and in preparing enzyme-antibody conjugates. Chemically, the cleavable crosslinkers specifically include, without limitation, disulfide-based, hydrazone, and peptide linkers. A well-known and much studied enzyme-labile linker is a valine-citrulline linker, but other peptide linkers are also known and suitable. Typical representatives of non-cleavable linkers include thioethers, such as SMCC (N-succinimidyl-4-(N-maleimidomethyl)-cyclohexane-1-carboxylate). For further details see, e.g., Ducry L and Stump B, *Bioconjugate Chem.* 2010, 21:5-13, the entire disclosure of which is expressly incorporated by reference herein. For listing of further suitable linkers see, e.g., Klein et al., *Protein Engineering, Design & Selection;* 2014, 27(10): 325-330, the entire disclosure of which is expressly incorporated by reference herein.

In some embodiments, a modified J-chain comprises one extraneous ADME-modulating moiety. In some embodiments, a modified J-chain comprises more than one ADME-modulating moiety. For example, in some embodiments, one ADME-modulating moiety is introduced into a modified J-chain at either the N-terminus or the C-terminus. In some embodiments, a first ADME-modulating moiety is introduced into a modified J-chain at the N-terminus, and a second ADME-moiety is introduced into the same modified J-chain at the C-terminus. In some embodiments, an ADME-modulating moiety is introduced into a modified J-chain, and a binding moiety is introduced into the same modified J-chain. For examples, in some embodiments, an ADME-modulating moiety is introduced into a modified J-chain at the N-terminus, and a binding moiety (e.g., a CD3-binding antibody fragment, e.g., a CD3-binding scFv antibody fragment) is introduced into the same modified J-chain at the C-terminus. In some embodiments, an ADME-modulating moiety is introduced into a modified J-chain at the C-terminus, and a binding moiety (e.g., a CD3-binding antibody fragment, e.g., a CD3-binding scFv antibody fragment) is introduced into the same modified J-chain at the N-terminus. A binding molecule that comprises a binding moiety at both the N-terminus and the C-terminus of the J-chain is referred to herein as a binding molecule that comprises a "bidentate" J-chain.

The modified J-chain may be produced by well-known techniques of recombinant DNA technology, e.g., by expressing a nucleic acid encoding the modified J-chain in a suitable prokaryotic or eukaryotic host organism, such as CHO cells or *E. coli*. Thus, the modified J-chain may, for example, be expressed in *E. coli*, as described by Symersky et al., *Mol Immunol* 2000, 37:133-140.

In one embodiment, the J-chain can be initially modified by insertion of an enzyme recognition site, and post-translationally modified by a peptide or non-peptide linker, which can tether any extraneous ADME-modulating moiety to the J-chain.

The modified J-chain can also be co-expressed with the heavy and light chains of the recipient IgM, IgA, IgG/IgM or IgG/IgA antibody. Although due to its complex structure, the large scale production of recombinant IgM has been difficult, several recombinant production systems for IgM using non-lymphoid cells have been reported, including co-expression of the IgM heavy (H) and light (L) chains in C6 glioma cells, CHO cells, and HeLa cells (see, e.g., WO89/01975 and Wood et al., *J. Immunol.* 145, 3011-3016 (1990) for expression in CHO cells). Expression of an IgM monoclonal antibody in *E. coli*, with or without a J-chain is described, e.g., in Azuma et al., *Clin Cancer Res* 2007, 13(9):2745-2750. Production of IgM in an immortalized human retina cell line expressing E1A and E1B proteins of an adenovirus is described in U. S. Application Publication No. 20060063234.

The recipient IgM, IgA, IgG/IgM or IgG/IgA antibody may be monospecific, bispecific or multi-specific. Bispecific and multi-specific IgM and IgA binding molecules, including antibodies, are described, for example, in PCT Application No. PCT/US2014/054079 and PCT/US2015/015268, the entire disclosures of which are expressly incorporated by reference herein.

A subject binding molecule can bind to any binding target via the IgM, IgA, IgG/IgM or IgG/IgA antibody, while an ADME-modulating moiety located on the J-chain modulates one or more ADME characteristics of the binding molecule. As such, the subject binding molecules can be used to provide high avidity binding to a target that is targeted by the IgM, IgA, IgG/IgM or IgG/IgA antibody, while the ADME-modulating moiety on the J-chain modulates one or more ADME characteristics of the binding molecule. Different types of ADME-modulating moieties are described herein, as are different classes of targets that can be targeted by an antibody portion of a subject binding molecule.

ADME-Modulating Moieties that Reduce Clearance

Aspects of the invention include binding molecules having an ADME-modulating moiety that reduces clearance of a binding molecule from the circulation of a subject, thereby increasing the half-life of the binding molecule in the subject. Albumin binding is known in the art as a general strategy for improving the pharmacokinetics of a protein. For example, non-covalent association with albumin has been shown to extend the half-life of short lived proteins. E.g., Dennis, Mark S. et al., *J. Biol. Chem.*, 2002, 277: 35035-35043, the disclosure of which is incorporated by reference herein in its entirety. As such, the use of albumin (human serum albumin), albumin-like proteins, albumin binding peptides, albumin binding antibody moieties (e.g., albumin binding scFv antibody fragments) as ADME-modulating moieties in a subject binding molecule provides an effective strategy for manipulating the pharmacokinetics of a binding molecule. In addition, the neonatal Fc receptor (FcRn) is known to provide a recycling pathway that provides immunoglobulin molecules with a longer circulating half-life. E.g., Roopenian D. C. et al., *Nature Reviews Immunology* 7, 715-725 (2007). As such, the use of FcRn-binding proteins, Fc domains that bind to FcRn, or antibody moieties that bind to FcRn, also provide an effective strategy for manipulating the pharmacokinetics of a binding molecule. Without being held to theory, in some embodiments, ADME-modulating moieties that bind to FcRn provide an extended half-life by accessing an FcRn-mediated recycling pathway, rather than merely providing extended half-life due to an increase in the molecular weight of the binding compound.

In some embodiments, an ADME-modulating moiety comprises an albumin protein. Albumin proteins are soluble, non-glycosylated proteins that are commonly found in blood plasma. Albumin proteins are known to interact with the FcRn-mediated recycling pathway, and as a result, have an extraordinarily long circulatory half-life.

In certain embodiments, an ADME-modulating moiety binds to an albumin protein, thereby connecting itself to an albumin protein and taking advantage of the FcRn-mediated recycling pathway. As such, in certain embodiments, an ADME-modulating moiety comprises an albumin binding peptide. Non-limiting examples of albumin-binding peptides are described in US Patent Publication No. US20050287153, the disclosure of which is incorporated by reference herein in its entirety. In some embodiments, an ADME-modulating moiety comprises an albumin-binding antibody moiety. Non-limiting examples of antibody moieties that bind to albumin include anti-albumin scFv, anti-albumin VHH, anti-albumin scFab, and anti-albumin dAb.

In some embodiments, an ADME-modulating moiety comprises an FcRn-binding peptide. In certain embodiments, an ADME-modulating moiety comprises an FcRn-binding antibody moiety. In some embodiments, an ADME-modulating moiety comprises an Fc domain of an immunoglobulin molecule that is bound by an FcRn receptor. Non-limiting examples of ADME-modulating moieties that reduce the clearance of a binding molecule are provided below in Table 1. Non-limiting examples of proteins that can be used to generate an antibody moiety that can be used as an ADME-modulating moiety in the subject binding molecules are provided in Table 1.

TABLE 1

| Sequence information for ADME-modulating moieties | |
|---|---|
| ADME-modulating moiety | Amino acid sequence information |
| albumin | GenBank Accession No.: NP_000468.1 |
| albumin binding peptide | DLCLRDWGCLW (SEQ ID NO: 2) |
| albumin binding peptide | DICLPRWGCLW (SEQ ID NO: 3) |
| albumin binding peptide | MEDICLPRWGCLWGD (SEQ ID NO: 4) |

TABLE 1-continued

Sequence information for ADME-modulating moieties

| ADME-modulating moiety | Amino acid sequence information |
|---|---|
| albumin binding peptide | QRLMEDICLPRWGCLWEDDE (SEQ ID NO: 5) |
| albumin binding peptide | QGLIGDICLPRWGCLWGRSV (SEQ ID NO: 6) |
| albumin binding peptide | QGLIGDICLPRWGCLWGRSVK (SEQ ID NO: 7) |
| albumin binding peptide | EDICLPRWGCLWEDD (SEQ ID NO: 8) |
| albumin binding peptide | RLMEDICLPRWGCLWEDD (SEQ ID NO: 9) |
| albumin binding peptide | MEDICLPRWGCLWEDD (SEQ ID NO: 10) |
| albumin binding peptide | MEDICLPRWGCLWED (SEQ ID NO: 11) |
| albumin binding peptide | RLMEDICLARWGCLWEDD (SEQ ID NO: 12) |
| albumin binding peptide | EVRSFCTRWPAEKSCKPLRG (SEQ ID NO: 13) |
| albumin binding peptide | RAPESFVCYWETICFERSEQ (SEQ ID NO: 14) |
| albumin binding peptide | EMCYFPGICWM (SEQ ID NO: 15) |
| FcRn | GenBank Accession No.: P55899.1 |
| Fc domain of IgG1 | GenBank Accession No.: AAB24269.1 |
| Fc domain of IgG2 | GenBank Accession No.: AAR26706.1 |
| Fc domain of IgG3 | GenBank Accession No.: ACO54886.1 |
| Fc domain of IgG4 | GenBank Accession No.: AAG00912.1 |

ADME-Modulating Moieties that Enhance Penetration of the Blood Brain Barrier

Aspects of the invention include binding molecules having an ADME-modulating moiety that enhances the ability of a binding molecule to penetrate the blood brain barrier of a subject, thereby increasing the concentration of the binding molecule in the brain extracellular fluid and central nervous system. The blood brain barrier is formed by brain endothelial cells, which are connected by tight junctions. The blood brain barrier permits selective transport of certain molecules into the brain extracellular fluid and the central nervous system, while denying passage to others.

Aspects of the invention include binding molecules having a moiety that binds to one or more targets in a receptor-mediated transcytosis (RMT) pathway, thereby facilitating transportation of a binding molecule across the blood brain barrier. Specific non-limiting examples of binding targets that are associated with an RMT pathway include: transferrin, transferrin receptor, insulin, insulin receptor, IGF-1, IGF-1 receptor, leptin, leptin receptor, basigin, Glut1 and CD98hc. RMT pathways are known in the art to facilitate passage of their respective ligands through the blood brain barrier and into the brain extracellular fluid and central nervous system of a mammalian subject. E.g., Dennis et al., *Neuropsychopharmacology Reviews* (2012) 37, 302-303, the disclosure of which is incorporated by reference herein in its entirety; Joy Yu Zuchero et al., Neuron 89, 70-82 (2016), the disclosure of which is incorporated by reference herein in its entirety. As such, the use of RMT binding moieties (e.g., antibody moieties that bind to an RMT pathway target (e.g., an RMT-associated cell surface receptor and/or its associated ligand)) as ADME-modulating moieties in a subject binding molecule provides an effective strategy for enhancing penetration of the blood brain barrier and increasing the concentration of the binding molecule in the brain extracellular fluid and the central nervous system. Non-limiting examples of antibody moieties that can bind to an RMT pathway target include scFv, $V_HH$, scFab, and dAb moieties.

In some embodiments, an ADME-modulating moiety comprises an antibody moiety that binds to a receptor in an RMT pathway. In some embodiments, an ADME-modulating moiety comprises an antibody moiety that binds to a ligand in an RMT pathway. In some embodiments, an ADME-modulating moiety comprises a ligand, or a portion of a ligand that is capable of binding to a receptor, in an RMT pathway (e.g., comprises a transferrin protein, or comprises at least a portion of a transferrin protein that is capable of binding to a transferrin receptor).

In some embodiments, an ADME-modulating moiety comprises a transferrin receptor-binding antibody moiety (e.g., a transferrin receptor-binding scFv). In some embodiments, an ADME-modulating moiety comprises a transferrin-binding antibody moiety (e.g., a transferrin-binding scFv). In certain embodiments, an ADME-modulating moiety comprises an insulin receptor-binding antibody moiety (e.g., an insulin receptor-binding scFv). In certain embodiments, an ADME-modulating moiety comprises an insulin-binding antibody moiety (e.g., an insulin-binding scFv). In certain embodiments, an ADME-modulating moiety comprises an IGF-1 receptor-binding antibody moiety (e.g., an IGF-1 receptor-binding scFv). In certain embodiments, an ADME-modulating moiety comprises an IGF-1-binding antibody moiety (e.g., an IGF-1-binding scFv). In certain embodiments, an ADME-modulating moiety comprises a leptin receptor-binding antibody moiety (e.g., a leptin receptor-binding scFv). In certain embodiments, an ADME-modulating moiety comprises a leptin-binding antibody moiety (e.g., a leptin-binding scFv). In some embodiments, an ADME-modulating moiety comprises a basigin-binding antibody moiety (e.g., a basigin-binding scFv). In some embodiments, an ADME-modulating moiety comprises a Glut1-binding antibody moiety (e.g., a Glut1-binding scFv). In some embodiments, an ADME-modulating moiety comprises a CD98hc-binding antibody moiety (e.g., a CD98hc-binding scFv).

In some embodiments, an ADME-modulating moiety comprises a transferrin protein. In some embodiments, an ADME-modulating moiety comprises an IGF-1 protein. In some embodiments, an ADME-modulating moiety comprises a leptin protein. In some embodiments, an ADME-modulating moiety comprises a basigin protein. In some embodiments, an ADME-modulating moiety comprises a Glut1 protein. In some embodiments, an ADME-modulating moiety comprises a CD98hc protein. Non-limiting examples of proteins that can be used to generate an antibody moiety that can be used as an ADME-modulating moiety that enhances penetration of the blood brain barrier are provided in Table 2.

TABLE 2

Sequence information for ADME-modulating moieties

| ADME-modulating moiety | GenBank Accession No. |
|---|---|
| Transferrin receptor | AAA61153.1 |
| Insulin receptor | P06213.4 |
| IGF-1 receptor | P08069.1 |
| Leptin receptor | P48357.2 |
| Transferrin | AAB22049.1 |
| Leptin | AAH69452.1 |
| Insulin | AAA59172.1 |
| IGF-1 | CAA01954.1 |
| basigin | BAA08109.1 |
| Glut1 | P11166.2 |
| CD98hc (4F2 cell-surface antigen heavy chain) | P08195.3 |

ADME-Modulating Moieties that Increase Half-Life in Extra-Vascular Spaces

Aspects of the invention include binding molecules having an ADME-modulating moiety that increases a half-life of a binding molecule in an extra-vascular space of a subject. Therapeutic proteins that are delivered directly to extra-vascular spaces such as intra-articular spaces, or intra-vitreal spaces, typically have a characteristically short half-life in the extra-vascular space. E.g., Mordenti, J. et al., *Toxicological Sciences* 52, 101-106 (1999); Mordenti, J. et al., *Toxicological Sciences* 27(5), 536-544 (1999).

Hyaluronic acid is an anionic, non-sulfated glycosaminoglycan that is a major component of the extracellular matrix in certain extra-vascular spaces, such as intra-articular spaces and intra-vitreal spaces. As such, the use of compounds that bind to hyaluronic acid as ADME-modulating moieties provides an effective strategy for retaining a therapeutic molecule in such an extracellular space. The structure of hyaluronic acid is provided in FIG. 15.

Tumor necrosis factor-inducible gene 6 protein (TSG-6) is a 30 kDa secreted protein that contains a hyaluronan-binding domain. The hyaluronan-binding domain interacts with extracellular matrix in extra-vascular spaces and is involved with cell migration. As such, the use of TSG-6 as an ADME-modulating moiety provides an effective strategy for retaining a therapeutic molecule in an extracellular space.

In some embodiments, an ADME-modulating moiety comprises a hyaluronic acid binding protein (HABP). In some embodiments, an ADME-modulating moiety comprises a TSG-6 protein. In certain embodiments, an ADME-modulating moiety comprises a hyaluronic acid-binding antibody moiety. In certain embodiments, an ADME-modulating moiety comprises a TSG-6-binding antibody moiety. Non-limiting examples of antibody moieties include scFv, VHH, scFab, and dAb moieties. Non-limiting examples of ADME-modulating moieties that retain a binding molecule in an extracellular space are provided below in Table 3.

TABLE 3

Sequence information for ADME-modulating moieties

| ADME-modulating moiety | Amino acid sequence information |
|---|---|
| Hyaluronic acid binding protein (HABP) | GenBank Accession No.: 2207280A |
| TSG-6 | GenBank Accession No.: CAD13434.1 |

Antagonist Targets

Aspects of the invention include binding molecules having an IgM, IgA, IgG/IgM or IgG/IgA antibody that antagonizes a T-cell inhibitory signaling pathway. T-cell inhibitory signaling pathways are known in the art, and include, without limitation, those described in Pardoll et al. Non-limiting examples of T-cell inhibitory signaling pathways and components thereof are described in further detail below.

One example of a T-cell inhibitory signaling pathway is the signaling pathway involving programmed cell death-1 (PD-1) and its ligand, programmed cell death ligand-1 (PD-L1). PD-1 is an inhibitory cell surface receptor protein of the immunoglobulin superfamily, and is involved in the regulation of T-cell function in immunity and self-tolerance. PD-L1 interacts with PD-1 on the surface of T-cells, and inhibits proliferation of T-cells by blocking cell cycle progression and cytokine production. Id.

Another example of a T-cell inhibitory signaling pathway is the signaling pathway involving T-cell immunoglobulin and mucin domain 3 (TIM3). TIM3 is a cell surface glycoprotein that is expressed on the surface of T-cells, and functions as an inhibitory molecule that is involved in the termination of Th1 cells. Id.

Another example of a T-cell inhibitory signaling pathway is the signaling pathway involving lymphocyte-activation gene 3 (LAG3). LAG3 belongs to the immunoglobulin superfamily, and functions as an inhibitor of cellular proliferation, activation and homeostasis of T-cells. Id.

As reviewed above, the subject binding molecules comprise a J-chain that comprises an ADME-modulating moiety. In some embodiments, an IgM, IgA, IgG/IgM or IgG/IgA antibody binds to a target that is involved in a T-cell inhibitory signaling pathway and antagonizes the inhibitory signaling pathway, thereby blocking or diminishing inhibitory signals that are received by a T-cell via the pathway, while the ADME-modulating moiety on the J-chain modulates an ADME characteristic of the binding molecule. Due to their higher avidity, the subject IgM, IgA, IgG/IgM or IgG/IgA antibodies act more effectively as antagonists when directed against T-cell inhibitory signaling pathway targets, as compared to IgG antibodies, which only have two binding sites. As a result, the T-cell's immune response is not blocked, halted or diminished, or, at least, the inhibition of the T-cell's immune response is reduced or diminished. The antibody of a subject binding molecule can be used to antagonize any T-cell inhibitory signaling pathway, including but not limited to the inhibitory signaling pathways that involve the proteins listed in Table 4, below. The GenBank Accession Numbers corresponding to the human protein sequences of these T-cell inhibitory signaling pathway targets are provided in Table 4, below.

TABLE 4

Sequence information for T-cell stimulatory signaling pathway targets

| T-cell stimulatory signaling pathway member: | GenBank Accession No. |
|---|---|
| PD-1 | AAC51773.1 |
| PD-L1 | Q9NZQ7.1 |
| TIM3 | AAL65158.1 |
| LAG3 | AAH52589.1 |

Agonist Targets

Aspects of the invention include binding molecules having an IgM, IgA, IgG/IgM or IgG/IgA antibody that agonizes a T-cell stimulatory signaling pathway. T-cell stimulatory signaling pathways are known in the art, and include, without limitation, those described in Pardoll et al. Non-limiting examples of T-cell stimulatory signaling pathways and components thereof are described in further detail below.

CD137 is a member of the tumor necrosis factor receptor (TNF-R) superfamily, and is expressed on the surface of T-cells. Its function is to stimulate T-cell proliferation and cytokine secretion. E.g., Pardoll at 254. OX40 is another member of the tumor necrosis factor receptor superfamily that is expressed on T-cells, and it functions by delivering a stimulatory signal to T-cells that helps to maintain the immune response over time. Id.

Another T-cell stimulatory signaling pathway involves CD40. CD40 is a member of the tumor necrosis factor receptor superfamily, and is expressed on antigen presenting cells. Engagement of CD40 with its ligand CD40L results in various T-cell stimulatory signals. Id.

Another T-cell stimulatory signaling pathway involves gluococorticoid-induced TNFR-related protein (GITR). GITR is a member of the tumor necrosis factor receptor superfamily, and is expressed on T-cells. It functions by increasing T-cell proliferation, activation and cytokine production. E.g., Nocentini, G. et al., Proc Natl Acad Sci USA. 1997 Jun. 10; 94(12):6216-21.

CD27 is another protein that is involved in a T-cell stimulatory signaling pathway. Another member of the tumor necrosis factor receptor superfamily, CD27 is expressed on the surface of T-cells and functions by delivering a stimulatory signal to T-cells when it interacts with CD70. E.g., Pardoll at 254.

Another T-cell stimulatory signaling pathway involves herpesvirus entry mediator (HVEM). HVEM is a member of the tumor necrosis factor receptor superfamily, and is expressed on the surface of antigen presenting cells. When HVEM interacts with certain ligands, such as CD258, it delivers a stimulatory signal to T-cells. Id.

As reviewed above, the subject binding molecules comprise ADME-modulating moiety on the J-chain that modulates an ADME characteristic of the binding molecule. In some embodiments, an IgM, IgA, IgG/IgM or IgG/IgA antibody binds to a target that is involved in a T-cell stimulatory signaling pathway and agonizes the stimulatory signaling pathway, thereby maintaining or increasing stimulatory signals that are received by a T-cell via the pathway, while the ADME-modulating moiety on the J-chain modulates an ADME characteristic of the binding molecule. Due to their higher avidity, the subject IgM, IgA, IgG/IgM or IgG/IgA antibodies act more effectively as agonists when directed against T-cell stimulatory signaling pathway targets, as compared to IgG antibodies, which only have two binding sites. As a result, a T-cell's immune response is maintained or increased. An antibody of a subject binding molecule can be used to agonize any T-cell stimulatory signaling pathway, including but not limited to the stimulatory signaling pathways that involve the proteins listed in Table 5, below. The GenBank Accession Numbers corresponding to the human protein sequences of these T-cell stimulatory signaling pathway targets are provided in Table 5, below.

TABLE 5

Sequence information for T-cell stimulatory signaling pathway targets

| T-cell stimulatory signaling pathway member: | GenBank Accession No. |
|---|---|
| CD137 (4-1BB) | NP_001552.2 |
| OX40 | CAE11757.1 |
| CD40 | P25942.1 |
| GITR | Q9Y5U5.1 |
| CD27 | P26842.2 |
| HVEM | AAQ89238.1 |

Other non-limiting examples of T-cell stimulatory signaling pathways include those mediated by: TNFR1 (DR1) (GenBank Accession No. P19438.1); TNFR2 (GenBank Accession No. P20333.3); Fas (CD95, Apo1, DR2) (GenBank Accession No. AAH12479.1); CD30 (GenBank Accession No. AAA51947.1); TRAILR1 (DR4, Apo2) (GenBank Accession No. 000220.3); DR5 (TRAILR2) (GenBank Accession No. 014763.2); TRAILR3 (DcR1) (GenBank Accession No. 014798.3); TRAILR4 (DcR2) (GenBank Accession No. Q9UBN6.1); OPG (OCIF) (GenBank Accession No. 000300.3); TWEAKR (FN14) (GenBank Accession No. Q9NP84.1); DcR3 (GenBank Accession No. O95407.1); DR3 (GenBank Accession No. AAQ88676.1); EDAR (GenBank Accession No. Q9UNE0.1); and XEDAR (GenBank Accession No. AAQ89952.1). See, e.g., Aggarwal et al., Blood, 119:651-665, 2012, the disclosure of which is herein incorporated by reference in its entirety. In some embodiments, an IgM, IgA, IgG/IgM or IgG/IgA antibody binds to any one of these targets and agonizes a T-cell stimulatory signaling pathway, thereby maintaining or increasing stimulatory signals that are received by a T-cell via the pathway, while the ADME-modulating moiety on the J-chain modulates an ADME characteristic of the binding molecule.

Low Level Expression Targets

Aspects of the invention include binding molecules having an IgM, IgA, IgG/IgM or IgG/IgA antibody that binds to a low level expression target. Due to their higher avidity, the subject binding molecules are more potent than IgG antibodies. As such, the subject binding molecules can be employed in settings where a particular binding target is expressed at a low level, and where higher avidity is beneficial in facilitating binding between an antibody and a target. An antibody of a subject binding molecule can be used to target any low level expression target. Specific examples of low level expression targets that may be targeted by an IgM, IgA, IgG/IgM or IgG/IgA antibody of the subject binding molecules include, without limitation, EGFR, HER2, HER3, EpCAM, CEACAM, Gp100, MAGE1 and PD-L1. The GenBank Accession Numbers corresponding to the human protein sequences of these targets are provided in Table 6, below.

TABLE 6

Sequence information for low level expression targets

| Target Name | GenBank Accession No. |
| --- | --- |
| EGFR | AAI18666.1 |
| HER2 | P04626.1 |
| HER3 | P21860.1 |
| EpCAM | P16422.2 |
| CEACAM | P06731.3 |
| Gp100 | AAC60634.1 |
| MAGE1 | NP_004979.3 |
| PD-L1 | Q9NZQ7.1 |

Low Affinity Targets

Figure 14:
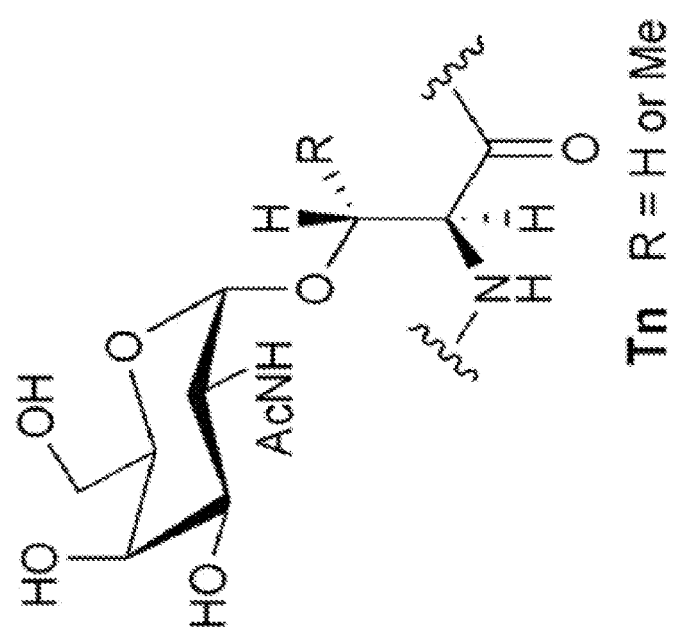
FIG. 14 is an illustration of the structure of Tn antigen.
Figure 15:
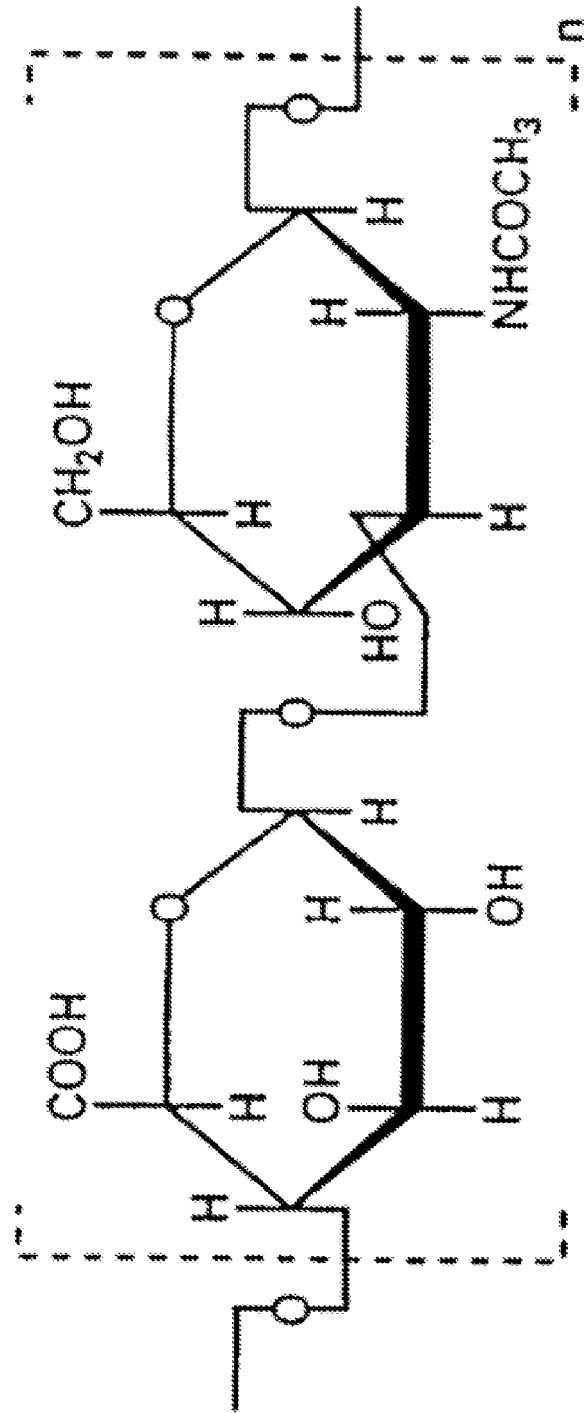
FIG. 15 is an illustration of the structure of hyaluronic acid.

Aspects of the invention include binding molecules having an IgM, IgA, IgG/IgM or IgG/IgA antibody that binds to a low affinity target. Due to their higher avidity, the subject binding molecules are more potent than IgG antibodies. As such, the subject binding molecules can be employed in settings where a particular binding target has a low binding affinity, and where higher avidity is beneficial in facilitating binding between an antibody and a target. An antibody of a subject binding molecule can be used to target any low affinity target. Specific examples of low affinity targets that may be targeted by an IgM, IgA, IgG/IgM or IgG/IgA antibody of the subject binding molecules include, without limitation, NY-ESO-1, Sialyl Lewis X antigen, and Tn antigen. The GenBank Accession Numbers corresponding to the human protein sequences of NY-ESO-1 and Sialyl Lewis X antigen are provided in Table 7, below. The structure of Tn antigen is provided in FIG. 14.

TABLE 7

Sequence information for low affinity targets

| Target Name | GenBank Accession No. |
| --- | --- |
| NY-ESO-1 | CAA05908.1 |
| Sialyl Lewis X antigen | NP_001241688.1 |

Hematologic Cancer Targets

Aspects of the invention include binding molecules having an IgM, IgA, IgG/IgM or IgG/IgA antibody that binds to a hematologic cancer target. Due to their higher avidity, the subject binding molecules are more potent than IgG antibodies. As such, the subject binding molecules can be employed in settings where a particular binding target is expressed at a low level, as is the case in certain hematologic cancers. The higher avidity of the subject binding molecules facilitates binding between an antibody and a target. An antibody of a subject binding molecule can be used to target any binding target, such as a low level expression target on a hematologic cancer cell. Specific examples of hematologic cancer targets that can be targeted by an IgM, IgA, IgG/IgM or IgG/IgA antibody of the subject binding molecules include, without limitation, CD19, CD20, CD22, CD33, CD38, CD52 and CD70. The GenBank Accession Numbers corresponding to the human protein sequences of these targets are provided in Table 8, below.

TABLE 8

Sequence information for hematologic cancer targets

| Target Name | GenBank Accession No. |
| --- | --- |
| CD19 | AAA69966.1 |
| CD20 | NP_690605.1 |
| CD22 | P20273.2 |
| CD33 | P20138.2 |
| CD38 | BAA18966.1 |
| CD52 | AJC19276.1 |
| CD70 | NP_001243.1 |

Other Binding Targets

Aspects of the invention include binding molecules having an IgM, IgA, IgG/IgM or IgG/IgA antibody that binds to a target that is associated with a particular disease or disorder. Due to their higher avidity, the subject binding molecules are more potent than IgG antibodies. As such, the subject binding molecules can be employed in settings where high avidity binding to a particular binding target is desirable. An antibody of a subject binding molecule can be used to target any binding target. Specific examples of binding targets that can be targeted by an IgM, IgA, IgG/IgM or IgG/IgA antibody of the subject binding molecules include, without limitation, VEGF, TNF-alpha, amyloid beta, and Beta-secretase 1 (BACE) proteins. The GenBank Accession Numbers corresponding to the human protein sequences of these targets are provided in Table 9, below.

TABLE 9

Sequence information for other binding targets

| Target Name | GenBank Accession No. |
| --- | --- |
| VEGF | AAP86646.1 |
| TNF alpha | CAA26669.1 |
| Amyloid beta A4 | P05067.3 |
| BACE (Beta-secretase 1) | P56817.2 |

Applications of Binding Molecules with ADME-Modulating Moieties

Binding molecules comprising a modified J-chain that comprises an ADME-modulating moiety have widespread therapeutic and diagnostic applications, including but not limited to the treatment of various diseases by modulating one or more ADME characteristics of a binding molecule.

In some embodiments, the subject binding molecules comprising a modified J-chain may broadly be used for the treatment of any of a variety of cancers. It is anticipated that any type of tumor and any type of tumor-associated antigen may be targeted by the subject binding molecules. Examples of cancer types include, without limitation, acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer. However, the skilled artisan will realize that tumor-associated antigens are known in the art for virtually any type of cancer.

In some embodiments, the J-chain of a subject binding molecule includes an ADME-modulating moiety that reduces clearance of the binding molecule from the circulation of a subject, while the antibody antagonizes a T-cell inhibitory signaling pathway. Without being held to theory, the purpose of such a binding molecule is to increase the half-life of the binding molecule via the J-chain ADME-modulating moiety, while simultaneously blocking or decreasing T-cell inhibitory signaling via the antibody. Due to their increased avidity, the subject IgM, IgA, IgG/IgM and IgG/IgA antibodies act as effective antagonists when directed to certain binding targets, such as members of a T-cell inhibitory signaling pathway, as described above. Such binding molecules find utility, for example, in the treatment of diseases wherein blocking or decreasing the inhibition of a T-cell immune response is desirable, such as, e.g., certain cancers and immune disorders. Such cancers include, but are not limited to, epithelial cancers as well as hematologic cancers.

Epithelial cancers that are suitable for treatment with the subject binding molecules having an antagonist antibody and an ADME-modulating moiety on the J-chain include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. Hematologic cancers that are suitable for treatment with the subject binding molecules having an antagonist antibody and an ADME-modulating moiety on the J-chain include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, the J-chain of a subject binding molecule includes an ADME-modulating moiety that enhances penetration of the blood brain barrier by the binding molecule, while the antibody antagonizes a T-cell inhibitory signaling pathway. Without being held to theory, the purpose of such a binding molecule is to increase the concentration of the binding molecule in the brain extracellular fluid and the central nervous system via the J-chain ADME-modulating moiety, while simultaneously blocking or decreasing T-cell inhibitory signaling via the antibody. Due to their increased avidity, the subject IgM, IgA, IgG/IgM and IgG/IgA antibodies act as effective antagonists when directed to certain binding targets, such as members of a T-cell inhibitory signaling pathway, as described above. Such binding molecules find utility, for example, in the treatment of diseases wherein blocking or decreasing the inhibition of a T-cell immune response is desirable, such as, e.g., certain cancers and immune disorders of the brain and central nervous system. Such cancers include, but are not limited to, glioma, astrocytoma, meningioma, neuroma and oligodendroglioma.

In some embodiments, the J-chain of the subject binding molecules includes an ADME-modulating moiety that reduces clearance of the binding molecule from the circulation of a subject, while the antibody agonizes a T-cell stimulatory signaling pathway. Without being held to theory, the purpose of such a binding molecule is to increase the half-life of the binding molecule via the ADME-modulating moiety on the J-chain, while simultaneously maintaining or increasing T-cell stimulatory signaling via the antibody. Due to their increased avidity, the subject IgM, IgA, IgG/IgM and IgG/IgA antibodies act as super agonists when directed to certain binding targets, such as members of a T-cell stimulatory signaling pathway, as described above. Such binding molecules find utility, for example, in the treatment of diseases wherein maintenance or activation of a T-cell immune response is desirable, such as, e.g., certain cancers and immune disorders. Such cancers include, but are not limited to, epithelial cancers as well as hematologic cancers.

Epithelial cancers that are suitable for treatment with the subject binding molecules having an agonist antibody and an ADME-modulating moiety include on the J-chain include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. Hematologic cancers that are suitable for treatment with the subject binding molecules having an agonist antibody and an ADME-modulating moiety include on the J-chain include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, the J-chain of a subject binding molecule includes an ADME-modulating moiety that enhances penetration of the blood brain barrier by the binding molecule, while the antibody agonizes a T-cell stimulatory signaling pathway. Without being held to theory, the purpose of such a binding molecule is to increase the concentration of the binding molecule in the brain extracellular fluid and the central nervous system via the ADME-modulating moiety on the J-chain, while simultaneously maintaining or increasing T-cell stimulatory signaling via the antibody. Due to their increased avidity, the subject IgM, IgA, IgG/IgM and IgG/IgA antibodies act as super agonists when directed to certain binding targets, such as members of a T-cell stimulatory signaling pathway, as described above. Such binding molecules find utility, for example, in the treatment of diseases wherein maintenance or activation of a T-cell immune response is desirable, such as, e.g., certain cancers and immune disorders of the brain and central nervous system. Such cancers include, but are not limited to, glioma, astrocytoma, meningioma and oligodendroglioma.

In some embodiments, the J-chain of a subject binding molecule includes an ADME-modulating moiety that increases the half-life of the binding molecule, while the antibody binds to a low level expression target. Without being held to theory, the purpose of such a binding molecule is to increase the half-life of the binding molecule via the ADME-modulating moiety on the J-chain, while simultaneously binding to a low level expression target using the higher avidity of the subject IgM, IgA, IgG/IgM and IgG/IgA antibodies. Such binding molecules find utility in the treatment of diseases wherein high avidity binding to a low level expression target is beneficial, such as, for example, in certain cancers and immune disorders. For example, certain epithelial cancers are known to express tumor antigens that have a low level of expression, as described above. Such epithelial cancers include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. In some embodiments, the subject binding molecules find use in the treatment of any of these conditions.

In some embodiments, the J-chain of the subject binding molecules includes an ADME-modulating moiety that increases the half-life of the binding molecule, while the antibody binds to a low affinity target. Without being held to theory, the purpose of such a binding molecule is to increase the half-life of the binding molecule via the ADME-modulating moiety on the J-chain, while simultaneously binding to a low affinity target using the higher avidity of the subject IgM, IgA, IgG/IgM and IgG/IgA antibodies. As reviewed above, due to their increased avidity, the subject IgM, IgA, IgG/IgM and IgG/IgA antibodies, comprising a modified J-chain comprising an ADME-modulating moiety are especially advantageous in situations where IgG antibodies bind to their target with low affinity. Thus, in some embodiments, the IgM, IgA, IgG/IgM and IgG/IgA antibodies herein may comprise the binding domain of a therapeutic IgG antibody. Such binding molecules find utility in the treatment of diseases wherein high avidity binding to a low affinity target is beneficial, such as, for example, in certain cancers and immune disorders. For example, certain epithelial cancers are known to express tumor antigens that have a low binding affinity, as described above. Such epithelial cancers include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. In some embodiments, the subject binding molecules find use in the treatment of any of these conditions.

In some embodiments, the J-chain of a subject binding molecule includes an ADME-modulating moiety that increases the half-life of the binding molecule, while the antibody binds to a target on a hematologic cancer cell. Without being held to theory, the purpose of such a binding molecule is to increase the half-life of the binding molecule via the ADME-modulating moiety on the J-chain, while simultaneously binding to a hematologic cancer target using the higher avidity of the subject IgM, IgA, IgG/IgM and IgG/IgA antibodies. Such binding molecules find utility in the treatment of hematologic cancers wherein high avidity binding to a tumor antigen is beneficial. For example, certain hematologic cancers are known to express tumor antigens at a low level, as described above. Such hematologic cancers include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, the J-chain of a subject binding molecule includes an ADME-modulating moiety that increases the retention of the binding molecule in an extra-vascular space, while the antibody binds to a binding target in the extra-vascular space. Without being held to theory, the purpose of such a binding molecule is to increase the residence time of the binding molecule in the extra-vascular space via the ADME-modulating moiety on the J-chain, while simultaneously binding to a binding target using the higher avidity of the subject IgM, IgA, IgG/IgM and IgG/IgA antibodies. Such binding molecules find utility in the treatment of diseases or disorders wherein high avidity binding to a binding target in an extra-vascular space is beneficial. For example, tumor necrosis factor alpha (TNF alpha) is a binding target in the treatment of rheumatoid arthritis, which is an autoimmune disease that affects the joints of a subject. The subject binding molecules find use in the treatment of rheumatoid arthritis by providing high avidity binding to TNF alpha via the IgM, IgA, IgG/IgM or IgG/IgA antibody, while also providing extended retention time within an intra-articular space via the ADME-modulating moiety on the modified J-chain.

In another non-limiting example, vascular endothelial growth factor (VEGF) is a binding target in the treatment of age-related macular degeneration (AMD), which is a disease that affects the retina of a subject. The subject binding molecules find use in the treatment of AMD by providing high avidity binding to VEGF via the IgM, IgA, IgG/IgM or IgG/IgA antibody, while also providing extended retention time in an intra-vitreal space via the ADME-modulating moiety on the modified J-chain.

In some embodiments, the J-chain of a subject binding molecule includes an ADME-modulating moiety that enhances penetration of the blood brain barrier by the binding molecule, while the antibody binds to a binding target in the brain extracellular fluid or a central nervous system tissue. Without being held to theory, the purpose of such a binding molecule is to increase the concentration of the binding molecule in the brain extracellular fluid and central nervous system tissue via the ADME-modulating moiety on the J-chain, while simultaneously binding to a binding target using the higher avidity of the subject IgM, IgA, IgG/IgM and IgG/IgA antibodies. Such binding molecules find utility in the treatment of diseases or disorders wherein high avidity binding to a binding target in the brain extracellular fluid or central nervous system tissue is beneficial. For example, amyloid beta is a binding target in the treatment of Alzheimer's disease, which is a disease that affects the central nervous system of a subject. Beta secretase 1 (BACE) is also a binding target in the treatment of Alzheimer's disease. The subject binding molecules find use in the treatment of Alzheimer's disease by providing high avidity binding to, e.g., amyloid beta or BACE via the IgM, IgA, IgG/IgM or IgG/IgA antibody, while also providing increased concentration of the binding molecule within the brain extracellular fluid or central nervous system tissue via the ADME-modulating moiety on the modified J-chain.

Examples of IgM, IgA, IgG/IgM, or IgG/IgA antibodies including a modified J-chain that modulates an ADME characteristic of a binding molecule can include the binding regions of known IgG antibodies to tumor-associated antigens, such as, for example, blinatumomab (also known as MT103) (anti-CD19), CD19hA19 (anti-CD19, U.S. Pat. No. 7,109,304), hPAM4 (anti-mucin, U.S. Pat. No. 7,282,567), hA20 (anti-CD20, U.S. Pat. No. 7,251,164), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the disclosures of which are expressly incorporated by reference herein.

Other antibodies that can provide binding regions for use in combination with a modified J-chain that increases the half-life of a subject binding molecule include, for example, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), atalizumab (anti-.alpha.4 integrin), omalizumab (anti-IgE); anti-TNF-.alpha. antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), BENLYSTA® (Human Genome Sciences); antibodies for therapy of Alzheimer's disease such as Alz 50 (Ksiezak-Reding et al., 1987, J Biol Chem 263:7943-47), gantenerumab, solanezumab and infliximab; anti-fibrin antibodies like 59D8, T2G1s, MH1; anti-CD38 antibodies such as MOR03087 (MorphoSys AG), MOR202 (Celgene), HuMax-CD38 (Genmab) or daratumumab (Johnson & Johnson); trastuzumab (anti-HER2); tremelimumab (anti-CTLA4); urelumab (anti-CD137 (4-1BB)); vorsetuzumab (anti-CD70); duligotumab (anti-HER3); dacetuzumab (anti-CD40); varlilumab (anti-CD27); atezolizumab (anti-PD-L1); anti-MAGE1 antibodies such as MA454 (Thermo Scientific, Rockford, Ill.); anti-OX-40 antibodies such as ACT35 (Affymetrix eBioscience, San Diego, Calif.); anti-GITR antibodies such as 621 (BioLegend, San Diego, Calif.); anti-HVEM antibodies such as 122 (BioLegend, San Diego, Calif.); anti-TIM3 antibodies such as F38-2E2 (BioLegend, San Diego, Calif.); anti-LAG3 antibodies such as 3DS223H (Affymetrix eBioscience, San Diego, Calif.); anti-BTLA antibodies such as MIH26 (BioLegend, San Diego, Calif.); anti-VISTA antibodies such as MAB71261 (R&D Systems, Minneapolis, Minn.); anti-TIGIT antibodies such as MBSA43 (Affymetrix eBioscience, San Diego, Calif.); anti-CEACAM antibodies such as D14HD11 (abcam, Cambridge, Mass.); anti-Gp100 antibodies such as ab52058 (abcam, Cambridge, Mass.); anti-NY-ESO-1 antibodies such as E978 (Thermo Scientific, Rockford, Ill.); anti-Sialyl Lewis X antigen antibodies such as MAB2096 (EMD Millipore, Billerica, Mass.); anti-Tn antigen antibodies such as MA1-90544 (Thermo Scientific, Rockford, Ill.); anti-HIV antibodies such as P4/D10 (U.S. Pat. No. 8,333,971), Ab 75, Ab 76, Ab 77 (Paulik et al., 1999, Biochem Pharmacol 58:1781-90), as well as the anti-HIV antibodies described in U.S. Pat. Nos. 5,831,034, 5,911,989, and Vcelar et al., AIDS 2007; 21(16):2161-2170 and Joos et al., Antimicrob. Agents Chemother. 2006; 50(5): 1773-9; anti-albumin antibodies such as ab106582 (abcam, Cambridge, Mass.); anti-FcRn antibodies such as sc-271745 (Santa Cruz Biotechnology, Santa Cruz, Calif.); anti-transferrin receptor antibodies such as ab61021 (abcam, Cambridge, Mass.); anti-insulin receptor antibodies such as ab5500 (abcam, Cambridge, Mass.); anti-IGF-1 receptor antibodies such as ab5681 (abcam, Cambridge, Mass.); anti-leptin receptor antibodies such as ab5593 (abcam, Cambridge, Mass.); anti-TNF alpha antibodies such as ab31908 (abcam, Cambridge, Mass.); anti-amyloid beta antibodies such as ab2539 (abcam, Cambridge, Mass.); anti-hyaluronic acid antibodies such as ab53842 (abcam, Cambridge, Mass.); anti-BACE antibodies such as ab2077 (abcam, Cambridge, Mass.); anti-TSG-6 antibodies such as ab204049 (abcam, Cambridge, Mass.).

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or

IgG/IgA antibody binds to CD137 and agonizes a CD137-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to EGFR has an ADME-modulating moiety on the J-chain that comprises human serum albumin. In one specific embodiment, a binding molecule whose IgM, IgA, IgG/IgM, or IgG/IgA antibody binds to EGFR has an ADME-modulating moiety on the J-chain that comprises a human serum albumin-binding peptide. In one specific embodiment, a binding molecule whose IgM, IgA, IgG/IgM, or IgG/IgA antibody binds to EGFR has an ADME-modulating moiety on the J-chain that comprises a human serum albumin-binding antibody moiety. In one specific embodiment, a binding molecule whose IgM, IgA, IgG/IgM, or IgG/IgA antibody binds to EGFR has an ADME-modulating moiety on the J-chain that comprises a human serum albumin-binding scFv antibody fragment. In one specific embodiment, a binding molecule whose IgM, IgA, IgG/IgM, or IgG/IgA antibody binds to EGFR has an ADME-modulating moiety on the J-chain that comprises an FcRn-binding antibody moiety. In one specific embodiment, a binding molecule whose IgM, IgA, IgG/IgM, or IgG/IgA antibody binds to EGFR has an ADME-modulating moiety on the J-chain that comprises an FcRn-binding scFv antibody fragment. In one specific embodiment, a binding molecule whose IgM, IgA, IgG/IgM, or IgG/IgA antibody binds to EGFR has an ADME-modulating moiety on the J-chain that comprises an Fc domain.

In one specific embodiment, a binding molecule whose IgM, IgA, IgG/IgM, or IgG/IgA antibody binds to HER2 has an ADME-modulating moiety on the J-chain that comprises human serum albumin. In one specific embodiment, a binding molecule whose IgM, IgA, IgG/IgM, or IgG/IgA antibody binds to HER2 has an ADME-modulating moiety on the J-chain that comprises a human serum albumin-binding peptide. In one specific embodiment, a binding molecule whose IgM, IgA, IgG/IgM, or IgG/IgA antibody binds to HER2 has an ADME-modulating moiety on the J-chain that comprises a human serum albumin-binding antibody moiety. In one specific embodiment, a binding molecule whose IgM, IgA, IgG/IgM, or IgG/IgA antibody binds to HER2 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to HER2 has an ADME-modulating moiety on the J-chain that comprises an FcRn-binding antibody moiety. In one specific embodiment, a binding molecule whose IgM, IgA, IgG/IgM, or IgG/IgA antibody binds to HER2 has an ADME-modulating moiety on the J-chain that comprises an FcRn-binding scFv antibody fragment. In one specific embodiment, a binding molecule whose IgM, IgA, IgG/IgM, or IgG/IgA antibody binds to HER2 has an ADME-modulating moiety on the J-chain that comprises an Fc domain.

In one specific embodiment, a binding molecule whose IgM, IgA, IgG/IgM, or IgG/IgA antibody binds to HER3 has an ADME-modulating moiety on the J-chain that comprises human serum albumin. In one specific embodiment, a binding molecule whose IgM, IgA, IgG/IgM, or IgG/IgA antibody binds to HER3 has an ADME-modulating moiety on the J-chain that comprises a human serum albumin-binding peptide. In one specific embodiment, a binding molecule whose IgM, IgA, IgG/IgM, or IgG/IgA antibody binds to HER3 has an ADME-modulating moiety on the J-chain that comprises a human serum albumin-binding antibody moiety. In one specific embodiment, a binding molecule whose IgM, IgA, IgG/IgM, or IgG/IgA antibody binds to HER3 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to HER3 has an ADME-modulating moiety on the J-chain that comprises an FcRn-binding antibody moiety. In one specific embodiment, a binding molecule whose IgM, IgA, IgG/IgM, or IgG/IgA antibody binds to HER3 has an ADME-modulating moiety on the J-chain that comprises an FcRn-binding scFv antibody fragment. In one specific embodiment, a binding molecule whose IgM, IgA, IgG/IgM, or IgG/IgA antibody binds to HER3 has an ADME-modulating moiety on the J-chain that comprises an Fc domain.

In one specific embodiment, a binding molecule whose IgM, IgA, IgG/IgM, or IgG/IgA antibody binds to EPCAM has an ADME-modulating moiety on the J-chain that comprises human serum albumin. In one specific embodiment, a binding molecule whose IgM, IgA, IgG/IgM, or IgG/IgA antibody binds to EPCAM has an ADME-modulating moiety on the J-chain that comprises a human serum albumin-binding peptide. In one specific embodiment, a binding molecule whose IgM, IgA, IgG/IgM, or IgG/IgA antibody binds to EPCAM has an ADME-modulating moiety on the J-chain that comprises a human serum albumin-binding antibody moiety. In one specific embodiment, a binding molecule whose IgM, IgA, IgG/IgM, or IgG/IgA antibody binds to EPCAM has an ADME-modulating moiety on the J-chain that comprises a human serum albumin-binding scFv antibody fragment. In one specific embodiment, a binding molecule whose IgM, IgA, IgG/IgM, or IgG/IgA antibody binds to EPCAM has an ADME-modulating moiety on the J-chain that comprises an FcRn-binding antibody moiety. In one specific embodiment, a binding molecule whose IgM, IgA, IgG/IgM, or IgG/IgA antibody binds to EPCAM has an ADME-modulating moiety on the J-chain that comprises an FcRn-binding scFv antibody fragment. In one specific embodiment, a binding molecule whose IgM, IgA, IgG/IgM, or IgG/IgA antibody binds to EPCAM has an ADME-modulating moiety on the J-chain that comprises an Fc domain.

In one specific embodiment, a binding molecule whose IgM, IgA, IgG/IgM, or IgG/IgA antibody binds to CEACAM has an ADME-modulating moiety on the J-chain that comprises human serum albumin. In one specific embodiment, a binding molecule whose IgM, IgA, IgG/IgM, or IgG/IgA antibody binds to CEACAM has an ADME-modulating moiety on the J-chain that comprises a human serum albumin-binding peptide. In one specific embodiment, a binding molecule whose IgM, IgA, IgG/IgM, or IgG/IgA antibody binds to CEACAM has an ADME-modulating moiety on the J-chain that comprises a human serum albumin-binding antibody moiety. In one specific embodiment, a binding molecule whose IgM, IgA, IgG/IgM, or IgG/IgA antibody binds to CEACAM has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CEACAM has an ADME-modulating moiety on the J-chain that comprises an FcRn-binding antibody moiety. In one specific embodiment, a binding molecule whose IgM, IgA, IgG/IgM, or IgG/IgA antibody binds to CEACAM has an ADME-modulating moiety on the J-chain that comprises an FcRn-binding scFv antibody fragment. In one specific embodiment, a binding molecule whose IgM, IgA, IgG/IgM, or IgG/IgA antibody binds to CEACAM has an ADME-modulating moiety on the J-chain that comprises an Fc domain.

In one specific embodiment, a binding molecule whose IgM, IgA, IgG/IgM, or IgG/IgA antibody binds to GP100 has an ADME-modulating moiety on the J-chain that comprises human serum albumin. In one specific embodiment, a binding molecule whose IgM, IgA, IgG/IgM, or IgG/IgA antibody binds to GP100 has an ADME-modulating moiety on the J-chain that comprises a human serum albumin-binding peptide. In one specific embodiment, a binding molecule whose IgM, IgA, IgG/IgM, or IgG/IgA antibody binds to GP100 has an ADME-modulating moiety on the J-chain that comprises a human serum albumin-binding antibody moiety. In one specific embodiment, a binding molecule whose IgM, IgA, IgG/IgM, or IgG/IgA antibody binds to GP100 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to GP100 has an ADME-modulating moiety on the J-chain that comprises an FcRn-binding antibody moiety. In one specific embodiment, a binding molecule whose IgM, IgA, IgG/IgM, or IgG/IgA antibody binds to GP100 has an ADME-modulating moiety on the J-chain that comprises an FcRn-binding scFv antibody fragment. In one specific embodiment, a binding molecule whose IgM, IgA, IgG/IgM, or IgG/IgA antibody binds to GP100 has an ADME-modulating moiety on the J-chain that comprises an Fc domain.

In one specific embodiment, a binding molecule whose IgM, IgA, IgG/IgM, or IgG/IgA antibody binds to MAGE1 has an ADME-modulating moiety on the J-chain that comprises human serum albumin. In one specific embodiment, a binding molecule whose IgM, IgA, IgG/IgM, or IgG/IgA antibody binds to MAGE1 has an ADME-modulating moiety on the J-chain that comprises a human serum albumin-binding peptide. In one specific embodiment, a binding molecule whose IgM, IgA, IgG/IgM, or IgG/IgA antibody binds to MAGE1 has an ADME-modulating moiety on the J-chain that comprises a human serum albumin-binding antibody moiety. In one specific embodiment, a binding molecule whose IgM, IgA, IgG/IgM, or IgG/IgA antibody binds to MAGE1 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to MAGE1 has an ADME-modulating moiety on the J-chain that comprises an FcRn-binding antibody moiety. In one specific embodiment, a binding molecule whose IgM, IgA, IgG/IgM, or IgG/IgA antibody binds to MAGE1 has an ADME-modulating moiety on the J-chain that comprises an FcRn-binding scFv antibody fragment. In one specific embodiment, a binding molecule whose IgM, IgA, IgG/IgM, or IgG/IgA antibody binds to MAGE1 has an ADME-modulating moiety on the J-chain that comprises an Fc domain.

In one specific embodiment, a binding molecule whose IgM, IgA, IgG/IgM, or IgG/IgA antibody binds to NY-ESO-1 has an ADME-modulating moiety on the J-chain that comprises human serum albumin. In one specific embodiment, a binding molecule whose IgM, IgA, IgG/IgM, or IgG/IgA antibody binds to NY-ESO-1 has an ADME-modulating moiety on the J-chain that comprises a human serum albumin-binding peptide. In one specific embodiment, a binding molecule whose IgM, IgA, IgG/IgM, or IgG/IgA antibody binds to NY-ESO-1 has an ADME-modulating moiety on the J-chain that comprises a human serum albumin-binding antibody moiety. In one specific embodiment, a binding molecule whose IgM, IgA, IgG/IgM, or IgG/IgA antibody binds to NY-ESO-1 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to NY-ESO-1 has an ADME-modulating moiety on the J-chain that comprises an FcRn-binding antibody moiety. In one specific embodiment, a binding molecule whose IgM, IgA, IgG/IgM, or IgG/IgA antibody binds to NY-ESO-1 has an ADME-modulating moiety on the J-chain that comprises an FcRn-binding scFv antibody fragment. In one specific embodiment, a binding molecule whose IgM, IgA, IgG/IgM, or IgG/IgA antibody binds to NY-ESO-1 has an ADME-modulating moiety on the J-chain that comprises an Fc domain.

In one specific embodiment, a binding molecule whose IgM, IgA, IgG/IgM, or IgG/IgA antibody binds to Sialyl Lewis X antigen has an ADME-modulating moiety on the J-chain that comprises human serum albumin. In one specific embodiment, a binding molecule whose IgM, IgA, IgG/IgM, or IgG/IgA antibody binds to Sialyl Lewis X antigen has an ADME-modulating moiety on the J-chain that comprises a human serum albumin-binding peptide. In one specific embodiment, a binding molecule whose IgM, IgA, IgG/IgM, or IgG/IgA antibody binds to Sialyl Lewis X antigen has an ADME-modulating moiety on the J-chain that comprises a human serum albumin-binding antibody moiety. In one specific embodiment, a binding molecule whose IgM, IgA, IgG/IgM, or IgG/IgA antibody binds to Sialyl Lewis X antigen has an ADME-modulating moiety on the J-chain that comprises a human serum albumin-binding scFv antibody fragment. In one specific embodiment, a binding molecule whose IgM, IgA, IgG/IgM, or IgG/IgA antibody binds to Sialyl Lewis X antigen has an ADME-modulating moiety on the J-chain that comprises an FcRn-binding antibody moiety. In one specific embodiment, a binding molecule whose IgM, IgA, IgG/IgM, or IgG/IgA antibody binds to Sialyl Lewis X antigen has an ADME-modulating moiety on the J-chain that comprises an FcRn-binding scFv antibody fragment. In one specific embodiment, a binding molecule whose IgM, IgA, IgG/IgM, or IgG/IgA antibody binds to Sialyl Lewis X antigen has an ADME-modulating moiety on the J-chain that comprises an Fc domain.

In one specific embodiment, a binding molecule whose IgM, IgA, IgG/IgM, or IgG/IgA antibody binds to Tn antigen has an ADME-modulating moiety on the J-chain that comprises human serum albumin. In one specific embodiment, a binding molecule whose IgM, IgA, IgG/IgM, or IgG/IgA antibody binds to Tn antigen has an ADME-modulating moiety on the J-chain that comprises a human serum albumin-binding peptide. In one specific embodiment, a binding molecule whose IgM, IgA, IgG/IgM, or IgG/IgA antibody binds to Tn antigen has an ADME-modulating moiety on the J-chain that comprises a human serum albumin-binding antibody moiety. In one specific embodiment, a binding molecule whose IgM, IgA, IgG/IgM, or IgG/IgA antibody binds to Tn antigen has an ADME-modulating moiety on the J-chain that comprises a human serum albumin-binding scFv antibody fragment. In one specific embodiment, a binding molecule whose IgM, IgA, IgG/IgM, or IgG/IgA antibody binds to Tn antigen has an ADME-modulating moiety on the J-chain that comprises an FcRn-binding antibody moiety. In one specific embodiment, a binding molecule whose IgM, IgA, IgG/IgM, or IgG/IgA antibody binds to Tn antigen has an ADME-modulating moiety on the J-chain that comprises an FcRn-binding scFv antibody fragment. In one specific embodiment, a binding molecule whose IgM, IgA, IgG/IgM, or IgG/IgA antibody binds to Tn antigen has an ADME-modulating moiety on the J-chain that comprises an Fc domain.

In one specific embodiment, a binding molecule whose IgM, IgA, IgG/IgM, or IgG/IgA antibody binds to CD19 has an ADME-modulating moiety on the J-chain that comprises human serum albumin. In one specific embodiment, a binding molecule whose IgM, IgA, IgG/IgM, or IgG/IgA antibody binds to CD19 has an ADME-modulating moiety on the J-chain that comprises a human serum albumin-binding peptide. In one specific embodiment, a binding molecule whose IgM, IgA, IgG/IgM, or IgG/IgA antibody binds to CD19 has an ADME-modulating moiety on the J-chain that comprises a human serum albumin-binding antibody moiety. In one specific embodiment, a binding molecule whose IgM, IgA, IgG/IgM, or IgG/IgA antibody binds to CD19 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD19 has an ADME-modulating moiety on the J-chain that comprises an FcRn-binding antibody moiety. In one specific embodiment, a binding molecule whose IgM, IgA, IgG/IgM, or IgG/IgA antibody binds to CD19 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD19 has an ADME-modulating moiety on the J-chain that comprises an Fc domain.

In one specific embodiment, a binding molecule whose IgM, IgA, IgG/IgM, or IgG/IgA antibody binds to CD20 has an ADME-modulating moiety on the J-chain that comprises human serum albumin. In one specific embodiment, a binding molecule whose IgM, IgA, IgG/IgM, or IgG/IgA antibody binds to CD20 has an ADME-modulating moiety on the J-chain that comprises a human serum albumin-binding peptide. In one specific embodiment, a binding molecule whose IgM, IgA, IgG/IgM, or IgG/IgA antibody binds to CD20 has an ADME-modulating moiety on the J-chain that comprises a human serum albumin-binding antibody moiety. In one specific embodiment, a binding molecule whose IgM, IgA, IgG/IgM, or IgG/IgA antibody binds to CD20 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD20 has an ADME-modulating moiety on the J-chain that comprises an FcRn-binding antibody moiety. In one specific embodiment, a binding molecule whose IgM, IgA, IgG/IgM, or IgG/IgA antibody binds to CD20 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD20 has an ADME-modulating moiety on the J-chain that comprises an Fc domain.

In one specific embodiment, a binding molecule whose IgM, IgA, IgG/IgM, or IgG/IgA antibody binds to CD22 has an ADME-modulating moiety on the J-chain that comprises human serum albumin. In one specific embodiment, a binding molecule whose IgM, IgA, IgG/IgM, or IgG/IgA antibody binds to CD22 has an ADME-modulating moiety on the J-chain that comprises a human serum albumin-binding peptide. In one specific embodiment, a binding molecule whose IgM, IgA, IgG/IgM, or IgG/IgA antibody binds to CD22 has an ADME-modulating moiety on the J-chain that comprises a human serum albumin-binding antibody moiety. In one specific embodiment, a binding molecule whose IgM, IgA, IgG/IgM, or IgG/IgA antibody binds to CD22 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD22 has an ADME-modulating moiety on the J-chain that comprises an FcRn-binding antibody moiety. In one specific embodiment, a binding molecule whose IgM, IgA, IgG/IgM, or IgG/IgA antibody binds to CD22 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD22 has an ADME-modulating moiety on the J-chain that comprises an Fc domain.

In one specific embodiment, a binding molecule whose IgM, IgA, IgG/IgM, or IgG/IgA antibody binds to CD33 has an ADME-modulating moiety on the J-chain that comprises human serum albumin. In one specific embodiment, a binding molecule whose IgM, IgA, IgG/IgM, or IgG/IgA antibody binds to CD33 has an ADME-modulating moiety on the J-chain that comprises a human serum albumin-binding peptide. In one specific embodiment, a binding molecule whose IgM, IgA, IgG/IgM, or IgG/IgA antibody binds to CD33 has an ADME-modulating moiety on the J-chain that comprises a human serum albumin-binding antibody moiety. In one specific embodiment, a binding molecule whose IgM, IgA, IgG/IgM, or IgG/IgA antibody binds to CD33 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD33 has an ADME-modulating moiety on the J-chain that comprises an FcRn-binding antibody moiety. In one specific embodiment, a binding molecule whose IgM, IgA, IgG/IgM, or IgG/IgA antibody binds to CD33 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD33 has an ADME-modulating moiety on the J-chain that comprises an Fc domain.

In one specific embodiment, a binding molecule whose IgM, IgA, IgG/IgM, or IgG/IgA antibody binds to CD38 has an ADME-modulating moiety on the J-chain that comprises human serum albumin. In one specific embodiment, a binding molecule whose IgM, IgA, IgG/IgM, or IgG/IgA antibody binds to CD38 has an ADME-modulating moiety on the J-chain that comprises a human serum albumin-binding peptide. In one specific embodiment, a binding molecule whose IgM, IgA, IgG/IgM, or IgG/IgA antibody binds to CD38 has an ADME-modulating moiety on the J-chain that comprises a human serum albumin-binding antibody moiety. In one specific embodiment, a binding molecule whose IgM, IgA, IgG/IgM, or IgG/IgA antibody binds to CD38 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD38 has an ADME-modulating moiety on the J-chain that comprises an FcRn-binding antibody moiety. In one specific embodiment, a binding molecule whose IgM, IgA, IgG/IgM, or IgG/IgA antibody binds to CD38 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD38 has an ADME-modulating moiety on the J-chain that comprises an Fc domain.

In one specific embodiment, a binding molecule whose IgM, IgA, IgG/IgM, or IgG/IgA antibody binds to CD52 has an ADME-modulating moiety on the J-chain that comprises human serum albumin. In one specific embodiment, a binding molecule whose IgM, IgA, IgG/IgM, or IgG/IgA antibody binds to CD52 has an ADME-modulating moiety on the J-chain that comprises a human serum albumin-binding peptide. In one specific embodiment, a binding molecule whose IgM, IgA, IgG/IgM, or IgG/IgA antibody binds to CD52 has an ADME-modulating moiety on the J-chain that comprises a human serum albumin-binding antibody moiety. In one specific embodiment, a binding molecule whose IgM, IgA, IgG/IgM, or IgG/IgA antibody binds to CD52 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD52 has an ADME-modulating moiety on the J-chain that comprises an FcRn-binding antibody moiety. In one specific embodiment, a binding molecule whose IgM, IgA, IgG/IgM, or IgG/IgA antibody binds to CD52 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD52 has an ADME-modulating moiety on the J-chain that comprises an Fc domain.

In one specific embodiment, a binding molecule whose IgM, IgA, IgG/IgM, or IgG/IgA antibody binds to CD70 has an ADME-modulating moiety on the J-chain that comprises human serum albumin. In one specific embodiment, a binding molecule whose IgM, IgA, IgG/IgM, or IgG/IgA antibody binds to CD70 has an ADME-modulating moiety on the J-chain that comprises a human serum albumin-binding peptide. In one specific embodiment, a binding molecule whose IgM, IgA, IgG/IgM, or IgG/IgA antibody binds to CD70 has an ADME-modulating moiety on the J-chain that comprises a human serum albumin-binding antibody moiety. In one specific embodiment, a binding molecule whose IgM, IgA, IgG/IgM, or IgG/IgA antibody binds to CD70 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD70 has an ADME-modulating moiety on the J-chain that comprises an FcRn-binding antibody moiety. In one specific embodiment, a binding molecule whose IgM, IgA, IgG/IgM, or IgG/IgA antibody binds to CD70 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD70 has an ADME-modulating moiety on the J-chain that comprises an Fc domain.

In one specific embodiment, a binding molecule whose IgM, IgA, IgG/IgM, or IgG/IgA antibody binds to VEGF has an ADME-modulating moiety on the J-chain that comprises human serum albumin. In one specific embodiment, a binding molecule whose IgM, IgA, IgG/IgM, or IgG/IgA antibody binds to VEGF has an ADME-modulating moiety on the J-chain that comprises a human serum albumin-binding peptide. In one specific embodiment, a binding molecule whose IgM, IgA, IgG/IgM, or IgG/IgA antibody binds to VEGF has an ADME-modulating moiety on the J-chain that comprises a human serum albumin-binding antibody moiety. In one specific embodiment, a binding molecule whose IgM, IgA, IgG/IgM, or IgG/IgA antibody binds to VEGF has an ADME-modulating moiety on the J-chain that comprises a human serum albumin-binding scFv antibody fragment. In one specific embodiment, a binding molecule whose IgM, IgA, IgG/IgM, or IgG/IgA antibody binds to VEGF has an ADME-modulating moiety on the J-chain that comprises an FcRn-binding antibody moiety. In one specific embodiment, a binding molecule whose IgM, IgA, IgG/IgM, or IgG/IgA antibody binds to VEGF has an ADME-modulating moiety on the J-chain that comprises an FcRn-binding scFv antibody fragment. In one specific embodiment, a binding molecule whose IgM, IgA, IgG/IgM, or IgG/IgA antibody binds to VEGF has an ADME-modulating moiety on the J-chain that comprises an Fc domain. In one specific embodiment, a binding molecule whose IgM, IgA, IgG/IgM, or IgG/IgA antibody binds to VEGF has an ADME-modulating moiety on the J-chain that comprises a hyaluronic acid binding protein (HABP). In one specific embodiment, a binding molecule whose IgM, IgA, IgG/IgM, or IgG/IgA antibody binds to VEGF has an ADME-modulating moiety on the J-chain that comprises TSG-6. In one specific embodiment, a binding molecule whose IgM, IgA, IgG/IgM, or IgG/IgA antibody binds to VEGF has an ADME-modulating moiety on the J-chain that comprises a hyaluronic acid-binding antibody moiety. In one specific embodiment, a binding molecule whose IgM, IgA, IgG/IgM, or IgG/IgA antibody binds to VEGF has an ADME-modulating moiety on the J-chain that comprises a hyaluronic acid-binding scFv antibody fragment. In one specific embodiment, a binding molecule whose IgM, IgA, IgG/IgM, or IgG/IgA antibody binds to VEGF has an ADME-modulating moiety on the J-chain that comprises a TSG-6-binding antibody moiety. In one specific embodiment, a binding molecule whose IgM, IgA, IgG/IgM, or IgG/IgA antibody binds to VEGF has an ADME-modulating moiety on the J-chain that comprises a TSG-6-binding scFv antibody fragment.

In one specific embodiment, a binding molecule whose IgM, IgA, IgG/IgM, or IgG/IgA antibody binds to TNF alpha has an ADME-modulating moiety on the J-chain that comprises human serum albumin. In one specific embodiment, a binding molecule whose IgM, IgA, IgG/IgM, or IgG/IgA antibody binds to TNF alpha has an ADME-modulating moiety on the J-chain that comprises a human serum albumin-binding peptide. In one specific embodiment, a binding molecule whose IgM, IgA, IgG/IgM, or IgG/IgA antibody binds to TNF alpha has an ADME-modulating moiety on the J-chain that comprises a human serum albumin-binding antibody moiety. In one specific embodiment, a binding molecule whose IgM, IgA, IgG/IgM, or IgG/IgA antibody binds to TNF alpha has an ADME-modulating moiety on the J-chain that comprises a human serum albumin-binding scFv antibody fragment. In one specific embodiment, a binding molecule whose IgM, IgA, IgG/IgM, or IgG/IgA antibody binds to TNF alpha has an ADME-modulating moiety on the J-chain that comprises an FcRn-binding antibody moiety. In one specific embodiment, a binding molecule whose IgM, IgA, IgG/IgM, or IgG/IgA antibody binds to TNF alpha has an ADME-modulating moiety on the J-chain that comprises an FcRn-binding scFv antibody fragment. In one specific embodiment, a binding molecule whose IgM, IgA, IgG/IgM, or IgG/IgA antibody binds to TNF alpha has an ADME-modulating moiety on the J-chain that comprises an Fc domain. In one specific embodiment, a binding molecule whose IgM, IgA, IgG/IgM, or IgG/IgA antibody binds to TNF alpha has an ADME-modulating moiety on the J-chain that comprises a hyaluronic acid binding protein (HABP). In one specific embodiment, a binding molecule whose IgM, IgA, IgG/IgM, or IgG/IgA antibody binds to TNF alpha has an ADME-modulating moiety on the J-chain that comprises TSG-6. In one specific embodiment, a binding molecule whose IgM, IgA, IgG/IgM, or IgG/IgA antibody binds to TNF alpha has an ADME-modulating moiety on the J-chain that comprises a hyaluronic acid-binding antibody moiety. In one specific embodiment, a binding molecule whose IgM, IgA, IgG/IgM, or IgG/IgA antibody binds to TNF alpha has an ADME-modulating moiety on the J-chain that comprises a hyaluronic acid-binding scFv antibody fragment. In one specific embodiment, a binding molecule whose IgM, IgA, IgG/IgM, or IgG/IgA antibody binds to TNF alpha has an ADME-modulating moiety on the J-chain that comprises a TSG-6-binding antibody moiety. In one specific embodiment, a binding molecule whose IgM, IgA, IgG/IgM, or IgG/IgA antibody binds to TNF alpha has an ADME-modulating moiety on the J-chain that comprises a TSG-6-binding scFv antibody fragment.

In one specific embodiment, a binding molecule whose IgM, IgA, IgG/IgM, or IgG/IgA antibody binds to amyloid beta has an ADME-modulating moiety on the J-chain that comprises human serum albumin. In one specific embodiment, a binding molecule whose IgM, IgA, IgG/IgM, or IgG/IgA antibody binds to amyloid beta has an ADME-modulating moiety on the J-chain that comprises a human serum albumin-binding peptide. In one specific embodiment, a binding molecule whose IgM, IgA, IgG/IgM, or IgG/IgA antibody binds to amyloid beta has an ADME-modulating moiety on the J-chain that comprises a human serum albumin-binding antibody moiety. In one specific embodiment, a binding molecule whose IgM, IgA, IgG/IgM, or IgG/IgA antibody binds to amyloid beta has an ADME-modulating moiety on the J-chain that comprises a human serum albumin-binding scFv antibody fragment. In one specific embodiment, a binding molecule whose IgM, IgA, IgG/IgM, or IgG/IgA antibody binds to amyloid beta has an ADME-modulating moiety on the J-chain that comprises an FcRn-binding antibody moiety. In one specific embodiment, a binding molecule whose IgM, IgA, IgG/IgM, or IgG/IgA antibody binds to amyloid beta has an ADME-modulating moiety on the J-chain that comprises an FcRn-binding scFv antibody fragment. In one specific embodiment, a binding molecule whose IgM, IgA, IgG/IgM, or IgG/IgA antibody binds to amyloid beta has an ADME-modulating moiety on the J-chain that comprises an Fc domain.

In one specific embodiment, a binding molecule whose IgM, IgA, IgG/IgM, or IgG/IgA antibody binds to amyloid beta has an ADME-modulating moiety on the J-chain that comprises transferrin. In one specific embodiment, a binding molecule whose IgM, IgA, IgG/IgM, or IgG/IgA antibody binds to amyloid beta has an ADME-modulating moiety on the J-chain that comprises a transferrin-binding antibody moiety. In one specific embodiment, a binding molecule whose IgM, IgA, IgG/IgM, or IgG/IgA antibody binds to amyloid beta has an ADME-modulating moiety on the J-chain that comprises a transferrin-binding scFv antibody fragment. In one specific embodiment, a binding molecule whose IgM, IgA, IgG/IgM, or IgG/IgA antibody binds to amyloid beta has an ADME-modulating moiety on the J-chain that comprises a transferrin receptor-binding antibody moiety. In one specific embodiment, a binding molecule whose IgM, IgA, IgG/IgM, or IgG/IgA antibody binds to amyloid beta has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises leptin. In one specific embodiment, a binding molecule whose IgM, IgA, IgG/IgM, or IgG/IgA antibody binds to amyloid beta has an ADME-modulating moiety on the J-chain that comprises a leptin-binding antibody moiety. In one specific embodiment, a binding molecule whose IgM, IgA, IgG/IgM, or IgG/IgA antibody binds to amyloid beta has an ADME-modulating moiety on the J-chain that comprises a leptin-binding scFv antibody fragment. In one specific embodiment, a binding molecule whose IgM, IgA, IgG/IgM, or IgG/IgA antibody binds to amyloid beta has an ADME-modulating moiety on the J-chain that comprises a leptin receptor-binding antibody moiety. In one specific embodiment, a binding molecule whose IgM, IgA, IgG/IgM, or IgG/IgA antibody binds to amyloid beta has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises insulin. In one specific embodiment, a binding molecule whose IgM, IgA, IgG/IgM, or IgG/IgA antibody binds to amyloid beta has an ADME-modulating moiety on the J-chain that comprises an insulin-binding antibody moiety. In one specific embodiment, a binding molecule whose IgM, IgA, IgG/IgM, or IgG/IgA antibody binds to amyloid beta has an ADME-modulating moiety on the J-chain that comprises an insulin-binding scFv antibody fragment. In one specific embodiment, a binding molecule whose IgM, IgA, IgG/IgM, or IgG/IgA antibody binds to amyloid beta has an ADME-modulating moiety on the J-chain that comprises an insulin receptor-binding antibody moiety. In one specific embodiment, a binding molecule whose IgM, IgA, IgG/IgM, or IgG/IgA antibody binds to amyloid beta has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises IGF-1. In one specific embodiment, a binding molecule whose IgM, IgA, IgG/IgM, or IgG/IgA antibody binds to amyloid beta has an ADME-modulating moiety on the J-chain that comprises an IGF-1-binding antibody moiety. In one specific embodiment, a binding molecule whose IgM, IgA, IgG/IgM, or IgG/IgA antibody binds to amyloid beta has an ADME-modulating moiety on the J-chain that comprises an IGF-1-binding scFv antibody fragment. In one specific embodiment, a binding molecule whose IgM, IgA, IgG/IgM, or IgG/IgA antibody binds to amyloid beta has an ADME-modulating moiety on the J-chain that comprises an IGF-1 receptor-binding antibody moiety. In one specific embodiment, a binding molecule whose IgM, IgA, IgG/IgM, or IgG/IgA antibody binds to amyloid beta has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises basigin. In one specific embodiment, a binding molecule whose IgM, IgA, IgG/IgM, or IgG/IgA antibody binds to amyloid beta has an ADME-modulating moiety on the J-chain that comprises a basigin-binding antibody moiety. In one specific embodiment, a binding molecule whose IgM, IgA, IgG/IgM, or IgG/IgA antibody binds to amyloid beta has an ADME-modulating moiety on the J-chain that comprises a basigin-binding scFv antibody fragment.

In one specific embodiment, a binding molecule whose IgM, IgA, IgG/IgM, or IgG/IgA antibody binds to amyloid beta has an ADME-modulating moiety on the J-chain that comprises Glut1. In one specific embodiment, a binding molecule whose IgM, IgA, IgG/IgM, or IgG/IgA antibody binds to amyloid beta has an ADME-modulating moiety on the J-chain that comprises a Glut1-binding antibody moiety. In one specific embodiment, a binding molecule whose IgM, IgA, IgG/IgM, or IgG/IgA antibody binds to amyloid beta has an ADME-modulating moiety on the J-chain that comprises a Glut1-binding scFv antibody fragment.

In one specific embodiment, a binding molecule whose IgM, IgA, IgG/IgM, or IgG/IgA antibody binds to amyloid beta has an ADME-modulating moiety on the J-chain that comprises CD98hc. In one specific embodiment, a binding molecule whose IgM, IgA, IgG/IgM, or IgG/IgA antibody binds to amyloid beta has an ADME-modulating moiety on the J-chain that comprises a CD98hc-binding antibody moiety. In one specific embodiment, a binding molecule whose IgM, IgA, IgG/IgM, or IgG/IgA antibody binds to amyloid beta has an ADME-modulating moiety on the J-chain that comprises a CD98hc-binding scFv antibody fragment.

In one specific embodiment, a binding molecule whose IgM, IgA, IgG/IgM, or IgG/IgA antibody binds to BACE has an ADME-modulating moiety on the J-chain that comprises human serum albumin. In one specific embodiment, a binding molecule whose IgM, IgA, IgG/IgM, or IgG/IgA antibody binds to BACE has an ADME-modulating moiety on the J-chain that comprises a human serum albumin-binding peptide. In one specific embodiment, a binding molecule whose IgM, IgA, IgG/IgM, or IgG/IgA antibody binds to BACE has an ADME-modulating moiety on the J-chain that comprises a human serum albumin-binding antibody moiety. In one specific embodiment, a binding molecule whose IgM, IgA, IgG/IgM, or IgG/IgA antibody binds to BACE has an ADME-modulating moiety on the J-chain that comprises a human serum albumin-binding scFv antibody fragment. In one specific embodiment, a binding molecule whose IgM, IgA, IgG/IgM, or IgG/IgA antibody binds to BACE has an ADME-modulating moiety on the J-chain that comprises an FcRn-binding antibody moiety. In one specific embodiment, a binding molecule whose IgM, IgA, IgG/IgM, or IgG/IgA antibody binds to BACE has an ADME-modulating moiety on the J-chain that comprises an FcRn-binding scFv antibody fragment. In one specific embodiment, a binding molecule whose IgM, IgA, IgG/IgM, or IgG/IgA antibody binds to BACE has an ADME-modulating moiety on the J-chain that comprises an Fc domain.

In one specific embodiment, a binding molecule whose IgM, IgA, IgG/IgM, or IgG/IgA antibody binds to BACE has an ADME-modulating moiety on the J-chain that comprises transferrin. In one specific embodiment, a binding molecule whose IgM, IgA, IgG/IgM, or IgG/IgA antibody binds to BACE has an ADME-modulating moiety on the J-chain that comprises a transferrin-binding antibody moiety. In one specific embodiment, a binding molecule whose IgM, IgA, IgG/IgM, or IgG/IgA antibody binds to BACE has an ADME-modulating moiety on the J-chain that comprises a transferrin-binding scFv antibody fragment. In one specific embodiment, a binding molecule whose IgM, IgA, IgG/IgM, or IgG/IgA antibody binds to BACE has an ADME-modulating moiety on the J-chain that comprises a transferrin receptor-binding antibody moiety. In one specific embodiment, a binding molecule whose IgM, IgA, IgG/IgM, or IgG/IgA antibody binds to BACE has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to BACE has an ADME-modulating moiety on the J-chain that comprises leptin. In one specific embodiment, a binding molecule whose IgM, IgA, IgG/IgM, or IgG/IgA antibody binds to BACE has an ADME-modulating moiety on the J-chain that comprises a leptin-binding antibody moiety. In one specific embodiment, a binding molecule whose IgM, IgA, IgG/IgM, or IgG/IgA antibody binds to BACE has an ADME-modulating moiety on the J-chain that comprises a leptin-binding scFv antibody fragment. In one specific embodiment, a binding molecule whose IgM, IgA, IgG/IgM, or IgG/IgA antibody binds to BACE has an ADME-modulating moiety on the J-chain that comprises a leptin receptor-binding antibody moiety. In one specific embodiment, a binding molecule whose IgM, IgA, IgG/IgM, or IgG/IgA antibody binds to BACE has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to BACE has an ADME-modulating moiety on the J-chain that comprises insulin. In one specific embodiment, a binding molecule whose IgM, IgA, IgG/IgM, or IgG/IgA antibody binds to BACE has an ADME-modulating moiety on the J-chain that comprises an insulin-binding antibody moiety. In one specific embodiment, a binding molecule whose IgM, IgA, IgG/IgM, or IgG/IgA antibody binds to BACE has an ADME-modulating moiety on the J-chain that comprises an insulin receptor-binding antibody moiety. In one specific embodiment, a binding molecule whose IgM, IgA, IgG/IgM, or IgG/IgA antibody binds to BACE has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to BACE has an ADME-modulating moiety on the J-chain that comprises IGF-1. In one specific embodiment, a binding molecule whose IgM, IgA, IgG/IgM, or IgG/IgA antibody binds to BACE has an ADME-modulating moiety on the J-chain that comprises an IGF-1-binding antibody moiety. In one specific embodiment, a binding molecule whose IgM, IgA, IgG/IgM, or IgG/IgA antibody binds to BACE has an ADME-modulating moiety on the J-chain that comprises an IGF-1-binding scFv antibody fragment. In one specific embodiment, a binding molecule whose IgM, IgA, IgG/IgM, or IgG/IgA antibody binds to BACE has an ADME-modulating moiety on the J-chain that comprises an IGF-1 receptor-binding antibody moiety. In one specific embodiment, a binding molecule whose IgM, IgA, IgG/IgM, or IgG/IgA antibody binds to BACE has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to BACE has an ADME-modulating moiety on the J-chain that comprises basigin. In one specific embodiment, a binding molecule whose IgM, IgA, IgG/IgM, or IgG/IgA antibody binds to BACE has an ADME-modulating moiety on the J-chain that comprises a basigin-binding antibody moiety. In one specific embodiment, a binding molecule whose IgM, IgA, IgG/IgM, or IgG/IgA antibody binds to BACE has an ADME-modulating moiety on the J-chain that comprises a basigin-binding scFv antibody fragment.

In one specific embodiment, a binding molecule whose IgM, IgA, IgG/IgM, or IgG/IgA antibody binds to BACE has an ADME-modulating moiety on the J-chain that comprises Glut1. In one specific embodiment, a binding molecule whose IgM, IgA, IgG/IgM, or IgG/IgA antibody binds to BACE has an ADME-modulating moiety on the J-chain that comprises a Glut1-binding antibody moiety. In one specific embodiment, a binding molecule whose IgM, IgA, IgG/IgM, or IgG/IgA antibody binds to BACE has an ADME-modulating moiety on the J-chain that comprises a Glut1-binding scFv antibody fragment.

In one specific embodiment, a binding molecule whose IgM, IgA, IgG/IgM, or IgG/IgA antibody binds to BACE has an ADME-modulating moiety on the J-chain that comprises CD98hc. In one specific embodiment, a binding molecule whose IgM, IgA, IgG/IgM, or IgG/IgA antibody binds to BACE has an ADME-modulating moiety on the J-chain that comprises a CD98hc-binding antibody moiety. In one specific embodiment, a binding molecule whose IgM, IgA, IgG/IgM, or IgG/IgA antibody binds to BACE has an ADME-modulating moiety on the J-chain that comprises a CD98hc-binding scFv antibody fragment.

It is to be understood that an IgM, IgA, IgG/IgM or IgG/IgA antibody that binds to any of the listed targets described herein can be combined with a modified J-chain with any of the ADME-modulating moieties listed herein to create a binding molecule. Thus, any antibody target listed herein can be combined with any ADME-modulating moiety listed herein. FIG. 13 provides a list of non-limiting examples of antibody targets and ADME-modulating moieties that can be included on a J-chain of a binding molecule in accordance with aspects of the invention. Any of the antibody targets listed in the left column of FIG. 13 can be combined with any of the ADME-modulating moieties listed in the right column of FIG. 13.

While certain preferred embodiments are specifically referred to herein, it is to be understood that IgM, IgA, IgG/IgM and IgG/IgA antibodies with binding specificity to any target, such as any tumor antigen, comprising a modified J-chain with any ADME-modulating moiety described herein are contemplated and are within the scope of the present invention.

In a preferred embodiment, the multi-specific IgM, IgA, IgG/IgM or IgG/IgA antibody binds to one or more of the tumor targets listed herein, while the J-chain comprises an ADME-modulating moiety.

In another preferred embodiment, the J-chain of the subject binding molecules includes an ADME-modulating moiety that is an scFv, and that reduces clearance of the binding molecule by binding to albumin. In one preferred embodiment, the ADME-modulating moiety on the J-chain is an scFv that binds to albumin.

In one preferred embodiment, a binding molecule includes an IgM antibody that binds to CD20, and the ADME-modulating moiety on the J-chain is human serum albumin (HSA). In another preferred embodiment, a binding molecule includes an IgM antibody that binds to CD20, and the ADME-modulating moiety on the J-chain is an anti-albumin scFv.

In one preferred embodiment, a binding molecule includes an IgM antibody that binds to DR5, and the ADME-modulating moiety on the J-chain is human serum albumin (HSA). In another preferred embodiment, a binding molecule includes an IgM antibody that binds to DR5, and the ADME-modulating moiety on the J-chain is an anti-albumin scFv.

In one preferred embodiment, a binding molecule includes an IgM antibody that binds to BACE, and the ADME-modulating moiety on the J-chain is transferrin. In another preferred embodiment, a binding molecule includes an IgM antibody that binds to BACE, and the ADME-modulating moiety on the J-chain is an anti-transferrin receptor scFv. In one preferred embodiment, a binding molecule includes an IgM antibody that binds to BACE, and the ADME-modulating moiety on the J-chain is an anti-transferrin scFv.

In one preferred embodiment, a binding molecule includes an IgM antibody that binds to VEGF, and the ADME-modulating moiety on the J-chain is hyaluronic acid binding protein (HABP). In another preferred embodiment, a binding molecule includes an IgM antibody that binds to VEGF, and the ADME-modulating moiety on the J-chain is an anti-hyaluronic acid scFv.

In one preferred embodiment, a binding molecule includes an IgM antibody that binds to TNF alpha, and the ADME-modulating moiety on the J-chain is hyaluronic acid binding protein (HABP). In another preferred embodiment, a binding molecule includes an IgM antibody that binds to TNF alpha, and the ADME-modulating moiety on the J-chain is an anti-hyaluronic acid scFv.

In all embodiments, an ADME-modulating moiety of the modified J-chain may be introduced before or after the J-chain. Thus, a modified J-chain with an anti-albumin scFv ADME-modulating moiety that increases the retention of the binding molecule in the circulation by binding to albumin may have an anti-albumin scFv-J or a J-anti-albumin scFv configuration. A schematic illustration of two non-limiting examples of such configurations are provided in FIGS. 4A and 4B.

Due to their increased avidity, the subject binding molecules are superior relative to bispecific IgG antibodies. For example, as a result, they are suitable for targeting low level expression targets, such as Rittman-resistant Burkitt lymphoma cells characterized by a low level of CD20 expression. In addition, the IgM, IgA, IgG/IgM and IgG/IgA antibodies herein comprising a modified J-chain have greatly enhanced potency relative to bispecific IgG antibodies.

Pharmaceutical Compositions of Antibodies with Modified J-Chain

For therapeutic uses, the subject binding molecules can be formulated into pharmaceutical compositions. A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The compositions may also contain adjuvants such as preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

The following examples, sequence listing and figures are provided to aid the understanding of the present invention, the true scope of which is set forth in the appended claims.

It is understood that modifications can be made in the procedures set forth without departing from the spirit of the invention.

Further details of the invention are illustrated by the following non-limiting Examples.

Example 1: IgMs can be Conjugated to Multiple scFvs on Either End of the J-Chain with No Effect on Functional Activity The J-chain of an IgM molecule can be linked in frame with an scFv designed to bind a target of interest at either its C- or N-terminus, and the resultant bispecific IgMs are not perturbed in structure or function as evidenced by no diminution in their CDC activity.

1. Generation of DNA Constructs with Designed Mutations

DNA construct synthesis. All the DNA constructs with designed mutations are synthesized by commercial vendors (Genescript), with compatible restriction sites at both ends for sub-cloning into respective expression vectors.

Constructing expression vectors. The synthesized DNA constructs are re-suspended in Tris-EDTA buffer at 1 µg/ml. DNA (1 µg) is subjected to enzyme digestion and the synthesized gene is separated from the carrier plasmid DNA by electrophoresis. The digested DNA is ligated to pre-digested plasmid DNA (pCAGGS for J-chain, Gene 108 (1991) 193-200) by standard molecular biology techniques. The ligated DNA is transformed into competent bacteria and plated on LB plates with multiple selective antibiotics. Several bacterial colonies are picked and DNA preparations are made by standard molecular biology techniques. The prepared DNA are verified by sequencing. Only the bacterial clones with 100% match of DNA sequence with the designed DNA sequence are used for plasmid DNA preparation and subsequently for cell transfection.

IgM heavy chain: This heavy chain construct has a full length µ chain for an anti-CD20 IgM which binds CD20 on the surface of B-cells:

IgM Heavy chain sequence of an anti-CD20 antibody:

(SEQ ID: 16)
MGWSYIILFLVATATGVHSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSSGSASAPTLFP

LVSCENSPSDTSSVAVGCLAQDFLPDSITFSWKYKNNSDISSTRGFPSVL

RGGKYAATSQVLLPSKDVMQGTDEHVVCKVQHPNGNKEKNVPLPVIAELP

PKVSVFVPPRDGFFGNPRKSKLICQATGFSPRQIQVSWLREGKQVGSGVT

TDQVQAEAKESGPTTYKVTSTLTIKESDWLSQSMFTCRVDHRGLTFQQNA

SSMCVPDQDTAIRVFAIPPSFASIFLTKSTKLTCLVTDLTTYDSVTISWT

RQNGEAVKTHTNISESHPNATFSAVGEASICEDDWNSGERFTCTVTHTDL

PSPLKQTISRPKGVALHRPDVYLLPPAREQLNLRESATITCLVTGFSPAD

VFVQWMQRGQPLSPEKYVTSAPMPEPQAPGRYFAHSILTVSEEEWNTGET

YTCVVAHEALPNRVTERTVDKSTGKPTLYNVSLVMSDTAGTCY

This heavy chain construct has a molecular weight about 64 kD and when co-expressed with light chain, the resultant IgM is able to bind to CDIM positive B cells.

IgM Light chain sequence of an anti-CD20 antibody:

(SEQ ID NO: 17)
MDMRVPAQLLGLLLLWLRGARCQIVLSQSPAILSASPGEKVTMTCRASSS

VSYIHWFQQKPGSSPKPWIYATSNLASGVPVRFSGSGSGTSYSLTISRVE

AEDAATYYCQQWTSNPPTFGGGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

The light chain construct has a molecular weight of about 24 kD and when co-expressed with the appropriate heavy chain (SEQ ID NO: 16) is able to bind to CDIM positive B cells.

Different J-chains. In order to demonstrate that J-chain variants were able to couple with IgM, two different J-chain variants are constructed with distinct fusion sites incorporating anti-CD3 antibody (OKT3 scFv).

i. This construct is composed of an scFv of OKT3 (anti-CD3) fused with N-terminus of human J-chain (CD3scFv-15 aa Linker-J, O15J):

(SEQ ID NO: 18)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYSLDYWGQGTTLTVSSGGGGSGGGGSGGGGSQIVLTQSPAIMSASPG

EKVTMTCSASSSVSYMNWYQQKSGTSPKRWIYDTSKLASGVPAHFRGSGS

GTSYSLTISGMEAEDAATYYCQQWSSNPFTFGSGTKLEIKGGGGSGGGGS

GGGGSQEDERIVLVDNKCKCARITSRIIRSSEDPNEDIVERNIRIIVPLN

NRENISDPTSPLRTRFVYHLSDLCKKCDPTEVELDNQIVTATQSNICDED

SATETCYTYDRNKCYTAVVPLVYGGETKMVETALTPDACYPDGGGSEQKL

ISEEDLNSAVDHHHHHH

This construct has a molecular weight about 45 kD and is able to bind to soluble epsilon chain of CD3 (Sino Biological), or T cells; and is able to bind to anti-myc monoclonal antibody 4A6 or other anti-myc antibodies.

ii. This construct is composed of a scFv of OKT3 (anti-CD3) fused with C-terminus of human J-chain (J-15 aa Linker-CD3scFv, J15O):

(SEQ ID NO: 19)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPDGGGGSGGGGSGGG

GSQVQLQQSGAELARPGASVKMSCKASGYTFTRYTMHWVKQRPGQGLEWI

GYINPSRGYTNYNQKFKDKATLTTDKSSSTAYMQLSSLTSEDSAVYYCAR

YYDDHYSLDYWGQGTTLTVSSGGGGSGGGGSGGGGSQIVLTQSPAIMSAS

PGEKVTMTCSASSSVSYMNWYQQKSGTSPKRWIYDTSKLASGVPAHFRGS

GSGTSYSLTISGMEAEDAATYYCQQWSSNPFTFGSGTKLEIKEQKLISEE

DLNSAVDHHHHHH-

This J-CD3scFv construct has a molecular weight about 45 kD and is able to bind to soluble epsilon chain of CD3 (Sino Biological), or T cells; and is able to bind to anti-myc monoclonal antibody 4A6 or other anti-myc antibodies.

To establish that assembly of bispecific IgM is feasible with a modified J-chain carrying an anti-CD3 scFv of a different sequence than that used in Examples 1 and 2, a J-chain carrying the variable regions from the antibody Visilizumab (Nuvion) was performed. Shown below are the sequences for two J-chains with the scFv corresponding to Visilizumab (V) fused to the J-chain through a linker containing 15 amino acid residues in two different orientations—V15J and J15V.

J chain sequence for V15J:

(SEQ ID NO: 20)
MGWSYIILFLVATATGVHSQVQLVQSGAEVKKPGASVKVSCKASGYTFIS

YTMHWVRQAPGQGLEWMGYINPRSGYTHYNQKLKDKATLTADKSASTAYM

ELSSLRSEDTAVYYCARSAYYDYDGFAYWGQGTLVTVSSGGGGSGGGGSG

GGGSDIQMTQSPSSLSASVGDRVTITCSASSSVSYMNWYQQKPGKAPKRL

IYDTSKLASGVPSRFSGSGSGTDFTLTISSLQPEDFATYYCQQWSSNPPT

FGGGTKLEIKGGGGSGGGGSGGGGSQEDERIVLVDNKCKCARITSRIIRS

SEDPNEDIVERNIRIIVPLNNRENISDPTSPLRTRFVYHLSDLCKKCDPT

EVELDNQIVTATQSNICDEDSATETCYTYDRNKCYTAVVPLVYGGETKMV

ETALTPDACYPD

J-chain sequence for J15V:

(SEQ ID NO: 21)
MKNHLLFWGVLAVFIKAVHVKAQEDERIVLVDNKCKCARITSRIIRSSED

PNEDIVERNIRIIVPLNNRENISDPTSPLRTRFVYHLSDLCKKCDPTEVE

LDNQIVTATQSNICDEDSATETCYTYDRNKCYTAVVPLVYGGETKMVETA

LTPDACYPDGGGGSGGGGSGGGGSQVQLVQSGAEVKKPGASVKVSCKASG

YTFISYTMHWVRQAPGQGLEWMGYINPRSGYTHYNQKLKDKATLTADKSA

STAYMELSSLRSEDTAVYYCARSAYYDYDGFAYWGQGTLVTVSSGGGGSG

GGGSGGGGSDIQMTQSPSSLSASVGDRVTITCSASSSVSYMNWYQQKPGK

APKRLIYDTSKLASGVPSRFSGSGSGTDFTLTISSLQPEDFATYYCQQWS

SNPPTFGGGTKLEIK

Figure 6:
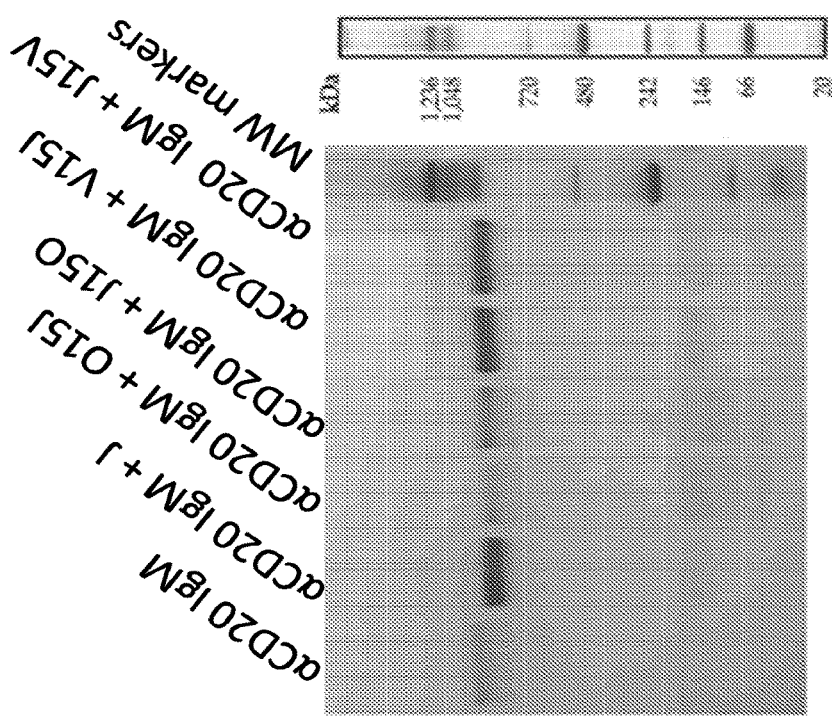
FIG. 6 shows SDS PAGE analysis of anti-CD20 IgM antibodies with or without various anti-CD3 binding moieties on the J-chain in either orientation. J-chain containing IgM pentamers are easily distinguished from the hexameric IgM without J-chain.

DNA corresponding to these sequences was synthesized and transfected into HEK293 cells along with the heavy and light chains for anti-CD20 IgM to produce protein which was then purified using the camelid antibody affinity matrix specific for IgM. As shown in FIG. 6, J-chains fused to the new anti-CD3 scFv with the 15 aa linker are able to incorporate into the IgM and the pentameric form of bi-specific IgM with the corresponding J-chain is clearly distinguishable from the hexameric form without a J-chain.

2. Protein Expression, Purification and Characterization
   a. Transfection. Heavy, Light and Modified J-chain DNA is transfected into CHO cells. DNA for expression vectors are mixed typically in 1:1:1 ratio with PEI and then added to CHO-S cells. PEI transfection with CHO-S cells is conducted according to established techniques (see Biotechnology and Bioengineering, Vol 87, 553-545).
   b. Immunoprecipitation
      i. Capture Select IgM (BAC, Thermo Fisher). IgM proteins from transfected CHO cell supernatants are partially purified by immuno-precipitation with Capture Select IgM affinity matrix according to manufacturers' protocol (GE Life Sciences). After incubation at room temperature for 2 hours, the affinity matrix is separated from the supernatant by centrifugation. The matrix is further washed with PBS for 3 times before the PBS is carefully removed. The captured protein is eluted from the matrix by incubating with NuPage LDS protein buffer (Life Technology) for 5 minutes.
      ii. Anti-myc agarose affinity matrix (Sigma). IgM proteins from transfected CHO cell supernatants are partially purified by immunoprecipitation with anti-myc affinity matrix according to manufacturers' protocol. After incubation at room temperature for 2 hours, the affinity matrix is separated from the supernatant by centrifugation. The matrix is further washed with PBS for 3 times before the PBS is carefully removed after the final wash. The captured protein is eluted from the matrix by incubating with NuPage LDS protein buffer (Life Technology) for 5 minutes.
   c. Gel Electrophoresis
      i. Non-reducing SDS PAGE separates native IgM and its mutant forms according to size. Pentameric IgM, composed of homodimeric heavy and light chains, produces a protein band of approximately 1,000,000 molecular weight. NuPage LDS Sample Buffer (Life Technologies) is added to IgM protein samples at 25 C for 30 minutes before loading onto the gel. NativePage Novex 3-12% Bis-Tris Gel (Life Technologies) is used with Novex Tris-Acetate SDS Running Buffer (Life Technologies). Run gel until the dye front reaches the bottom of the gel.
      ii. Reducing SDS-PAGE. NuPage LDS sample buffer (Life Technologies) and NuPage reducing agent dithiothreitol (Life Technologies) are added to IgM protein samples and heated to 80° C. for 10 minutes before loading on NuPage Novex 4-12% Bis-Tris Gel (Life Technologies). NuPage MES SDS Running Buffer (Life Technologies) is used for gel electrophoresis. Gels are run until the dye front reaches the bottom of the gel. After electrophoresis is complete, remove gel from apparatus and stain the gel using Colloidal Blue Staining (Life Technologies).
      iii. The DNA corresponding to these heavy and light chains as well as that corresponding to either the wild-type (wt) J-chain, O15J or J15O J-chain sequences described above were co-transfected into HEK293 cells and proteins expressed and purified using the camelid resin as described before. As shown in FIG. 6, all four proteins express well. The anti-CD20 IgM hexamer without J-chain is clearly resolved from the J-chain containing pentamers for the IgM pentamer with the wild type J-chain as well as for the bispecific IgMs where the anti-CD3 scFv is linked to the J-chain in either orientation (O15J or J15O).

Figure 7:
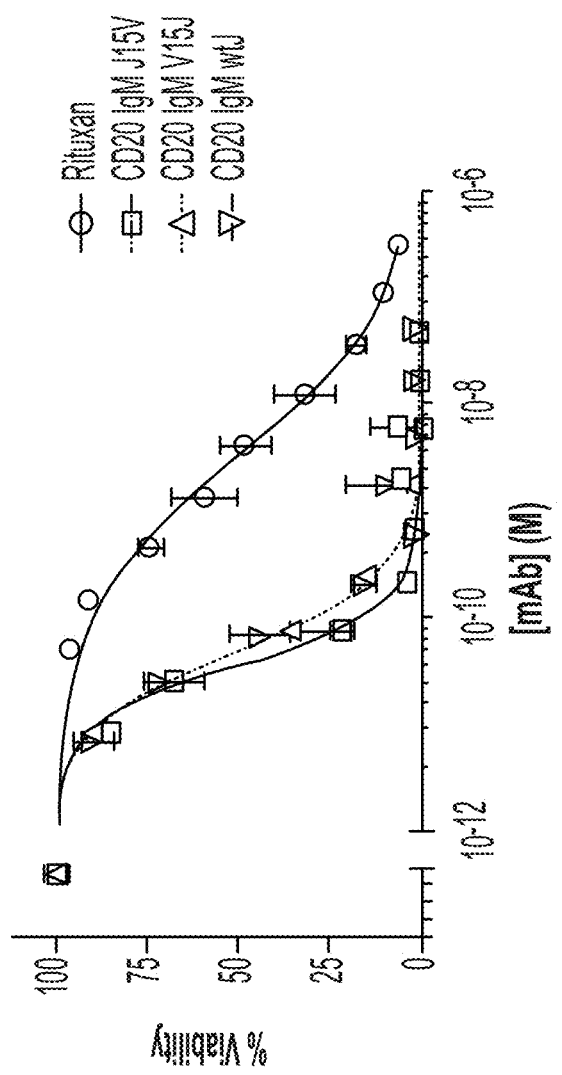
FIG. 7 is a graph showing cell viability as a function of antibody concentration for various antibody constructs in a complement dependent cytotoxicity assay in the presence of IgG, IgM or IgM's carrying various J-chains. A table is provided with the EC50 values for each construct.

Analysis of Complement Dependent Cytotoxicity for Family of IgMs with and without Incorporated J-Chains Complement dependent cytotoxicity is a key mechanism for cell killing by antibodies. IgM antibodies are known to have enhanced complement dependent cell killing (CDC) due to their multimeric form. A key aspect of this invention was to test if incorporation of modified J-chains, which carry scFv or camelid Vhh binders of effector cells at either their C- or N-termini, causes interference with binding of C1q—the key component of the complement pathway, and therefore may inhibit CDC. The CDC activity of each of the IgM and bispecific IgM constructs was measured. As shown in FIG. 7, incorporation of the modified J-chain has, unexpectedly, no deleterious effect on the CDC activity of the bispecific IgMs. Moreover, with the linker lengths tested, it was found that the bispecific IgMs have CDC activity between 60-100 fold enhanced over the corresponding IgG on a molar basis (FIG. 7).

Example 2: Bispecific IgMs can Bind Two Targets Simultaneously and Show Functional Effects The DNA corresponding to these heavy and light chains as well as that corresponding to either the wild-type (wt) J-chain (FIG. 3), V15J or J15V J-chain sequences shown above were co-transfected into HEK293 cells and proteins expressed and purified using the camelid resin as described before. As shown in FIG. 6, all four proteins express well. The anti-CD20 IgM hexamer without J-chain is clearly resolved from the J-chain containing pentamers for the IgM pentamer with the wild type J-chain as well as for the bispecific IgMs where the anti-CD3 scFv is linked to the J-chain in either orientation.

Figure 8:
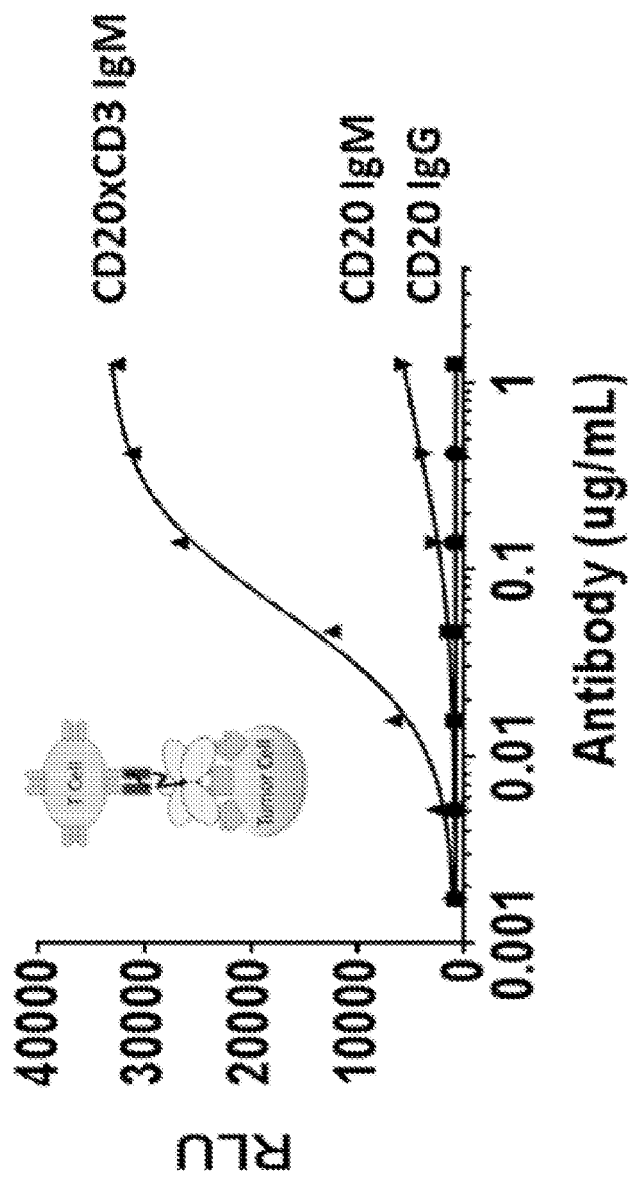
FIG. 8 is a graph showing results of a T-cell activation assay comparing the ability of an anti-CD20 IgM with a CD3 binding moiety on the J-chain to activate T-cells, as compared to anti-CD20 IgM antibodies without a CD3 binding moiety on the J-chain, as well as anti-CD20 IgG antibodies.

Purified proteins were analyzed for T-cell activation using a commercially available Luciferase reporter gene based kit (Promega). Briefly, purified protein was added to 7500 Ramos and 25000 engineered Jurkat cells (Promega CS176403) in 40 uL RPMI with 10% FBS. Mixture was incubated for 5 h 37 C with 5% $CO_2$. Cells were mixed with lysis buffer containing luciferin to measure luciferase reporter activity. Light output was measured by EnVision plate reader and analyzed by Prism software. As shown in FIG. 8, only the antibodies that carried the CD3 specific scFv binding moiety on the J-chain are able to show dose dependent activation, whereas the IgM antibody lacking the modified J-chain or the IgG are unable to show any signal in this assay.

Figure 9:
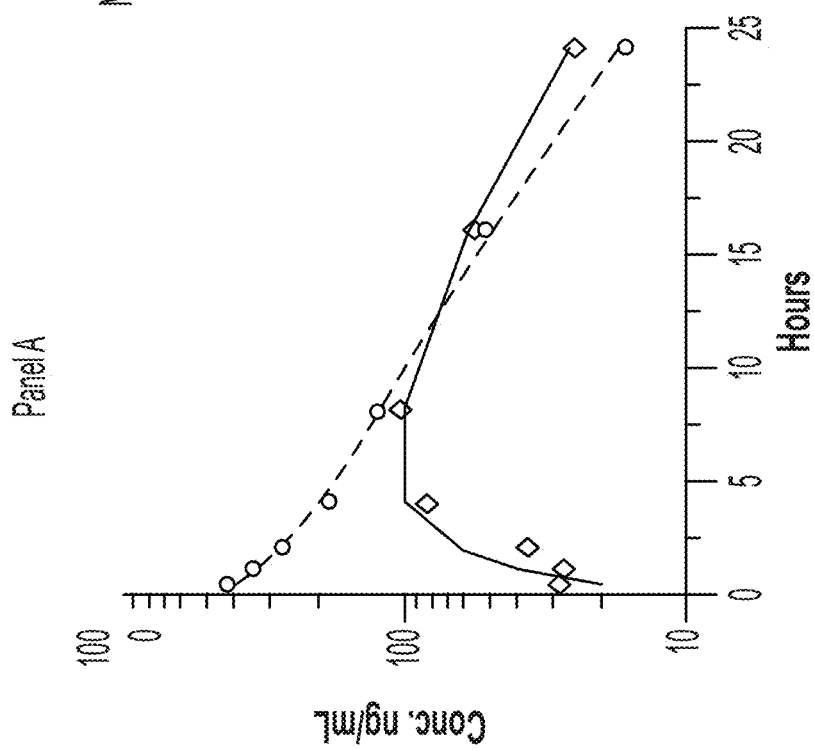
FIG. 9, Panel A is a graph showing IgM concentration in mice in the absence of half-life extension for CDIM binding IgM 55.5. Panel B is a table providing PK parameters.

Example 3: Construction and Testing of Anti-CD20 Antibody with Albumin Binding Domain Tethered to J-Chain The half-life of IgMs in human plasma is estimated to be around 2-3 days and shorter still in mice (FIG. 9). This is significantly shorter than for IgGs, which interact with the neonatal Fc receptor (FcRn) and are recycled after endocytosis enabling a much longer half-life of roughly 21 days. In order to increase the half-life of IgMs, tethering of scFvs to either terminus of the J-chain was performed, without significantly altering the effector functions of IgMs such as CDC (FIG. 7).

There are several approaches that have been described in the art to enable half-life extension of biologics. These include tethering of mutants of human serum albumin (Andersen et al, JBC VOL. 289, NO. 19, pp. 13492-13502, 2014), peptides (Dennis et al, *J. Biol. Chem.* 2002, 277: 35035-35043) or scFvs that can bind human serum albumin (Muller et al mAbs 4:6, 673-685; 2012), Shown below is the sequence of an example J-chain that can be used to extend the half-life of IgMs by utilizing an albumin binding domain designed for binding to human serum albumin with high affinity (Hopp et al PEDS 23:pp 827-833 (2010)).

```
Albumin binding domain:
                                     (SEQ ID NO: 22)
QHDEAVDANSLAEAKVLANRELDKYGVSDYYKNLINNAKTVEGVKALIDE

ILAALP
```

```
Wt J-chain:
                                      (SEQ ID NO: 1)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPD

A15J:
                                     (SEQ ID NO: 23)
QHDEAVDANSLAEAKVLANRELDKYGVSDYYKNLINNAKTVEGVKALIDE

ILAALPGGGGSGGGGSGGGGSQEDERIVLVDNKCKCARITSRIIRSSEDP

NEDIVERNIRIIVPLNNRENISDPTSPLRTRFVYHLSDLCKKCDPTEVEL

DNQIVTATQSNICDEDSATETCYTYDRNKCYTAVVPLVYGGETKMVETAL

TPDACYPD
```

Expression and assembly of this ABD-J-chain fusion into IgMs was tested using the IgM sequence described in Example 1. In addition, fusion of this ABD to J-chain was verified not to perturb the CDC activity on anti-CD20 IgM on target cell lines carrying CD20 on their surface (eg. Ramos) as described in Example 1. Finally, the affinity of ABD in the context of the IgM, for binding to HSA was measured using immobilized HSA using surface plasmon resonance (Biacore).

Example 4: Construction and Testing of Anti-CD20 Antibody with Transferrin Binding scFv Delivery of biologic drugs to targets in the central nervous system, particularly the brain, is a challenging problem because of the Blood Brain Barrier (BBB). The transferrin receptor (TfR) is overexpressed in the endothelium of the BBB. It is thought to act as a shuttle to transport nutrients such as iron from the periphery to the brain. Receptor mediated transcytosis (RMT) has been used by several groups to deliver biologics to the brain. For example, Jones et al have described the use of transferrin binding antibodies as a method of shuttling biologics across the BBB (Jones, A. R., and E. V. Shusta. 2007. Blood-brain barrier transport of therapeutics via receptor-mediation. Pharm. Res. 24:1759-1771).

One such transferrin binding sequence was used (Vh sequence selected from phage display by Yang et al) to make an in-frame fusion with our J-chain as shown below.

Transferrin receptor binding Vh sequence:

```
                                     (SEQ ID NO: 24)
M A Q V Q L L E S G G G L V Q P G G S L R L S C A

A S G F I F N T E Y M A W V R Q A P G K G L E W V

S A I K E Q S G S T Y Y A D S V K G R F T I S R D

N S K N T L Y L Q M N S L R A E D T A V Y Y C A A

Q M H H E A E V K F W G Q G T L V T V S
```

Transferrin receptor binding Vh sequence fused to J-chain at N-terminus:

```
                                     (SEQ ID NO: 25)
M A Q V Q L L E S G G G L V Q P G G S L R L S C A

A S G F I F N T E Y M A W V R Q A P G K G L E W V
```

-continued

```
S A I K E Q S G S T Y Y A D S V K G R F T I S R D

N S K N T L Y L Q M N S L R A E D T A V Y Y C A A

Q M H H E A E V K F W G Q G T L VTVSGGGGSGGGGSGGG

GSQEDERIVLVDNKCKCARITSRIIRSSEDPNEDIVERNIRIIVPLNNR

ENISDPTSPLRTRFVYHLSDLCKKCDPTEVELDNQIVTATQSNICDEDS

ATETCYTYDRNKCYTAVVPLVYGGETKMVETALTPDACYPD
```

The fusion J-chain was incorporated into a relevant IgM (for example the CD20 IgM described previously). In addition to the assays described earlier for expression and assembly, antigen binding, cell binding and cell internalization assays were carried out to verify that the resultant IgM+TfR J-chain is functional.

Figure 10:
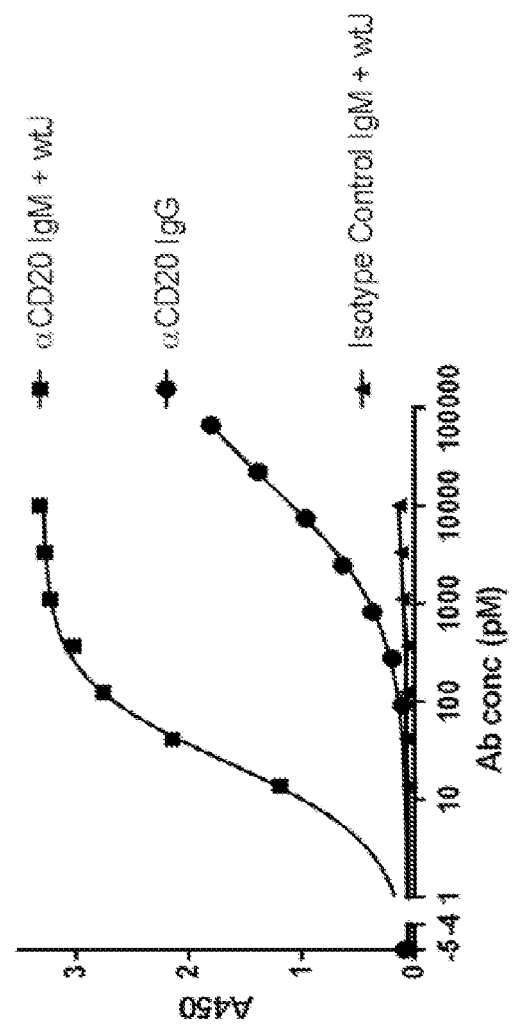
FIG. 10 is a graph showing results of a multimer specific ELISA for anti-CD20 IgM antibodies demonstrating the vastly tighter binding of IgM.

Antigen binding was tested using ELISAs with commercially available recombinant human transferin receptor (R&D Systems) immobilized on plates. Briefly, ~100 ng of human tansferrin receptor was added to a 96-Wellplate (Nunc Maxisorb plate) per well at 4 C, overnight. The plate was washed with PBS-0.05% Tween-20 three times and blocked with StartingBlock (Pierce) at 37 C for 1 hour. Then the plate was washed with PBST three times after the blocking solution was removed. The bispecific antibodies with different concentrations were added to each well and the plate was allowed to stand at 37 C for 1 hour. After three PBST washes, HRP-conjugated anti-human IgG Fc antibody (Abcam, diluted in StartingBlock at a ratio of 1:10,000) was added to each well, and the plate was further incubated at 37° C. for 1 hour. After three PBST washes, colorimetric TMB substrate (US Biological) was added to each well to perform a peroxidase reaction. After the addition of stop solution (1 M H2SO4), the absorbance was monitored at 450 nm and the equilibrium constant ($K_D$) for the antibody was calculated by fitting the resultant data with Graph Pad Prism. For testing CD20 binding, an ELISA using immobilized CD2O-Fc (Acros Biosystems) was used as illustrated in FIG. 10. Detection antibody for this ELISA is a mouse anti-human kappa light chain antibody conjugated with HRP (Southern Biotech, 9230-05). Capture, detection and development are carried out as detailed above.

To verify that the resultant IgM binds to target cells by using FACS based assay such as those described in Example 1, on tumor cell lines known to overexpress the transferrin receptor for example the human erythroleukemia cell line K562. Mean fluorescence intensity readings were analyzed using GraphPad Prism to calculate a $K_d$.

Example 5: Use of Site Specific Chemoenzymatic Labeling to Generate Imaging Agents and Antibody Drug Conjugates with IgMs IgMs are very large biomolecules (>1 MDa with J-chain). Labeling of IgMs to enable visualization in animal studies is problematic because of the numerous free lysine residues. In order to enable labeling with stoichiometry and positions that retain the activity of IgMs, site specific labeling is carried out using chemo-enzymatic approaches as reviewed in Kline et al (Pharm Res 2014 Dec. 16).

One method for site specifically labeling IgM molecules is to use a glycan labeling strategy as described in Houghton et al (PNAS (52) 15850-15855). The method uses a combination of enzymes—beta galactosidase to remove a terminal galactose residue and then a promiscuous galactose transferase (GalTY289L) to install an azide labeled sugar (GlcNAz) that can be used to post-synthetically add a DIBO labeled dye or cytotoxin. Because the heavy chain of IgMs carries five glycans as opposed to the single glycan on each heavy chain of an IgG antibody, much more efficient labeling is expected using this approach with an antibody to dye/drug ratio of up to 1:102 if the glycan on the J-chain is also derivatized. As shown in FIG. 10, using an example IgM (1.5.3V15J15HSA) efficient labeling was demonstrated with this approach, and an Alexa 647 DIBO dye. Clearly, a similar approach can also be used to generate IgMs that are labeled with PET tracers and cytotoxic molecules.

As a second example of using an acceptor sequence on the J-chain for post-translational site-specific labeling, the "LLQGA" recognition site of microbial transglutaminase (mTGase) is added to the C-terminus of J-chain as shown below (FIG. 12).

J chain with "Q Tag":

```
                                          (SEQ ID NO: 26)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPDGGGGSGGGGSGGG

GSLLQGA
```

Next, dye molecules with a primary amine at its terminus e.g Alexa 488 Cadaverine (Thermo Scientific) was reacted with IgMs incorporating this J-chain in the presence of mTGAse under standard conditions (Strop et al Bioconjugate Chemistry 2015 26(4) 650-9). After incubation overnight at room temperature with 5× molar excess of dye, free dye was separated from labeled IgM using size exclusion chromatography on a NAP-5 column (Biorad). Incorporation of dye was quantitated using absorbance at 488 nm.

It follows that such methods can also be used with other enzymes that can be used for chemo-enzymatic modification as well as other small molecules (e.g., cytotoxic drugs) that carry appropriate handles for functionalization.

Example 6: In Vivo Bio-Distribution Studies Using IgMs Labeled with Near Infra-Red Dye VivoTag680 (Perkin Elmer)

In order to follow the bio-distribution of IGM-55.5 in mice, the molecule was labeled with a near infra-red dye VivoTag680 (Perkin Elmer) using standard amine coupling with an NHS ester at neutral pH (Vasquez et al, PLoS One. 2011; 6: e20594). The injected group received an intravenous injection with 2 nmol/mouse of the labeled IgM molecule. The background control group remained un-injected as a way to distinguish the fluorescence signal of the labeled antibodies from low level background signal, which is primarily from food in the gut. The t0 imaging time point was performed immediately after injection with antibody. Mice were sacrificed after the final in vivo imaging timepoint, followed by resection of tissues and ex vivo imaging.

A generalized schematic of a temporal biodistribution model assessed by in vivo 3D FMT is presented in FIG. 11 Panel A. This type of study is well suited to non-invasively determine both the blood PK of labeled antibodies (determined from the decrease in fluorescence signal of blood in the heart), as well as kinetic biodistribution into various organ systems (brain, lungs, heart, liver, kidneys, stomach, intestines, bladder, and skin). For each animal at each time point, the blood fluorescence signal was subtracted from the total signal of each of the other organs to provide a more accurate determination of tissue accumulation. The in vivo tissues were also assessed ex vivo at the terminal time point by epifluorescence. Ex vivo epifluorescence measurements were also obtained for gall bladder, muscle, spleen, pancreas, white blood cells, lymph nodes, and intestines (which were flushed prior to imaging to remove fecal material).

Whole body and head bio-distribution imaging was performed on the FMT4000 at 0, 1, 2, 4, 8, 24, 48, and 96 h post-injection. Additional animals were bled at 0, 1, 2, 4, 8, 24, 48, 96 h, and these blood samples were shipped to IGM Biosciences for assay. For tomographic imaging, animals were positioned in the supine position within an imaging cassette that provided gentle restraint and mild compression. All images were successfully acquired at the planned timepoints. Whole body non-invasive biodistribution and blood pharmacokinetics showed rapid blood clearance (t½=20 minutes) and dominant liver accumulation with some stomach and kidney signal. Un-injected controls showed only low level signal within the stomach and intestines, and data from IgM-injected mice were corrected for these background levels. The accumulation in liver, kidney and stomach was very rapid and achieved the highest levels at 1 h post-injection, partially clearing by 96 h. The majority of the signal resided in the liver (approximately 5× that of the other tissues); but when normalizing for tissue weight, comparable signal intensity could be seen in the stomach, with somewhat lower signal intensity in the kidneys (FIG. 11, Panel B). Such in vivo studies can also be carried out with the IgMs carrying modified J-chains to assess the increase in half-life or tissue distribution.

Example 7: Pharmacokinetics of IgG v. IgM with J-Chain

Pharmacokinetic (PK) studies were conducted in Balb/c mice to assess clearance of IgG and IgM antibodies, with and without an attached modified J-chain. 100 ug of each antibody was administered to the mice via intravenous infusion. Approximately 500 uL of blood was collected by terminal cardiac puncture at each timepoint, with 3 mice per timepoint, and 8 or 15 timepoints total. ELISA was used to measure the concentration of each antibody in the blood. Quality metrics were verified on all ELISAs, and PK parameters were derived using standard curve fitting techniques.

Figure 16:
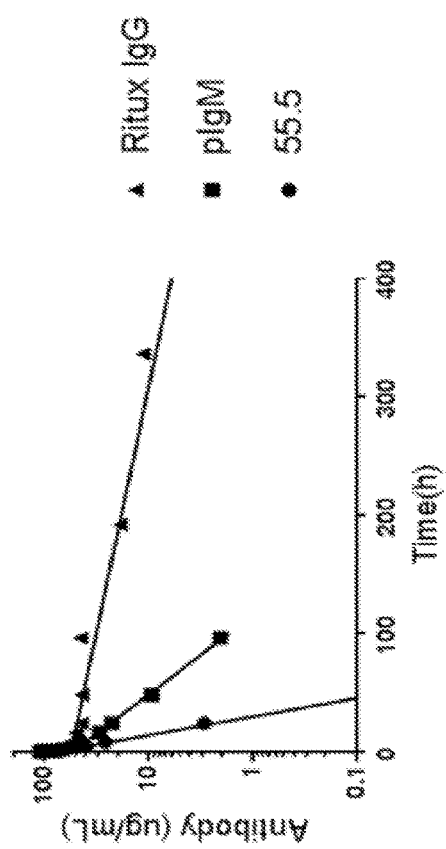
FIG. 16, Panel A, is a graph showing antibody concentration as a function of time in a BALB/c mouse PK experiment for a model IgG (Rituximab), serum derived polyclonal IgM from humans, and an engineered CHO cell derived IgM (55.5). Panel B is a table showing alpha and beta half-life, and AUC for these three different antibodies.

PK results from Rituximab, polyclonal IgM and IgM 55.5 are provided in FIG. 16. These results demonstrate that IgM half-life in mice is significantly shorter that IgG half-life, as evidenced by the fact Rituximab (IgG) had a longer half-life than either the polyclonal IgM of the IgM 55.5. In addition, the half-life of IgM 55.5, produced in CHO cells, was shorter than that of human polyclonal IgM.

Figure 17:
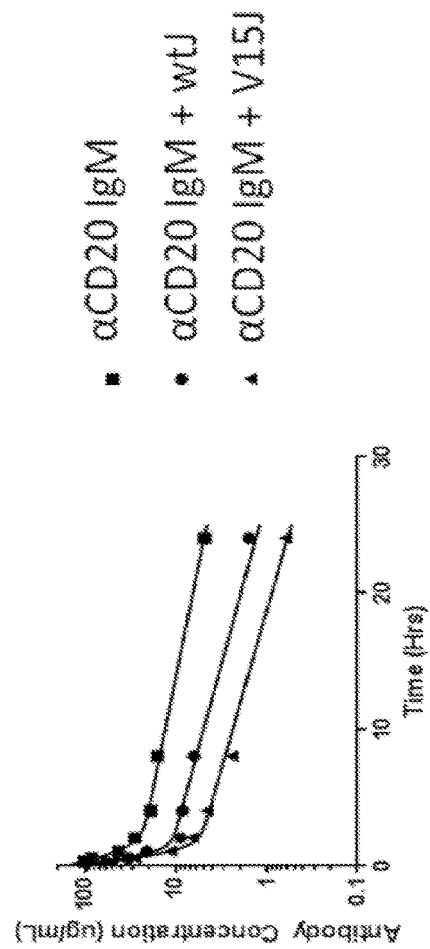
FIG. 17, Panel A, is a graph showing antibody concentration as a function of time in a PK experiment in BALB/c mice testing the effect of J-chain incorporation in IgM. Panel B is a table showing alpha and beta half-life, and AUC for three different IgM antibodies with wild type (wt) or J-chain fused with an scFv configured to bind T-cells.

Results from IgM 1.5.3 with and without J-chain are provided in FIG. 17. As shown, the half-life of IgM 1.5.3 with no J-chain (1.5.3 IgM) was comparable to the half-life of IgM 55.5. The addition of a wild-type J-chain reduced the half-life of IgM 1.5.3. Addition of a J-chain having the V-linker-J orientation (1.5.3. V15J) further reduced the half-life of the antibody. These results demonstrate that the addition of J-chain to an IgM antibody reduces the half-life of the antibody.

Example 8: Fusion of an Albumin Binding Domain to the J-Chain Significantly Reduces Clearance of IgMs As noted above, the pharmacokinetics of IgMs indicate rapid blood clearance. Experiments were performed to determine the serum half-life-extending effects of tethering an albumin binding domain (ABD) (SEQ ID NO: 22) to an IgM J-chain. DNA corresponding to the IgM heavy and light chains as shown in Example 1, as well as that corresponding to either the V15J sequence of Example 1 (Visilizumab (V) fused to the J-chain through a linker containing 15 amino acid residues) or the A15J sequence of Example 3 (an albumin-binding domain fused to the J-chain through a linker containing 15 amino acid residues) were co-transfected into HEK293 cells, and the proteins were expressed and purified using the camelid resin as described before. Three groups of mice received an intravenous injection with 100 ug/mouse of either V15J-1.5.3-IgM, A15J-1.5.3-IgM, or Rituximab (IgG). Blood samples were taken periodically following the initial injection, and the serum concentration of each injected antibody was measured in the samples using an ELISA that was adapted to measure the concentration of the tested antibodies in serum.

Figure 18:
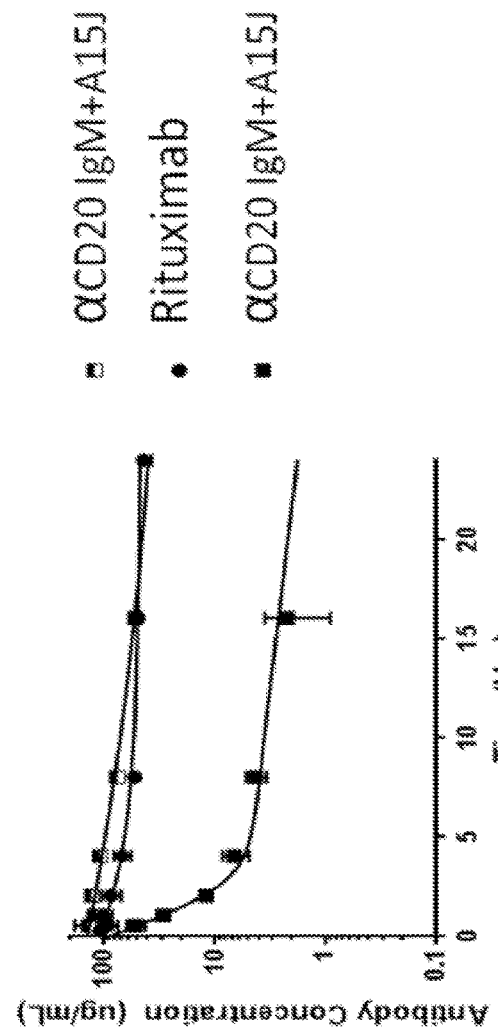
FIG. 18 is a graph showing serum concentration as a function of time for three different model antibodies: Rituximab(IgG); an anti-CD20 IgM with a domain configured to bind T-cells fused to the N-terminus of the J-chain; and an anti-CD20 IgM with an albumin binding domain (ABD) fused to the N-terminus of the J-chain with a 15-amino acid linker (A15J).

The data demonstrate that fusion of an albumin-binding domain to the J-chain resulted in a significant and relatively large increase in the half-life of IgMs. As shown in FIG. 18, the beta half-life of V15J-1.5.3-IgM, which did not include the albumin binding domain, was only 7 hours. By contrast, the beta half-life of A15J-1.5.3-IgM, which did include the albumin-binding domain on the J-chain, was 32 hours, which was comparable to Rituximab.

Example 9: IgM Albumin J-Chain Assembly and Expression

J-chain constructs that incorporate a human serum albumin (HSA) were prepared as provided in Example 1. Constructs were prepared with the HSA positioned at the N-terminus of the J-chain (HSA-15-J), and at the C-terminus of the J-chain (J-15-HSA). To verify that IgM antibodies incorporating J-chains containing HSA in either of these configurations could be assembled and expressed, SDS-PAGE gels under reducing conditions and Western blots were conducted.

Reducing SDS-PAGE: NuPage LDS sample buffer (Life Technologies) and NuPage reducing agent dithiothreitol (Life Technologies) were added to IgM protein samples and heated to 80° C. for 10 minutes before loading on NuPage Novex 4-12% Bis-Tris Gel (Life Technologies). NuPage MES SDS Running Buffer (Life Technologies) was used for gel electrophoresis. Gels were run until the dye front reached the bottom of the gel. After electrophoresis was complete, the gel was removed from the apparatus and stained using Colloidal Blue Staining (Life Technologies).

Western Blot: An acrylamide gel run under conditions described above was washed in a 20% ethanol solution for 10 minutes and then the protein was transferred to an iBlot PVDF membrane (Invitrogen) using the iBlot Dry Blotting System (Invitrogen) at 20V for 10 minutes. After transfer the PVDF membrane was blocked using 2% bovine serum albumin, 0.05% Tween 20 for at least 12 hours. A 1/500 dilution of Pierce J-chain antibody (ThermoFisher) was added to the membrane, incubated for 1 hour, and then a 1/5000 dilution of peroxidase-conjugated goat anti-rabbit IgG (Jackson ImmunoResearch) was added and allowed to incubate in darkness for 30 minutes. Finally, Super Signal West Pico Chemiluminescent Substrate (ThermoFisher) was added to the blot and the resulting signal was visualized using the ChemiDoc-It HR410 Imaging System (UVP) or by exposing the blot to X-ray film.

Figure 19:
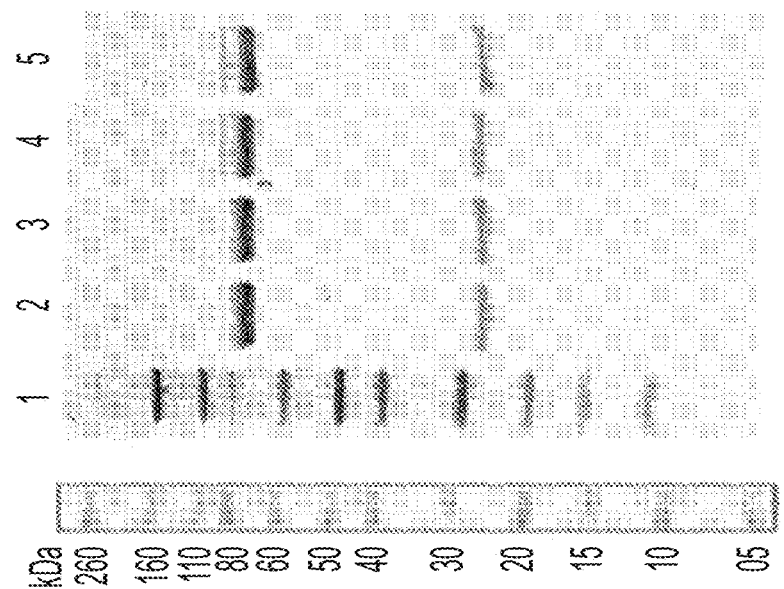
FIG. 19 is an image of a reducing PAGE gel and a Western blot analysis of the antibodies listed in the table. Incorporation of the J-chain with or without fused human serum albumin in either orientation with respect to J-chain is visualized using western blotting with an anti-J chain antibody.

The results are provided in FIG. 19, and demonstrate that J-chains having either of these configurations can be successfully incorporated into IgM antibodies, and that the resulting IgM antibodies can be assembled and expressed by CHO cells.

Example 10: CDC Activity of ABD/HSA-Containing J-Chains

Complement-dependent cytotoxicity (CDC) assays were conducted using IgM antibodies incorporating a J-chain having the HSA-15-J (HSA at the N-terminus of the J-chain, followed by a 15 amino acid linker sequence) or the J-15-HSA (HSA at the C-terminus of the J-chain, preceded by a 15 amino acid linker sequence) configuration.

Ramos, a CD20+ cell line, was seeded in 96 well half area white plates at 25,000 cells/well. The protein under evaluation and human complement (5% final, Quidel) were added to initiate the CDC analysis and the number of viable cells were measured using Cell Titer Glo and manufacturer's protocol. Luminescence was measured on an Envision multimode reader (Perkin Elmer) using 0.1 s integration time per well. The percentage of viable cells was calculated by normalizing the luminescence values (Relative luminescence units—RLU) versus wells with no added test compound. Data were analyzed using GraphPad Prism and a four parameter fit with top and bottom values fixed at 100 and 0% viability respectively.

Figure 20:
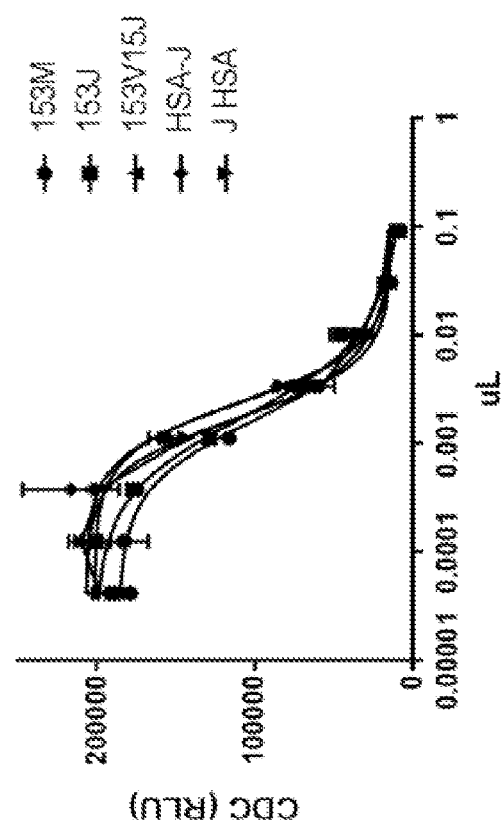
FIG. 20, is a graph showing CDC activity as a function of concentration for four IgM antibodies demonstrating that incorporating a moiety as large as 65 KDa HSA does not disrupt the CDC activity of IgM.

The results are provided in FIG. 20. The results demonstrate that the assembled IgM+HSA J-chain antibodies are functionally active in CDC assays in both orientations.

Example 11: Pharmacokinetics of J-HSA and HSA-J Constructs

Figure 21:
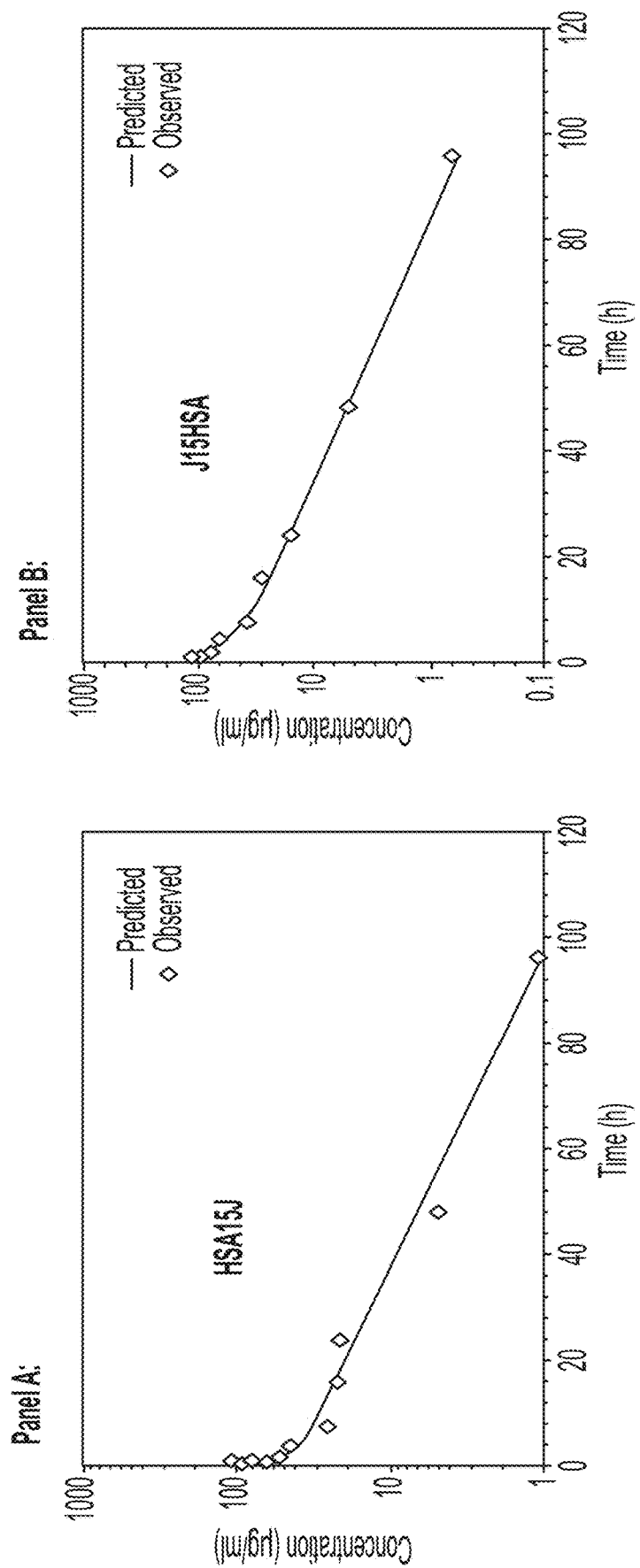
FIG. 21, Panel A, is a graph showing concentration as a function of time in a mouse pharmacokinetics experiment, for an IgM antibody that has an HSA-15-J configuration on the J-chain. Panel B is a graph showing concentration as a function of time for a mouse PK experiment with IgM antibody that has a J-15-HSA configuration on the J-chain.

PK studies, as described above, were conducted in mice to evaluate the PK characteristics of IgM antibodies incorporating a J-chain having the HSA-15-J or the J-15-HSA orientation. The results are provided in FIG. 21 and FIG. 22. The results demonstrate an orientation effect, wherein the HSA positioned at the N-terminus (HSA-15-J orientation) had diminished half-life in comparison to the J-15-HSA orientation (HSA located at the C-terminus).

Example 12: Assembly and Expression of "Bidentate" J-Chain Constructs

Assembly and expression studies were conducted as described above in Example 9 for constructs containing both a CD3-binding moiety (abbreviated as "V") and a half-life extending moiety (either an albumin-binding domain protein, abbreviated "ABD", or a human serum albumin protein, abbreviated as "HSA"). These constructs are referred to as "bidentate" constructs. A summary of all the constructs that were evaluated is provided below in Table 10.

Figure 23:
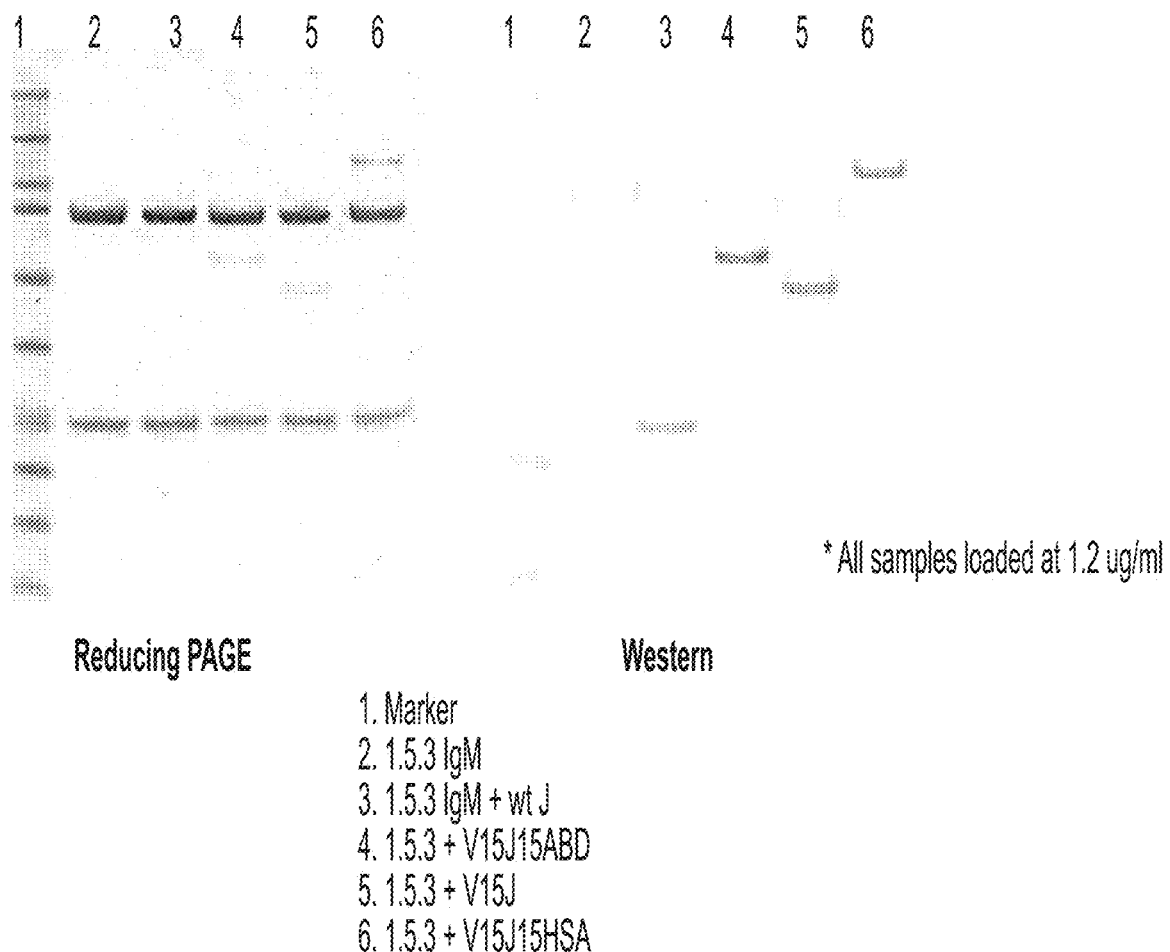
FIG. 23 is an image of a reducing PAGE gel and a Western blot analysis of the antibodies listed in the table, one of which (1.5.3V15J15ABD) has bidentate J-chain configuration.

Constructs were prepared with the half-life extending moiety (e.g., the "ABD" or the "HSA") positioned at the C-terminus of the J-chain, and the CD3-binding moiety (e.g., "V") positioned at the N-terminus. To verify that IgM antibodies incorporating J-chains having any of these configurations could be assembled and expressed, SDS-PAGE gels under reducing conditions and Western blots were conducted, as described above. The results are provided in FIG. 23, and demonstrate that J-chains having either of these configurations can be successfully incorporated into IgM molecules, and that the resulting IgM molecules can be assembled and expressed by CHO cells.

Example 13: CDC Activity of Bidentate J-Chain Constructs

Figure 24:
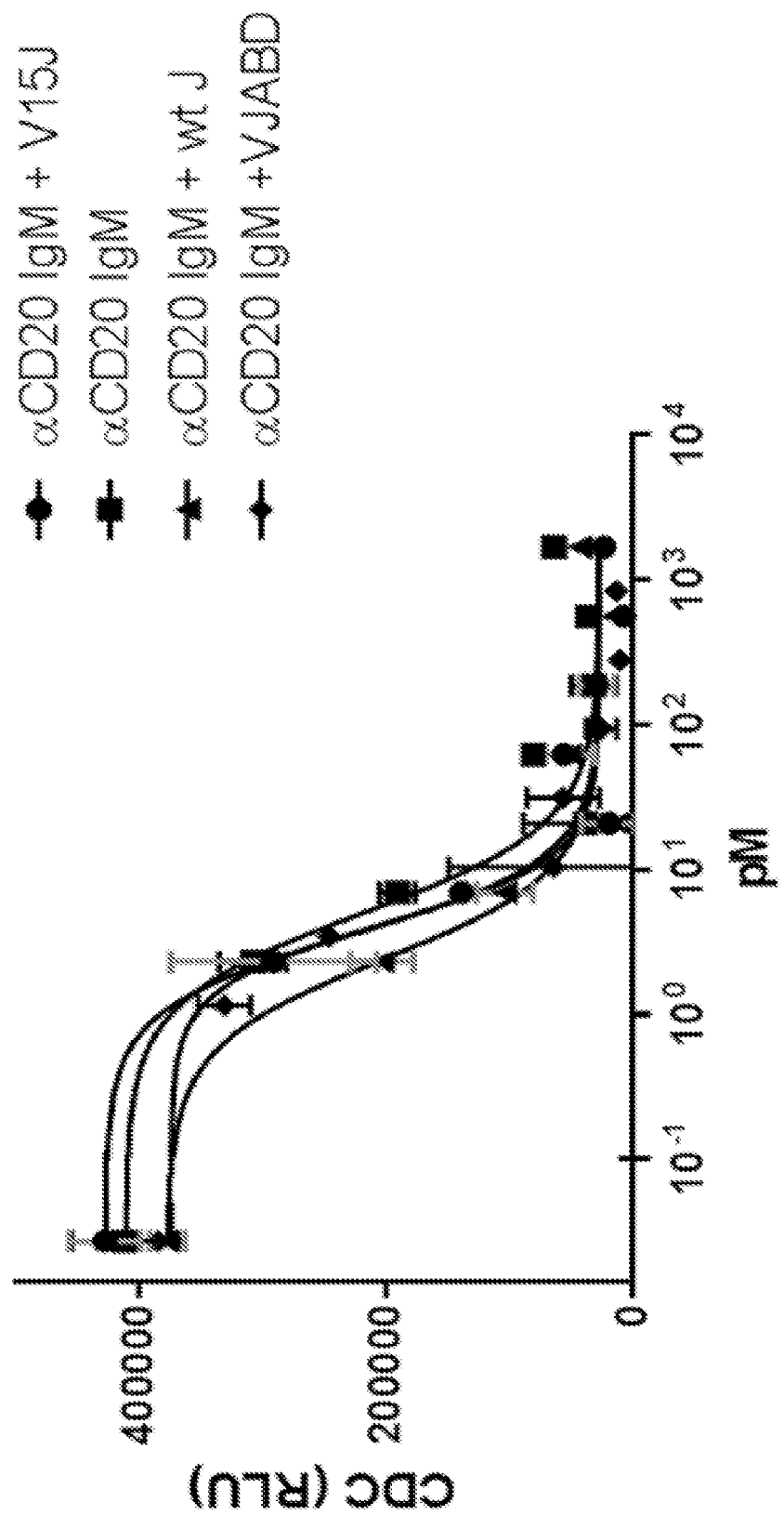
FIG. 24, is a graph showing CDC activity as a function of concentration for antibodies having the indicated J-chain configuration. The bidentate ABD-IgM has essentially the same activity as IgM with or without J-chain.
Figure 25:
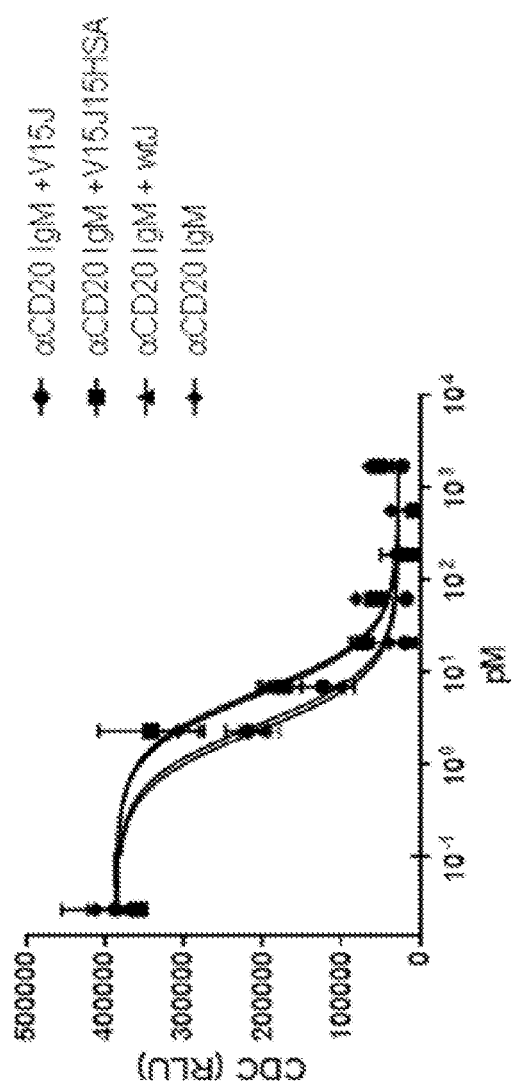
FIG. 25, is a graph showing CDC activity as a function of concentration for antibodies having the indicated J-chain configuration. The bidentate HSA-IgM has essentially the same activity as IgM with or without J-chain.

CDC assays, as described above in Example 10, were conducted using IgM antibodies incorporating the bidentate J-chains described above in Example 12. The results are provided in FIG. 24, and in FIG. 25. The results demonstrate that the bidentate J-chains that were evaluated did not diminish the CDC activity of the IgM antibodies that were tested.

Example 14: Pharmacokinetics of Bidentate J-Chain Constructs

PK studies, as described above, were conducted in mice to evaluate the PK characteristics of the IgM antibodies incorporating the bidentate J-chains described above in Example 12. The results are provided in FIG. 26 and FIG. 27. The results demonstrate that both the V-J-ABD and V-J-HSA bidentate J-chains exhibited good alpha and beta half-life, and that the overall $AUC_{0-inf}$ showed an approximately 60% increase as compared to 1.5.3 IgM J-15-HSA.

Example 15: In-Vivo Activity of Bidentate J-Chain Constructs

CD34+ humanized NSG mouse studies were performed by In-Vivo Technologies, Inc. The mice were purchased from the Jackson Laboratory, and dosed with test articles through tail vein injection. Blood samples were collected at designated time points through facial vein. Blood samples from both the CD34+ mouse studies were sent back to IGM Biosciences Inc. for lymphocyte analysis. Blood samples were stained for human CD56, CD3, CD19 and CD45 markers to identify different populations of human lymphocytes. CountBright Absolute Counting Beads (LifeTechnologies, C36950) were used to quantify the absolute number of lymphocytes in the blood samples. The lymphocyte levels were plotted and analyzed using GraphPad Prism. As shown in FIG. 28, Panels A and B, the B-lymphocyte levels were essentially reduced to <10% of pre-dose levels, and this level was retained at the 24 hour timepoint for both 1.5.3V15J15HSA(K573P) and 1.5.3V15J15HSAwt with as little as 10 ug of article dosed one single time.

TABLE 10

Sequence Summary

| SEQ ID NO: | Short Name | Sequence |
|---|---|---|
| 27 | Rituximab VH | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSA |
| 28 | Rituximab HCDR1 | SYNMH |

TABLE 10-continued

Sequence Summary

| SEQ ID NO: | Short Name | Sequence |
|---|---|---|
| 29 | Rituximab HCDR2 | AIYPGNGDTSYNQKFKG |
| 30 | Rituximab HCDR3 | STYYGGDWYFNV |
| 31 | Rituximab VL | QIVLSQSPAILSASPGEKVTMTCRASSSVSYTHWQQKPGSSPKPWIYATSNLASGVPVRFSGSGSGTSYSLTISRVEAEDAATYYCQQWTSNPPTFGGGTKLEIKR |
| 32 | Rituximab LCDR1 | RASSSVSYIH |
| 33 | Rituximb LCDR2 | ATSNLAS |
| 34 | Rituximb LCDR3 | QQWTSNPPT |
| 35 | 900 VH | EVQLVESGGG LVQPGGSLRL SCAASGYTFT SYNMHWVRQA PGKGLEWVGA IYPGNGDTSY NQKFKGRFTI SVDKSKNTLY LQMNSLRAED TAVYYCARVV YYSNSYWYFD VWGQGTLVTV SSASTKGPSV FPLAPSSKST SGGTAALGCL VKDYFPEPVT VSWNSGALTS GVHTFPAVLQ SSGLYSLSSV VTVPSSSLGT |
| 36 | 900HCDR3 | VVYYSNSYWYFDV |
| 37 | 900 VL | DIQMTQSPSS LSASVGDRVT ITCRASSSVS YMHWYQQKPG KAPKPLIYAP SNLASGVPSR FSGSGSGTDF TLTISSLQPE DFATYYCQQW SFNPPTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL |
| 38 | 900LCDR1 | RASSSVSYMH |
| 39 | 900LCDR2 | APSNLAS |
| 40 | 900LCDR3 | QQWSFNPPT |
| 41 | 125 VH | EVQLVQSGAEVKKPGESLKISCKGSGRTFTSYNMHWVRQMPGKGLEWMGAIYPLTGDTSYNQKSKLQVTISADKSISTAYLQWSSLKASDTAMYYCARSTYVGGDWQFDVWGKGTTVTVSS |
| 42 | 125HCDR2 | AIYPLTGDTSYNQKSKL |
| 43 | 125HCDR3 | STYVGGDWQFDV |
| 44 | 125 VL | EIVLTQSPGTLSLSPGERATLSCRASSSVPYIHWYQQKPGQAPRLLIYATSALASGIPDRFSGSGSGTDFTLTISRLEPEDFAVYYCQQWLSNPPTFGQGTKLEIK |
| 45 | 125LCDR1 | RASSSVPYIH |
| 46 | 125LCDR2 | ATSALAS |
| 47 | 125LCDR3 | QQWLSNPPT |
| 48 | 844 VH #2 | QVQLQQPGAELKKPGASVKVSCKASGYTFTSYNMHWVKQTPGRGLEWTGAIYPGNGDTSYNQKFKGKTTLTADKSSSTAYMELSSLRSEDTAVYYCARSTYYGGDWYFNVWGAGTTVTVSA |
| 49 | 844 VH #3 | QVQLQQPGAELKKPGASVKVSCKASGYTFTSYNMHWVKQTPGRGLEWIGAIYPGNGDTSYNQKFKGKTTLTADKSSSTAYMELSSLRSEDTAVYYCARSTYYGGDWYFNVWGAGTTVTVSA |
| 50 | 844 VL #5 | QIVLSQSPAIITASPGEKVTMTCRASTSASYIHWFQQKPTSSPKPWIYATSNLASGVPSRFSGSGSGTTYSMTISSLEAEDAATYYCQQWTSNPPTFGGGTKLEIK |
| 51 | 844 VL #5 LCDR1 | RASTSASYIH |
| 52 | 844 VL #6 | QIVLSQSPAIITASPGEKVTMTCRASTSVSYIHWFQQKPTSSPKPWIYATSNLASGVPSRFSGSGSGTTYSMTISSLEAEDAATYYCQQWTSNPPTFGGGTKLEIK |
| 53 | 844 VL #6, #7 LCDR1 | RASTSVSYIH |
| 54 | 844 VL #7 | QIVLSQSPAIITASPGEKVTMTCRASTSVSYIHWFQQKPGSSPKPWIYATSNLASGVPSRFSGSGSGTTYSMTISSLEAEDAATYYCQQWTSNPPTFGGGTKLEIK |

TABLE 10-continued

Sequence Summary

| SEQ ID NO: | Short Name | Sequence |
|---|---|---|
| 55 | 844 VL #8 | QIVLSQSPAIITASPGEKVTMTCRASSSVSYIHWFQQKPGSSPKPWIYATSNLASGVPSRFSGSGSGTTYSMTISSLEAEDAATYYCQQWTSNPPTFGGGTKLEIK |
| 56 | 844 VH #10 | EVQLQQSGAELKKPGASVKVSCKASGYTFTSYNMHWVKQTPGQGLEWIGAIYPGNGDTSYNQKFKGKTTLTADKSSSTAYMELSSLRSEDTAVYYCARSNYYGSSYWFFDVWGTGTTVTVSS |
| 57 | 844 VH #10 HCDR3 | SNYYGSSYWFFDV |
| 58 | 844 VL #12 | DIVLTQSPAIITASPGEKVTMTCRASSSVNYMDWYQKKPGSSPKPWIYATSNLASGVPSRFSGSGSGTTYSMTISSLEAEDAATYYCQQWSFNPPTFGGGTKLEIK |
| 59 | 844 VL #12 LCDR1 | RASSSVNYMD |
| 60 | 844 VL #12 LCDR3 | QQWSFNPPT |
| 61 | 164 VH | QVQLQQSGAEVKKPGSSVKVSCKASGYTFTSYNMHWVKQAPGQGLEWIGAIYPGNGDTSYNQKFKGKATLTADESTNTAYMELSSLRSEDTAFYYCARSTYYGGDWYFDVWGQGTTVTVSS |
| 62 | 164 VH HCDR3 | STYYGGDWYFDV |
| 63 | 164 VL | MGWSCIILFLVATATGVHSDIQLTQSPSSLSASVGDRVTMTCRASSSVSYIHWFQQKPGKAPKPWIYATSNLASGVPVRFSGSGSGTDYTFTISSLQPEDIATYYCQQWTSNPPTFGGGTKLEIK |
| 64 | 1.5.3 VH | EVQLVQSGAEVKKPGESLKISCKGSGYSFTSYWIGWVRQMPGKGLEWMGIIYPGDSDTRYSPSFQGQVTISADKSITTAYLQWSSLKASDTAMYYCARHPSYGSGSPNFDYWGQGTLVTVSS |
| 65 | 1.5.3 HCDR1 | GYSFTSYWIG |
| 66 | 1.5.3 HCDR2 | IIYPGDSDTRYSPSFQG |
| 67 | 1.5.3 HCDR3 | HPSYGSGSPNFDY |
| 68 | 1.5.3 VL | DIVMTQTPLSSPVTLGQPASISCRSSQSLVYSDGNTYLSWLQQRPGQPPRLLIYKISNRFSGVPDRFSGSGAGTDFTLKISRVEAEDVGVYYCVQATQFPLTFGGGTKVEIK |
| 69 | 1.5.3 LCDR1 | RSSQSLVYSDGNTYLS |
| 70 | 1.5.3 LCDR2 | KISNRFS |
| 71 | 1.5.3 LCDR3 | VQATQFPLT |
| 72 | human IgM constant region DNA | GCCCCAACCCTTTTCCCCCTCGTCTCCTGTGAGAATTCCCCGTCGGATACGAGCAGCGTGGCCGTTGGCTGCCTCGCACAGGACTTCCTTCCCGACTCCATCACTTTCTCCTGGAAATACAAGAACAACTCTGACATCAGCAGCACCCGGGGCTTCCCATCAGTCCTGAGAGGGGGCAAGCACGCAGCCACCTCACAGGTGCTGCTGCCTTCCAAGGACGTCATGCAGGGCACAGACGAACACGTGGTGTGCAAAGTCCAGCACCCCAACGGCAACAAAGAAAAGAACGTGCCTCTTCCAGTGATTGCTGAGCTGCCTCCCAAAGTGAGCGTCTTCGTCCCACCCCGCGACGGCTTCTTCGGCAACCCCCGCAAGTCCAAGCTCATCTGCCAGGCCACGGGTTTCAGTCCCCGGCAGATTCAGGTGTCCTGGCTGCGCGAGGGGAAGCAGGTGGGGTCTGGCGTCACCACGGACCAGGTGCAGGCTGAGGCAAAGGAGTCTGGGACCACGACCTACAAGGTGACCAGCACACTGACCATCAAAGAGAGCGACTGGCTCAGCCAGAGCATGTTCACCTGCCGCGTGGATCACAGGGGCCTGACCTTCCAGCAGAATGCGTCCTCCATGTGTGGCCCCGATCAAGACACAGCCATCCGGGTCTTCTCCATCCCCCCATCCTTTGCCAGCATCTTCCTCACCAAGTCCACCAAGTTGACCTGCCTGGTCACAGACCTGACCACCTATGACAGCGTGACCATCTCCTGGACCCGCCAGAATGGCGAAGCTGTGAAAACCCACACCAACATCTCCGAGAGCCACCCCAATGCCACTTTCAGCGCCGTGGGTGAGGCCAGCATCTGCGAGGATGACTGGAATTCCGGGGAGAGGTTCACGTGCACCGTGACCCACACAGACCTGCCCTCGCCACTGAAGCAGACCATCTCCCGGCCCAAGGGGGTGGCCCTGCACAGGCCCGATGTCTACTTGCTGCCACCAGCCCGGGAGCAGCTGAACCTGCGGGAGTCGGCCACCATCACGTGCCTGGTGACGGGCTTCTCTCCCGCGGACGTCTTCGTCCAGTGGATGCAGAGGGGGCAGCCCTTGTCCCCGGAGAAGTATGTGACCAGCGCCCCAATGCCTGAGCCCCAGGCCCCAGGCCGGTACTTCGCCCACAGCATCCTGACCGTGTCCGAAGAGGAATGGAACACGGGGGAGACCTACACCTGCGTGGTGGCCCATGAGGCCCTGCCCAACAGGGTCACCGAGAGGACCGTGGACAAGTCCACCGGTAAACCCACCCTGTACAACGTGTCCCTGGTCATGTCCGACACAGCTGGCACCTGCTAC |

TABLE 10-continued

Sequence Summary

| SEQ ID NO: | Short Name | Sequence |
|---|---|---|
| 73 | human IgM constant region AA | GSASAPTLFPLVSCENSPSDTSSVAVGCLAQDFLPDSITFSWKYKNNSDISSTRGFPS VLRGGKYAATSQVLLPSKDVMQGTDEHVVCKVQHPNGNKEKNVPLPVIAELPPKVSVF VPPRDGFFGNPRKSKLICQATGFSPRQIQVSWLREGKQVGSGVTTDQVQAEAKESGPT TYKVTSTLTIKESDWLSQSMFTCRVDHRGLTFQQNASSMCVPDQDTAIRVFAIPPSFA SIFLTKSTKLTCLVTDLTTYDSVTISWTRQNGEAVKTHTNISESHPNATFSAVGEASI CEDDWNSGERFTCTVTHTDLPSPLKQTISRPKGVALHRPDVYLLPPAREQLNLRESAT ITCLVTGFSPADVFVQWMQRGQPLSPEKYVTSAPMPEPQAPGRYFAHSILTVSEEEWN TGETYTCVVAHEALPNRVTERTVDKSTGKPTLYNVSLVMSDTAGTCY |
| 74 | J Chain DNA | ATGAAGAACCATTTGCTTTTCTGGGGAGTCCTGGCGGTTTTTATTAAGGCTGTTCATG TGAAAGCCCAAGAAGATGAAAGGATTGTTCTTGTTGACAACAAATGTAAGTGTGCCCG GATTACTTCCAGGATCATCCGTTCTTCCGAAGATCCTAATGAGGACATTGTGGAGAGA AACATCCGAATTATTGTTCCTCTGAACAACAGGGAGAATATCTCTGATCCCACCTCAC CATTGAGAACCAGATTTGTGTACCATTTGTCTGACCTCTGTAAAAAATGTGATCCTAC AGAAGTGGAGCTGGATAATCAGATAGTTACTGCTACCCAGAGCAATATCTGTGATGAA GACAGTGCTACAGAGACCTGCTACACTTATGACAGAAACAAGTGCTACACAGCTGTGG TCCCACTCGTATATGGTGGTGAGACCAAAATGGTGGAAACAGCCTTAACCCCAGATGC CTGCTATCCTGACTAA |
| 75 | J Chain AA | MKNHLLFWGVLAVFIKAVHVKAQEDERIVLVDNKCKCARITSRIIRSSEDPNEDIVER NIIIVPLNNRENISDPTSPLRTRFVYHLSDLCKKCDPTEVELDNQIVTATQSNICDED SATETCYTYDRNKCYTAVVPLVYGGETKMVETALTPDACYPD |
| 76 | human CD20 amino acid | MTTPRNSVNGTFPAEPMKGPIAMQSGPKPLFRRMSSLVGPTQSFFMRESKTLGAVQIM NGLFHIALGGLLMIPAGIYAPICVTVWYPLWGGIMYIISGSLLAATEKNSRKCLVKGK MIMNSLSLFAAISGMILSIMDILNIKISHFLKMESLNFIRAHTPYINIYNCEPANPSE KNSPSTQYCYSIQSLFLGILSVMLIFAFFQELVIAGIVENEWKRTCSRPKSNIVLLSA EEKKEQTIEIKEEVVGLTETSSQPKNEEDIEIIPIQEEEEEETETNFPEPPQDQESSP IENDSSP |
| 77 | Ritux-IgM heavy chain DNA | CAGGTTCAGCTGCAGCAGCCCGGAGCCGAGCTGGTCAAACCTGGCGCTAGTGTGAAAA TGTCATGCAAGGCATCCGGATACACATTCACTAGCTATAACATGCACTGGGTGAAGCA GACCCCCGGCAGGGGTCTGGAGTGGATCGGAGCTATCTACCCCGGCAACGGAGACACA TCTTATAATCAGAAGTTTAAAGGCAAGGCCACCCTGACAGCTGATAAGTCCAGCTCTA CCGCATACATGCAGCTGAGTTCACTGACAAGCGAGGACTCCGCCGTGTACTATTGCGC CCGGTCCACTTACTATGGCGGAGATTGGTATTTCAATGTGTGGGGAGCAGGCACCACA GTCACCGTCTCGAGCGGCAGTGCTAGCGCCCCAACCCTTTTCCCCCTCGTCTCCTGTG AGAATTCCCCGTCGGATACGAGCAGCGTGGCCGTTGGCTGCCTCGCACAGGACTTCCT TCCCGACTCCATCACTTTCTCCTGGAAATACAAGAACAACTCTGACATCAGCAGCACC CGGGGCTTCCCATCAGTCCTGAGAGGGGGCAAGTACGCAGCCACCTCACAGGTGCTGC TGCCTTCCAAGGACGTCATGCAGGGCACAGACGAACACGTGGTGTGCAAAGTCCAGCA CCCCAACGGCAACAAAGAAAAGAACGTGCCTCTTCCAGTGATTGCTGAGCTGCCTCCC AAAGTGAGCGTCTTCGTCCCACCCCGCGACGGCTTCTTCGGCAACCCCCGCAAGTCCA AGCTCATCTGCCAGGCCACGGGTTTCAGTCCCCGGCAGATTCAGGTGTCCTGGCTGCG CGAGGGGAAGCAGGTGGGGTCTGGCGTCACCACGGACAGGTGCAGGCTGAGGCCAAA GAGTCTGGGCCCACGACCTACAAGGTGACCAGCACACTGACCATCAAAGAGAGCGACT GGCTCAGCCAGAGCATGTTCACCTGCCGCGTGGATCACAGGGGCCTGACCTTCCAGCA GAATGCGTCCTCCATGTGTGTCCCCGATCAAGACACAGCCATCCGGGTCTTCGCCATC CCCCCATCCTTTGCCAGCATCTTCCTCACCAAGTCCACCAAGTTGACCTGCCTGGTCA CAGACCTGACCACCTATGACAGCGTGACCATCTCCTGGACCCGCCAGAATGGCGAAGC TGTGAAAACCCACACCAACATCTCCGAGAGCCACCCCAATGCCACTTTCAGCGCCGTG GGTGAGGCCAGCATCTGCGAGGATGACTGGAATTCCGGGGAGAGGTTCACGTGCACCG TGACCCACACAGACCTGCCCTCGCCACTGAAGCAGACCATCTCCCGGCCCAAGGGGGT GGCCCTGCACAGGCCCGATGTCTACTTGCTGCCACCAGCCCGGGAGCAGCTGAACCTG CGGGAGTCGGCCACCATCACGTGCCTGGTGACGGGCTTCTCTCCCGCGGACGTCTTCG TGCAGTGGATGCAGAGGGGGCAGCCCTTGTCCCCGGAGAAGTATGTGACCAGCGCCCC AATGCCTGAGCCCCAGGCCCCAGGCCGGTACTTCGCCCACAGCATCCTGACCGTGTCC GAAGAGGAATGGAACACGGGGGAGACCTACACCTGCGTGGTGGCCCATGAGGCCCTGC CCAACAGGGTCACCGAGAGGACCGTGGACAAGTCCACCGGTAAACCCACCCTGTACAA CGTGTCCCTGGTCATGTCCGACACAGCTGGCACCTGCTACTGA |
| 78 | Ritux-IgM heavy chain AA | QVQLQQPGAELVKPGASVKMSCKASGYTFTSYNMHWVKQTPGRGLEWIGAIYPGNGDT SYNQKFKGKATLTADKSSSTAYMQLSSLTSEDSAVYYCARSTYYGGDWYFNVWGAGTT VTVSSGSASAPTLFPLVSCENSPSDTSSVAVGCLAQDFLPDSITFSWKYKNNSDISST RGFPSVLRGGKYAATSQVLLPSKDVMQGTDEHVVCKVQHPNGNKEKNVPLPVIAELPP KVSNFVPPRDGFFGNPRKSKLICQATGFSPRQIQVSWLREGKQVGSGVTTDQVQAEAK ESGPTTYKVTSTLTIKESDWLSQSMFTCRVDHRGLTFQQNASSMCVPDQDTAIRVFAI PPSFASTFLTKSTKLTCLVTDLTTYDSVTISWTRQNGEAVKTHTNISESHPNATFSAV GEASICEDDWNSGERFTCTVTHTDLPSPLKQTISRPKGVALHRPDVYLLPPAREQLNL RESATITCLVTGFSPADVFVQWMQRGQPLSPEKYVTSAPMPEPQAPGRYFAHSILTVS EEEWNTGETYTCVVAHEALPNRVTERTVDKSTGKPTLYNVSLVMSDTAGTCY- |

TABLE 10-continued

Sequence Summary

| SEQ ID NO:Short Name | Sequence |
|---|---|
| 79  Ritux-light chain DNA | CAAATTGTGCTGTCTCAGAGTCCAGCTATCCTGAGCGCATCTCCCGGAGAGAAGGTGA CCATGACATGCAGAGCCTCCAGCTCTGTCTCCTACATCCACTGGTTCCAGCAGAAGCC CGGCTCCTCCCCAAAACCCTGGATCTACGCCACCTCTAACCTGGCTAGTGGTGTGCCT GTCAGGTTTAGTGGATCAGGGTCCGGCACCAGCTACTCTCTGACAATCAGCCGGGTGG AGGCTGAAGACGCCGCTACATACTATTGCCAGCAGTGGACTTCTAATCCCCCTACCTT CGGCGGAGGGACAAAGCTGGAGATCAAGCGTACGGTGGCTGCACCATCTGTCTTCATC TTCCCGCCATCTGATGAGCAGTTGAAATCTGGAACTGCCTCTGTTGTGTGCCTGCTGA ATAACTTCTATCCCAGAGAGGCCAAAGTACAGTGGAAGGTGGATAACGCCCTCCAATC GGGTAACTCCCAGGAGAGTGTCACAGAGCAGGACAGCAAGGACAGCACCTACAGCCTC AGCAGCACCCTGACGCTGAGCAAAGCAGACTACGAGAAACACAAAGTCTACGCCTGCG AAGTCACCCATCAGGGCCTGAGCTCGCCCGTCACAAAGAGCTTCAACAGGGGAGAGTG TTAG |
| 80  Ritux-light chain AA | QIVLSQSPAILSASPGEKVTMTCRASSSVSYIHWFQQKPGSSPKPWIYATSNLASGVP VRFSGSGSGTSYSLTISRVEAEDAATYYCQQWTSNPPTFGGGTKLEIKRTVAAPSVFI FPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC- |
| 81  1.5.3 -IgM heavy chain DNA | GAGGTGCAGCTGGTGCAGTCCGGCGCCGAGGTGAAGAAGCCCGGCGAGTCCCTGAAGA TCTCCTGCAAGGGCTCCGGCTACTCCTTCACCTCCTACTGGATCGGCTGGGTGAGGCA GATGCCCGGCAAGGGCCTGGAGTGGATGGGCATCATCTACCCCGGCGACTCCGACACC AGGTACTCCCCCTCCTTCCAGGGCCAGGTGACCATCTCCGCCGACAAGTCCATCACCA CCGCCTACCTGCAGTGGTCCTCCCTGAAGGCCTCCGACACCGCCATGTACTACTGCGC CAGGCACCCCTCCTACGGCTCCGGCTCCCCCAACTTCGACTACGGGGCAGGGCACC CTGGTGACCGTGTCCTCCGGCAGTGCTAGCGCCCCAACCCTTTTCCCCCTCGTCTCCT GTGAGAATTCCCCGTCGGATACGAGCAGCGTGGCCGTTGGCTGCCTCGCACAGGACTT CCTTCCCGACTCCATCACTTTCTCCTGGAAATACAAGAACAACTCTGACATCAGCAGC ACCCGGGGCTTCCCATCAGTCCTGAGAGGGGGCAAGTACGCAGCCACCTCACAGGTGC TGCTGCCTTCCAAGGACGTCATGCAGGGCACAGACGAACACGTGGTGTGCAAAGTCCA GCACCCCAACGGCAACAAAGAAAAGAACGTGCCTCTTCCAGTGATTGCTGAGCTGCCT CCCAAAGTGAGCGTCTTCGTCCCACCCCGCGACGGCTTCTTCGGCAACCCCCGCAAGT CCAAGCTCATCTGCCAGGCCACGGGTTTCAGTCCCCGGCAGATTCAGGTGTCCTGGCT GCGCGAGGGGAAGCAGGTGGGGTCTGGCGTCACCACGGACCAGGTGCAGGCTGAGGCC AAAGAGTCTGGGCCCACGACCTACAAGGTGACCAGCACACTGACCATCAAAGAGAGCG ACTGGCTCAGCCAGAGCATGTTCACCTGCCGCGTGGATCACAGGGGCCTGACCTTCCA GCAGAATGCGTCCTCCATGTGTGTCCCCGATCAAGACACAGCCATCCGGGTCTTCGCC ATCCCCCCATCCTTTGCCAGCATCTTCCTCACCAAGTCCACCAAGTTGACCTGCCTGG TCACAGACCTGACCACCTATGACAGCGTGACCATCTCCTGGACCCGCCAGAATGGCGA AGCTGTGAAAACCCACACCAACATCTCCGAGAGCCACCCCAATGCCACTTTCAGCGCC GTGGGTGAGGCCAGCATCTGCGAGGATGACTGGAATTCCGGGGAGAGGTTCACGTGCA CCGTGACCCACACAGACCTGCCCTCGCCACTGAAGCAGACCATCTCCCGGCCCAAGGG GGTGGCCCTGCACAGGCCCGATGTCTACTTGCTGCCACCAGCCCGGGAGCAGCTGAAC CTGCGGGAGTCGGCCACCATCACGTGCCTGGTGACGGGCTTCTCTCCCGCGGACGTCT TCGTGCAGTGGATGCAGAGGGGGCAGCCCTTGTCCCCGGAGAAGTATGTGACCAGCGC CCCAATGCCTGAGCCCCAGGCCCCAGGCCGGTACTTCGCCCACAGCATCCTGACCGTG TCCGAAGAGGAATGGAACACGGGGGAGACCTACACCTGCGTGGTGGCCCATGAGGCCC TGCCCAACAGGGTCACCGAGAGGACCGTGGACAAGTCCACCGGTAAACCCACCCTGTA CAACGTGTCCCTGGTCATGTCCGACACAGCTGGCACCTGCTACTGA |
| 82  1.5.3 -IgM heavy chain AA | EVQLVQSGAEVKKPGESLKISCKGSGYSFTSYWIGWVRQMPGKGLEWMGIIYPGDSDT RYSPSFQGQVTISADKSITTAYLQWSSLKASDTAMYYCARHPSYGSGSPNFDYWGQGT LVTVSSGSASAPTLFPLVSCENSPSDTSSVAVGCLAQDFLPDSITFSWKYKNNSDISS TRGFPSVLRGGKYAATSQVLLPSKDVMQGTDEHVVCKVQHPNGNKEKNVPLPVIAELP PKVSVFVPPRDGFFGNPRKSKLICQATGFSPRQIQVSWLREGKQVGSGVTTDQVQAEA KESGPTTYKVTSTLTIKESDWLSQSMFTCRVDHRGLTFQQNASSMCVPDQDTAIRVFA IPPSFASIFLTKSTKLTCLVTDLTTYDSVTISWTRQNGEAVKTHTNISESHPNATFSA VGEASICEDDWNSGERFTCTVTHTDLPSPLKQTISRPKGVALHRPDVYLLPPAREQLN LRESATITCLVTGFSPADVFVQWMQRGQPLSPEKYVTSAPMPEPQAPGRYFAHSILTV SEEEWNTGETYTCVVAHEALPNRVTERTVDKSTGKPTLYNVSLVMSDTAGTCY- |
| 83  1.5.3 light chain DNA | GACATCGTGATGACCCAGACCCCCCTGTCCTCCCCCGTGACCCTGGGCCAGCCCGCCT CCATCTCCTGCAGGTCCTCCCAGTCCCTGGTGTACTCCGACGGCAACACCTACCTGTC CTGGCTGCAGCAGAGGCCCGGCCAGCCCCCCAGGCTGCTGATCTACAAGATCTCCAAC AGGTTCTCCGGCGTGCCCGACAGGTTCTCCGGCTCCGGCGCCGGCACCGACTTCACCC TGAAGATCTCCAGGGTGGAGGCCGAGGACGTGGGCGTGTACTACTGCGTGCAGGCCAC CCAGTTCCCCCTGACCTTCGGCGGCGGCACCAAGGTGGAGATCAAGCGTACGGTGGCT GCACCATCTGTCTTCATCTTCCCGCCATCTGATGAGCAGTTGAAATCTGGAACTGCCT CTGTTGTGTGCCTGCTGAATAACTTCTATCCCAGAGAGGCCAAAGTACAGTGGAAGGT GGATAACGCCCTCCAATCGGGTAACTCCCAGGAGAGTGTCACAGAGCAGGACAGCAAG GACAGCACCTACAGCCTCAGCAGCACCCTGACGCTGAGCAAAGCAGACTACGAGAAAC ACAAAGTCTACGCCTGCGAAGTCACCCATCAGGGCCTGAGCTCGCCCGTCACAAAGAG CTTCAACAGGGGAGAGTGTTAG |

TABLE 10-continued

Sequence Summary

| SEQ ID NO: | Short Name | Sequence |
|---|---|---|
| 84 | 1.5.3 light chain AA | DIVMTQTPLSSPVTLGQPASISCRSSQSLVYSDGNTYLSWLQQRPGQPPRLLIYKISN RFSGVPDRFSGSGAGTDFTLKISRVEAEDVGVYYCVQATQFPLTFGGGTKVEIKRTVA APSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC- |
| 85 | human IgA1 constant region aa P01876 | ASPTSPKVFPLSLCSTQPDGNVVIACLVQGFFPQEPLSVTWSESGQGVTARNFPPSQD ASGDLYTTSSQLTLPATQCLAGKSVTCHVKHYTNPSQDVTVPCPVPSTPPTPSPSTPP TPSPSCCHPRLSLHRPALEDLLLGSEANLTCTLTGLRDASGVTFTWTPSSGKSAVQGP PERDLCGCYSVSSVLPGCAEPWNHGKTFTCTAAYPESKTPLTATLSKSGNTFRPEVHL LPPPSEELALNELVTLTCLARGFSPKDVLVRWLQGSQELPREKYLTWASRQEPSQGTT TFAVTSILRVAAEDWKKGDTFSCMVGHEALPLAFTQKTIDRLAGKPTHVNVSVVMAEV DGTCY |
| 86 | human IgA2 constant region aa P01877 | ASPTSPKVFPLSLDSTPQDGNVVVACLVQGFFPQEPLSVTWSESGQNVTARNFPPSQD ASGDLYTTSSQLTLPATQCPDGKSVTCHVKHYTNPSQDVTVPCPVPPPPPCCHPRLSL HRPALEDLLLGSEANLTCTLTGLRDASGATFTWTPSSGKSAVQGPPERDLCGCYSVSS VLPGCAQPWNHGETFTCTAAHPELKTPLTANITKSGNTFRPEVHLLPPPSEELALNEL VTLTCLARGFSPKDVLVRWLQGSQELPREKYLTWASRQEPSQGTTTFAVTSILRVAAE DWKKGDTFSCMVGHEALPLAFTQKTIDRMAGKPTHVNVSVVMAEVDGTCY |
| 87 | Human Secretory Component Precursor | MLLFVLTCLLAVFPAISTKSPIFGPEEVNSVEGNSVSITCYYPPTSVNRHTRKYWCRQ GARGGCITLISSEGYVSSKYAGRANLTNFPENGTFVVNIAQLSQDDSGRYKCGLGINS RGLSFDVSLEVSQGPGLLNDTKVYTVDLGRTVTINCPFKTENAQKRKSLYKQIGLYPV LVIDSSGYVNPNYTGRIRLDIQGTGQLLFSVVINQLRLSDAGQYLCQAGDDSNSNKKN ADLQVLKPEPELVYEDLRGSVTFHCALGPEVANVAKFLCRQSSGENCDVVVNTLGKRA PAFEGRILLNPQDKDGSFSVVITGLRKEDAGRYLCGAHSDGQLQEGSPIQAWQLFVNE ESTIPRSPTVVKGVAGGSVAVLCPYNRKESKSIKYWCLWEGAQNGRCPLLVDSEGWVK AQYEGRLSLLEEPGNGTFTVILNQLTSRDAGFYWCLTNGDTLWRTTVEIKIIEGEPNL KVPGNVTAVLGETLKVPCHFPCKFSSYEKYWCKWNNTGCQALPSQDEGPSKAFVNCDE NSRLVSLTLNLVTRADEGWYWCGVKQGHFYGETAAVYVAVEERKAAGSRDVSLAKADA APDEKVLDSGFREIENKAIQDPRLFAEEKAVADTRDQADGSRASVDSGSSEEQGGSSR ALVSTLVPLGLVLAVGAVAVGVARARHRKNVDRVSIRSYRTDISMSDFENSREFGAND NMGASSITQETSLGGKEEFVATTESTTETKEPKKAKRSSKEEAEMAYKDFLLQSSTVA AEAQDGPQEA |
| 88 | human secretory component mature | KSPIFGPEEVNSVEGNSVSITCYYPPTSVNRHTRKYWCRQGARGGCITLISSEGYVSS KYAGRANLTNFPENGTFVVNIAQLSQDDSGRYKCGLGINSRGLSFDVSLEVSQGPGLL NDTKVYTVDLGRTVTINCPFKTENAQKRKSLYKQIGLYPVLVIDSSGYVNPNYTGRIR IDIQGTGQLLFSVVINQLRLSDAGQYLCQAGDDSNSNKKNADLQVLKPEPELVYEDLR GSVTFHCALGPEVANVAKFLCRQSSGENCDVVVNTLGKRAPAFEGRILLNPQDKDGSF SVVITGLRKEDAGRYLCGAHSDGQLQEGSPIQAWQLFVNEESTIPRSPTVVKGVAGGS VAVLCPYNRKESKSIKYWCLWEGAQNGRCPLLVDSEGWVKAQYEGRLSLLEEPGNGTF TVILNQLTSRDAGFYWCLTNGDTLWRTTVEIKIIEGEPNLKVPGNVTAVLGETLKVPC HFPCKFSSYEKYWCKWNNTGCQALPSQDEGPSKAFVNCDENSRLVSLTLNLVTRADEG WYWCGVKQGHFYGETAAVYVAVEERKAAGSRDVSLAKADAAPDEKVLDSGFREIENKA IQDPR |
| 89 | J15ABD DNA | ATGGAATGGAGCTGGGTCTTTCTCTTCTTCCTGTCAGTAACGACTGGTGTCCACTCCC AGGAAGATGAGCGGATCGTGCTGGTGGACAACAAGTGCAAGTGCGCCAGATCACCTC CCGGATCATCCGGTCCTCCGAGGATCCCAACGAGGACATCGTGGAACGGAACATCAGA ATCATCGTGCCCCTGAACAACCGCGAGAACATCTCCGACCCCACCAGCCCTCTGCGGA CCAGATTCGTGTACCACCTGTCCGACCTGTGCAAGAAGTGCGACCCTACCGAGGTGGA ACTGGACAACCAGATCGTGACCGCCACCCAGTCCAACATCTGCGACGAGGACTCCGCC ACCGAGACATGCTACACCTACGACCGGAACAAGTGCTACACCGCCGTGGTGCCTCTGG TGTACGGCGGCGAGACAAAGATGGTGGAAACCGCCCTGACCCCCGACGCCTGCTATCC TGATGGAGGCGGAGGATCTGGTGGCGGTGGTTCTGGCGGAGGGGGCTCTCAGCACGAT GAGGCCGTGGACGCCAATTCTCTGGCCGAGGCTAAGGTGCTGGCCAACAGAGAGCTGG ATAAGTACGGCGTGTCCGACTACTACAAGAACCTGATCAACAACGCCAAGACCGTGGA AGGCGTGAAGGCCCTGATCGACGAGATCCTGGCTGCCCTGCCTTGA |
| 90 | J15ABD AA | MEWSWVFLFFLSVTTGVHSQEDERIVLVDNKCKCARITSRIIRSSEDPNEDIVERNIR IIVPLNNRENISDPTSPLRTRFVYHLSDLCKKCDPTEVELDNQIVTATQSNICDEDSA TETCYTYDRNKCYTAVVPLVYGGETKMVETALTPDACYPDGGGGSGGGGSGGGGSQHD EAVDANSLAEAKVLANRELDKYGVSDYYKNLINNAKTVEGVKALIDEILAALP |
| 91 | ABD15J DNA | ATGGAATGGAGCTGGGTCTTTCTCTTCTTCCTGTCAGTAACGACTGGTGTCCACTCCC AGCACGATGAGGCCGTGGACGCCAATTCTCTGGCCGAGGCTAAGGTGCTGGCCAACAG AGAGCTGGATAAGTACGGCGTGTCCGACTACTACAAGAACCTGATCAACAACGCCAAG ACCGTGGAAGGCGTGAAGGCCCTGATCGACGAGATCCTGGCTGCCCTGCCTGGAGGCG GAGGATCTGGTGGCGGTGGTTCTGGCGGAGGGGGCTCTCAGGAAGATGAGCGGATCGT GCTGGTGGACAACAAGTGCAAGTGCGCCCGGATCACCTCCCGGATCATCCGGTCCTCC GAGGATCCCAACGAGGACATCGTGGAACGGAACATCAGAATCATCGTGCCCCTGAACA ACCGCGAGAACATCTCCGACCCCACCAGCCCTCTGCGGACCAGATTCGTGTACCACCT GTCCGACCTGTGCAAGAAGTGCGACCCTACCGAGGTGGAACTGGACAACCAGATCGTG |

TABLE 10-continued

Sequence Summary

| SEQ ID NO:Short Name | | Sequence |
|---|---|---|
| | | ACCGCCACCCAGTCCAACATCTGCGACGAGGACTCCGCCACCGAGACATGCTACACCT<br>ACGACCGGAACAAGTGCTACACCGCCGTGGTGCCTCTGGTGTACGGCGGCGAGACAAA<br>GATGGTGGAAACCGCCCTGACCCCCGACGCCTGCTATCCTGATTGA |
| 92 | ABD15J<br>AA | MEWSWVFLFFLSVTTGVHSQHDEAVDANSLAEAKVLANRELDKYGVSDYYKNLINNAK<br>TVEGVKALIDEILAALPGGGGSGGGGSGGGGSQEDERIVLVDNKCKCARITSRIIRSS<br>EDPNEDIVERNIRIIVPLNNRENISDPTSPLRTRFVYHLSDLCKKCDPTEVELDNQIV<br>TATQSNICDEDSATETCYTYDRNKCYTAVVPLVYGGETKMVETALTPDACYPD |
| 93 | HSA15J<br>DNA | ATGAAATGGGTCACCTTTATCTCCCTGCTGTTCCTGTTCTCCTCCGCCTACTCTCGGG<br>GCGTGTTCAGAAGAGACGCCCACAAATCGGAGGTAGCGCACCGGTTCAAAGACTTGGG<br>AGAAGAAAACTTTAAGGCCCTTGTACTCATTGCGTTTGCGCAGTATTTGCAGCAGTGC<br>CCATTCGAGGACCATGTCAAACTTGTCAACGAAGTGACAGAGTTTGCGAAAACTTGCG<br>TCGCCGACGAATCCGCGGAGAACTGTGACAAGTCGCTGCATACGTTGTTCGGGGATAA<br>GCTCTGTACCGTAGCGACCTTGAGGGAAACTTACGGGGAAATGGCGGACTGTTGCGCT<br>AAGCAGGAGCCGGAACGGAACGAGTGTTTCCTTCAGCATAAGGATGACAACCCCAACC<br>TCCCTAGATTGGTCAGACCCGAAGTGGATGTGATGTGCACAGCATTCCATGACAATGA<br>GGAAACCTTTCTCAAAAAGTATTTGTACGAGATTGCCCGACGACACCCCTATTTCTAC<br>GCTCCCGAGTTGCTCTTCTTCGCGAAACGGTATAAAGCTGCCTTTACTGAATGCTGTC<br>AAGCAGCGGACAAGGCCGCATGCCTCCTTCCCAAATTGGATGAACTCCGCGATGAAGG<br>GAAGGCGTCATCGGCCAAACAGCGGCTTAAGTGCGCATCGCTTCAGAAATTCGGAGAG<br>AGGGCGTTCAAAGCGTGGGCCGTCGCGAGACTGTCGCAGAGATTCCCTAAGGCGGAAT<br>TTGCAGAGGTATCGAAGCTCGTGACAGACCTCACAAAGGTCCACACCGAATGTTGCCA<br>TGGAGACCTGCTTGAGTGCGCCGATGATAGGGCAGACCTCGCAAAGTACATTTGTGAG<br>AATCAGGACAGCATTAGCTCCAAGCTGAAAGAGTGCTGTGAGAAGCCTTTGCTGGAAA<br>AATCCCACTGTATCGCCGAGGTAGAAAACGATGAAATGCCCGCTGATCTTCCCTCGCT<br>GGCGGCAGACTTCGTCGAGTCGAAGGACGTCTGCAAGAATTACGCAGAGGCAAAAGAT<br>GTGTTCTTGGAATGTTCCTTTATGAGTATGCGAGAAGGCACCCGGATTATTCCGTGG<br>TACTGCTCTTGCGATTGGCGAAAACGTACGAAACAACGCTTGAGAAGTGTTGTGCGGC<br>TGCCGACCCGCATGAGTGCTACGCCAAGGTATTTGATGAGTTTAAACCTCTTGTCGAG<br>GAACCCCAGAATCTTATCAAGCAGAACTGCGAGCTTTTCAAGCAGTTGGGTGAATACA<br>AATTCCAGAACGCGCTTCTGGTGAGGTATACCAAGAAAGTACCTCAAGTCTCAACACC<br>CACACTCGTCGAGGTGTCACGGAACCTCGGGAAAGTAGGGTCGAAGTGCTGTAAACAC<br>CCAGAGGCCAAGCGCATGCCCTGTGCGGAGGACTACCTCTCGGTAGTGTTGAATCAAC<br>TGTGTGTCCTCCACGAAAAGACGCCGGTGTCAGACCGCGTCACAAAGTGCTGCACGGA<br>GAGCCTGGTCAATAGAGCGCCCTGCTTCTCAGCGCTGGAGGTGGATGAGACATACGTC<br>CCGAAAGAGTTTAACGCCGAAACGTTTACTTTTCATGCTGATATCTGTACGTTGTCAG<br>AGAAGGAAAGGCAAATCAAGAAACAAACTGCGCTTGTGGAACTGGTGAAGCACAAACC<br>GAAGGCGACTAAGGAACAGCTGAAGGCGGTGATGGATGACTTTGCCGCGTTCGTAGAG<br>AAATGCTGTAAAGCAGACGATAAGGAGACTTGTTTTGCGGAAGAGGGACCTAAACTTG<br>TTGCTGCAAGTCAAGCTGCCTTAGGCTTAGGAGGCGGAGGATCTGGTGGCGGTGGTTC<br>TGGCGGAGGGGGCTCTCAGGAAGATGAGCGGATCGTGCTGGTGGACAACAAGTGCAAG<br>TGCGCCCGGATCACCTCCCGGATCATCCGGTCCTCCGAGGATCCCAACGAGGACATCG<br>TGGAACGGAACATCAGAATCATCGTGCCCCTGAACAACCGCGAGAACATCTCCGACCC<br>CACCAGCCCTCTGCGGACCAGATTCGTGTACCACCTGTCCGACCTGTGCAAGAAGTGC<br>GACCCTACCGAGGTGGAACTGGACAACCAGATCGTGACCGCCACCCAGTCCAACATCT<br>GCGACGAGGACTCCGCCACCGAGACATGCTACACCTACGACCGGAACAAGTGCTACAC<br>CGCCGTGGTGCCTCTGGTGTACGGCGGCGAGACAAAGATGGTGGAAACCGCCCTGACC<br>CCCGACGCCTGCTATCCTGATTAG |
| 94 | HSA15J<br>AA | MKWVTFISLLFLFSSAYSRGVFRRDAHKSEVAHRFKDLGEENFKALVLIAFAQYLQQC<br>PFEDHVKLVNEVTEFAKTCVADESAENCDKSLHTLFGDKLCTVATLRETYGEMADCCA<br>KQEPERNECFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKCASLQKFGE<br>RAFKAWAVARLSQRFPKAEFAEVSKLVTDLTKVHTECCHGDLLECADDRADLAKYICE<br>NQDSISSKLKECCEKPLLEKSHCIAEVENDEMPADLPSLAADFVESKDVCKNYAEAKD<br>VFLGMFLYEYARRHPDYSVVLLLRLAKTYETTLEKCCAAADPHECYAKVFDEFKPLVE<br>EPQNLIKQNCELFKQLGEYKFQNALLVRYTKKVPQVSTPTLVEVSRNLGKVGSKCCKH<br>PEAKRMPCAEDYLSVVLNQLCVLHEKTPVSDRVTKCCTESLVNRRPCFSALEVDETYV<br>PKEFNAETFTFHADICTLSEKERQIKKQTALVELVKHKPKATKEQLKAVMDDFAAFVE<br>KCCKADDKETCFAEEGPKLVAASQAALGLGGGGSGGGGSGGGGSQEDERIVLVDNKCK<br>CARITSRIIRSSEDPNEDIVERNIRIIVPLNNRENISDPTSPLRTRFVYHLSDLCKKC<br>DPTEVELDNQIVTATQSNICDEDSATETCYTYDRNKCYTAVVPLVYGGETKMVETALT<br>PDACYPD |
| 95 | J15HSA<br>DNA | ATGAAGAACCATCTGCTGTTCTGGGGCGTGCTGGCCGTGTTCATCAAGGCCGTGCACG<br>TGAAGGCCCAGGAAGATGAGCGGATCGTGCTGGTGGACAACAAGTGCAAGTGCGCCCG<br>GATCACCTCCCGGATCATCCGGTCCTCCGAGGATCCCAACGAGGACATCGTGGAACGG<br>AACATCAGAATCATCGTGCCCCTGAACAACCGCGAGAACATCTCCGACCCCACCAGCC<br>CTCTGCGGACCAGATTCGTGTACCACCTGTCCGACCTGTGCAAGAAGTGCGACCCTAC<br>CGAGGTGGAACTGGACAACCAGATCGTGACCGCCACCCAGTCCAACATCTGCGACGAG<br>GACTCCGCCACCGAGACATGCTACACCTACGACCGGAACAAGTGCTACACCGCCGTGG<br>TGCCTCTGGTGTACGGCGGCGAGACAAAGATGGTGGAAACCGCCCTGACCCCCGACGC<br>CTGCTATCCTGATGAGGCGGAGGATCTGGTGGCGGTGGTTCTGGCGGAGGGGGCTCT<br>GACGCCCACAAATCGGAGGTAGCGCACCGGTTCAAAGACTTGGGAGAAGAAAACTTTA<br>AGGCCCTTGTACTCATTGCGTTTGCGCAGTATTTGCAGCAGTGCCCATTCGAGGACCA |

TABLE 10-continued

Sequence Summary

| SEQ ID NO:Short Name | Sequence |
|---|---|
| | TGTCAAACTTGTCAACGAAGTGACAGAGTTTGCGAAAACTTGCGTCGCCGACGAATCC<br>GCGGAGAACTGTGACAAGTCGCTGCATACGTTGTTCGGGGATAAGCTCTGTACCGTAG<br>CGACCTTGAGGGAAACTTACGGGGAAATGGCGGACTGTTGCGCTAAGCAGGAGCCGGA<br>ACGGAACGAGTGTTTCCTTCAGCATAAGGATGACAACCCCAACCTCCCTAGATTGGTC<br>AGACCCGAAGTGGATGTGATGTGCACAGCATTCCATGACAATGAGGAAACCTTTCTCA<br>AAAAGTATTTGTACGAGATTGCCCGACGACACCCCTATTTCTACGCTCCCGAGTTGCT<br>CTTCTTCGCGAAACGGTATAAAGCTGCCTTTACTGAATGCTGTCAAGCAGCGGACAAG<br>GCCGCATGCCTCCTTCCCAAATTGGATGAACTCCGCGATGAAGGGAAGGCGTCATCGG<br>CCAAACAGCGGCTTAAGTGCGCATCGCTTCAGAAATTCGGAGAGAGGGCGTTCAAAGC<br>GTGGGCCGTCGCGAGACTGTCGCAGAGATTCCCTAAGGCGGAATTTGCAGAGGTATCG<br>AAGCTCGTGACAGACCTCACAAAGGTCCACACCGAATGTTGCCATGGAGACCTGCTTG<br>AGTGCGCCGATGATAGGGCAGACCTCGCAAAGTACATTTGTGAGAATCAGGACAGCAT<br>TAGCTCCAAGCTGAAAGAGTGCTGTGAGAAGCCTTTGCTGGAAAAATCCCACTGTATC<br>GCCGAGGTAGAAAACGATGAAATGCCCGCTGATCTTCCCTCGCTGGCGGCAGACTTCG<br>TCGAGTCGAAGGACGTCTGCAAGAATTACGCAGAGGCAAAAGATGTGTTTCTTGGAAT<br>GTTCCTTTATGAGTATGCGAGAAGGCACCCGGATTATTCCGTGGTACTGCTCTTGCGA<br>TTGGCGAAAACGTACGAAACAACGCTTGAGAAGTGTTGTGCGGCTGCCGACCCGCATG<br>AGTGCTACGCCAAGGTATTTGATGAGTTTAAACCTCTTGTCGAGGAACCCCAGAATCT<br>TATCAAGCAGAACTGCGAGCTTTTCAAGCAGTTGGGTGAATACAAATTCCAGAACGCG<br>CTTCTGGTGAGGTATACCAAGAAAGTACCTCAAGTCTCAACACCCACACTCGTCGAGG<br>TGTCACGGAACCTCGGGAAAGTAGGGTCGAAGTGCTGTAAACACCCAGAGGCCAAGCG<br>CATGCCCTGTGCGGAGGACTACCTCTCGGTAGTGTTGAATCAACTGTGTGTCCTCCAC<br>GAAAAGACGCCGGTGTCAGACCGCGTCACAAAGTGCTGCACGGAGAGCCTGGTCAATA<br>GACGCCCCTGCTTCTCAGCGCTGGAGGTGGATGAGACATACGTCCCGAAAGAGTTTAA<br>CGCCGAAACGTTTACTTTTCATGCTGATATCGTACGTTGTCAGAGAAGGAAAGGCAA<br>ATCAAGAAACAAACTGCGCTTGTGGAACTGGTGAAGCACAAACCGAAGGCGACTAAGG<br>AACAGCTGAAGGCGGTGATGGATGACTTTGCCGCGTTCGTAGAGAAATGCTGTAAAGC<br>AGACGATAAGGAGACTTGTTTTGCGGAAGAGGGACCTAAACTTGTTGCTGCAAGTCAA<br>GCTGCCTTAGGCTTATAG |
| 96 J15HSA<br>AA | MKNHLLFWGVLAVFIKAVHVKAQEDERIVLVDNKCKCARITSRIIRSSEDPNEDIVER<br>NIRIIVPLNNRENISDPTSPLRTRFVYHLSDLCKKCDPTEVELDNQIVTATQSNICDE<br>DSATETCYTYDRNKCYTAVVPLVYGGETKMVETALTPDACYPDGGGSGGGGSGGGGS<br>DAHKSEVAHRFKDLGEENFKALVLIAFAQYLQQCPFEDHVKLVNEVTEFAKTCVADES<br>AENCDKSLHTLFGDKLCTVATLRETYGEMADCCAKQEPERNECFLQHKDDNPNLPRLV<br>RPEVDVMCTAFHDNEETFLKKYLYEIARRHPYFYAPELLFFAKRYKAAFTECCQAADK<br>AACLLPKLDELRDEGKASSAKQRLKCASLQKFGERAFKAWAVARLSQRFPKAEFAEVS<br>KLVTDLTKVHTECCHGDLLECADDRADLAKYICENQDSISSKLKECCEKPLLEKSHCI<br>AEVENDEMPADLPSLAADFVESKDVCKNYAEAKDVFLGMFLYEYARRHPDYSVVLLLR<br>LAKTYETTLEKCCAAADPHECYAKVFDEFKPLVEEPQNLIKQNCELFKQLGEYKFQNA<br>LLVRYTKKVPQVSTPTLVEVSRNLGKVGSKCCKHPEAKRMPCAEDYLSVVLNQLCVLH<br>EKTPVSDRVTKCCTESLVNRRPCFSALEVDETYVPKEFNAETFTFHADICTLSEKERQ<br>IKKQTALVELVKHKPKATKEQLKAVMDDFAAFVEKCCKADDKETCFAEEGPKLVAASQ<br>AALGL |
| 97 V15J15ABD<br>DNA | ATGGGGTGGTCCTACATTATCCTGTTCCTCGTGGCCACCGCCACTGGCGTGCACTCAC<br>AGGTGCAGCTGGTGCAGTCTGGCGCCGAAGTGAAGAAACCTGGCGCCTCCGTGAAGGT<br>GTCCTGCAAGGCCTCCGGCTACACCTTCATCAGCTACACCATGCACTGGGTGCGACAG<br>GCCCCTGGACAGGGCCTGGAATGGATGGGCTACATCAACCCTAGATCGGCTACACCC<br>ACTACAACCAGAAGCTGAAGGACAAGGCCACCCTGACCGCCGACAAGTCTGCCTCCAC<br>CGCCTACATGGAACTGTCCTCCCTGCGGAGCGAGGACACCGCCGTGTACTACTGTGCC<br>AGATCCGCCTACTACGACTACGACGGCTTCGCCTATTGGGGCCAGGGCACCCTCGTGA<br>CAGTGTCTAGCGGTGGCGGAGGATCTGGCGGAGGCGGTAGTGGCGGTGGCGGATCTGA<br>TATCCAGATGACCCAGTCCCCCTCCAGCCTGTCTGCCTCTGTGGGCGACAGAGTGACA<br>ATTACCTGCTCCGCCAGCTCCTCCGTGTCTTACATGAACTGGTATCAGCAGAAGCCCG<br>GCAAGGCCCCCAAGCGGCTGATCTACGACACCTCCAAGCTGGCCTCTGGCGTGCCCTC<br>CAGATTCTCCGGCTCTGGCTCTGGCACCGACTTTACCCTGACCATCAGCTCCCTGCAG<br>CCCGAGGACTTCGCCACCTACTACTGCCAGCAGTGGTCCTCCAACCCTCCCACCTTTG<br>GCGGAGGCACCAAGGTGGAAATCAAAGGCGGCGGAGGAAGCGGGGAGGCGGTTCTGG<br>GGGTGGTGGATCTCAGGAAGATGAGCGGATCGTGCTGGTGGACAACAAGTGCAAGTGC<br>GCCCGGATCACCTCCCGGATCATCCGGTCCTCCGAGGATCCCAACGAGGACATCGTGG<br>AACGGAACATCAGAATCATCGTGCCCCTGAACAACCGCGAGAACATCTCCGACCCCAC<br>CAGCCCTCTGCGGACCAGATTCGTGTACCACCTGTCCGACCTGTGCAAGAAGTGCGAC<br>CCTACCGAGGTGGAACTGGACAACCAGATCGTGACCGCCACCCAGTCCAACATCTGCG<br>ACGAGGACTCCGCCACCGAGACATGCTACACCTACGACCGGAACAAGTGCTACACCGC<br>CGTGGTGCCTCTGGTGTACGGCGGCGAGACAAAGATGGTGGAAACCGCCCTGACCCCC<br>GACGCCTGCTATCCTGATGGAGGCGGAGGATCTGGTGGCGGTGGTTCTGGCGGAGGGG<br>GCTCTCAGCACGATGAGGCCGTGGACGCCAATTCTCTGGCCGAGGCTAAGGTGCTGGC<br>CAACAGAGAGCTGGATAAGTACGGCGTGTCCGACTACTACAAGAACCTGATCAACAAC<br>GCCAAGACCGTGGAAGGCGTGAAGGCCCTGATCGACGAGATCCTGGCTGCCCTGCCTT<br>GA |

TABLE 10-continued

Sequence Summary

| SEQ ID NO:Short Name | | Sequence |
|---|---|---|
| 98 | V15J15ABD AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSQHDEAVDANSLAEAKVLANRELDKYGVSDYYKNLINN AKTVEGVKALIDEILAALP |
| 99 | V15J15HSA (K573P) DNA | ATGGGGTGGTCCTACATTATCCTGTTCCTCGTGGCCACCGCCACTGGCGTGCACTCAC AGGTGCAGCTGGTGCAGTCTGGCGCCGAAGTGAAGAAACCTGGCGCCTCCGTGAAGGT GTCCTGCAAGGCCTCCGGCTACACCTTCATCAGCTACACCATGCACTGGGTGCGACAG GCCCCTGGACAGGGCCTGGAATGGATGGGCTACATCAACCCTAGATCTGGCTACACCC ACTACAACCAGAAGCTGAAGGACAAGGCCACCCTGACCGCCGACAAGTCTGCCTCCAC CGCCTACATGGAACTGTCCTCCCTGCGGAGCGAGGACACCGCCGTGTACTACTGTGCC AGATCCGCCTACTACGACTACGACGGCTTCGCCTATTGGGGCCAGGGCACCCTCGTGA CAGTGTCTAGCGGTGGCGGAGGATCTGGCGGAGGCGGTAGTGGCGGTGGCGGATCTGA TATCCAGATGACCCAGTCCCCCTCCAGCCTGTCTGCCTCTGTGGGCGACAGAGTGACA ATTACCTGCTCCGCCAGCTCCTCCGTGTCTTACATGAACTGGTATCAGCAGAAGCCCG GCAAGGCCCCCAAGCGGCTGATCTACGACACCTCCAAGCTGGCCTCTGGCGTGCCCTC CAGATTCTCCGGCTCTGGCTCTGGCACCGACTTTACCCTGACCATCAGCTCCCTGCAG CCCGAGGACTTCGCCACCTACTACTGCCAGCAGTGGTCCTCCAACCCTCCCACCTTTG GCGGAGGCACCAAGGTGGAAATCAAAGGCGGCGGAGGAAGCGGGGGAGGCGGTTCTGG GGGTGGTGGATCTCAGGAAGATGAGCGGATCGTGCTGGTGGACAACAAGTGCAAGTGC GCCCGGATCACCTCCCGGATCATCCGGTCCTCCGAGGATCCCAACGAGGACATCGTGG AACGGAACATCAGAATCATCGTGCCCCTGAACAACCGCGAGAACATCTCCGACCCCAC CAGCCCTCTGCGGACCAGATTCGTGTACCACCTGTCCGACCTGTGCAAGAAGTGCGAC CCTACCGAGGTGGAACTGGACAACCAGATCGTGACCGCCACCCAGTCCAACATCTGCG ACGAGGACTCCGCCACCGAGACATGCTACACCTACGACCGGAACAAGTGCTACACCGC CGTGGTGCCTCTGGTGTACGGCGGCGAGACAAAGATGGTGGAAACCGCCCTGACCCCC GACGCCTGCTATCCTGATGGAGGCGGAGGATCTGGTGGCGGTGGTTCTGGCGGAGGGG GCTCTGACGCCCACAAATCGGAGGTAGCGCACCGGTTCAAAGACTTGGGAGAAGAAAA CTTTAAGGCCCTTGTACTCATTGCGTTTGCGCAGTATTTGCAGCAGTGCCCATTCGAG GACCATGTCAAACTTGTCAACGAAGTGACAGAGTTTGCGAAAACTTGCGTCGCCGACG AATCCGCGGAGAACTGTGACAAGTCGCTGCATACGTTGTTCGGGGATAAGCTCTGTAC CGTAGCGACCTTGAGGGAAACTTACGGGGAAATGGCGGACTGTTGCGCTAAGCAGGAG CCGGAACGGAACGAGTGTTTCCTTCAGCATAAGGATGACAACCCCAACCTCCCTAGAT TGGTCAGACCCGAAGTGGATGTGATGTGCACAGCATTCCATGACAATGAGGAAACCTT TCTCAAAAAGTATTTGTACGAGATTGCCCGACGACACCCCTATTTCTACGCTCCCGAG TTGCTCTTCTTCGCGAAACGGTATAAAGCTGCCTTTACTGAATGCTGTCAAGCAGCGG ACAAGGCCGCATGCCTCCTTCCCAAATTGGATGAACTCCGCGATGAAGGGAAGGCGTC ATCGGCCAAACAGCGGCTTAAGTGCGCATCGCTTCAGAAATTCGGAGAGAGGCGTTC AAAGCGTGGGCCGTCGCGAGACTGTCGCAGAGATTCCCTAAGGCGGAATTTGCAGAGG TATCGAAGCTCGTGACAGACCTCACAAAGGTCCACACCGAATGTTGCCATGGAGACGT GCTTGAGTGCGCCGATGATAGGGCAGACCTCGCAAAGTACATTTGTGAGAATCAGGAC AGCATTAGCTCCAAGCTGAAAGAGTGCTGTGAGAAGCCTTTGCTGGAAAAATCCCACT GTATCGCCGAGGTAGAAAACGATGAAATGCCCGCTGATCTTCCCTCGCTGGCGGCAGA CTTCGTCGAGTCGAAGGACGTCTGCAAGAATTACGCAGAGGCAAAAGATGTGTTTCTT GGAATGTTCCTTTATGAGTATGCGAGAAGGCACCCGGATTATTCCGTGGTACTGCTCT TGCGATTGGCGAAAACGTACGAAACAACGCTTGAGAAGTGTTGTGCGGCTGCCGACCC GCATGAGTGCTACGCCAAGGTATTTGATGAGTTTAAACCTCTTGTCGAGGAACCCCAG AATCTTATCAAGCAGAACTGCGAGCTTTTCAAGCAGTTGGGTGAATACAAATTCCAGA ACGCGCTTCTGGTGAGGTATACCAAGAAAGTACCTCAAGTCTCAACACCCACACTCGT CGAGGTGTCACGGAACCTCGGGAAGTAGGGTCGAAGTGCTGTAAACACCCAGAGGCC AAGCGCATGCCCTGTGCGGAGGACTACCTCTCGGTAGTGTTGAATCAACTGTGTGTCC TCCACGAAAAGACGCCGGTGTCAGACCGCGTCACAAAGTGCTGCACGGAGAGCCTGGT CAATAGACGCCCCTGCTTCTCAGCGCTGGAGGTGGATGAGACATACGTCCCGAAAGAG TTTAACGCCGAAACGTTTACTTTTCATGCTGATATCTGTACGTTGTCAGAGAAGGAAA GGCAAATCAAGAAACAAACTGCGCTTGTGGAACTGGTGAAGCACAAACCGAAGGCGAC TAAGGAACAGCTGAAGGCGGTGATGGATGACTTTGCCGCGTTCGTAGAGAAATGCTGT AAAGCAGACGATAAGGAGACTTGTTTTGCGGAAGAGGGACCTAAACTTGTTGCTGCAA GTCAAGCTGCCTTAGGCTTATAG |
| 100 | V15J15HSA (K573P) AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSIRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSDAHKSEVAHRFKDLGEENFKALVLIAFAQYLQQCPFE DHVKLVNEVTEFAKTCVADESAENCDKSLHTLFGDKLCTVATLRETYGEMADCCAKQE PERNECFLQHKDDNPNLPRLVRPEVDVMCTAFHDNEETFLKKYLYEIARRHPYFYAPE LLFFAKRYKAAFTECCQAADKAACLLPKLDELRDEGKASSAKQRLKCASLQKFGERAF |

US 11,542,342 B2

107 108

TABLE 10-continued

Sequence Summary

| SEQ ID NO:Short Name | Sequence |
|---|---|
| | KAWAVARLSQRFPKAEFAEVSKLVTDLTKVHTECCHGDLLECADDRADLAKYICENQD
SISSKLKECCEKPLLEKSHCIAEVENDEMPADLPSLAADFVESKDVCKNYAEAKDVFL
GMFLYEYARRHPDYSVVLLLRLAKTYETTLEKCCAAADPHECYAKVFDEFKPLVEEPQ
NLIKQNCELFKQLGEYKFQNALLVRYTKKVPQVSTPTLVEVSRNLGKVGSKCCKHPEA
KRMPCAEDYLSVVLNQLCVLHEKTPVSDRVTKCCTESLVNRRPCFSALEVDETYVPKE
FNAETFTFHADICTLSEKERQIKKQTALVELVKHKPKATKEQLKAVMDDFAAFVEKCC
KADDKETCFAEEGPKLVAASQAALGL |
| 101 V15J15HSA (wt) DNA | ATGGGGTGGTCCTACATTATCCTGTTCCTCGTGGCCACCGCCACTGGCGTGCACTCAC
AGGTGCAGCTGGTGCAGTCTGGCGCCGAAGTGAAGAAACCTGGCGCCTCCGTGAAGGT
GTCCTGCAAGGCCTCCGGCTACACCTTCATCAGCTACACCATGCACTGGGTGCGACAG
GCCCCTGGACAGGGCCTGGAATGGATGGGCTACATCAACCCTAGATCGGCTACACCC
ACTACAACCAGAAGCTGAAGGACAAGGCCACCCTGACCGCCGACAAGTCTGCCTCCAC
CGCCTACATGGAACTGTCCTCCCTGCGGAGCGAGGACACCGCCGTGTACTACTGTGCC
AGATCCGCCTACTACGACTACGACGGCTTCGCCTATTGGGGCCAGGGCACCCTCGTGA
CAGTGTCTAGCGGTGGCGGAGGATCTGGCGGAGGCGGTAGTGGCGGTGGCGGATCTGA
TATCCAGATGACCCAGTCCCCCTCCAGCCTGTCTGCCTCTGTGGGCGACAGAGTGACA
ATTACCTGCTCCGCCAGCTCCTCCGTGTCTTACATGAACTGGTATCAGCAGAAGCCCG
GCAAGGCCCCCAAGCGGCTGATCTACGACACCTCCAAGCTGGCCTCTGGCGTGCCCTC
CAGATTCTCCGGCTCTGGCTCTGGCACCGACTTTACCCTGACCATCAGCTCCCTGCAG
CCCGAGGACTTCGCCACCTACTACTGCCAGCAGTGGTCCTCCAACCCTCCCACCTTTG
GCGGAGGCACCAAGGTGGAAATCAAAGGCGGCGGAGGAAGCGGGGGAGGCGGTTCTGG
GGGTGGTGGATCTCAGGAAGATGAGCGGATCGTGCTGGTGGACAACAAGTGCAAGTGC
GCCCGGATCACCTCCCGGATCATCCGGTCCTCCGAGGATCCCAACGAGGACATCGTGG
AACGGAACATCAGAATCATCGTGCCCCTGAACAACCGCGAGAACATCTCCGACCCCAC
CAGCCCTCTGCGGACCAGATTCGTGTACCACCTGTCCGACCTGTGCAAGAAGTGCGAC
CCTACCGAGGTGGAACTGGACAACCAGATCGTGACCGCCACCCAGTCCAACATCTGCG
ACGAGGACTCCGCCACCGAGACATGCTACACCTACGACCGGAACAAGTGCTACACCGC
CGTGGTGCCTCTGGTGTACGGCGGCGAGACAAAGATGGTGGAAACCGCCCTGACCCCC
GACGCCTGCTATCCTGATGGAGGCGGAGGATCTGGTGGCGGTGGTTCTGGCGGAGGGG
GCTCTGACGCCCACAAATCGGAGGTAGCGCACCGGTTCAAAGACTTGGGAGAAGAAAA
CTTTAAGGCCCTTGTACTCATTGCGTTTGCGCAGTATTTGCAGCAGTGCCCATTCGAG
GACCATGTCAAACTTGTCAACGAAGTGACAGAGTTTGCGAAAACTTGCGTCGCCGACG
AATCCGCGGAGAACTGTGACAAGTCGCTGCATACGTTGTTCGGGGATAAGCTCTGTAC
CGTAGCGACCTTGAGGGAAACTTACGGGAAATGGCGGACTGTTGCGCTAAGCAGGAG
CCGGAACGGAACGAGTGTTTCCTTCAGCATAAGGATGACAACCCCAACCTCCCTAGAT
TGGTCAGACCCGAAGTGGATGTGATGTGCACAGCATTCCATGACAATGAGGAAACCTT
TCTCAAAAAGTATTTGTACGAGATTGCCCGACGACACCCCTATTTCTACGCTCCCGAG
TTGCTCTTCTTCGCGAAACGGTATAAAGCTGCCTTTACTGAATGCTGTCAAGCAGCGG
ACAAGGCCGCATGCCTCCTTCCCAAATTGGATGAACTCCGCGATGAAGGGAAGGCGTC
ATCGGCCAAACAGCGGCTTAAGTGCGCATCGCTTCAGAAATTCGGAGAGAGGGCGTTC
AAAGCGTGGGCCGTCGCGAGACTGTCGCAGAGATTCCCTAAGGCGGAATTTGCAGAGG
TATCGAAGCTCGTGACAGACCTCACAAAGGTCCACACCGAATGTTGCCATGGAGACCT
GCTTGAGTGCGCCGATGATAGGGCAGACCTCGCAAAGTACATTTGTGAGAATCAGGAC
AGCATTAGCTCCAAGCTGAAAGAGTGCTGTGAGAAGCCTTTGCTGGAAAATCCCACT
GTATCGCCGAGGTAGAAAACGATGAAATGCCCGCTGATCTTCCCTCGCTGGCGGCAGA
CTTCGTCGAGTCGAAGGACGTCTGCAAGAATTACGCAGAGGCAAAAGATGTGTTCTT
GGAATGTTCCTTTATGAGTATGCGAGAAGGCACCCGGATTATTCCGTGGTACTGCTCT
TGCGATTGGCGAAAACGTACGAAACAACGCTTGAGAAGTGTTGTGCGGCTGCCGACCC
GCATGAGTGCTACGCCAAGGTATTTGATGAGTTTAAACCTCTTGTCGAGGAACCCCAG
AATCTTATCAAGCAGAACTGCGAGCTTTTCAAGCAGTTGGGTGAATACAAATTCCAGA
ACGCGCTTCTGGTGAGGTATACCAAGAAAGTACCTCAAGTCTCAACACCCACACTCGT
CGAGGTGTCACGGAACCTCGGGAAGTAGGGTCGAAGTGCTGTAAACACCCAGAGGCC
AAGCGCATGCCCTGTGCGGAGGACTACCTCTCGGTAGTGTTGAATCAACTGTGTGTCC
TCCACGAAAAGACGCCGGTGTCAGACCGCGTCACAAAGTGCTGCACGGAGAGCCTGGT
CAATAGACGCCCCTGCTTCTCAGCGCTGGAGGTGGATGAGACATACGTCCCGAAAGAG
TTTAACGCCGAAACGTTTACTTTTCATGCTGATATCTGTACGTTGTCAGAGAAGGAAA
GGCAAATCAAGAAACAAACTGCGCTTGTGGAACTGGTGAAGCACAAACCGAAGGCGAC
TAAGGAACAGCTGAAGGCGGTGATGGATGACTTTGCCGCGTTCGTAGAGAAATGCTGT
AAAGCAGACGATAAGGAGACTTGTTTTGCGGAAGAGGGAAAGAAACTTGTTGCTGCAA
GTCAAGCTGCCTTAGGCTTATAG |
| 102 V15J15HSA (wt) AA | MGWSYIILFLVATATGVHSQVQLVQSGAEVKKPGASVKVSCKASGYTFISYTMHWVRQ
APGQGLEWMGYINPRSGYTHYNQKLKDKATLTADKSASTAYMELSSLRSEDTAVYYCA
RSAYYDYDGFAYWGQGTLVTVSSGGGGSGGGGSGGGGSDIQMTQSPSSLSASVGDRVT
ITCSASSSVSYMNWYQQKPGKAPKRLIYDTSKLASGVPSRFSGSGSGTDFTLTISSLQ
PEDFATYYCQQWSSNPPTFGGGTKVEIKGGGGSGGGGSGGGGSQEDERIVLVDNKCKC
ARITSRIIRSSEDPNEDIVERNIRIIVPLNNRENISDPTSPLRTRFVYHLSDLCKKCD
PTEVELDNQIVTATQSNICDEDSATETCYTYDRNKCYTAVVPLVYGGETKMVETALTP
DACYPDGGGSGGGGSGGGGSDAHKSEVAHRFKDLGEENFKALVLIAFAQYLQQCPFE
DHVKLVNEVTEFAKTCVADESAENCDKSLHTLFGDKLCTVATLRETYGEMADCCAKQE
PERNECFLQHKDDNPNLPRLVRPEVDVMCTAFHDNEETFLKKYLYEIARRHPYFYAPE
LLFFAKRYKAAFTECCQAADKAACLLPKLDELRDEGKASSAKQRLKCASLQKFGERAF
KAWAVARLSQRFPKAEFAEVSKLVTDLTKVHTECCHGDLLECADDRADLAKYICENQD
SISSKLKECCEKPLLEKSHCIAEVENDEMPADLPSLAADFVESKDVCKNYAEAKDVFL
GMFLYEYARRHPDYSVVLLLRLAKTYETTLEKCCAAADPHECYAKVFDEFKPLVEEPQ |

TABLE 10-continued

Sequence Summary

| SEQ ID NO:Short Name | Sequence |
|---|---|
| | NLIKQNCELFKQLGEYKFQNALLVRYTKKVPQVSTPTLVEVSRNLGKVGSKCCKHPEA<br>KRMPCAEDYLSVVLNQLCVLHEKTPVSDRVTKCCTESLVNRRPCFSALEVDETYVPKE<br>FNAETFTFHADICTLSEKERQIKKQTALVELVKHKPKATKEQLKAVMDDFAAFVEKCC<br>KADDKETCFAEEGKKLVAASQAALGL |

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. Various examples of changes, substitutions, and alterations are ascertainable by one skilled in the art and could be made without departing from the spirit and scope disclosed herein.

The invention claimed is:

1. A polymeric antibody comprising two or five immunoglobulin monomers and a modified J-chain, wherein the modified J-chain comprises a moiety introduced into a J-chain, wherein each immunoglobulin monomer comprises two heavy chains, and wherein each heavy chain comprises a tail-piece domain and a heavy chain constant domain, wherein the moiety comprises an albumin protein.

2. The polymeric antibody of claim 1, wherein the J-chain is a native human J-chain.

3. The polymeric antibody of claim 2, wherein the native human J-chain comprises SEQ ID NO: 1.

4. The polymeric antibody of claim 3, wherein the moiety is introduced into the J-chain by indirect fusion through a peptide linker.

5. The polymeric antibody of claim 4, wherein the peptide linker is located at or around the C- or N-terminus of the moiety.

6. The polymeric antibody of claim 4, wherein the moiety is introduced at the C-terminus of the J-chain.

7. The polymeric antibody of claim 4, wherein the moiety is introduced at the N-terminus of the J-chain.

8. The polymeric antibody of claim 4, wherein the peptide linker is about 10 to 20 amino acids long.

9. The polymeric antibody of claim 4, wherein the peptide linker is 15 amino acids long.

10. The polymeric antibody of claim 4, wherein the modified J chain further comprising a binding moiety.

11. The polymeric antibody of claim 10, wherein the binding moiety is a polypeptide introduced into the J-chain by direct or indirect fusion.

12. The polymeric antibody of claim 10, wherein the moiety is located at an N-terminus of the modified J-chain, and the binding moiety is located at a C-terminus of the modified J-chain.

13. The polymeric antibody of claim 10, wherein the moiety is located at a C-terminus of the modified J-chain, and the binding moiety is located at an N-terminus of the modified J-chain.

14. The polymeric antibody of claim 10, wherein the binding moiety binds human CD3.

15. The polymeric antibody of claim 14, wherein the binding moiety comprises a human CD3-binding scFv.

16. The polymeric antibody of claim 1, which comprises five immunoglobulin monomers to form a pentamer, wherein the two heavy chains of each immunoglobulin monomer comprise an IgM tail-piece (µtp) and a Cµ4 domain.

17. The polymeric antibody of claim 16, wherein the two heavy chains of each immunoglobulin monomer each further comprise a Cµ1 domain, a Cµ2 domain, and a Cµ3 domain.

18. The polymeric antibody of claim 1, wherein each immunoglobulin monomer further comprises two light chains associated with the two heavy chains.

19. The polymeric antibody of claim 16, wherein the two heavy chains of immunoglobulin monomer are hybrid heavy chains further comprising one or more heavy chain constant region domains of a non-IgM isotype.

20. The polymeric antibody of claim 19, wherein the non-IgM isotype is IgG.

21. The polymeric antibody of claim 1, which comprises two immunoglobulin monomers to form a dimer, wherein each immunoglobulin monomer comprise an IgA tail-piece (αtp) and a Cα3 domain.

22. The polymeric antibody of claim 21, wherein the two heavy chains of each immunoglobulin monomer each further comprise a Cα1 domain, and a Cα2 domain.

23. The polymeric antibody of claim 22, wherein the two heavy chains of each immunoglobulin monomer comprise a heavy chain variable domain (VH), and wherein each heavy chain comprises, starting at the N-terminus, the VH, the Cα1 domain, the Cα2 domain, the Cα3 domain, and the αtp.

24. The polymeric antibody of claim 23, wherein each immunoglobulin monomer further comprises two light chains associated with the two heavy chains.

25. The polymeric antibody of claim 21, wherein the two heavy chains of immunoglobulin monomer are hybrid heavy chains further comprising one or more heavy chain constant region domains of a non-IgA isotype.

26. The polymeric antibody of claim 25, wherein the non-IgA isotype is IgG.

27. The polymeric antibody of claim 1, wherein the albumin protein is human serum albumin.

* * * * *